(12) United States Patent
Fukumoto et al.

(10) Patent No.: US 8,895,035 B2
(45) Date of Patent: Nov. 25, 2014

(54) ALKOXYIMINO DERIVATIVE AND PEST CONTROL AGENT

(75) Inventors: Shunichirou Fukumoto, Shizuoka (JP); Daisuke Shikama, Shizuoka (JP); Keiji Toriyabe, Shizuoka (JP); Toshihiro Nagata, Shizuoka (JP); Masaaki Komatsu, Shizuoka (JP); Takeshi Matsuda, Shizuoka (JP); Yuki Nakano, Tokyo (JP)

(73) Assignees: Kumiai Chemical Industry Co., Ltd, Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/806,317

(22) PCT Filed: Jun. 21, 2011

(86) PCT No.: PCT/JP2011/003522
§ 371 (c)(1),
(2), (4) Date: Dec. 21, 2012

(87) PCT Pub. No.: WO2011/161945
PCT Pub. Date: Dec. 29, 2011

(65) Prior Publication Data
US 2013/0102568 A1   Apr. 25, 2013

(30) Foreign Application Priority Data
Jun. 24, 2010   (JP) ................. 2010-143577

(51) Int. Cl.
| | |
|---|---|
| *A01N 43/54* | (2006.01) |
| *A01N 55/00* | (2006.01) |
| *A01N 37/50* | (2006.01) |
| *A01N 43/08* | (2006.01) |
| *A01N 43/10* | (2006.01) |
| *A01N 43/20* | (2006.01) |
| *A01N 43/40* | (2006.01) |
| *A01N 43/50* | (2006.01) |
| *A01N 43/56* | (2006.01) |
| *A01N 43/653* | (2006.01) |
| *A01N 43/713* | (2006.01) |
| *A01N 43/78* | (2006.01) |
| *A01N 43/82* | (2006.01) |
| *C07C 259/02* | (2006.01) |
| *A01N 43/84* | (2006.01) |
| *C07D 249/10* | (2006.01) |
| *C07D 401/12* | (2006.01) |
| *C07D 403/12* | (2006.01) |
| *C07D 413/06* | (2006.01) |
| *C07D 413/12* | (2006.01) |
| *C07D 417/06* | (2006.01) |
| *C07F 7/10* | (2006.01) |
| *C07D 403/06* | (2006.01) |
| *C07D 405/12* | (2006.01) |
| *C07D 417/12* | (2006.01) |
| *A01N 47/18* | (2006.01) |
| *C07F 7/08* | (2006.01) |

(52) U.S. Cl.
CPC ................. *A01N 55/00* (2013.01); *A01N 37/50* (2013.01); *A01N 43/08* (2013.01); *A01N 43/10* (2013.01); *A01N 43/20* (2013.01); *A01N 43/40* (2013.01); *A01N 43/50* (2013.01); *A01N 43/56* (2013.01); *A01N 43/653* (2013.01); *A01N 43/713* (2013.01); *A01N 43/78* (2013.01); *A01N 43/82* (2013.01); *C07C 259/02* (2013.01); *A01N 43/84* (2013.01); *C07D 249/10* (2013.01); *C07D 401/12* (2013.01); *C07D 403/12* (2013.01); *C07D 413/06* (2013.01); *C07D 413/12* (2013.01); *C07D 417/06* (2013.01); *C07F 7/10* (2013.01); *C07D 403/06* (2013.01); *C07D 405/12* (2013.01); *C07D 417/12* (2013.01); *A01N 47/18* (2013.01); *C07F 7/0812* (2013.01)
USPC .............................. 424/400; 514/63; 514/236

(58) Field of Classification Search
CPC ............................... A01N 37/50; A01N 43/56
USPC ..................................... 424/400; 514/63, 236
See application file for complete search history.

(56) References Cited

U.S. PATENT DOCUMENTS

| | | | |
|---|---|---|---|
| 4,358,408 A | 11/1982 | Kruger et al. | |
| 5,411,990 A | 5/1995 | Tsuji et al. | |

(Continued)

FOREIGN PATENT DOCUMENTS

| | | |
|---|---|---|
| AU | A-91777/82 | 12/1982 |
| GB | 1443555 A | 7/1976 |

(Continued)

*Primary Examiner* — Johann R Richter
*Assistant Examiner* — Yanzhi Zhang
(74) *Attorney, Agent, or Firm* — Bacon & Thomas, PLLC

(57) ABSTRACT

The present invention provides a novel alkoxyimino derivative or a salt thereof, as well as to a pest control agent containing the derivative or salt thereof as an active ingredient, which shows an excellent pest control effect on a wide range of pests in the agricultural and horticultural field and is also capable of controlling resistant pests. The novel alkoxyimino derivative is characterized by being represented by general formula [I]

[Chemcial formula 1]

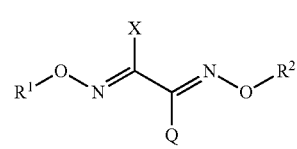

[I]

(in the formula, X, $R^1$, $R^2$ and Q are as defined in the specification) and the post control agent is characterized by containing as an active ingredient the alkoxyimino derivative or a salt thereof.

16 Claims, No Drawings

(56) References Cited

U.S. PATENT DOCUMENTS

| | | | |
|---|---|---|---|
| 6,130,247 A | 10/2000 | Bayer et al. | |
| 6,225,349 B1 * | 5/2001 | Bayer et al. | 514/538 |
| 2004/0023806 A1 * | 2/2004 | Ziegler et al. | 504/244 |

FOREIGN PATENT DOCUMENTS

| | | | |
|---|---|---|---|
| JP | 49-55833 | | 5/1974 |
| JP | 52136120 | A | 11/1977 |
| JP | 58110569 | A | 7/1983 |
| JP | 6-40811 | A | 2/1994 |
| JP | 11-512446 | A | 10/1999 |
| JP | 2000506902 | A1 | 6/2000 |
| JP | 2001-513782 | A | 9/2001 |
| JP | 2003-516384 | A | 5/2003 |
| WO | 9711065 | A1 | 3/1997 |
| WO | 01/36399 | A1 | 5/2001 |

* cited by examiner

ALKOXYIMINO DERIVATIVE AND PEST CONTROL AGENT

TECHNICAL FIELD

The present invention relates to a novel alkoxyimino derivative or a salt thereof, as well as to a pest control agent containing the derivative or salt thereof as an active ingredient.

BACKGROUND ART

For example, the following patent literature 1 or patent literature 2 is already known as a literature regarding compounds similar to the alkoxyimino derivative of the present invention.

The patent literature 1 discloses a hydroximoylazole derivative. However, this derivative is restricted to compounds having a carbamic acid ester structure, and the literature does not disclose the alkoxyimino derivative of the present invention.

The patent literature 2 discloses a hydroximoyl derivative. However, this derivative is restricted to O-acyl derivatives, and the literature does not disclose the alkoxyimino derivative of the present invention.

PRIOR ART LITERATURES

Patent Literatures

Patent literature 1: DE-3150984
Patent literature 2: JP-1995-41704

SUMMARY OF THE INVENTION

Task to be Achieved by the Invention

It is desired that pest control agents such as insecticide, acaricide and the like, used to useful crops are safe to man and livestock, are small in influence to environment, and exhibit a sufficient effect to pests at a low dose. Use of insecticides and acaricides for past many years has generated resistant pests, making it difficult to control pests completely with conventional chemicals.

The task of the present invention is to provide an excellent pest control agent which solves the above-mentioned problems of conventional pest control agents.

Means for Achieving the Task

In order to develop a pest control agent having the above-mentioned advantageous features, the present inventors synthesized various alkoxyimino derivatives and studied physiological activities thereof. As a result, it was found that an alkoxyimino derivative represented by the general formula [I] shown below shows a high effect to pests and resistant pests. The finding has led to the completion of the present invention.

The present invention has a scope characterized as shown below.

(1) An alkoxyimino derivative characterized by being represented by the following general formula [I] or an agriculturally acceptable salt thereof.

[Formula 1]

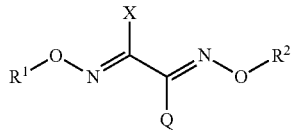

[in the formula,

X is a hydrogen atom, a halogen atom, a cyano group, a $C_1$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkylthio group, a $C_1$~$C_6$ alkylsulfinyl group, a $C_1$~$C_6$ alkylsulfonyl group, a $C_1$~$C_5$ alkylthio $C_1$~$C_6$ alkyl group, a $C_1$~$C_6$ alkylsulfinyl $C_1$~$C_6$ alkyl group, a $C_1$~$C_8$ alkylsulfonyl $C_1$~$C_6$ alkyl group, a $C_1$~$C_6$ alkoxy group, a $C_1$~$C_6$ alkoxy $C_1$~$C_6$ alkyl group, a thiocarbamoyl group, a $R^4R^5NC(=O)$ group, a $R^6R^7N$ group, a $C_1$~$C_6$ alkoxycarbonyl group, a carboxyl group, a $R^8O(HN=)C$ group, a $R^9ON=(R^{10})C$ group, a $R^{11}S(O=)C$ group, a $R^{12}R^{13}NSO_2NH$ group, a hydroxy $C_1$~$C_6$ alkyl group, a cyano $C_1$~$C_6$ alkyl group, a $C_1$~$C_6$ alkylcarbonyl group, a phenyl group which may be substituted with substituent(s) selected from substituent group α shown later, or a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1$~$C_6$ alkyl group, $C_1$~$C_6$ haloalkyl group, $C_1$~$C_6$ alkoxy group, oxo group or cyano group), $R^1$ is a $C_1$~$C_{10}$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_2$~$C_6$ haloalkenyl group, a $C_2$~$C_6$ haloalkynyl group, a $C_1$~$C_6$ alkylthio $C_1$~$C_6$ alkyl group, a $C_1$~$C_6$ alkylsulfinyl $C_1$~$C_6$ alkyl group, a $C_1$~$C_6$ alkylsulfonyl $C_1$~$C_6$ alkyl group, a $C_1$~$C_6$ alkoxy $C_1$~$C_6$ alkyl group, a $C_1$~$C_6$ haloalkoxy $C_1$~$C_6$ alkyl group, a $C_1$~$C_6$ alkoxyimino $C_1$~$C_6$ alkyl group, a tri ($C_1$~$C_6$ alkyl)silyl $C_1$~$C_6$ alkyl group, a cyano $C_1$~$C_6$ alkyl group, a gem-di ($C_1$~$C_6$ alkoxy) $C_1$~$C_6$ alkyl group, a hydroxy $C_1$~$C_6$ alkyl group, an amino $C_1$~$C_6$ alkyl group (the group may be substituted with $R^{14}$ and $R^{15}$), a phenyl group which may be substituted with substituent(s) selected from the substituent group α, a phenyl $C_1$~$C_6$ alkyl group which may be substituted with substituent(s) selected from the substituent group α, a phenyl $C_2$~$C_6$ alkenyl group which may be substituted with substituent(s) selected from the substituent group α, a phenoxy $C_1$~$C_6$ alkyl group which may be substituted with substituent(s) selected from the substituent group α, a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1$~$C_6$ alkyl group, $C_1$~$C_6$ haloalkyl group, $C_1$~$C_6$ alkoxy group, or cyano group), a $C_1$~$C_6$ alkyl group substituted with a heterocyclic ring of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1\sim C_6$ alkyl group, $C_1\sim C_6$ haloalkyl group, $C_1\sim C_6$ alkoxy group, oxo group or cyano group), or a $C_2\sim C_6$ alkenyl group substituted with a heterocyclic ring of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1\sim C_6$ alkyl group, $C_1\sim C_6$ haloalkyl group, $C_1\sim C_6$ alkoxy group, or a cyano group, when the heterocyclic ring group contains nitrogen atom, the nitrogen atom may be oxidized to form N-oxide, $R^2$ is a $C_1\sim C_6$ alkyl group, a $C_2\sim C_6$ alkenyl group, a $C_2\sim C_6$ alkynyl group, a $C_3\sim C_6$ cycloalkyl group, a $C_1\sim C_6$ haloalkyl group, a $C_2\sim C_6$ haloalkenyl group, a $C_2\sim C_6$ haloalkynyl group, a $C_1\sim C_6$ alkylthio $C_1\sim C_6$ alkyl group, a $C_1\sim C_6$ alkylsulfinyl $C_1\sim C_6$ alkyl group, a $C_1\sim C_6$ alkylsulfonyl $C_1\sim C_6$ alkyl group, a $C_1\sim C_6$ alkoxy $C_1\sim C_6$ alkyl group, a $C_1\sim C_6$ haloalkoxy $C_1\sim C_6$ alkyl group, a cyano $C_1\sim C_6$ alkyl group, or a phenyl $C_1\sim C_6$ alkyl group which may be substituted with the substituent group α, Q is a heterocyclic ring group represented by the following formula [Q-1] or formula [Q-2],

[formula 2]

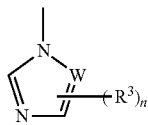
[Q-1]

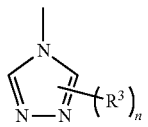
[Q-2]

or a halogen atom, in the formula [Q-1], W is a nitrogen atom or a methine group, the nitrogen atom(s) of the heterocyclic ring group of formula [Q-1] and formula [Q-2] may be oxidized to form N-oxide, in the formula [Q-1] and formula [Q-2], $R^3$ is a halogen atom, a cyano group, a nitro group, a hydroxyl group, a mercapto group, a $C_1\sim C_6$ alkyl group, a $C_1\sim C_6$ haloalkyl group, a $C_1\sim C_6$ alkoxy group, a $C_1\sim C_6$ alkylthio group, a $C_1\sim C_6$ alkylsulfinyl group, a $C_1\sim C_6$ alkylsulfonyl group, a formyl group, or a hydroxyimino $C_1\sim C_4$ alkyl group, in the formula [Q-1] and formula [Q-2], n is 0, 1 or 2 when W is a nitrogen atom and 0, 1, 2 or 3 when W is a methine group, $R^4$, $R^5$, $R^6$, $R^7$, $R^{12}$, $R^{13}$, $R^{14}$ and $R^{15}$ are each a hydrogen atom, a $C_1\sim C_6$ alkyl group, a $C_1\sim C_6$ alkoxy group, a $C_1\sim C_6$ alkoxy $C_1\sim C_6$ alkyl group, a $C_1\sim C_6$ alkylcarbonyl group, a $C_1\sim C_6$ alkoxycarbonyl group, a $C_1\sim C_6$ haloalkyl group, a $C_3\sim C_6$ cycloalkyl group, a $C_3\sim C_6$ cycloalkyl $C_1\sim C_6$ alkyl group, a $C_1\sim C_6$ alkylsulfonyl group, a cyano $C_1\sim C_6$ alkyl group, or a phenyl group which may be substituted with substituent(s) selected from the substituent group α, $R^4$ and $R^5$, $R^6$ and $R^7$, $R^{12}$ and $R^{13}$, and $R^{14}$ and $R^{15}$ may respectively be combined together to form an $C_2\sim C_7$ alkylene chain and thereby may form, together with the nitrogen atom to which they bond, a 3- to 8-membered ring, wherein the alkylene chain may contain one oxygen atom, sulfur atom or nitrogen atom and also may be substituted with halogen atom, $C_1\sim C_6$ alkyl group and oxo group, $R^8$ and $R^9$ are each a hydrogen atom, a $C_1\sim C_6$ alkyl group, a $C_1\sim C_6$ haloalkyl group, or a $C_1\sim C_6$ alkoxycarbonyl group, $R^{10}$ is a $R^6R^7N$ group or Q, and $R^{11}$ is a $C_1\sim C_6$ alkyl group.]

Substituent Group α

Halogen atom, $C_1\sim C_6$ alkyl group, $C_1\sim C_6$ haloalkyl group, $C_1\sim C_6$ alkoxy group, $C_1\sim C_6$ haloalkoxy group, $C_1\sim C_6$ alkoxycarbonyl group, nitro group, and cyano group (2) An alkoxyimino derivative or an agriculturally acceptable salt thereof, set forth in (1), wherein X is a hydrogen atom, a halogen atom, a cyano group, a $C_1\sim C_8$ alkyl group, a $C_3\sim C_6$ cycloalkyl group, a $C_1\sim C_6$ haloalkyl group, a $C_1\sim C_6$ alkylthio group, a $C_1\sim C_6$ alkylsulfinyl group, a $C_1\sim C_5$ alkylsulfonyl group, a $C_1\sim C_6$ alkoxy group, a thiocarbamoyl group, a $R^4R^5NC(=O)$ group, a $R^6R^7N$ group, a $C_1\sim C_6$ alkoxycarbonyl group, a carboxyl group, a $R^8O(HN=)C$ group, a $R^9ON=(R^{10})C$ group, a $R^{11}S(O=)C$ group, a $R^{12}R^{13}NSO_2NH$ group, a hydroxy $C_1\sim C_6$ alkyl group, a cyano $C_1\sim C_6$ alkyl group, a $C_1\sim C_6$ alkylcarbonyl group, a phenyl group which may be substituted with substituent(s) selected from the substituent group α, or a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1\sim C_6$ alkyl group, $C_1\sim C_6$ haloalkyl group, $C_1\sim C_6$ alkoxy group, oxo group or cyano group), $R^1$ is a $C_1\sim C_{10}$ alkyl group, a $C_2\sim C_6$ alkenyl group, a $C_2\sim C_6$ alkynyl group, a $C_3\sim C_6$ cycloalkyl group, a $C_3\sim C_6$ cycloalkyl $C_1\sim C_6$ alkyl group, a $C_1\sim C_6$ haloalkyl group, a $C_2\sim C_6$ haloalkenyl group, a $C_1\sim C_6$ alkylthio $C_1\sim C_6$ alkyl group, a $C_1\sim C_6$ alkoxy $C_1\sim C_6$ alkyl group, a $C_1\sim C_6$ haloalkoxy $C_1\sim C_6$ alkyl group, a tri ($C_1\sim C_6$ alkyl)silyl $C_1\sim C_6$ alkyl group, a cyano $C_1\sim C_6$ alkyl group, a gem-di ($C_1\sim C_6$ alkoxy) $C_1\sim C_6$ alkyl group, a hydroxy $C_1\sim C_6$ alkyl group, an amino $C_1\sim C_6$ alkyl group (the group may be substituted with $R^{14}$ and $R^{15}$), a phenyl group which may be substituted with substituent(s) selected from the substituent group α, a phenyl $C_1\sim C_6$ alkyl group which may be substituted with substituent(s) selected from the substituent group α, a phenyl $C_2\sim C_6$ alkenyl group which may be substituted with substituent(s) selected from the substituent group α, a phenoxy $C_1\sim C_6$ alkyl group which may be substituted with substituent(s) selected from the substituent group α, a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1\sim C_6$ alkyl group, $C_1\sim C_6$ haloalkyl group, $C_1\sim C_6$ alkoxy group, or cyano group), or a $C_1\sim C_6$ alkyl group substituted with a heterocyclic ring of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1\sim C_6$ alkyl group, $C_1\sim C_6$ haloalkyl group, $C_1\sim C_6$ alkoxy group, oxo group or cyano group), when the heterocyclic ring group contains nitrogen atom, the nitrogen atom may be oxidized to form N-oxide, $R^2$ is a $C_1\sim C_6$ alkyl group, a $C_2\sim C_6$ alkenyl group, a $C_2\sim C_5$ alkynyl group, a $C_3\sim C_6$ cycloalkyl group, a $C_1\sim C_6$ haloalkyl group, a $C_1\sim C_6$ alkoxy $C_1\sim C_6$ alkyl group, a cyano $C_1\sim C_6$ alkyl group, or a phenyl $C_1$~$C_6$ alkyl group which may be substituted with the substituent group α, Q is a heterocyclic ring group represented by the following formula [Q-1] or formula [Q-2],

[formula 3]

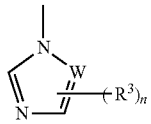
[Q-1]

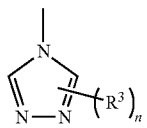
[Q-2]

or a halogen atom, in the formula [Q-1], W is a nitrogen atom or a methine group, in the formula [Q-1] and formula [Q-2], $R^3$ is a mercapto group or a $C_1$~$C_6$ haloalkyl group, in the formula [Q-1] and formula [Q-2], n is 0 or 1, $R^4$, $R^5$, $R^6$, $R^7$, $R^{12}$, $R^{13}$, $R^{14}$ and $R^{15}$ are each a hydrogen atom, a $C_1$~$C_6$ alkyl group, a $C_1$=$C_6$ alkoxy group, a $C_1$~$C_6$ alkylcarbonyl group, a $C_1$~$C_6$ alkoxycarbonyl group, a $C_1$~$C_6$ haloalkyl group, a $C_3$~$C_6$ cycloalkyl $C_1$~$C_6$ alkyl group, a cyano $C_1$~$C_6$ alkyl group, or a phenyl group which may be substituted with substituent(s) selected from the substituent group α, $R^4$ and $R^5$, $R^6$ and $R^7$, $R^{12}$ and $R^{13}$, and $R^{14}$ and $R^{15}$ may respectively be combined together to form an $C_2$~$C_7$ alkylene chain and thereby may form, together with the nitrogen atom to which they bond, a 3- to 8-membered ring, wherein the alkylene ring may contain one oxygen atom, sulfur atom or nitrogen atom, $R^8$ and $R^9$ are each a hydrogen atom, a $C_1$~$C_6$ alkyl group, or a $C_1$~$C_6$ alkoxycarbonyl group, $R^{10}$ is a $R^6R^7N$ group or Q, and $R^{11}$ is a $C_1$~$C_6$ alkyl group.

(3) An alkoxyimino derivative or an agriculturally acceptable salt thereof, set forth in (1) or (2), wherein Q is a halogen atom.

(4) An alkoxyimino derivative or an agriculturally acceptable salt thereof, set forth in (1) or (2), wherein Q is a heterocyclic ring group represented by the following formula [Q-1].

[Formula 4]

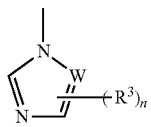
[Q-1]

(5) A pest control agent characterized by containing, as an active ingredient, an alkoxyimino derivative or an agriculturally acceptable salt thereof, set forth in any of (1) to (4).

(6) A pest control agent according to (5), which is an insecticide.

(7) A method for pest control, which is characterized by using, in an effective amount, an alkoxyimino derivative or an agriculturally acceptable salt thereof, set forth in any of (1) to (4).

(8) A method for pest control according to (7), which comprises using an alkoxyimino derivative or an agriculturally acceptable salt thereof as an insecticide.

The alkoxyimino derivative or agriculturally acceptable salt thereof, of the present invention is a novel compound. The pest control agent containing the compound as an active ingredient shows an excellent control effect to a variety of pests in agricultural and horticultural fields, can control even resistant pests, and is highly effective particularly to Hemipteran pests such as *Nilaparvata lugens* (brown rice planthopper), *Laodelphax striatella* (small brown planthopper), *Sogatella furcifera* (white backed rice planthopper), *Nephotettix cincticeps* (green rice leafhoper), *Aphis gossipii* (aphid), *Benisia tabaci* (white fly) and the like.

BEST MODE FOR CARRYING OUT THE INVENTION

Description is made on the symbols and terms used in the Description.

In the present invention, pest control agent means pest control agents targeted for injurious orthopods, used in agricultural and horticultural fields, livestock industry, sanitation field, etc. (insecticide and acaricide agents for agricultural and horticultural fields, control agents for internal and external parasites of mammals and birds as livestock or pet animal, and control agents for sanitary pests and uncomfortable pests, for household use and business use).

In the present invention, agricultural chemical means insecticides, acaricides, nematicides, etc. used in agricultural and horticultural fields.

Halogen atom refers to fluorine atom, chlorine atom, bromine atom or iodine atom.

$C_1$~$C_6$ alkyl group refers to a straight chain or branched chain alkyl group of 1 to 6 carbon atoms, unless otherwise specified. There can be mentioned, for example, methyl, ethyl, n-propyl, isopropyl, n-butyl, sec-butyl, isobutyl, tert-butyl, n-pentyl, 1-methylbutyl, 2-methylbutyl, isopentyl, 1-ethylpropyl, 1,1-dimethylpropyl, 1,2-dimethylpropyl, neopentyl, n-hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, and 1-ethyl-1-methylpropyl groups.

$C_1$~$C_8$ alkyl group refers to a straight chain or branched chain alkyl group of 1 to 8 carbon atoms, unless otherwise specified. There can be mentioned, for example, those groups mentioned for the $C_1$~$C_6$ alkyl group; and n-heptyl, 1-methylhexyl, 5-methylhexyl, 4,4-dimethylpentyl, n-octyl, 1-methylheptyl, 6-methylhexptyl and 5,5-dimethylhexyl groups.

$C_1$~$C_{10}$ alkyl group refers to a straight chain or branched chain alkyl group of 1 to 10 carbon atoms, unless otherwise specified. There can be mentioned, for example, those groups mentioned for the $C_1$~$C_8$ alkyl group; and n-nonyl, isononyl, n-decanyl, isodecanyl, 7,7-dimethyloctyl and n-undecanyl groups.

$C_2$~$C_6$ alkenyl group refers to a straight chain or branched chain alkenyl group of 2 to 6 carbon atoms, unless otherwise specified. There can be mentioned, for example, vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl and 2,4-hexadienyl groups.

$C_2$~$C_6$ alkynyl group refers to a straight chain or branched chain alkynyl group of 2 to 6 carbon atoms, unless otherwise specified. There can be mentioned, for example, ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexnynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexnynyl, 1-ethyl-3-butynyl, 1-ethyl-1-methyl-2-propynyl, 1-(isopropyl)-2-propynyl, 1,1-dimethyl-2-butynyl and 2,2-dimethyl-3-butynyl groups.

$C_3$~$C_6$ cycloalkyl group refers to a cycloalkyl group of 3 to 6 carbon atoms, unless otherwise specified. There can be mentioned, for example, cyclopropyl, cyclobutyl, cyclopentyl and cyclohexyl groups.

$C_3$~$C_6$ cycloalkyl $C_1$~$C_6$ alkyl group refers, unless otherwise specified, to a ($C_3$~$C_6$ cycloalkyl)-($C_1$~$C_6$ alkyl) group wherein the cycloalkyl moiety and the alkyl moiety have each the above-mentioned meaning. There can be mentioned, for example, cyclopropylmethyl, cyclobutylmethyl, cyclopentylmethyl and cyclohexylmethyl groups.

$C_1$~$C_6$ alkoxy group refers, unless otherwise specified, to a ($C_1$~$C_6$ alkyl)-O— group wherein the alkyl moiety has the above-mentioned meaning. There can be mentioned, for example, methoxy, ethoxy, n-propoxy, isopropxy, n-butoxy, isobutoxy, tert-butoxy, pentyloxy, isopentyloxy, hexyloxy and isohexyloxy groups.

$C_1$~$C_6$ haloalkyl group refers, unless otherwise specified, to a straight chain or branched chain alkyl group of 1 to 6 carbon atoms, substituted with 1 to 13, preferably 1 to 5 same or different halogen atoms. There can be mentioned, for example, 2-fluoroethyl, 2,2,2-trifluoroethyl, 3,3,3-trifluoropropyl and 2,2,2-trichloroethyl groups.

$C_2$~$C_6$ haloalkenyl group refers, unless otherwise specified, to a straight chain or branched chain alkenyl group of 2 to 6 carbon atoms, substituted with 1 to 11, preferably 1 to 5 same or different halogen atoms. There can be mentioned, for example, 3-chloro-2-propenyl, 2-chloro-2-propenyl, 3,3-dichloro-2-propenyl and 4,4-difluoro-3-butenyl groups.

$C_2$~$C_6$ haloalkynyl group refers, unless otherwise specified, to a straight chain or branched chain alkynyl group of 2 to 6 carbon atoms, substituted with 1 to 4 same or different halogen atoms. There can be mentioned, for example, 3-chloro-2-propynyl, 3-bromo-2-propynyl, 3-iodo-2-propynyl, 3-chloro-1-propynyl and 5-chloro-4-pentynyl groups.

$C_1$~$C_6$ haloalkoxy group refers, unless otherwise specified, to a straight chain or branched chain alkyl-O— group of 1 to 6 carbon atoms, substituted with 1 to 11, preferably 1 to 5 same or different halogen atoms, wherein the haloalkyl moiety has the above-mentioned meaning. There can be mentioned, for example, chloromethoxy, difluoromethoxy, chlorodifluoromethoxy, trifluoromethoxy and 2,2,2-trifluoroethoxy groups.

$C_1$~$C_6$ alkylthio group refers, unless otherwise specified, to a straight chain or branched chain alkyl-Sgroup of 1 to 6 carbon atoms wherein the alkyl moiety of alkylthio has the above-mentioned meaning. There can be mentioned, for example, methylthio and ethylthio groups.

$C_1$~$C_6$ alkylsulfinyl group refers, unless otherwise specified, to a straight chain or branched chain alkyl-S(O)— group of 1 to 6 carbon atoms wherein the alkyl moiety of alkylsulfinyl has the above-mentioned meaning. There can be mentioned, for example, methylsulfinyl and ethylsulfinyl groups.

$C_1$~$C_6$ alkylsulfonyl group refers, unless otherwise specified, to a straight chain or branched chain alkyl-$S(O)_2$— group of 1 to 6 carbon atoms wherein the alkyl moiety of alkylsulfonyl has the above-mentioned meaning. There can be mentioned, for example, methylsulfonyl and ethylsulfonyl groups.

$C_1$~$C_6$ alkylthio $C_1$~$C_6$ alkyl group refers, unless otherwise specified, to an alkyl group of 1 to 6 carbon atoms, substituted with alkylthio group of 1 to 6 carbon atoms, wherein the alkyl moiety and the alkyl moiety of alkylthio have the above-mentioned meaning. There can be mentioned, for example, methylthiomethyl and ethylthiomethyl groups.

$C_1$~$C_6$ alkylsulfinyl $C_1$~$C_6$ alkyl group refers, unless otherwise specified, to an alkyl group of 1 to 6 carbon atoms, substituted with alkylsulfinyl group of 1 to 6 carbon atoms, wherein the alkyl moiety and the alkyl moiety of alkylsulfinyl have each the above-mentioned meaning. There can be mentioned, for example, methylsulfinylmethyl and ethylsulfinylmethyl groups.

$C_1$~$C_6$ alkylsulfonyl $C_1$~$C_6$ alkyl group refers, unless otherwise specified, to an alkyl group of 1 to 6 carbon atoms, substituted with alkylsulfonyl group of 1 to 6 carbon atoms, wherein the alkyl moiety and the alkyl moiety of alkylsulfonyl have each the above-mentioned meaning. There can be mentioned, for example, methylsulfonylmethyl and ethylsulfonylmethyl groups.

$C_1$~$C_6$ alkoxy $C_1$~$C_6$ alkyl group refers, unless otherwise specified, to an alkyl group of 1 to 6 carbon atoms, substituted with alkoxy group of 1 to 6 carbon atoms, wherein the alkyl moiety and the alkoxy moiety have each the above-mentioned meaning. There can be mentioned, for example, methoxymethyl, ethoxymethyl, isopropoxymethyl, pentyloxymethyl, methoxyethyl and butoxyethyl groups.

Phenoxy $C_1$~$C_6$ alkyl group refers, unless otherwise specified, to an alkyl group of 1 to 6 carbon atoms, substituted with phenyl-O— group, wherein the alkyl moiety has the above-mentioned meaning. There can be mentioned, for example, phenoxyethyl, 4-trifluoromethylphenoxypropyl and 2-(2-chlorophenoxy)propyl groups.

$C_1$~$C_6$ haloalkoxy $C_1$~$C_6$ alkyl group refers, unless otherwise specified, to an alkyl group of 1 to 6 carbon atoms, substituted with haloalkoxy group of 1 to 6 carbon atoms, wherein the haloalkoxy moiety and the alkyl moiety have each the above-mentioned meaning. There can be mentioned, for example, chloromethoxymethyl, difluoromethoxymethyl, chlorodifuloromethoxymethyl, trifluoromethoxymethyl and 2,2,2-trifluoroethoxymethyl groups.

$C_1$~$C_6$ alkoxyimino $C_1$~$C_6$ alkyl group refers, unless otherwise specified, to an alkyl group of 1 to 6 carbon atoms, substituted with (alkoxy)-N= of 1 to 6 carbon atoms, wherein the alkoxy moiety and the alkyl moiety have each the above-mentioned meaning. There can be mentioned, for example, 2-methoxyiminoethyl, 3-methoxyiminopropyl and 1-methoxyiminoethyl groups.

Hydroxyimino $C_1$~$C_4$ alkyl group refers, unless otherwise specified, to an alkyl group of 1 to 4 carbon atoms, substituted with HO—N=. There can be mentioned, for example, hydroxyiminomethyl and hydroxyiminoethyl groups.

Tri ($C_1$~$C_6$ alkyl)silyl $C_1$~$C_6$ alkyl group refers, unless otherwise specified, to an alkyl group of 1 to 6 carbon atoms, substituted with tri($C_1$~$C_6$ alkyl)-Si— group, wherein the alkyl moiety has the above-mentioned meaning. There can be mentioned, for example, trimethylsilylmethyl group, 2-trimethylsilylethyl group, 3-trimethylsilylpropyl group and 4-trimethylsilylbutyl group.

Phenyl $C_1$~$C_6$ alkyl group refers, unless otherwise specified, to an alkyl group of 1 to 6 carbon atoms, substituted with phenyl group, wherein the alkyl moiety has the above-mentioned meaning. There can be mentioned, for example, benzyl, 1-phenylethyl and 2-phenylethyl groups.

Phenyl $C_2$~$C_6$ alkenyl group refers, unless otherwise specified, to an alkenyl group of 2 to 6 carbon atoms, substituted with phenyl group, wherein the alkyl moiety has the above-mentioned meaning. There can be mentioned, for example, styryl and 3-phenyl-2-propenyl groups.

As heterocyclic ring group of 1 to 9 carbon atoms, having 1 to 5 hetero atoms which may be the same or different and which are selected from oxygen atom, sulfur atom and nitrogen atom, there can be mentioned, unless otherwise specified, for example, pyridine, pyrimidine, pyrazine, pyridazine, 1,3,5-triazine, 1,2,4-triazine, pyrrole, pyrazole, imidazole, 1,3,4-triazole, 1,2,4-triazole, 1,2,3-triazole, tetrazole, furan, oxazole, isoxazole, 1,2,4-oxadiazole, 1,3,4-oxadiazole, thiophene, thiazole, isothiazole, 1,3,4-thiadiazole, 1,2,4-thiadiazole, 1,2,3-thiadiazole, quinoline, indole, benzofuran, benzothiophene, benzoimidazole, benzoxazole, benzisoxazole, benzothiazole, benzisothiazole, oxirane, oxorane and isoxazoline groups. Incidentally, when the heterocyclic ring group contains nitrogen atom, the nitrogen atom may be oxidized to form N-oxide.

$C_1$~$C_6$ alkyl group substituted with heterocyclic ring of 1 to 9 carbon atoms, having 1 to 5 hetero atoms which may be the same or different and which are selected from oxygen atom, sulfur atom and nitrogen atom, refers, unless otherwise specified, to an alkyl group of 1 to 6 carbon atoms, substituted with heterocyclic ring, wherein the alkyl moiety has the above-mentioned meaning. There can be mentioned, for example, (tetrahydrofuran-2-yl)methyl, (4,5-dihydroisoxazol-5-yl) methyl, (isoxazol-5-yl)methyl and (thiophen-2-yl)methyl groups.

$C_2$~$C_6$ alkenyl group substituted with heterocyclic ring of 1 to 9 carbon atoms, having 1 to 5 hetero atoms which may be the same or different and which are selected from oxygen atom, sulfur atom and nitrogen atom, refers, unless otherwise specified, to an alkyl group of 1 to 6 carbon atoms, substituted with heterocyclic ring, wherein the alkyl moiety has the above-mentioned meaning. There can be mentioned, for example, 5-(tetrahydrofuran-2-yl)vinyl and 3-(4,5-dihydroisoxazol-5-yl)-2-propenyl groups.

Cyano $C_1$~$C_6$ alkyl group refers, unless otherwise specified, to an alkyl group of 1 to 6 carbon atoms, substituted with cyano group, wherein the alkyl moiety has the above-mentioned meaning. There can be mentioned, for example, cyanomethyl group and 1-cyanobutyl group.

gem-di ($C_1$~$C_6$ alkoxy) $C_1$~$C_6$ alkyl group refers, unless otherwise specified, to an alkyl group of 1 to 6 carbon atoms wherein one carbon atom is substituted with two alkoxy groups having the above-mentioned meaning. There can be mentioned, for example, diethoxymethyl and 2-dimethoxypropyl groups.

Hydroxy $C_1$~$C_6$ alkyl group refers, unless otherwise specified, to an alkyl group of 1 to 6 carbon atoms wherein the alkyl moiety is substituted with hydroxyl group. There can be mentioned, for example, 2-hydroxyethyl, 3-hydroxy-n-butyl and 3-hydroxy-n-propyl groups.

$C_1$~$C_6$ alkylcarbonyl group refers, unless otherwise specified, to alkyl-C(=O)— wherein the alkyl moiety has the above-mentioned meaning. There can be mentioned, for example, acetyl and isobutanoyl groups.

$C_1$~$C_6$ alkoxycarbonyl group refers, unless otherwise specified, to alkoxy-C(=O)— wherein the alkoxy moiety has the above-mentioned meaning. There can be mentioned, for example, methoxycarbonyl and isopropoxycarbonyl groups.

Amino $C_1$~$C_6$ alkyl group refers, unless otherwise specified, to an alkyl group of 1 to 6 carbon atoms wherein the alkyl moiety is substituted with amino group. There can be mentioned, for example, 2-aminoethyl, 3-amino-n-butyl and 3-amino-n-propyl groups.

As the agriculturally acceptable salt, there can be mentioned, for example, a salt of alkali metal (e.g. sodium or potassium); a salt of alkaline earth metal (e.g. calcium, magnesium or barium); a salt of transition metal (e.g. manganese, copper, zinc or iron); an ammonium salt (the nitrogen atom may be, as necessary, substituted with 1 to 4 alkyl groups of 1 to 4 carbon atoms and/or one phenyl or benzyl group), preferably diisopropyl ammonium, tetramethyl ammonium, tetrabutyl ammonium, or trimethylbenzyl ammonium; a salt with an inorganic acid (e.g. hydrochloric acid, hydrobromic acid, phosphoric acid or sulfuric acid); and a salt with an organic acid such as $C_1$~$C_4$ alkylsulfonic acid (e.g. methanesulfonic acid), aromatic sulfonic acid (e.g. benzenesulfonic acid or toluenesulfonic acid), oxalic acid, maleic acid, fumaric acid, lactic acid, tartaric acid, adipic acid, benzoic acid or the like.

Next, representative compounds of the present invention compound of the general formula [I] are shown in Tables 1 to 63. However, the present compound is not restricted thereto. The No. of each compound shown in each Table is referred to in the later description.

The compounds included in the present invention contain, in some cases, E-isomers and Z-isomers depending upon the kind of substituent. The present invention includes the E-isomers, the Z-isomers, and mixtures of any mixing ratio of E-isomer and Z-isomer. Further, the compounds included in the present invention contain, in some cases, optical isomers due to the presence of at least one asymmetric carbon atom and asymmetric sulfur atom. The present invention includes all optical active compounds, racemic modifications and diastereomers.

In the present invention, the following expressions refer to corresponding groups.

Me: methyl group
Et: ethyl group
Pr-n: n-propyl group
Pr-i: isopropyl group
Pr-c: cyclopropyl group
Bu-n: n-butyl group
Bu-s: sec-butyl group
Bu-i: isobutyl group
Bu-t: tert-butyl group
Pen-n: n-pentyl group
Pen-c: cyclopentyl group
Pen-i: isopentyl group
Pen-neo: neopentyl group
Pen-2: 2-pentyl group
Pen-3: 3-pentyl group
Hex-n: n-hexyl group
Hex-c: cyclohexyl group Also, for example, the following expressions have corresponding meanings.
5-CF$_3$: substituted with trifluoromethyl group at 5-position
3-Cl-5-CF$_3$: substituted with chlorine atom at 3-position and with trifluoromethyl group at 5-position
2,6-(Cl)$_2$: substituted with chlorine atom at 2- and 6-positions

TABLE 1

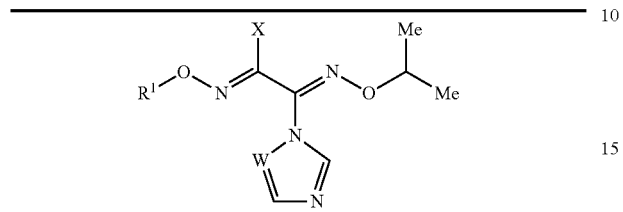

| Compound No. | R$^1$ | X | W |
|---|---|---|---|
| I-1 | Me | Cl | N |
| I-2 | Et | Cl | N |
| I-3 | Pr-n | Cl | N |
| I-4 | Pr-i | Cl | N |
| I-5 | Bu-n | Cl | N |
| I-6 | Bu-i | Cl | N |
| I-7 | Bu-s | Cl | N |
| I-8 | Bu-t | Cl | N |
| I-9 | Pen-n | Cl | N |
| I-10 | Pen-i | Cl | N |
| I-11 | Pen-neo | Cl | N |
| I-12 | Pen-2 | Cl | N |
| I-13 | Pen-3 | Cl | N |
| I-14 | Hex-n | Cl | N |
| I-15 | CH$_2$CH$_2$C(Me)$_3$ | Cl | N |
| I-16 | Pen-c | Cl | N |
| I-17 | Hex-c | Cl | N |
| I-18 | CH$_2$Pr-c | Cl | N |
| I-19 | CH$_2$Bu-c | Cl | N |
| I-20 | CH$_2$Pen-c | Cl | N |
| I-21 | CH$_2$CH=CH$_2$ | Cl | N |
| I-22 | CH$_2$C≡CH | Cl | N |
| I-23 | CH$_2$C≡CCH$_3$ | Cl | N |
| I-24 | Me | H | N |
| I-25 | Et | H | N |
| I-26 | Pr-n | H | N |
| I-27 | Pr-i | H | N |
| I-28 | Bu-n | H | N |
| I-29 | Bu-i | H | N |
| I-30 | Bu-s | H | N |
| I-31 | Bu-t | H | N |
| I-32 | Pen-n | H | N |

TABLE 2

| Compound No. | R$^1$ | X | W |
|---|---|---|---|
| I-33 | Pen-i | H | N |
| I-34 | Pen-neo | H | N |
| I-35 | Pen-2 | H | N |
| I-36 | Pen-3 | H | N |
| I-37 | Hex-n | H | N |
| I-38 | CH$_2$CH$_2$C(Me)$_3$ | H | N |
| I-39 | Pen-c | H | N |
| I-40 | Hex-c | H | N |
| I-41 | CH$_2$Pr-c | H | N |
| I-42 | CH$_2$Bu-c | H | N |
| I-43 | CH$_2$Pen-c | H | N |
| I-44 | CH$_2$CH=CH$_2$ | H | N |
| I-45 | CH$_2$C≡CH | H | N |
| I-46 | CH$_2$C≡CCH$_3$ | H | N |
| I-47 | Me | CN | N |
| I-48 | Et | CN | N |
| I-49 | Pr-n | CN | N |
| I-50 | Pr-i | CN | N |
| I-51 | Bu-n | CN | N |
| I-52 | Bu-i | CN | N |
| I-53 | Bu-s | CN | N |
| I-54 | Bu-t | CN | N |
| I-55 | Pen-n | CN | N |
| I-56 | Pen-i | CN | N |
| I-57 | Pen-neo | CN | N |
| I-58 | Pen-2 | CN | N |
| I-59 | Pen-3 | CN | N |
| I-60 | Hex-n | CN | N |
| I-61 | CH$_2$CH$_2$C(Me)$_3$ | CN | N |
| I-62 | Pen-c | CN | N |
| I-63 | Hex-c | CN | N |
| I-64 | CH$_2$Pr-c | CN | N |
| I-65 | CH$_2$Bu-c | CN | N |
| I-66 | CH$_2$Pen-c | CN | N |
| I-67 | CH$_2$CH=CH$_2$ | CN | N |
| I-68 | CH$_2$C≡CH | CN | N |

TABLE 3

| Compound No. | R$^1$ | X | W |
|---|---|---|---|
| I-69 | CH$_2$C≡CCH$_3$ | CN | N |
| I-70 | Me | CONH$_2$ | N |
| I-71 | Et | CONH$_2$ | N |
| I-72 | Pr-n | CONH$_2$ | N |
| I-73 | Pr-i | CONH$_2$ | N |
| I-74 | Bu-n | CONH$_2$ | N |
| I-75 | Bu-i | CONH$_2$ | N |
| I-76 | Bu-s | CONH$_2$ | N |
| I-77 | Bu-t | CONH$_2$ | N |
| I-78 | Pen-n | CONH$_2$ | N |
| I-79 | Pen-i | CONH$_2$ | N |
| I-80 | Pen-neo | CONH$_2$ | N |
| I-81 | Pen-2 | CONH$_2$ | N |
| I-82 | Pen-3 | CONH$_2$ | N |
| I-83 | Hex-n | CONH$_2$ | N |
| I-84 | CH$_2$CH$_2$C(Me)$_3$ | CONH$_2$ | N |
| I-85 | Pen-c | CONH$_2$ | N |
| I-86 | Hex-c | CONH$_2$ | N |
| I-87 | CH$_2$Pr-c | CONH$_2$ | N |
| I-88 | CH$_2$Bu-c | CONH$_2$ | N |
| I-89 | CH$_2$Pen-c | CONH$_2$ | N |
| I-90 | CH$_2$CH=CH$_2$ | CONH$_2$ | N |
| I-91 | CH$_2$C≡CH | CONH$_2$ | N |
| I-92 | CH$_2$C≡CCH$_3$ | CONH$_2$ | N |
| I-93 | Me | Me | N |
| I-94 | Et | Me | N |
| I-95 | Pr-n | Me | N |
| I-96 | Pr-i | Me | N |
| I-97 | Bu-n | Me | N |
| I-98 | Bu-i | Me | N |
| I-99 | Bu-s | Me | N |
| I-100 | Bu-t | Me | N |
| I-101 | Pen-n | Me | N |
| I-102 | Pen-i | Me | N |
| I-103 | Pen-neo | Me | N |
| I-104 | Pen-2 | Me | N |
| I-105 | Pen-3 | Me | N |
| I-106 | Hex-n | Me | N |

TABLE 4

| Compound No. | R$^1$ | X | W |
|---|---|---|---|
| I-107 | CH$_2$CH$_2$C(Me)$_3$ | Me | N |
| I-108 | Pen-c | Me | N |
| I-109 | Hex-c | Me | N |
| I-110 | CH$_2$Pr-c | Me | N |
| I-111 | CH$_2$Bu-c | Me | N |
| I-112 | CH$_2$Pen-c | Me | N |
| I-113 | CH$_2$CH=CH$_2$ | Me | N |

TABLE 4-continued

| Compound No. | R¹ | X | W |
|---|---|---|---|
| I-114 | CH₂C≡CH | Me | N |
| I-115 | CH₂C≡CCH₃ | Me | N |
| I-116 | Me | NH₂ | N |
| I-117 | Et | NH₂ | N |
| I-118 | Pr-n | NH₂ | N |
| I-119 | Pr-i | NH₂ | N |
| I-120 | Bu-n | NH₂ | N |
| I-121 | Bu-i | NH₂ | N |
| I-122 | Bu-s | NH₂ | N |
| I-123 | Bu-t | NH₂ | N |
| I-124 | Pen-n | NH₂ | N |
| I-125 | Pen-i | NH₂ | N |
| I-126 | Pen-neo | NH₂ | N |
| I-127 | Pen-2 | NH₂ | N |
| I-128 | Pen-3 | NH₂ | N |
| I-129 | Hex-n | NH₂ | N |
| I-130 | CH₂CH₂C(Me)₃ | NH₂ | N |
| I-131 | Pen-c | NH₂ | N |
| I-132 | Hex-c | NH₂ | N |
| I-133 | CH₂Pr-c | NH₂ | N |
| I-134 | CH₂Bu-c | NH₂ | N |
| I-135 | CH₂Pen-c | NH₂ | N |
| I-136 | CH₂CH=CH₂ | NH₂ | N |
| I-137 | CH₂C≡CH | NH₂ | N |
| I-138 | CH₂C≡CCH₃ | NH₂ | N |
| I-139 | Me | Br | N |
| I-140 | Et | Br | N |
| I-141 | Pr-n | Br | N |
| I-142 | Pr-i | Br | N |
| I-143 | Bu-n | Br | N |

TABLE 5

| Compound No. | R¹ | X | W |
|---|---|---|---|
| I-144 | Bu-i | Br | N |
| I-145 | Bu-s | Br | N |
| I-146 | Bu-t | Br | N |
| I-147 | Pen-n | Br | N |
| I-148 | Pen-i | Br | N |
| I-149 | Pen-neo | Br | N |
| I-150 | Pen-2 | Br | N |
| I-151 | Pen-3 | Br | N |
| I-152 | Hex-n | Br | N |
| I-153 | CH₂CH₂C(Me)₃ | Br | N |
| I-154 | Pen-c | Br | N |
| I-155 | Hex-c | Br | N |
| I-156 | CH₂Pr-c | Br | N |
| I-157 | CH₂Bu-c | Br | N |
| I-158 | CH₂Pen-c | Br | N |
| I-159 | CH₂CH=CH₂ | Br | N |
| I-160 | CH₂C≡CH | Br | N |
| I-161 | CH₂C≡CCH₃ | Br | N |
| I-162 | Me | OMe | N |
| I-163 | Et | OMe | N |
| I-164 | Pr-n | OMe | N |
| I-165 | Pr-i | OMe | N |
| I-166 | Bu-n | OMe | N |
| I-167 | Bu-i | OMe | N |
| I-168 | Bu-s | OMe | N |
| I-169 | Bu-t | OMe | N |
| I-170 | Pen-n | OMe | N |
| I-171 | Pen-i | OMe | N |
| I-172 | Pen-neo | OMe | N |
| I-173 | Pen-2 | OMe | N |
| I-174 | Pen-3 | OMe | N |
| I-175 | Hex-n | OMe | N |
| I-176 | CH₂CH₂C(Me)₃ | OMe | N |
| I-177 | Pen-c | OMe | N |
| I-178 | Hex-c | OMe | N |
| I-179 | CH₂Pr-c | OMe | N |
| I-180 | CH₂Bu-c | OMe | N |

TABLE 6

| Compound No. | R¹ | X | W |
|---|---|---|---|
| I-181 | CH₂Pen-c | OMe | N |
| I-182 | CH₂CH=CH₂ | OMe | N |
| I-183 | CH₂C≡CH | OMe | N |
| I-184 | CH₂C≡CCH₃ | OMe | N |
| I-185 | Me | C(NH₂)=NOH | |
| I-186 | Et | C(NH₂)=NOH | N |
| I-187 | Pr-n | C(NH₂)=NOH | N |
| I-188 | Pr-i | C(NH₂)=NOH | N |
| I-189 | Bu-n | C(NH₂)=NOH | N |
| I-190 | Bu-i | C(NH₂)=NOH | N |
| I-191 | Bu-s | C(NH₂)=NOH | N |
| I-192 | Bu-t | C(NH₂)=NOH | N |
| I-193 | Pen-n | C(NH₂)=NOH | N |
| I-194 | Pen-i | C(NH₂)=NOH | N |
| I-195 | Pen-neo | C(NH₂)=NOH | N |
| I-196 | Pen-2 | C(NH₂)=NOH | N |
| I-197 | Pen-3 | C(NH₂)=NOH | N |
| I-198 | Hex-n | C(NH₂)=NOH | N |
| I-199 | CH₂CH₂C(Me)₃ | C(NH₂)=NOH | N |
| I-200 | Pen-c | C(NH₂)=NOH | N |
| I-201 | Hex-c | C(NH₂)=NOH | N |
| I-202 | CH₂Pr-c | C(NH₂)=NOH | N |
| I-203 | CH₂Bu-c | C(NH₂)=NOH | N |
| I-204 | CH₂Pen-c | C(NH₂)=NOH | N |
| I-205 | CH₂CH=CH₂ | C(NH₂)=NOH | N |
| I-206 | CH₂C≡CH | C(NH₂)=NOH | N |
| I-207 | CH₂C≡CCH₃ | C(NH₂)=NOH | N |
| I-208 | Pr-i | 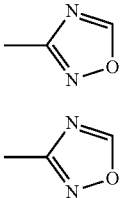 | N |
| I-209 | Bu-i | 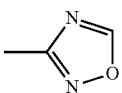 | N |
| I-210 | Pr-i | 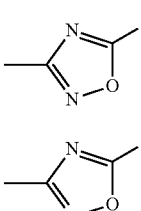 | N |
| I-211 | Bu-i | 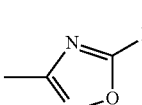 | N |

TABLE 7

| Compound No. | R¹ | X | W |
|---|---|---|---|
| I-212 | Pr-i | 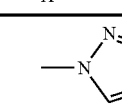 | N |
| I-213 | Pr-i | 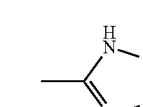 | N |
| I-214 | Pr-i | 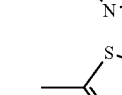 | N |
| I-215 | Pr-i | 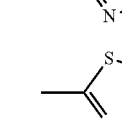 | N |

TABLE 7-continued

| Compound No. | R¹ | X | W |
|---|---|---|---|
| I-216 | Pr-i | NHCOMe | N |
| I-217 | Bu-i | NHCOMe | N |
| I-218 | CH$_2$Pr-c | NHCOMe | N |
| I-219 | Bu-i | NHCO$_2$Me | N |
| I-220 | Pr-i | NMe$_2$ | N |
| I-221 | Pr-i | CO$_2$Me | N |
| I-222 | Pr-i | COSMe | N |
| I-223 | Pr-i | C(=NH)OMe | N |
| I-224 | Pr-i | CSNH$_2$ | N |
| I-225 | Pr-i | CONHMe | N |
| I-226 | Pr-i | CONMe$_2$ | N |
| I-227 | Pr-i | CON(Me)OMe | N |
| I-228 | Pr-i | SMe | N |
| I-229 | Pr-i | CF$_3$ | N |
| I-230 | Pr-i | Et | N |

TABLE 7-continued

| Compound No. | R¹ | X | W |
|---|---|---|---|
| I-231 | Pr-i | Pr-i | N |
| I-232 | Pr-i | Bu-t | N |
| I-233 | CH$_2$(CH$_2$)$_5$CH$_3$ | Cl | N |
| I-234 | CH$_2$(CH$_2$)$_8$CH$_3$ | NH$_2$ | N |
| I-235 | CH$_2$(CH$_2$)$_8$CH$_3$ | Cl | N |
| I-236 | CH$_2$CF$_3$ | CN | N |
| I-237 | CH$_2$CF$_3$ | CONH$_2$ | N |
| I-238 | CH$_2$CF$_3$ | H | N |
| I-239 | CH$_2$Ph | Cl | N |
| I-240 | CH$_2$Ph | CN | N |
| I-241 | CH$_2$Ph | CONH$_2$ | N |
| I-242 | CH$_2$CH$_2$CH(OMe)CH$_3$ | NH$_2$ | N |
| I-243 | CH$_2$CH$_2$CH(OMe)CH$_3$ | Cl | N |

TABLE 8

| Compound No. | R¹ | X | W |
|---|---|---|---|
| I-244 | CH$_2$CH$_2$OCH$_2$CH$_3$ | H | N |
| I-245 | CH(Me)CH$_2$OCH$_3$ | NH$_2$ | N |
| I-246 | CH(Me)CH$_2$OCH$_3$ | Cl | N |
| I-247 | CH$_2$CH$_2$OC(CH$_3$)$_3$ | NH$_2$ | N |
| I-248 | CH$_2$CH$_2$OH | Cl | N |
| I-249 | CH$_2$CH$_2$SC(CH$_3$)$_3$ | NH$_2$ | N |
| I-250 | CH$_2$CH$_2$SCH(CH$_3$)$_2$ | CN | N |
| I-251 | CH$_2$CH$_2$SCH(CH$_3$)$_2$ | CONH$_2$ | N |
| I-252 | CH$_2$CH$_2$SOCH(CH$_3$)$_2$ | CONH$_2$ | N |
| I-253 | CH$_2$CH$_2$SO$_2$CH(CH$_3$)$_2$ | CONH$_2$ | N |
| I-254 | 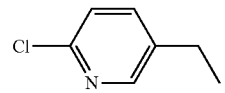 | CN | N |
| I-255 | 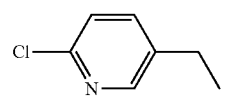 | CONH$_2$ | N |
| I-256 | 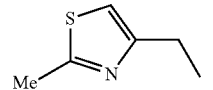 | CONH$_2$ | N |
| I-257 | CH$_2$Si(CH$_3$)$_3$ | NH$_2$ | N |
| I-258 | CH$_2$Si(CH$_3$)$_3$ | Cl | N |
| I-259 | CH$_2$(CH$_2$)$_2$Si(CH$_3$)$_3$ | NH$_2$ | N |
| I-260 | CH$_2$(CH$_2$)$_2$Si(CH$_3$)$_3$ | Cl | N |
| I-261 | CH$_2$CH$_2$C(CH$_3$)$_3$ | C(NMe$_2$)=NOMe | N |
| I-262 | Et | C(NH$_2$)=NOBu-i | N |
| I-263 | Et | C(Cl)=NOBu-i | N |
| I-264 | Et | C(NH$_2$)=NOCH$_2$CH$_2$C(Me)$_3$ | N |
| I-265 | Et | C(Cl)=NOCH$_2$CH$_2$C(Me)$_3$ | N |
| I-266 | Et | 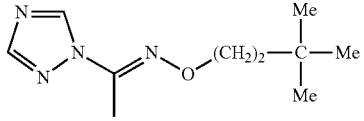 | N |
| I-267 | Me | OBu-i | N |
| I-268 | COCH$_2$CH$_2$C(CH$_3$)$_3$ | NH$_2$ | N |
| I-269 | Pr-i | NH$_2$ | CH |
| I-270 | Pr-i | Cl | CH |
| I-271 | Pr-i | CN | CH |
| I-272 | Pr-i | CONH$_2$ | CH |
| I-273 | Pr-i | Me | CH |
| I-274 | CH$_2$CF$_3$ | CN | CH |

TABLE 9

| Compound No. | R$^1$ | X | W |
|---|---|---|---|
| I-275 | CH$_2$CF$_3$ | CONH$_2$ | CH |
| I-276 | Bu-i | CONH$_2$ | CH |
| I-277 | CH$_2$Pr-c | CONH$_2$ | CH |
| I-278 | Ph | CONH$_2$ | N |
| I-279 | 3-chloro-2-methyl-5-(trifluoromethyl)pyridin-yl | CONH$_2$ | N |
| I-280 | 4-methyl-5-iodopyrimidin-yl | CONH$_2$ | N |
| I-281 | CH(Me)Ph | CONH$_2$ | N |
| I-282 | 4-(morpholin-4-yl)propyl | CONH$_2$ | N |
| I-283 | 2-ethyloxiranyl | CONH$_2$ | N |
| I-284 | 4-ethyl-1,3-dioxolan-2-one-yl | CONH$_2$ | N |
| I-285 | 2-ethyl-1,3-dioxolan-yl | CONH$_2$ | N |
| I-286 | 2-ethyltetrahydrofuran-yl | CN | N |
| I-287 | 2-ethyltetrahydrofuran-yl | CONH$_2$ | N |
| I-288 | CH$_2$CH(CH$_3$)CH$_2$CH$_3$ | CN | N |
| I-289 | CH$_2$CH(CH$_3$)CH$_2$CH$_3$ | CONH$_2$ | N |
| I-290 | CH$_2$CN | CONH$_2$ | N |
| I-291 | Pr-i | SOMe | N |
| I-292 | Pr-i | SO$_2$Me | N |
| I-293 | Pr-i | CH$_2$Pr-c | N |
| I-294 | Pr-i | CH$_2$CH=CH$_2$ | N |
| I-295 | Pr-i | CH$_2$C≡CH | N |
| I-296 | CH$_2$C(CH$_3$)=CH$_2$ | CN | N |
| I-297 | CH$_2$C(CH$_3$)=CH$_2$ | CONH$_2$ | N |
| I-298 | CH$_2$C(Cl)=CH$_2$ | CN | N |
| I-299 | CH$_2$C(Cl)=CH$_2$ | CONH$_2$ | N |
| I-300 | CH$_2$C(Cl)=CHCl(trans) | CN | N |

TABLE 10

| Compound No. | R$^1$ | X | W |
|---|---|---|---|
| I-301 | CH$_2$C(Cl)=CHCl(trans) | CONH$_2$ | N |
| I-302 | CH$_2$C(Cl)=CHCl(cis) | CONH$_2$ | N |
| I-303 | Pr-i | C(NH$_2$)=NOCH$_2$CF$_3$ | N |
| I-304 | Pr-i | C(NH$_2$)=NOCO$_2$Et | N |
| I-305 | 2-chloro-5-ethylthiazol-yl | CN | N |
| I-306 | 2-chloro-5-ethylthiazol-yl | CONH$_2$ | N |
| I-307 | Bu-c | CN | N |
| I-308 | Bu-c | CONH$_2$ | N |
| I-309 | Pr-i | Pr-c | N |
| I-310 | Pr-i | CO$_2$H | N |
| I-311 | Pr-i | Ph | N |
| I-312 | Pr-i | 2-methyl-4-oxo-thiazolin-yl | N |
| I-313 | Pr-i | 2-methyl-oxazolin-yl | N |
| I-314 | Pr-i | 2-methyl-imidazolin-yl | N |
| I-315 | Pr-i | 3-methyl-5-oxo-1,2,4-oxadiazol-yl | N |
| I-316 | BrCH$_2$CH$_2$CH$_2$CH$_2$ | CN | N |
| I-317 | BrCH$_2$CH$_2$CH$_2$CH$_2$ | CONH$_2$ | N |
| I-318 | CH$_2$Si(CH$_3$)$_3$ | CN | N |
| I-319 | CH$_2$Si(CH$_3$)$_3$ | CONH$_2$ | N |
| I-320 | CHF$_2$ | CN | N |
| I-321 | CHF$_2$ | CONH$_2$ | N |
| I-322 | Pr-i | CONHCH$_2$CH$_2$Cl | N |
| I-323 | 1-cyclopropylethyl | CN | N |
| I-324 | 1-cyclopropylethyl | CONH$_2$ | N |

TABLE 11

| Compound No. | R$^1$ | X | W |
|---|---|---|---|
| I-325 | cyclopropylethyl | CN | N |
| I-326 | cyclopropylethyl | CONH$_2$ | N |
| I-327 | CH$_2$Ph(4-CN) | CN | N |

TABLE 11-continued

| Compound No. | R¹ | X | W |
|---|---|---|---|
| I-328 | CH₂Ph(4-CN) | CONH₂ | N |
| I-329 | CH₂Ph(3-CF₃) | CN | N |
| I-330 | CH₂Ph(3-CF₃) | CONH₂ | N |
| I-331 | CH₂Ph(4-CF₃) | CN | N |
| I-332 | CH₂Ph(4-CF₃) | CONH₂ | N |
| I-333 | CH₂Ph(4-OCH₃) | CN | N |
| I-334 | CH₂Ph(4-OCH₃) | CONH₂ | N |
| I-335 | CH₂Ph(4-Cl) | CN | N |
| I-336 | CH₂Ph(4-Cl) | CONH₂ | N |
| I-337 | CH₂Ph(4-CH₃) | CN | N |
| I-338 | CH₂Ph(4-CH₃) | CONH₂ | N |
| I-339 | CH₂CH₂Ph | CN | N |
| I-340 | CH₂CH₂Ph | CONH₂ | N |
| I-341 | CH₂CH₂CH₂Ph | CN | N |
| I-342 | CH₂CH₂CH₂Ph | CONH₂ | N |
| I-343 | CH(CH₃)Ph | CN | N |
| I-344 | CH(CH₃)Ph | CONH₂ | N |
| I-345 | Pr-i | Ph(2-CF₃) | N |
| I-346 | Pr-i | Ph(2-CF₃) | N |
| I-347 | CH₂Ph(3-CN) | CN | N |
| I-348 | CH₂Ph(3-OCH₃) | CN | N |
| I-349 | CH₂Ph(3-OCH₃) | CONH₂ | N |
| I-350 | Pen-neo | CSNH₂ | N |
| I-351 | CH₂(CH₂)₆CH₃ | CN | N |
| I-352 | CH₂(CH₂)₆CH₃ | CONH₂ | N |
| I-353 | Pr-i | Ph(4-Cl) | N |
| I-354 | Pr-i | Ph(4-F) | N |
| I-355 | CH₂(CH₂)₈CH₃ | CN | N |
| I-356 | CH₂(CH₂)₈CH₃ | CONH₂ | N |
| I-357 | CH₂Ph(4-F) | CN | N |
| I-358 | CH₂Ph(4-F) | CONH₂ | N |
| I-359 | CH₂(CF₂)₂CF₃ | CN | N |
| I-360 | CH₂(CF₂)₂CF₃ | CONH₂ | N |

TABLE 12

| Compound No. | R¹ | X | W |
|---|---|---|---|
| I-361 | CH₂Ph(2-CF₃) | CN | N |
| I-362 | CH₂Ph(2-CF₃) | CONH₂ | N |
| I-363 | CH₂Ph(2-CN) | CN | N |
| I-364 | CH₂Ph(2-CN) | CONH₂ | N |
| I-365 | CH₂Ph(4-CO₂CH₂CH₃) | CN | N |
| I-366 | CH₂C≡CI | CONH₂ | N |
| I-367 | CH₂Ph(2-OCH₃) | CN | N |
| I-368 | CH₂Ph(2-OCH₃) | CONH₂ | N |
| I-369 | CH₂CH=C(CH₃)₂ | CN | N |
| I-370 | CH₂CH=C(CH₃)₂ | CONH₂ | N |
| I-371 | Pr-i | Ph(2-Cl) | N |
| I-372 | Pr-i | Ph(3-Cl) | N |
| I-373 | CH₂Pr-c | NHSO₂NHCO₂Bu-t | N |
| I-374 | CH₂CF₂CF₃ | CN | N |
| I-375 | CH₂CF₂CF₃ | CONH₂ | N |
| I-376 | CH₂CH₂OCH₂CH₃ | CN | N |
| I-377 | CH₂CH₂OCH₂CH₃ | CONH₂ | N |
| I-378 | Pr-i | Ph(2-OCH₃) | N |
| I-379 | CH(CH₃)CF₃ | CN | N |
| I-380 | CH(CH₃)CF₃ | CONH₂ | N |
| I-381 | CH₂CH₂OCH(CH₃)₂ | CN | N |
| I-382 | CH₂CH₂OCH(CH₃)₂ | CONH₂ | N |
| I-383 | CH₂Ph(2-CH₃) | CN | N |
| I-384 | CH₂Ph(2-CH₃) | CONH₂ | N |
| I-385 | CH₂Ph(3-CH₃) | CN | N |
| I-386 | CH₂Ph(3-CH₃) | CONH₂ | N |
| I-387 | CH₂Ph(2,6-di-CH₃) | CN | N |
| I-388 | CH₂Ph(2,6-di-CH₃) | CONH₂ | N |
| I-389 | Pr-i | CONHPh | N |
| I-390 | Pr-i | CONHCH₂CN | N |
| I-391 | Pr-i | CH₂OH | N |
| I-392 | Pr-i | CH₂Cl | N |
| I-393 | Pr-i | CH₂CN | N |
| I-394 | Pr-i | COCH₃ | N |
| I-395 | Pr-i | SO₂CH₃ | N |
| I-396 | Pr-i | SOCH₃ | N |

TABLE 12-continued

| Compound No. | R¹ | X | W |
|---|---|---|---|
| I-397 | Pr-i | I | N |
| I-398 | Pr-i | Ph(2-CH₃) | N |

TABLE 13

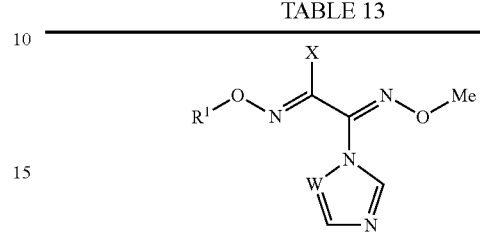

| Compound No. | R¹ | X | W |
|---|---|---|---|
| II-1 | Me | Cl | N |
| II-2 | Et | Cl | N |
| II-3 | Pr-n | Cl | N |
| II-4 | Pr-i | Cl | N |
| II-5 | Bu-n | Cl | N |
| II-6 | Bu-i | Cl | N |
| II-7 | Bu-s | Cl | N |
| II-8 | Bu-t | Cl | N |
| II-9 | Pen-n | Cl | N |
| II-10 | Pen-i | Cl | N |
| II-11 | Pen-neo | Cl | N |
| II-12 | Pen-2 | Cl | N |
| II-13 | Pen-3 | Cl | N |
| II-14 | Hex-n | Cl | N |
| II-15 | CH₂CH₂C(Me)₃ | Cl | N |
| II-16 | Pen-c | Cl | N |
| II-17 | Hex-c | Cl | N |
| II-18 | CH₂Pr-c | Cl | N |
| II-19 | CH₂Bu-c | Cl | N |
| II-20 | CH₂Pen-c | Cl | N |
| II-21 | CH₂CH=CH₂ | Cl | N |
| II-22 | CH₂C≡CH | Cl | N |
| II-23 | CH₂C≡CCH₃ | Cl | N |
| II-24 | Me | H | N |
| II-25 | Et | H | N |
| II-26 | Pr-n | H | N |
| II-27 | Pr-i | H | N |
| II-28 | Bu-n | H | N |
| II-29 | Bu-i | H | N |
| II-30 | Bu-s | H | N |
| II-31 | Bu-t | H | N |
| II-32 | Pen-n | H | N |

TABLE 14

| Compound No. | R¹ | X | W |
|---|---|---|---|
| II-33 | Pen-i | H | N |
| II-34 | Pen-neo | H | N |
| II-35 | Pen-2 | H | N |
| II-36 | Pen-3 | H | N |
| II-37 | Hex-n | H | N |
| II-38 | CH₂CH₂C(Me)₃ | H | N |
| II-39 | Pen-c | H | N |
| II-40 | Hex-c | H | N |
| II-41 | CH₂Pr-c | H | N |
| II-42 | CH₂Bu-c | H | N |
| II-43 | CH₂Pen-c | H | N |
| II-44 | CH₂CH=CH₂ | H | N |
| II-45 | CH₂C≡CH | H | N |
| II-46 | CH₂C≡CCH₃ | H | N |
| II-47 | Me | CN | N |
| II-48 | Et | CN | N |
| II-49 | Pr-n | CN | N |
| II-50 | Pr-i | CN | N |
| II-51 | Bu-n | CN | N |

TABLE 14-continued

| Compound No. | R¹ | X | W |
|---|---|---|---|
| II-52 | Bu-i | CN | N |
| II-53 | Bu-s | CN | N |
| II-54 | Bu-t | CN | N |
| II-55 | Pen-n | CN | N |
| II-56 | Pen-i | CN | N |
| II-57 | Pen-neo | CN | N |
| II-58 | Pen-2 | CN | N |
| II-59 | Pen-3 | CN | N |
| II-60 | Hex-n | CN | N |
| II-61 | $CH_2CH_2C(Me)_3$ | CN | N |
| II-62 | Pen-c | CN | N |
| II-63 | Hex-c | CN | N |
| II-64 | $CH_2Pr$-c | CN | N |
| II-65 | $CH_2Bu$-c | CN | N |
| II-66 | $CH_2Pen$-c | CN | N |
| II-67 | $CH_2CH=CH_2$ | CN | N |
| II-68 | $CH_2C\equiv CH$ | CN | N |
| II-69 | $CH_2C\equiv CCH_3$ | CN | N |

TABLE 15

| Compound No. | R¹ | X | W |
|---|---|---|---|
| II-70 | Me | $CONH_2$ | N |
| II-71 | Et | $CONH_2$ | N |
| II-72 | Pr-n | $CONH_2$ | N |
| II-73 | Pr-i | $CONH_2$ | N |
| II-74 | Bu-n | $CONH_2$ | N |
| II-75 | Bu-i | $CONH_2$ | N |
| II-76 | Bu-s | $CONH_2$ | N |
| II-77 | Bu-t | $CONH_2$ | N |
| II-78 | Pen-n | $CONH_2$ | N |
| II-79 | Pen-i | $CONH_2$ | N |
| II-80 | Pen-neo | $CONH_2$ | N |
| II-81 | Pen-2 | $CONH_2$ | N |
| II-82 | Pen-3 | $CONH_2$ | N |
| II-83 | Hex-n | $CONH_2$ | N |
| II-84 | $CH_2CH_2C(Me)_3$ | $CONH_2$ | N |
| II-85 | Pen-c | $CONH_2$ | N |
| II-86 | Hex-c | $CONH_2$ | N |
| II-87 | $CH_2Pr$-c | $CONH_2$ | N |
| II-88 | $CH_2Bu$-c | $CONH_2$ | N |
| II-89 | $CH_2Pen$-c | $CONH_2$ | N |
| II-90 | $CH_2CH=CH_2$ | $CONH_2$ | N |
| II-91 | $CH_2C\equiv CH$ | $CONH_2$ | N |
| II-92 | $CH_2C\equiv CCH_3$ | $CONH_2$ | N |
| II-93 | Me | Me | N |
| II-94 | Et | Me | N |
| II-95 | Pr-n | Me | N |
| II-96 | Pr-i | Me | N |
| II-97 | Bu-n | Me | N |
| II-98 | Bu-i | Me | N |
| II-99 | Bu-s | Me | N |
| II-100 | Bu-t | Me | N |
| II-101 | Pen-n | Me | N |
| II-102 | Pen-i | Me | N |
| II-103 | Pen-neo | Me | N |
| II-104 | Pen-2 | Me | N |
| II-105 | Pen-3 | Me | N |
| II-106 | Hex-n | Me | N |

TABLE 16

| Compound No. | R¹ | X | W |
|---|---|---|---|
| II-107 | $CH_2CH_2C(Me)_3$ | Me | N |
| II-108 | Pen-c | Me | N |
| II-109 | Hex-c | Me | N |
| II-110 | $CH_2Pr$-c | Me | N |
| II-111 | $CH_2Bu$-c | Me | N |
| II-112 | $CH_2Pen$-c | Me | N |
| II-113 | $CH_2CH=CH_2$ | Me | N |
| II-114 | $CH_2C\equiv CH$ | Me | N |

TABLE 16-continued

| Compound No. | R¹ | X | W |
|---|---|---|---|
| II-115 | $CH_2C\equiv CCH_3$ | Me | N |
| II-116 | Me | $NH_2$ | N |
| II-117 | Et | $NH_2$ | N |
| II-118 | Pr-n | $NH_2$ | N |
| II-119 | Pr-i | $NH_2$ | N |
| II-120 | Bu-n | $NH_2$ | N |
| II-121 | Bu-i | $NH_2$ | N |
| II-122 | Bu-s | $NH_2$ | N |
| II-123 | Bu-t | $NH_2$ | N |
| II-124 | Pen-n | $NH_2$ | N |
| II-125 | Pen-i | $NH_2$ | N |
| II-126 | Pen-neo | $NH_2$ | N |
| II-127 | Pen-2 | $NH_2$ | N |
| II-128 | Pen-3 | $NH_2$ | N |
| II-129 | Hex-n | $NH_2$ | N |
| II-130 | $CH_2CH_2C(Me)_3$ | $NH_2$ | N |
| II-131 | Pen-c | $NH_2$ | N |
| II-132 | Hex-c | $NH_2$ | N |
| II-133 | $CH_2Pr$-c | $NH_2$ | N |
| II-134 | $CH_2Bu$-c | $NH_2$ | N |
| II-135 | $CH_2Pen$-c | $NH_2$ | N |
| II-136 | $CH_2CH=CH_2$ | $NH_2$ | N |
| II-137 | $CH_2C\equiv CH$ | $NH_2$ | N |
| II-138 | $CH_2C\equiv CCH_3$ | $NH_2$ | N |
| II-139 | Me | Br | N |
| II-140 | Et | Br | N |
| II-141 | Pr-n | Br | N |
| II-142 | Pr-i | Br | N |
| II-143 | Bu-n | Br | N |

TABLE 17

| Compound No. | R¹ | X | W |
|---|---|---|---|
| II-144 | Bu-i | Br | N |
| II-145 | Bu-s | Br | N |
| II-146 | Bu-t | Br | N |
| II-147 | Pen-n | Br | N |
| II-148 | Pen-i | Br | N |
| II-149 | Pen-neo | Br | N |
| II-150 | Pen-2 | Br | N |
| II-151 | Pen-3 | Br | N |
| II-152 | Hex-n | Br | N |
| II-153 | $CH_2CH_2C(Me)_3$ | Br | N |
| II-154 | Pen-c | Br | N |
| II-155 | Hex-c | Br | N |
| II-156 | $CH_2Pr$-c | Br | N |
| II-157 | $CH_2Bu$-c | Br | N |
| II-158 | $CH_2Pen$-c | Br | N |
| II-159 | $CH_2CH=CH_2$ | Br | N |
| II-160 | $CH_2C\equiv CH$ | Br | N |
| II-161 | $CH_2C\equiv CCH_3$ | Br | N |
| II-162 | Me | OMe | N |
| II-163 | Et | OMe | N |
| II-164 | Pr-n | OMe | N |
| II-165 | Pr-i | OMe | N |
| II-166 | Bu-n | OMe | N |
| II-167 | Bu-i | OMe | N |
| II-168 | Bu-s | OMe | N |
| II-169 | Bu-t | OMe | N |
| II-170 | Pen-n | OMe | N |
| II-171 | Pen-i | OMe | N |
| II-172 | Pen-neo | OMe | N |
| II-173 | Pen-2 | OMe | N |
| II-174 | Pen-3 | OMe | N |
| II-175 | Hex-n | OMe | N |
| II-176 | $CH_2CH_2C(Me)_3$ | OMe | N |
| II-177 | Pen-c | OMe | N |
| II-178 | Hex-c | OMe | N |
| II-179 | $CH_2Pr$-c | OMe | N |
| II-180 | $CH_2Bu$-c | OMe | N |

TABLE 18

| Compound No. | R¹ | X | W |
|---|---|---|---|
| II-181 | CH₂Pen-c | OMe | N |
| II-182 | CH₂CH=CH₂ | OMe | N |
| II-183 | CH₂C≡CH | OMe | N |
| II-184 | CH₂C≡CCH₃ | OMe | N |
| II-185 | Me | C(NH₂)=NOH | N |
| II-186 | Et | C(NH₂)=NOH | N |
| II-187 | Pr-n | C(NH₂)=NOH | N |
| II-188 | Pr-i | C(NH₂)=NOH | N |
| II-189 | Bu-n | C(NH₂)=NOH | N |
| II-190 | Bu-i | C(NH₂)=NOH | N |
| II-191 | Bu-s | C(NH₂)=NOH | N |
| II-192 | Bu-t | C(NH₂)=NOH | N |
| II-193 | Pen-n | C(NH₂)=NOH | N |
| II-194 | Pen-i | C(NH₂)=NOH | N |
| II-195 | Pen-neo | C(NH₂)=NOH | N |
| II-196 | Pen-2 | C(NH₂)=NOH | N |
| II-197 | Pen-3 | C(NH₂)=NOH | N |
| II-198 | Hex-n | C(NH₂)=NOH | N |
| II-199 | CH₂CH₂C(Me)₃ | C(NH₂)=NOH | N |
| II-200 | Pen-c | C(NH₂)=NOH | N |
| II-201 | Hex-c | C(NH₂)=NOH | N |
| II-202 | CH₂Pr-c | C(NH₂)=NOH | N |
| II-203 | CH₂Bu-c | C(NH₂)=NOH | N |
| II-204 | CH₂Pen-c | C(NH₂)=NOH | N |
| II-205 | CH₂CH=CH₂ | C(NH₂)=NOH | N |
| II-206 | CH₂C≡CH | C(NH₂)=NOH | N |
| II-207 | CH₂C≡CCH₃ | C(NH₂)=NOH | N |
| II-208 | Pr-i | 3-methyl-1,2,4-oxadiazol-5-yl | N |
| II-209 | Bu-i | 3-methyl-1,2,4-oxadiazol-5-yl | N |
| II-210 | Pr-i | 3,5-dimethyl-1,2,4-oxadiazol-yl | N |
| II-211 | Bu-i | 3,5-dimethyl-1,2,4-oxadiazol-yl | N |

TABLE 19

| Compound No. | R¹ | X | W |
|---|---|---|---|
| II-212 | Pr-i | 1H-1,2,4-triazol-1-yl | N |
| II-213 | Pr-i | 5-methyl-1H-tetrazol-yl | N |
| II-214 | Pr-i | 2-methylthiazol-yl | N |
| II-215 | Pr-i | 2-methyl-4,5-dihydrothiazol-yl | N |
| II-216 | Pr-i | NHCOMe | N |
| II-217 | Bu-i | NHCOMe | N |
| II-218 | CH₂Pr-c | NHCOMe | N |
| II-219 | Bu-i | NHCO₂Me | N |
| II-220 | Pr-i | NMe₂ | N |
| II-221 | Pr-i | CO₂Me | N |
| II-222 | Pr-i | COSEt | N |
| II-223 | Pr-i | C(=NM)OMe | N |
| II-224 | Pr-i | CSNH₂ | N |
| II-225 | Pr-i | CONHMe | N |
| II-226 | Pr-i | CONMe₂ | N |
| II-227 | Pr-i | CON(Me)OMe | N |
| II-228 | Pr-i | SMe | N |
| II-229 | Pr-i | CF₃ | N |
| II-230 | Pr-i | Et | N |
| II-231 | Pr-i | Pr-i | N |
| II-232 | Pr-i | Bu-t | N |
| II-233 | CH₂(CH₂)₅CH₃ | Cl | N |
| II-234 | CH₂(CH₂)₈CH₃ | NH₂ | N |
| II-235 | CH₂(CH₂)₆CH₃ | CN | N |
| II-236 | CH₂(CH₂)₈CH₃ | CN | N |
| II-237 | CH₂(CH₂)₆CH₃ | CONH₂ | N |
| II-238 | CH₂(CH₂)₈CH₃ | CONH₂ | N |
| II-239 | CH₂(CH₂)₈CH₃ | Cl | N |
| II-240 | CH₂CF₃ | CN | N |
| II-241 | CH₂CF₃ | CONH₂ | N |
| II-242 | CH₂CF₃ | H | N |

TABLE 20

| Compound No. | R¹ | X | W |
|---|---|---|---|
| II-243 | CH₂Ph | Cl | N |
| II-244 | CH₂Ph | CN | N |
| II-245 | CH₂Ph | CONH₂ | N |
| II-246 | PhCH=CHCH₂ | CN | N |
| II-247 | PhCH=CHCH₂ | CONH₂ | N |
| II-248 | CH₂CH₂CH(OMe)CH₃ | NH₂ | N |
| II-249 | CH₂CH₂CH(OMe)CH₃ | Cl | N |
| II-250 | CH₂CH₂OCH₂CH₃ | H | N |
| II-251 | CH(Me)CH₂OCH₃ | NH₂ | N |
| II-252 | CH(Me)CH₂OCH₃ | Cl | N |
| II-253 | CH₂CH₂OC(CH₃)₃ | NH₂ | N |

TABLE 20-continued

| Compound No. | R¹ | X | W |
|---|---|---|---|
| II-254 | CH₂CH₂OH | Cl | N |
| II-255 | CH₂CH₂SC(CH₃)₃ | NH₂ | N |
| II-256 | CH₂Si(CH₃)₃ | NH₂ | N |
| II-257 | CH₂Si(CH₃)₃ | Cl | N |
| II-258 | CH₂(CH₂)₂Si(CH₃)₃ | NH₂ | N |
| II-259 | CH₂(CH₂)₂Si(CH₃)₃ | Cl | N |
| II-260 | Et | C(NH₂)=NOBu-i | N |
| II-261 | Et | C(Cl)=NOBu-i | N |
| II-262 | Et | C(NH₂)=NOCH₂C(Me)₃ | N |
| II-263 | Et | CONHCH₂OCH₃ | N |
| II-264 | Et | triazolyl-C(=N-O-(CH₂)₂-C(Me)₃)- | N |
| II-265 | Me | OBu-i | N |
| II-266 | CH₂CH(CH₃)CH₂CH₃ | CN | N |
| II-267 | CH₂CH(CH₃)CH₂CH₃ | CONH₂ | N |
| II-268 | CH₂CH₂OCH₃ | CN | N |
| II-269 | CH₂CH₂OCH₃ | CONH₂ | N |
| II-270 | Pr-i | Cl | CH |
| II-271 | Pr-i | CN | CH |
| II-272 | Pr-i | CONH₂ | CH |
| II-273 | Pr-i | Me | CH |
| II-274 | CH₂CF₃ | CN | CH |

TABLE 21

| Compound No. | R¹ | X | W |
|---|---|---|---|
| II-275 | CH₂CF₃ | CONH₂ | CH |
| II-276 | Bu-i | CONH₂ | CH |
| II-277 | CH₂Pr-c | CONH₂ | CH |
| II-278 | CH₂CH₂CH=CH₂ | CN | N |
| II-279 | CH₂CH₂CH=CH₂ | CONH₂ | N |
| II-280 | ClCH=CHCH₂CH₃ | CN | N |
| II-281 | ClCH=CHCH₂CH₃ | CONH₂ | N |
| II-282 | (oxiranyl)CH₂CH₃ | CN | N |
| II-283 | (oxiranyl)CH₂CH₃ | CONH₂ | N |
| II-284 | (tetrahydrofuran-2-yl)CH₂CH₃ | CN | N |
| II-285 | (tetrahydrofuran-2-yl)CH₂CH₃ | CONH₂ | N |
| II-286 | 4-(butoxy)phenyl-C(=O)OMe | CN | N |

TABLE 21-continued

| Compound No. | R¹ | X | W |
|---|---|---|---|
| II-287 | 4-BuO-C₆H₄-C(=O)-OMe (methyl 4-butoxybenzoate group) | CONH₂ | N |
| II-288 | CH₂Hex-c | CN | N |
| II-289 | CH₂Hex-c | CONH₂ | N |
| II-290 | Bu-t | CONHBu-t | N |
| II-291 | Bu-i | Pr-c | N |
| II-292 | Bu-i | CH₂CH₂SCH₃ | N |
| II-293 | Bu-i | CH₂CH₂SOCH₃ | N |
| II-294 | Bu-i | CH₂CH₂SO₂CH₃ | N |
| II-295 | Pr-i | CH₂OCH₃ | N |
| II-296 | Pr-i | Ph | N |
| II-297 | Pr-i | Ph(2-F) | N |
| II-298 | Pr-i | CH₂C(=NOMe)CH₃ | N |

TABLE 22

| Compound No. | R¹ | X | W |
|---|---|---|---|
| II-299 | 1,1-dimethyl-2-ethylcyclopropyl | CN | N |
| II-300 | 1,1-dimethyl-2-ethylcyclopropyl | CONH₂ | N |
| II-301 | 1,1-difluoro-2-ethylcyclopropyl | CN | N |
| II-302 | 1,1-difluoro-2-ethylcyclopropyl | CONH₂ | N |
| II-303 | 1-(cyclopropyl)ethyl | CN | N |
| II-304 | 1-(cyclopropyl)ethyl | CONH₂ | N |
| II-305 | 1-methyl-2-ethylcyclopropyl | CN | N |
| II-306 | 1-methyl-2-ethylcyclopropyl | CONH₂ | N |
| II-307 | 2-ethylcyclopropyl | CN | N |
| II-308 | 2-ethylcyclopropyl | CONH₂ | N |
| II-309 | CH₂CH₂CH₂N(CH₃)₂ | CN | N |
| II-310 | CH₂CH₂CH₂N(CH₃)₂ | CONH₂ | N |
| II-311 | Pen-neo | CSNH₂ | N |
| II-312 | CH₂C(CH₃)₂CH₂CH₃ | CN | N |
| II-313 | CH₂C(CH₃)₂CH₂CH₃ | CONH₂ | N |
| II-314 | CH₂C(Cl)=CH₂ | CN | N |
| II-315 | CH₂C(Cl)=CH₂ | CONH₂ | N |
| II-316 | 1-chloro-2-ethylcyclopropyl | CN | N |
| II-317 | 1-chloro-2-ethylcyclopropyl | CONH₂ | N |
| II-318 | CH₂Pr-c | 2-(4,5-dihydrothiazolyl) | N |

TABLE 23

| Compound No. | R¹ | X | W |
|---|---|---|---|
| II-319 | CH₂C(CH₃)₂CN | CN | N |
| II-320 | CH₂C(CH₃)₂CN | CONH₂ | N |
| II-321 | CH₂C(CH₃)₂CH₂Cl | CN | N |
| II-322 | CH₂C(CH₃)₂CH₂Cl | CONH₂ | N |
| II-323 | CH₂Pr-c | NHSO₂NHCO₂Bu-t | N |
| II-324 | CH₂(CF₂)₂CF₃ | CN | N |
| II-325 | CH₂(CF₂)₂CF₃ | CONH₂ | N |
| II-326 | CH₂CF₂CF₃ | CN | N |
| II-327 | CH₂CF₂CF₃ | CONH₂ | N |
| II-328 | CH₂(CH₂)₂CF₃ | CN | N |
| II-329 | CH₂(CH₂)₂CF₃ | CONH₂ | N |
| II-330 | CH₂(CH₂)₂CF₂CF₃ | CN | N |
| II-331 | CH₂(CH₂)₂CF₂CF₃ | CONH₂ | N |
| II-332 | 1,1-dichloro-2-ethylcyclopropyl | CN | N |
| II-333 | 1,1-dichloro-2-ethylcyclopropyl | CONH₂ | N |

TABLE 23-continued

| Compound No. | R¹ | X | W |
|---|---|---|---|
| II-334 | CH₂CH₂CF₃ | CN | N |
| II-335 | CH₂CH₂CF₃ | CONH₂ | N |
| II-336 | CF₂CHF₂CF₃ | CN | N |
| II-337 | CF₂CHF₂CF₃ | CONH₂ | N |
| II-338 | 3-pyridyl-CH₂CH₂- | CN | N |
| II-339 | 3-pyridyl-CH₂CH₂- | CONH₂ | N |
| II-340 | 3-thienyl-CH₂CH₂- | CN | N |
| II-341 | 3-thienyl-CH₂CH₂- | CONH₂ | N |
| II-342 | 1-cyano-1-ethylcyclopropyl | CN | N |
| II-343 | 1-cyano-1-ethylcyclopropyl | CONH₂ | N |
| II-344 | CH(CH₂F)₂ | CN | N |

TABLE 24

| Compound No. | R¹ | X | W |
|---|---|---|---|
| II-345 | CH(CH₂F)₂ | CONH₂ | N |
| II-346 | CH₂Pr-c | 3-methyl-1,2,4-oxadiazol-5-yl | N |
| II-347 | 2-thienyl-CH₂CH₂- | CN | N |
| II-348 | 2-thienyl-CH₂CH₂- | CONH₂ | N |
| II-349 | CH₂CCH₃(CF₃)₂ | CN | N |
| II-350 | CH₂CCH₃(CF₃)₂ | CONH₂ | N |
| II-351 | CH₂CCH₃(CF₃)₂ | CN | CH |
| II-352 | CH₂CCH₃(CF₃)₂ | CONH₂ | CH |
| II-353 | 3-furyl-CH₂CH₂- | CN | N |
| II-354 | 3-furyl-CH₂CH₂- | CONH₂ | N |
| II-355 | CH₂Si(CH₃)₃ | CN | N |
| II-356 | CH₂Si(CH₃)₃ | CONH₂ | N |
| II-357 | CH₂CH₂OCH₂CF₃ | CN | N |
| II-358 | CH₂CH₂OCH₂CF₃ | CONH₂ | N |
| II-359 | CH(CH₃)CF₃ | CN | N |
| II-360 | CH(CH₃)CF₃ | CONH₂ | N |
| II-361 | CH₂CH₂OCH(CH₃)₂ | CN | N |
| II-362 | CH₂CH₂OCH(CH₃)₂ | CONH₂ | N |
| II-363 | CH₂Ph(1,2,3,4,5-penta-F) | CN | N |
| II-364 | CH₂Ph(1,2,3,4,5-penta-F) | CONH₂ | N |
| II-365 | CH₂Ph(3-F) | CN | N |
| II-366 | CH₂Ph(3-F) | CONH₂ | N |
| II-367 | CH₂Ph(4-F) | CN | N |
| II-368 | CH₂Ph(4-F) | CONH₂ | N |
| II-369 | 2-furyl-CH₂CH₂- | CN | N |
| II-370 | 2-furyl-CH₂CH₂- | CONH₂ | N |

TABLE 25

| Compound No. | R¹ | X | W |
|---|---|---|---|
| II-371 | CH₂Pr-c | 2-methylthiazol-4-yl | N |
| II-372 | 2-pyridyl-CH₂CH₂- | CONH₂ | N |
| II-373 | CH₂CF₂CF₃ | CN | CH |
| II-374 | CH₂CF₂CF₃ | CONH₂ | CN |
| II-375 | Me | 3-methyl-1,2,4-oxadiazol-5-yl | N |
| II-376 | Me | 2-methylthiazol-4-yl | N |
| II-377 | CH₂CH₂OCH₂CH₃ | CN | N |
| II-378 | CH₂CH₂OCH₂CH₃ | CONH₂ | N |
| II-379 | CH₂(CF₂)₃CHF₂ | CN | N |
| II-380 | CH₂(CF₂)₃CHF₂ | CONH₂ | N |
| II-381* | CH₂CF₂CF₃ | CONH₂ | CH |

*MeSO₂OH salt

TABLE 26

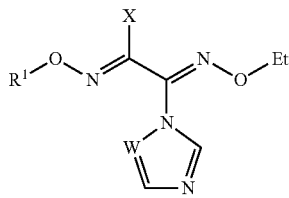

| Compound No. | R¹ | X | W |
|---|---|---|---|
| III-1 | Me | Cl | N |
| III-2 | Et | Cl | N |
| III-3 | Pr-n | Cl | N |
| III-4 | Pr-i | Cl | N |
| III-5 | Bu-n | Cl | N |
| III-6 | Bu-i | Cl | N |
| III-7 | Bu-s | Cl | N |
| III-8 | Bu-t | Cl | N |
| III-9 | Pen-n | Cl | N |
| III-10 | Pen-i | Cl | N |
| III-11 | Pen-neo | Cl | N |
| III-12 | Pen-2 | Cl | N |
| III-13 | Pen-3 | Cl | N |
| III-14 | Hex-n | Cl | N |
| III-15 | CH$_2$CH$_2$C(Me)$_3$ | Cl | N |
| III-16 | Pen-c | Cl | N |
| III-17 | Hex-c | Cl | N |
| III-18 | CH$_2$Pr-c | Cl | N |
| III-19 | CH$_2$Bu-c | Cl | N |
| III-20 | CH$_2$Pen-c | Cl | N |
| III-21 | CH$_2$CH=CH$_2$ | Cl | N |
| III-22 | CH$_2$C≡CH | Cl | N |
| III-23 | CH$_2$C≡CCH$_3$ | Cl | N |
| III-24 | Me | H | N |
| III-25 | Et | H | N |
| III-26 | Pr-n | H | N |
| III-27 | Pr-i | H | N |
| III-28 | Bu-n | H | N |
| III-29 | Bu-i | H | N |
| III-30 | Bu-s | H | N |
| III-31 | Bu-t | H | N |
| III-32 | Pen-n | H | N |

TABLE 27

| Compound No. | R¹ | X | W |
|---|---|---|---|
| III-33 | Pen-i | H | N |
| III-34 | Pen-neo | H | N |
| III-35 | Pen-2 | H | N |
| III-36 | Pen-3 | H | N |
| III-37 | Hex-n | H | N |
| III-38 | CH$_2$CH$_2$C(Me)$_3$ | H | N |
| III-39 | Pen-c | H | N |
| III-40 | Hex-c | H | N |
| III-41 | CH$_2$Pr-c | H | N |
| III-42 | CH$_2$Bu-c | H | N |
| III-43 | CH$_2$Pen-c | H | N |
| III-44 | CH$_2$CH=CH$_2$ | H | N |
| III-45 | CH$_2$C≡CH | H | N |
| III-46 | CH$_2$C≡CCH$_3$ | H | N |
| III-47 | Me | CN | N |
| III-48 | Et | CN | N |
| III-49 | Pr-n | CN | N |
| III-50 | Pr-i | CN | N |
| III-51 | Bu-n | CN | N |
| III-52 | Bu-i | CN | N |
| III-53 | Bu-s | CN | N |
| III-54 | Bu-t | CN | N |
| III-55 | Pen-n | CN | N |
| III-56 | Pen-i | CN | N |
| III-57 | Pen-neo | CN | N |
| III-58 | Pen-2 | CN | N |
| III-59 | Pen-3 | CN | N |
| III-60 | Hex-n | CN | N |

TABLE 27-continued

| Compound No. | R¹ | X | W |
|---|---|---|---|
| III-61 | CH$_2$CH$_2$C(Me)$_3$ | CN | N |
| III-62 | Pen-c | CN | N |
| III-63 | Hex-c | CN | N |
| III-64 | CH$_2$Pr-c | CN | N |
| III-65 | CH$_2$Bu-c | CN | N |
| III-66 | CH$_2$Pen-c | CN | N |
| III-67 | CH$_2$CH=CH$_2$ | CN | N |
| III-68 | CH$_2$C≡CH | CN | N |
| III-69 | CH$_2$C≡CCH$_3$ | CN | N |

TABLE 28

| Compound No. | R¹ | X | W |
|---|---|---|---|
| III-70 | Me | CONH$_2$ | N |
| III-71 | Et | CONH$_2$ | N |
| III-72 | Pr-n | CONH$_2$ | N |
| III-73 | Pr-i | CONH$_2$ | N |
| III-74 | Bu-n | CONH$_2$ | N |
| III-75 | Bu-i | CONH$_2$ | N |
| III-76 | Bu-s | CONH$_2$ | N |
| III-77 | Bu-t | CONH$_2$ | N |
| III-78 | Pen-n | CONH$_2$ | N |
| III-79 | Pen-i | CONH$_2$ | N |
| III-80 | Pen-neo | CONH$_2$ | N |
| III-81 | Pen-2 | CONH$_2$ | N |
| III-82 | Pen-3 | CONH$_2$ | N |
| III-83 | Hex-n | CONH$_2$ | N |
| III-84 | CH$_2$CH$_2$C(Me)$_3$ | CONH$_2$ | N |
| III-85 | Pen-c | CONH$_2$ | N |
| III-86 | Hex-c | CONH$_2$ | N |
| III-87 | CH$_2$Pr-c | CONH$_2$ | N |
| III-88 | CH$_2$Bu-c | CONH$_2$ | N |
| III-89 | CH$_2$Pen-c | CONH$_2$ | N |
| III-90 | CH$_2$CH=CH$_2$ | CONH$_2$ | N |
| III-91 | CH$_2$C≡CH | CONH$_2$ | N |
| III-92 | CH$_2$C≡CCH$_3$ | CONH$_2$ | N |
| III-93 | Me | Me | N |
| III-94 | Et | Me | N |
| III-95 | Pr-n | Me | N |
| III-96 | Pr-i | Me | N |
| III-97 | Bu-n | Me | N |
| III-98 | Bu-i | Me | N |
| III-99 | Bu-s | Me | N |
| III-100 | Bu-t | Me | N |
| III-101 | Pen-n | Me | N |
| III-102 | Pen-i | Me | N |
| III-103 | Pen-neo | Me | N |
| III-104 | Pen-2 | Me | N |
| III-105 | Pen-3 | Me | N |
| III-106 | Hex-n | Me | N |

TABLE 29

| Compound No. | R¹ | X | W |
|---|---|---|---|
| III-107 | CH$_2$CH$_2$C(Me)$_3$ | Me | N |
| III-108 | Pen-c | Me | N |
| III-109 | Hex-c | Me | N |
| III-110 | CH$_2$Pr-c | Me | N |
| III-111 | CH$_2$Bu-c | Me | N |
| III-112 | CH$_2$Pen-c | Me | N |
| III-113 | CH$_2$CH=CH$_2$ | Me | N |
| III-114 | CH$_2$C≡CH | Me | N |
| III-115 | CH$_2$C≡CCH$_3$ | Me | N |
| III-116 | Me | NH$_2$ | N |
| III-117 | Et | NH$_2$ | N |
| III-118 | Pr-n | NH$_2$ | N |
| III-119 | Pr-i | NH$_2$ | N |
| III-120 | Bu-n | NH$_2$ | N |
| III-121 | Bu-i | NH$_2$ | N |
| III-122 | Bu-s | NH$_2$ | N |
| III-123 | Bu-t | NH$_2$ | N |

TABLE 29-continued

| Compound No. | R¹ | X | W |
|---|---|---|---|
| III-124 | Pen-n | $NH_2$ | N |
| III-125 | Pen-i | $NH_2$ | N |
| III-126 | Pen-neo | $NH_2$ | N |
| III-127 | Pen-2 | $NH_2$ | N |
| III-128 | Pen-3 | $NH_2$ | N |
| III-129 | Hex-n | $NH_2$ | N |
| III-130 | $CH_2CH_2C(Me)_3$ | $NH_2$ | N |
| III-131 | Pen-c | $NH_2$ | N |
| III-132 | Hex-c | $NH_2$ | N |
| III-133 | $CH_2Pr$-c | $NH_2$ | N |
| III-134 | $CH_2Bu$-c | $NH_2$ | N |
| III-135 | $CH_2Pen$-c | $NH_2$ | N |
| III-136 | $CH_2CH=CH_2$ | $NH_2$ | N |
| III-137 | $CH_2C\equiv CH$ | $NH_2$ | N |
| III-138 | $CH_2C\equiv CCH_3$ | $NH_2$ | N |
| III-139 | Me | Br | N |
| III-140 | Et | Br | N |
| III-141 | Pr-n | Br | N |
| III-142 | Pr-i | Br | N |
| III-143 | Bu-n | Br | N |

TABLE 30

| Compound No. | R¹ | X | W |
|---|---|---|---|
| III-144 | Bu-i | Br | N |
| III-145 | Bu-s | Br | N |
| III-146 | Bu-t | Br | N |
| III-147 | Pen-n | Br | N |
| III-148 | Pen-i | Br | N |
| III-149 | Pen-neo | Br | N |
| III-150 | Pen-2 | Br | N |
| III-151 | Pen-3 | Br | N |
| III-152 | Hex-n | Br | N |
| III-153 | $CH_2CH_2C(Me)_3$ | Br | N |
| III-154 | Pen-c | Br | N |
| III-155 | Hex-c | Br | N |
| III-156 | $CH_2Pr$-c | Br | N |
| III-157 | $CH_2Bu$-c | Br | N |
| III-158 | $CH_2Pen$-c | Br | N |
| III-159 | $CH_2CH=CH_2$ | Br | N |
| III-160 | $CH_2C\equiv CH$ | Br | N |
| III-161 | $CH_2C\equiv CCH_3$ | Br | N |
| III-162 | Me | OMe | N |
| III-163 | Et | OMe | N |
| III-164 | Pr-n | OMe | N |
| III-165 | Pr-i | OMe | N |
| III-166 | Bu-n | OMe | N |
| III-167 | Bu-i | OMe | N |
| III-168 | Bu-s | OMe | N |
| III-169 | Bu-t | OMe | N |
| III-170 | Pen-n | OMe | N |
| III-171 | Pen-i | OMe | N |
| III-172 | Pen-neo | OMe | N |
| III-173 | Pen-2 | OMe | N |
| III-174 | Pen-3 | OMe | N |
| III-175 | Hex-n | OMe | N |
| III-176 | $CH_2CH_2C(Me)_3$ | OMe | N |
| III-177 | Pen-c | OMe | N |
| III-178 | Hex-c | OMe | N |
| III-179 | $CH_2Pr$-c | OMe | N |
| III-180 | $CH_2Bu$-c | OMe | N |

TABLE 31

| Compound No. | R¹ | X | W |
|---|---|---|---|
| III-181 | $CH_2Pen$-c | OMe | N |
| III-182 | $CH_2CH=CH_2$ | OMe | N |
| III-183 | $CH_2C\equiv CH$ | OMe | N |
| III-184 | $CH_2C\equiv CCH_3$ | OMe | N |
| III-185 | Me | $C(NH_2)=NOH$ | N |
| III-186 | Et | $C(NH_2)=NOH$ | N |

TABLE 31-continued

| Compound No. | R¹ | X | W |
|---|---|---|---|
| III-187 | Pr-n | $C(NH_2)=NOH$ | N |
| III-188 | Pr-i | $C(NH_2)=NOH$ | N |
| III-189 | Bu-n | $C(NH_2)=NOH$ | N |
| III-190 | Bu-i | $C(NH_2)=NOH$ | N |
| III-191 | Bu-s | $C(NH_2)=NOH$ | N |
| III-192 | Bu-t | $C(NH_2)=NOH$ | N |
| III-193 | Pen-n | $C(NH_2)=NOH$ | N |
| III-194 | Pen-i | $C(NH_2)=NOH$ | N |
| III-195 | Pen-neo | $C(NH_2)=NOH$ | N |
| III-196 | Pen-2 | $C(NH_2)=NOH$ | N |
| III-197 | Pen-3 | $C(NH_2)=NOH$ | N |
| III-198 | Hex-n | $C(NH_2)=NOH$ | N |
| III-199 | $CH_2CH_2C(Me)_3$ | $C(NH_2)=NOH$ | N |
| III-200 | Pen-c | $C(NH_2)=NOH$ | N |
| III-201 | Hex-c | $C(NH_2)=NOH$ | N |
| III-202 | $CH_2Pr$-c | $C(NH_2)=NOH$ | N |
| III-203 | $CH_2Bu$-c | $C(NH_2)=NOH$ | N |
| III-204 | $CH_2Pen$-c | $C(NH_2)=NOH$ | N |
| III-205 | $CH_2CH=CH_2$ | $C(NH_2)=NOH$ | N |
| III-206 | $CH_2C\equiv CH$ | $C(NH_2)=NOH$ | N |
| III-207 | $CH_2C\equiv CCH_3$ | $C(NH_2)=NOH$ | N |
| III-208 | Pr-i | 1,2,4-oxadiazol-3-yl | N |
| III-209 | Bu-i | 1,2,4-oxadiazol-3-yl | N |
| III-210 | Pr-i | 5-methyl-1,2,4-oxadiazol-3-yl | N |
| III-211 | Bu-i | 5-methyl-1,2,4-oxadiazol-3-yl | N |

TABLE 32

| Compound No. | R¹ | X | W |
|---|---|---|---|
| III-212 | Pr-i | 1-methyl-1,2,4-triazol-3-yl | N |
| III-213 | Pr-i | 1H-tetrazol-5-yl | N |
| III-214 | Pr-i | thiazol-2-yl | N |
| III-215 | Pr-i | 4,5-dihydrothiazol-2-yl | N |
| III-216 | Pr-i | NHCOMe | N |
| III-217 | Bu-i | NHCOMe | N |
| III-218 | $CH_2Pr$-c | NHCOMe | N |
| III-219 | Bu-i | $NHCO_2Me$ | N |
| III-220 | Pr-i | $NMe_2$ | N |
| III-221 | Pr-i | $CO_2Me$ | N |
| III-222 | Pr-i | COSEt | N |

TABLE 32-continued

| Compound No. | R¹ | X | W |
|---|---|---|---|
| III-223 | Pr-i | C(=NH)OMe | N |
| III-224 | Pr-i | CSNH$_2$ | N |
| III-225 | Pr-i | CONHMe | N |
| III-226 | Pr-i | CONMe$_2$ | N |
| III-227 | Pr-i | CON(Me)OMe | N |
| III-228 | Pr-i | SMe | N |
| III-229 | Pr-i | CF$_3$ | N |
| III-230 | Pr-i | Et | N |
| III-231 | Pr-i | Pr-i | N |
| III-232 | Pr-i | Bu-t | N |
| III-233 | CH$_2$(CH$_2$)$_6$CH$_3$ | CN | N |
| III-234 | CH$_2$(CH$_2$)$_6$CH$_3$ | CONH$_2$ | N |
| III-235 | CH$_2$(CH$_2$)$_5$CH$_3$ | Cl | N |
| III-236 | CH$_2$(CH$_2$)$_8$CH$_3$ | NH$_2$ | N |
| III-237 | CH$_2$(CH$_2$)$_8$CH$_3$ | Cl | N |
| III-238 | CH$_2$CF$_3$ | CN | N |
| III-239 | CH$_2$CF$_3$ | CONH$_2$ | N |
| III-240 | CH$_2$CF$_3$ | H | N |
| III-241 | CH$_2$Ph | Cl | N |
| III-242 | CH$_2$Ph | CN | N |

TABLE 33

| Compound No. | R¹ | X | W |
|---|---|---|---|
| III-243 | CH$_2$Ph | CONH$_2$ | N |
| III-244 | CH$_2$CH$_2$CH(OMe)CH$_3$ | NH$_2$ | N |
| III-245 | CH$_2$CH$_2$CH(OMe)CH$_3$ | Cl | N |
| III-246 | CH$_2$CH$_2$OCH$_2$CH$_3$ | H | N |
| III-247 | CH(Me)CH$_2$OCH$_3$ | NH$_2$ | N |
| III-248 | CH(Me)CH$_2$OCH$_3$ | Cl | N |
| III-249 | CH$_2$CH$_2$OC(CH$_3$)$_3$ | NH$_2$ | N |
| III-250 | CH$_2$CH$_2$OH | Cl | N |
| III-251 | CH$_2$CH$_2$SC(CH$_3$)$_3$ | NH$_2$ | N |
| III-252 | CH$_2$Si(CH$_3$)$_3$ | NH$_2$ | N |
| III-253 | CH$_2$Si(CH$_3$)$_3$ | Cl | N |
| III-254 | CH$_2$(CH$_2$)$_2$Si(CH$_3$)$_3$ | NH$_2$ | N |
| III-255 | CH$_2$(CH$_2$)$_2$Si(CH$_3$)$_3$ | Cl | N |
| III-256 | Et | C(NH$_2$)=NOBu-i | N |
| III-257 | Et | CONHPr-c | N |
| III-258 | Et | CONHCHF$_2$ | N |
| III-259 | Et | CONHSO$_2$CH$_3$ | N |
| III-260 | Et | [triazolyl-C(Me)=N-O-(CH$_2$)$_2$-C(Me)$_3$] | N |
| III-261 | Me | OBu-i | N |
| III-262 | CH$_2$CH$_2$OCH$_3$ | CN | N |
| III-263 | CH$_2$CH$_2$OCH$_3$ | CONH$_2$ | N |
| III-264 | Me | 3-methylpyridin-yl | N |
| III-265 | Me | 3-methylpyridine N-oxide | N |
| III-266 | Me | 2-chloro-3-methylpyridin-yl | N |

TABLE 33-continued

| Compound No. | R¹ | X | W |
|---|---|---|---|
| III-267 | Me | 2-methylthiophenyl | N |
| III-268 | Et | 3-CF$_3$-4-methyl-1-methyl-pyrazolyl | N |
| III-269 | (E)-ClCH=CHCH$_2$CH$_3$ | CN | N |

TABLE 34

| Compound No. | R¹ | X | W |
|---|---|---|---|
| III-270 | (E)-ClCH=CHCH$_2$CH$_3$ | CONH$_2$ | N |
| III-271 | (E)-3-pyridyl-CH=CHCH$_2$CH$_3$ | Me | N |
| III-272 | CH$_2$CH(CH$_3$)CH$_2$CH$_3$ | CN | N |
| III-273 | CH$_2$CH(CH$_3$)CH$_2$CH$_3$ | CONH$_2$ | N |
| III-274 | Pr-i | CO$_2$H | N |
| III-275 | CH$_2$CH$_2$OCH$_2$CF$_3$ | CN | N |
| III-276 | CH$_2$CH$_2$OCH$_2$CF$_3$ | CONH$_2$ | N |
| III-277 | CH$_2$OCH$_3$ | CN | N |
| III-278 | CH$_2$OCH$_3$ | CONH$_2$ | N |
| III-279 | CH$_2$(CH$_2$)$_2$OCH$_3$ | CN | N |
| III-280 | CH$_2$(CH$_2$)$_2$OCH$_3$ | CONH$_2$ | N |
| III-281 | 2-Me-cyclopropyl-Et | CN | N |
| III-282 | 2-Me-cyclopropyl-Et | CONH$_2$ | N |
| III-283 | 2,2-diCl-cyclopropyl-Et | CN | N |
| III-284 | 2,2-diCl-cyclopropyl-Et | CONH$_2$ | N |
| III-285 | 2,2-diMe-cyclopropyl-Et | CN | N |
| III-286 | 2,2-diMe-cyclopropyl-Et | CONH$_2$ | N |
| III-287 | 2,2-diF-cyclopropyl-Et | CN | N |

TABLE 34-continued

| Compound No. | R¹ | X | W |
|---|---|---|---|
| III-288 | (2,2-difluorocyclopropyl-ethyl) | CONH$_2$ | N |
| III-289 | (1-cyclopropyl-ethyl) | CN | N |
| III-290 | (1-cyclopropyl-ethyl) | CONH$_2$ | N |

TABLE 35

| Compound No. | R¹ | X | W |
|---|---|---|---|
| III-291 | (1-methyl-2-ethylcyclopropyl) | CN | N |
| III-292 | (1-methyl-2-ethylcyclopropyl) | CONH$_2$ | N |
| III-293 | (2-cyclopropyl-ethyl) | CN | N |
| III-294 | (2-cyclopropyl-ethyl) | CONH$_2$ | N |
| III-295 | CH$_2$C(CH$_3$)$_2$CH$_2$CH$_3$ | CN | N |
| III-296 | CH$_2$C(CH$_3$)$_2$CH$_2$CH$_3$ | CONH$_2$ | N |
| III-297 | CH$_2$(CF$_2$)$_2$CF$_3$ | CN | N |
| III-298 | CH$_2$(CF$_2$)$_2$CF$_3$ | CONH$_2$ | N |
| III-299 | CF$_2$CHFCF$_3$ | CN | N |
| III-300 | CH$_2$C(CH$_3$)$_2$CN | CN | N |
| III-301 | CH$_2$C(CH$_3$)$_2$CN | CONH$_2$ | N |
| III-302 | CH$_2$C(CH$_3$)$_2$CH$_2$Cl | CN | N |
| III-303 | CH$_2$C(CH$_3$)$_2$CH$_2$Cl | CONH$_2$ | N |
| III-304 | CH$_2$CF$_2$CF$_3$ | CN | N |
| III-305 | CH$_2$CF$_2$CF$_3$ | CONH$_2$ | N |
| III-306 | Bu-n | C(=NH)OCH$_3$ | N |
| III-307 | Bu-n | CO$_2$CH$_3$ | N |
| III-308 | CH$_2$(CF$_2$)$_3$CHF$_2$ | CN | N |
| III-309 | CH$_2$(CF$_2$)$_3$CHF$_2$ | CONH$_2$ | N |

TABLE 36

| Compound No. | R¹ | X | R² | W |
|---|---|---|---|---|
| IV-1 | Pr-i | Cl | Pr-n | N |
| IV-2 | Pr-i | Cl | Bu-n | N |
| IV-3 | Pr-i | Cl | Bu-i | N |
| IV-4 | Pr-i | Cl | Bu-t | N |
| IV-5 | Pr-i | Cl | Pen-i | N |
| IV-6 | Pr-i | Cl | CH$_2$Pr-c | N |
| IV-7 | Pr-i | Cl | CH$_2$CH=CH$_2$ | N |
| IV-8 | Pr-i | Cl | CH$_2$C≡CH | N |
| IV-9 | Pr-i | Cl | CH$_2$C≡CCH$_3$ | N |
| IV-10 | Pr-i | Cl | CH$_2$CF$_3$ | N |
| IV-11 | Pr-i | Cl | CH$_2$CH$_2$OCH$_3$ | N |
| IV-12 | Pr-i | Cl | CH$_2$CH$_2$OCH$_2$CH$_3$ | N |
| IV-13 | Pr-i | Cl | CH$_2$CH$_2$CH$_2$OCH$_3$ | N |
| IV-14 | Pr-i | Cl | CH$_2$(CH$_2$)$_3$OC(CH$_3$)$_3$ | N |
| IV-15 | Pr-i | CONH$_2$ | Pr-n | N |
| IV-16 | Pr-i | CONH$_2$ | Bu-n | N |
| IV-17 | Pr-i | CONH$_2$ | Bu-i | N |
| IV-18 | Pr-i | CONH$_2$ | Bu-s | N |
| IV-19 | Pr-i | CONH$_2$ | Bu-t | N |
| IV-20 | Pr-i | CONH$_2$ | Pen-i | N |
| IV-21 | Pr-i | CONH$_2$ | CH$_2$Pr-c | N |
| IV-22 | Pr-i | CONH$_2$ | CH$_2$CH=CH$_2$ | N |
| IV-23 | Pr-i | CONH$_2$ | CH$_2$C≡CH | N |
| IV-24 | Pr-i | CONH$_2$ | CH$_2$C≡CCH$_3$ | N |
| IV-25 | Pr-i | CONH$_2$ | CH$_2$CF$_3$ | N |
| IV-26 | Pr-i | CONH$_2$ | CH$_2$CH$_2$OCH$_3$ | N |
| IV-27 | Pr-i | CONH$_2$ | CH$_2$CH$_2$OCH$_2$CH$_3$ | N |
| IV-28 | Pr-i | CONH$_2$ | CH$_2$CH$_2$CH$_2$OCH$_3$ | N |
| IV-29 | Pr-i | CONH$_2$ | CH$_2$(CH$_2$)$_3$OC(CH$_3$)$_3$ | N |
| IV-30 | Pr-i | CN | Pr-n | N |
| IV-31 | Pr-i | CN | Bu-n | N |

TABLE 37

| Compound No. | R¹ | X | R² | W |
|---|---|---|---|---|
| IV-32 | Pr-i | CN | Bu-i | N |
| IV-33 | Pr-i | CN | Bu-s | N |
| IV-34 | Pr-i | CN | Bu-t | N |
| IV-35 | Pr-i | CN | Pen-i | N |
| IV-36 | Pr-i | CN | CH$_2$Pr-c | N |
| IV-37 | Pr-i | CN | CH$_2$CH=CH$_2$ | N |
| IV-38 | Pr-i | CN | CH$_2$C≡CH | N |
| IV-39 | Pr-i | CN | CH$_2$C≡CCH$_3$ | N |
| IV-40 | Pr-i | CN | CH$_2$CF$_3$ | N |
| IV-41 | Pr-i | CN | CH$_2$CH$_2$OCH$_3$ | N |
| IV-42 | Pr-i | CN | CH$_2$CH$_2$OCH$_2$CH$_3$ | N |
| IV-43 | Pr-i | CN | CH$_2$CH$_2$CH$_2$OCH$_3$ | N |
| IV-44 | Pr-i | CN | CH$_2$(CH$_2$)$_3$OC(CH$_3$)$_3$ | N |
| IV-45 | Me | Cl | Pr-n | N |
| IV-46 | Me | Cl | Bu-n | N |
| IV-47 | Me | Cl | Bu-i | N |
| IV-48 | Me | Cl | Bu-t | N |
| IV-49 | Me | Cl | Pen-i | N |
| IV-50 | Me | Cl | CH$_2$Pr-c | N |
| IV-51 | Me | Cl | CH$_2$CH=CH$_2$ | N |
| IV-52 | Me | Cl | CH$_2$C≡CH | N |
| IV-53 | Me | Cl | CH$_2$C≡CCH$_3$ | N |
| IV-54 | Me | Cl | CH$_2$CF$_3$ | N |
| IV-55 | Me | Cl | CH$_2$CH$_2$OCH$_3$ | N |
| IV-56 | Me | Cl | CH$_2$CH$_2$OCH$_2$CH$_3$ | N |
| IV-57 | Me | Cl | CH$_2$CH$_2$CH$_2$OCH$_3$ | N |
| IV-58 | Me | Cl | CH$_2$(CH$_2$)$_3$OC(CH$_3$)$_3$ | N |
| IV-59 | Me | CONH$_2$ | Pr-n | N |
| IV-60 | Me | CONH$_2$ | Bu-n | N |
| IV-61 | Me | CONH$_2$ | Bu-i | N |
| IV-62 | Me | CONH$_2$ | Bu-t | N |
| IV-63 | Me | CONH$_2$ | Pen-i | N |
| IV-64 | Me | CONH$_2$ | Pen-c | N |
| IV-65 | Me | CONH$_2$ | CH$_2$Pr-c | N |

TABLE 37-continued

| Compound No. | R¹ | X | R² | W |
|---|---|---|---|---|
| IV-66 | Me | CONH₂ | CH₂CH=CH₂ | N |
| IV-67 | Me | CONH₂ | CH₂C≡CH | N |

TABLE 38

| Compound No. | R¹ | X | R² | W |
|---|---|---|---|---|
| IV-68 | Me | CONH₂ | CH₂C≡CCH₃ | N |
| IV-69 | Me | CONH₂ | CH₂CF₃ | N |
| IV-70 | Me | CONH₂ | CH₂CH₂OCH₃ | N |
| IV-71 | Me | CONH₂ | CH₂CH₂OCH₂CH₃ | N |
| IV-72 | Me | CONH₂ | CH₂CH₂CH₂OCH₃ | N |
| IV-73 | Me | CONH₂ | CH₂(CH₂)₃OC(CH₃)₃ | N |
| IV-74 | Me | CN | Pr-n | N |
| IV-75 | Me | CN | Bu-n | N |
| IV-76 | Me | CN | Bu-i | N |
| IV-77 | Me | CN | Bu-t | N |
| IV-78 | Me | CN | Pen-i | N |
| IV-79 | Me | CN | Pen-c | N |
| IV-80 | Me | CN | CH₂Pr-c | N |
| IV-81 | Me | CN | CH₂CH=CH₂ | N |
| IV-82 | Me | CN | CH₂C≡CH | N |
| IV-83 | Me | CN | CH₂C≡CCH₃ | N |
| IV-84 | Me | CN | CH₂CF₃ | N |
| IV-85 | Me | CN | CH₂CH₂OCH₃ | N |
| IV-86 | Me | CN | CH₂CH₂OCH₂CH₃ | N |
| IV-87 | Me | CN | CH₂CH₂CH₂OCH₃ | N |
| IV-88 | Me | CN | CH₂(CH₂)₃OC(CH₃)₃ | N |
| IV-89 | Et | CN | Pr-n | N |
| IV-90 | Pr-n | CN | Pr-n | N |
| IV-91 | Bu-n | CN | Pr-n | N |
| IV-92 | Bu-i | CN | Pr-n | N |
| IV-93 | Bu-s | CN | Pr-n | N |
| IV-94 | Bu-t | CN | Pr-n | N |
| IV-95 | CH₂Pr-c | CN | Pr-n | N |
| IV-96 | CH₂CH=CH₂ | CN | Pr-n | N |
| IV-97 | CH₂C≡CH | CN | Pr-n | N |
| IV-98 | CH₂CF₃ | CN | Pr-n | N |
| IV-99 | CH₂Ph | CN | Pr-n | N |
| IV-100 | Et | CONH₂ | Pr-n | N |
| IV-101 | Pr-n | CONH₂ | Pr-n | N |
| IV-102 | Bu-n | CONH₂ | Pr-n | N |
| IV-103 | Bu-i | CONH₂ | Pr-n | N |

TABLE 39

| Compound No. | R¹ | X | R² | W |
|---|---|---|---|---|
| IV-104 | Bu-s | CONH₂ | Pr-n | N |
| IV-105 | Bu-t | CONH₂ | Pr-n | N |
| IV-106 | CH₂Pr-c | CONH₂ | Pr-n | N |
| IV-107 | CH₂CH=CH₂ | CONH₂ | Pr-n | N |
| IV-108 | CH₂C≡CH | CONH₂ | Pr-n | N |
| IV-109 | CH₂CF₃ | CONH₂ | Pr-n | N |
| IV-110 | CH₂Ph | CONH₂ | Pr-n | N |
| IV-111 | Bu-i | CN | Bu-i | N |
| IV-112 | Bu-i | CONH₂ | Bu-i | N |
| IV-113 | Pr-i | CN | CH₂CN | N |
| IV-114 | Pr-i | CONH₂ | CH₂CN | N |
| IV-115 | Bu-s | CN | Bu-s | N |
| IV-116 | Bu-s | CONH₂ | Bu-s | N |
| IV-117 | CH₂Pr-c | CN | CH₂Pr-c | N |
| IV-118 | CH₂Pr-c | CONH₂ | CH₂Pr-c | N |
| IV-119 | Pen-c | CN | Pen-c | N |
| IV-120 | Pen-c | CONH₂ | Pen-c | N |
| IV-121 | Me | CN | CH₂Ph | N |
| IV-122 | Me | CONH₂ | CH₂Ph | N |
| IV-123 | Pr-i | Cl | Bu-i | CH |
| IV-124 | Pr-i | Cl | CH₂Pr-c | CH |
| IV-125 | Pr-i | Me | Bu-i | CH |
| IV-126 | Pr-i | Me | CH₂Pr-c | CH |
| IV-127 | Me | CN | Pen-c | CH |
| IV-128 | Me | CONH₂ | Pen-c | CH |

TABLE 39-continued

| Compound No. | R¹ | X | R² | W |
|---|---|---|---|---|
| IV-129 | Pr-i | CN | Bu-i | CH |
| IV-130 | Pr-i | CN | CH₂Pr-c | CH |
| IV-131 | Pr-i | CN | Pen-i | CH |
| IV-132 | Pr-i | CONH₂ | Bu-i | CH |
| IV-133 | Pr-i | CONH₂ | CH₂Pr-c | CH |
| IV-134 | Pr-i | CONH₂ | Pen-i | CH |
| IV-135 | Pr-i | CONH₂ | CH₂CF₃ | CH |
| IV-136 | CH₂CF₃ | CONH₂ | Bu-i | CH |
| IV-137 | CH₂CF₃ | CONH₂ | CH₂Pr-c | CH |
| IV-138 | Bu-i | CONH₂ | Bu-i | CH |
| IV-139 | Bu-i | CONH₂ | CH₂Pr-c | CH |
| IV-140 | CH₂Pr-c | CONH₂ | Bu-i | CH |

TABLE 40

| Compound No. | R¹ | X | R² | W |
|---|---|---|---|---|
| IV-141 | CH₂Pr-c | CONH₂ | CH₂Pr-c | CH |
| IV-142 | Me | Cl | Bu-i | CH |
| IV-143 | Me | Cl | CH₂Pr-c | CH |
| IV-144 | Me | Me | Bu-i | CH |
| IV-145 | Me | Me | CH₂Pr-c | CH |
| IV-146 | Me | CN | Bu-i | CH |
| IV-147 | Me | CN | CH₂Pr-c | CH |
| IV-148 | Me | CN | CH₂CH₂OCH₂CH₃ | CH |
| IV-149 | Me | CN | Pen-i | CH |
| IV-150 | Me | CONH₂ | Bu-i | CH |
| IV-151 | Me | CONH₂ | CH₂Pr-c | CH |
| IV-152 | Me | CONH₂ | Pen-i | CH |
| IV-153 | Me | CONH₂ | CH₂CH₂OCH₂CH₃ | CH |
| IV-154 | Me | CONH₂ | CH₂CF₃ | CH |
| IV-155 | Me | CN | CH₂Ph | CH |
| IV-156 | Me | CONH₂ | CH₂Ph | CH |
| IV-157 | Me | CONH₂ | CH₂CF₃ | CH |
| IV-158 | Pr-i | CN | CH₂C(Cl)=CH₂ | N |
| IV-159 | Pr-i | CONH₂ | CH₂C(Cl)=CH₂ | N |
| IV-160 | Pr-i | Me | CH₂CH₂SCH₃ | N |
| IV-161 | Pr-i | Me | CH₂CH₂SOCH₃ | N |
| IV-162 | Pr-i | Me | CH₂CH₂SO₂CH₃ | N |
| IV-163 | Pr-i | Me | CH₂CH₂OCH₂CF₃ | N |
| IV-164 | Pen-c | CN | Pr-n | N |
| IV-165 | Pen-c | CONH₂ | Pr-n | N |
| IV-166 | Pen-3 | CN | Pr-n | N |
| IV-167 | Pen-3 | CONH₂ | Pr-n | N |
| IV-168 | Et | CN | Bu-t | N |
| IV-169 | Et | CONH₂ | Bu-t | N |
| IV-170 | Pr-n | CN | Bu-t | N |
| IV-171 | Pr-n | CONH₂ | Bu-t | N |
| IV-172 | Pr-i | CN | Pen-2 | N |
| IV-173 | Pr-i | CONH₂ | Pen-2 | N |
| IV-174 | Pr-i | CN | Pen-3 | N |
| IV-175 | Pr-i | CONH₂ | Pen-3 | N |
| IV-176 | Pen-neo | CN | Pr-n | N |
| IV-177 | Pen-neo | CONH₂ | Pr-n | N |
| IV-178 | Pen-i | CN | Pr-n | N |

TABLE 41

| Compound No. | R¹ | X | R² | W |
|---|---|---|---|---|
| IV-179 | Pen-i | CONH₂ | Pr-n | N |
| IV-180 | CH₂Pr-c | CONH₂ | CHF₂ | N |
| IV-181 | CH₂CF₂CF₃ | CN | Pr-n | N |
| IV-182 | CH₂CF₂CF₃ | CONH₂ | Pr-n | N |
| IV-183 | CH₂Ph | CN | CH₂CF₃ | N |
| IV-184 | CH₂Ph | CN | CH₂CF₃ | CH |
| IV-185 | CH₂CF₂CF₃ | CN | CH₂CF₃ | CH |
| IV-186 | CH₂CF₂CF₃ | CONH₂ | CH₂CF₃ | CH |
| IV-187 | CH₂CF₂CF₃ | CN | CH₂CF₃ | N |

TABLE 42

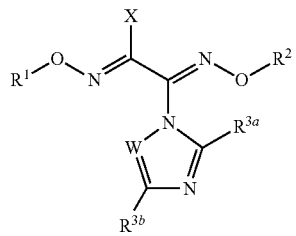

| Compound No. | R¹ | X | R² | R³ᵃ | R³ᵇ | W |
|---|---|---|---|---|---|---|
| V-1 | Pr-i | Cl | Pr-i | SH | H | N |
| V-2 | Pr-i | Cl | Pr-i | SMe | H | N |
| V-3 | Pr-i | Cl | Pr-i | SOMe | H | N |
| V-4 | Pr-i | Cl | Pr-i | SH | H | CH |
| V-5 | Pr-i | Cl | Pr-i | SMe | H | CH |
| V-6 | Pr-i | Cl | Pr-i | SOMe | H | CH |
| V-7 | Pr-i | Me | Pr-i | SH | H | N |
| V-8 | Pr-i | Me | Pr-i | SMe | H | N |
| V-9 | Pr-i | Me | Pr-i | SOMe | H | N |
| V-10 | Pr-i | Me | Pr-i | SH | H | CH |
| V-11 | Pr-i | Me | Pr-i | SMe | H | CH |
| V-12 | Pr-i | Me | Pr-i | SOMe | H | CH |
| V-13 | Pr-i | CN | Pr-i | SH | H | N |
| V-14 | Pr-i | CN | Pr-i | SMe | H | N |
| V-15 | Pr-i | CN | Pr-i | SOMe | H | N |
| V-16 | Pr-i | CN | Pr-i | SH | H | CH |
| V-17 | Pr-i | CN | Pr-i | SMe | H | CH |
| V-18 | Pr-i | CN | Pr-i | SOMe | H | CH |
| V-19 | Pr-i | CONH₂ | Pr-i | SH | H | N |
| V-20 | Pr-i | CONH₂ | Pr-i | SMe | H | N |
| V-21 | Pr-i | CONH₂ | Pr-i | SOMe | H | N |
| V-22 | Pr-i | CONH₂ | Pr-i | SH | H | CH |
| V-23 | Pr-i | CONH₂ | Pr-i | SMe | H | CH |
| V-24 | Pr-i | CONH₂ | Pr-i | SOMe | H | CH |
| V-25 | Pr-i | CF₃ | Pr-i | SH | H | N |
| V-26 | Pr-i | CF₃ | Pr-i | SMe | H | N |
| V-27 | Pr-i | CF₃ | Pr-i | SOMe | H | N |
| V-28 | Pr-i | CF₃ | Pr-i | SH | H | CH |
| V-29 | Pr-i | CF₃ | Pr-i | SMe | H | CH |
| V-30 | Pr-i | CF₃ | Pr-i | SOMe | H | CH |

TABLE 43

| Compound No. | R¹ | X | R² | R³ᵃ | R³ᵇ | W |
|---|---|---|---|---|---|---|
| V-31 | Pr-i | Cl | Et | SH | H | N |
| V-32 | Pr-i | Cl | Et | SMe | H | N |
| V-33 | Pr-i | Cl | Et | SOMe | H | N |
| V-34 | Pr-i | Cl | Et | SH | H | CH |
| V-35 | Pr-i | Cl | Et | SMe | H | CH |
| V-36 | Pr-i | Cl | Et | SOMe | H | CH |
| V-37 | Pr-i | Me | Et | SH | H | N |
| V-38 | Pr-i | Me | Et | SMe | H | N |
| V-39 | Pr-i | Me | Et | SOMe | H | N |
| V-40 | Pr-i | Me | Et | SH | H | CH |
| V-41 | Pr-i | Me | Et | SMe | H | CH |
| V-42 | Pr-i | Me | Et | SOMe | H | CH |
| V-43 | Pr-i | CN | Et | SH | H | N |
| V-44 | Pr-i | CN | Et | SMe | H | N |
| V-45 | Pr-i | CN | Et | SOMe | H | N |
| V-46 | Pr-i | CN | Et | SH | H | CH |
| V-47 | Pr-i | CN | Et | SMe | H | CH |
| V-48 | Pr-i | CN | Et | SOMe | H | CH |
| V-49 | Pr-i | CONH₂ | Et | SH | H | N |
| V-50 | Pr-i | CONH₂ | Et | SMe | H | N |
| V-51 | Pr-i | CONH₂ | Et | SOMe | H | N |
| V-52 | Pr-i | CONH₂ | Et | SH | H | CH |
| V-53 | Pr-i | CONH₂ | Et | SMe | H | CH |
| V-54 | Pr-i | CONH₂ | Et | SOMe | H | CH |
| V-55 | Pr-i | CF₃ | Et | SH | H | N |
| V-56 | Pr-i | CF₃ | Et | SMe | H | N |
| V-57 | Pr-i | CF₃ | Et | SOMe | H | N |
| V-58 | Pr-i | CF₃ | Et | SH | H | CH |
| V-59 | Pr-i | CF₃ | Et | SMe | H | CH |
| V-60 | Pr-i | CF₃ | Et | SOMe | H | CH |
| V-61 | Pr-i | Cl | Me | SH | H | N |
| V-62 | Pr-i | Cl | Me | SMe | H | N |
| V-63 | Pr-i | Cl | Me | SOMe | H | N |
| V-64 | Pr-i | Cl | Me | SH | H | CH |
| V-65 | Pr-i | Cl | Me | SMe | H | CH |
| V-66 | Pr-i | Cl | Me | SOMe | H | CH |

TABLE 44

| Compound No. | R¹ | X | R² | R³ᵃ | R³ᵇ | W |
|---|---|---|---|---|---|---|
| V-67 | Pr-i | Me | Me | SH | H | N |
| V-68 | Pr-i | Me | Me | SMe | H | N |
| V-69 | Pr-i | Me | Me | SOMe | H | N |
| V-70 | Pr-i | Me | Me | SH | H | CH |
| V-71 | Pr-i | Me | Me | SMe | H | CH |
| V-72 | Pr-i | Me | Me | SOMe | H | CH |
| V-73 | Pr-i | CN | Me | SH | H | N |
| V-74 | Pr-i | CN | Me | SMe | H | N |
| V-75 | Pr-i | CN | Me | SOMe | H | N |
| V-76 | Pr-i | CN | Me | SH | H | CH |
| V-77 | Pr-i | CN | Me | SMe | H | CH |
| V-78 | Pr-i | CN | Me | SOMe | H | CH |
| V-79 | Pr-i | CONH₂ | Me | SH | H | N |
| V-80 | Pr-i | CONH₂ | Me | SMe | H | N |
| V-81 | Pr-i | CONH₂ | Me | SOMe | H | N |
| V-82 | Pr-i | CONH₂ | Me | SH | H | CH |
| V-83 | Pr-i | CONH₂ | Me | SMe | H | CH |
| V-84 | Pr-i | CONH₂ | Me | SOMe | H | CH |
| V-85 | Pr-i | CF₃ | Me | SH | H | N |
| V-86 | Pr-i | CF₃ | Me | SMe | H | N |
| V-87 | Pr-i | CF₃ | Me | SOMe | H | N |
| V-88 | Pr-i | CF₃ | Me | SH | H | CH |
| V-89 | Pr-i | CF₃ | Me | SMe | H | CH |
| V-90 | Pr-i | CF₃ | Me | SOMe | H | CH |
| V-91 | Bu-i | Cl | Pr-i | SH | H | N |
| V-92 | Bu-i | Cl | Pr-i | SMe | H | N |
| V-93 | Bu-i | Cl | Pr-i | SOMe | H | N |
| V-94 | Bu-i | Cl | Pr-i | SH | H | CH |
| V-95 | Bu-i | Cl | Pr-i | SMe | H | CH |
| V-96 | Bu-i | Cl | Pr-i | SOMe | H | CH |
| V-97 | Bu-i | Me | Pr-i | SH | H | N |
| V-98 | Bu-i | Me | Pr-i | SMe | H | N |
| V-99 | Bu-i | Me | Pr-i | SOMe | H | N |
| V-100 | Bu-i | Me | Pr-i | SH | H | CH |
| V-101 | Bu-i | Me | Pr-i | SMe | H | CH |
| V-102 | Bu-i | Me | Pr-i | SOMe | H | CH |

TABLE 45

| Compound No. | R¹ | X | R² | R³ᵃ | R³ᵇ | W |
|---|---|---|---|---|---|---|
| V-103 | Bu-i | CN | Pr-i | SH | H | N |
| V-104 | Bu-i | CN | Pr-i | SMe | H | N |
| V-105 | Bu-i | CN | Pr-i | SOMe | H | N |
| V-106 | Bu-i | CN | Pr-i | SH | H | CH |
| V-107 | Bu-i | CN | Pr-i | SMe | H | CH |
| V-108 | Bu-i | CN | Pr-i | SOMe | H | CH |
| V-109 | Bu-i | CONH₂ | Pr-i | SH | H | N |
| V-110 | Bu-i | CONH₂ | Pr-i | SMe | H | N |
| V-111 | Bu-i | CONH₂ | Pr-i | SOMe | H | N |
| V-112 | Bu-i | CONH₂ | Pr-i | SH | H | CH |
| V-113 | Bu-i | CONH₂ | Pr-i | SMe | H | CH |
| V-114 | Bu-i | CONH₂ | Pr-i | SOMe | H | CH |
| V-115 | Bu-i | CF₃ | Pr-i | SH | H | N |
| V-116 | Bu-i | CF₃ | Pr-i | SMe | H | N |
| V-117 | Bu-i | CF₃ | Pr-i | SOMe | H | N |
| V-118 | Bu-i | CF₃ | Pr-i | SH | H | CH |

TABLE 45-continued

| Compound No. | R¹ | X | R² | R³ᵃ | R³ᵇ | W |
|---|---|---|---|---|---|---|
| V-119 | Bu-i | CF₃ | Pr-i | SMe | H | CH |
| V-120 | Bu-i | CF₃ | Pr-i | SOMe | H | CH |
| V-121 | Bu-i | Cl | Et | SH | H | N |
| V-122 | Bu-i | Cl | Et | SMe | H | N |
| V-123 | Bu-i | Cl | Et | SOMe | H | N |
| V-124 | Bu-i | Cl | Et | SH | H | CH |
| V-125 | Bu-i | Cl | Et | SMe | H | CH |
| V-126 | Bu-i | Cl | Et | SOMe | H | CH |
| V-127 | Bu-i | Me | Et | SH | H | N |
| V-128 | Bu-i | Me | Et | SMe | H | N |
| V-129 | Bu-i | Me | Et | SOMe | H | N |
| V-130 | Bu-i | Me | Et | SH | H | CH |
| V-131 | Bu-i | Me | Et | SMe | H | CH |
| V-132 | Bu-i | Me | Et | SOMe | H | CH |
| V-133 | Bu-i | CN | Et | SH | H | N |
| V-134 | Bu-i | CN | Et | SMe | H | N |
| V-135 | Bu-i | CN | Et | SOMe | H | N |
| V-136 | Bu-i | CN | Et | SH | H | CH |
| V-137 | Bu-i | CN | Et | SMe | H | CH |
| V-138 | Bu-i | CN | Et | SOMe | H | CH |

TABLE 46

| Compound No. | R¹ | X | R² | R³ᵃ | R³ᵇ | W |
|---|---|---|---|---|---|---|
| V-139 | Bu-i | CONH₂ | Et | SH | H | N |
| V-140 | Bu-i | CONH₂ | Et | SMe | H | N |
| V-141 | Bu-i | CONH₂ | Et | SOMe | H | N |
| V-142 | Bu-i | CONH₂ | Et | SH | H | CH |
| V-143 | Bu-i | CONH₂ | Et | SMe | H | CH |
| V-144 | Bu-i | CONH₂ | Et | SOMe | H | CH |
| V-145 | Bu-i | CF₃ | Et | SH | H | N |
| V-146 | Bu-i | CF₃ | Et | SMe | H | N |
| V-147 | Bu-i | CF₃ | Et | SOMe | H | N |
| V-148 | Bu-i | CF₃ | Et | SH | H | CH |
| V-149 | Bu-i | CF₃ | Et | SMe | H | CH |
| V-150 | Bu-i | CF₃ | Et | SOMe | H | CH |
| V-151 | Bu-i | Cl | Me | SH | H | N |
| V-152 | Bu-i | Cl | Me | SMe | H | N |
| V-153 | Bu-i | Cl | Me | SOMe | H | N |
| V-154 | Bu-i | Cl | Me | SH | H | CH |
| V-155 | Bu-i | Cl | Me | SMe | H | CH |
| V-156 | Bu-i | Cl | Me | SOMe | H | CH |
| V-157 | Bu-i | Me | Me | SH | H | N |
| V-158 | Bu-i | Me | Me | SMe | H | N |
| V-159 | Bu-i | Me | Me | SOMe | H | N |
| V-160 | Bu-i | Me | Me | SH | H | CH |
| V-161 | Bu-i | Me | Me | SMe | H | CH |
| V-162 | Bu-i | Me | Me | SOMe | H | CH |
| V-163 | Bu-i | CN | Me | SH | H | N |
| V-164 | Bu-i | CN | Me | SMe | H | N |
| V-165 | Bu-i | CN | Me | SOMe | H | N |
| V-166 | Bu-i | CN | Me | SH | H | CH |
| V-167 | Bu-i | CN | Me | SMe | H | CH |
| V-168 | Bu-i | CN | Me | SOMe | H | CH |
| V-169 | Bu-i | CONH₂ | Me | SH | H | N |
| V-170 | Bu-i | CONH₂ | Me | SMe | H | N |
| V-171 | Bu-i | CONH₂ | Me | SOMe | H | N |
| V-172 | Bu-i | CONH₂ | Me | SH | H | CH |
| V-173 | Bu-i | CONH₂ | Me | SMe | H | CH |
| V-174 | Bu-i | CONH₂ | Me | SOMe | H | CH |

TABLE 47

| Compound No. | R¹ | X | R² | R³ᵃ | R³ᵇ | W |
|---|---|---|---|---|---|---|
| V-175 | Bu-i | CF₃ | Me | SH | H | N |
| V-176 | Bu-i | CF₃ | Me | SMe | H | N |
| V-177 | Bu-i | CF₃ | Me | SOMe | H | N |
| V-178 | Bu-i | CF₃ | Me | SH | H | CH |
| V-179 | Bu-i | CF₃ | Me | SMe | H | CH |
| V-180 | Bu-i | CF₃ | Me | SOMe | H | CH |
| V-181 | Et | CN | Et | H | CF₃ | N |
| V-182 | Et | CONH₂ | Et | H | CF₃ | N |
| V-183 | Bu-i | Me | Et | CHO | H | N |
| V-184 | Bu-i | Me | Et | CH=NOH | H | N |
| V-185 | Bu-i | Me | Et | CN | H | N |
| V-186 | Pr-i | Me | Et | H | NO₂ | N |
| V-187 | Pr-i | Me | Et | Cl | H | N |
| V-188 | Pr-i | Me | Et | H | Me | N |
| V-189 | Pr-i | Me | Et | OH | H | N |
| V-190 | Pr-i | Me | Et | OCH₃ | H | N |
| V-191 | Pr-i | CF₃ | Me | SO₂Me | H | CH |

TABLE 48

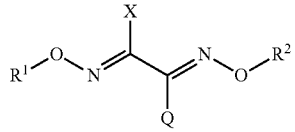

| Compound No. | R¹ | X | R² | Q |
|---|---|---|---|---|
| VI-1 | Me | Cl | Pr-i | Cl |
| VI-2 | Et | Cl | Pr-i | Cl |
| VI-3 | Pr-n | Cl | Pr-i | Cl |
| VI-4 | Pr-i | Cl | Pr-i | Cl |
| VI-5 | Bu-n | Cl | Pr-i | Cl |
| VI-6 | Bu-i | Cl | Pr-i | Cl |
| VI-7 | Bu-s | Cl | Pr-i | Cl |
| VI-8 | Bu-t | Cl | Pr-i | Cl |
| VI-9 | Pen-n | Cl | Pr-i | Cl |
| VI-10 | Pen-i | Cl | Pr-i | Cl |
| VI-11 | Pen-neo | Cl | Pr-i | Cl |
| VI-12 | Pen-2 | Cl | Pr-i | Cl |
| VI-13 | Pen-3 | Cl | Pr-i | Cl |
| VI-14 | Hex-n | Cl | Pr-i | Cl |
| VI-15 | CH₂CH₂C(Me)₃ | Cl | Pr-i | Cl |
| VI-16 | Pen-c | Cl | Pr-i | Cl |
| VI-17 | Hex-c | Cl | Pr-i | Cl |
| VI-18 | CH₂Pr-c | Cl | Pr-i | Cl |
| VI-19 | CH₂Bu-c | Cl | Pr-i | Cl |
| VI-20 | CH₂Pen-c | Cl | Pr-i | Cl |
| VI-21 | CH₂CH=CH₂ | Cl | Pr-i | Cl |
| VI-22 | CH₂C≡CH | Cl | Pr-i | Cl |
| VI-23 | CH₂C≡CCH₃ | Cl | Pr-i | Cl |
| VI-24 | Me | CN | Pr-i | Cl |
| VI-25 | Et | CN | Pr-i | Cl |
| VI-26 | Pr-n | CN | Pr-i | Cl |
| VI-27 | Pr-i | CN | Pr-i | Cl |
| VI-28 | Bu-n | CN | Pr-i | Cl |
| VI-29 | Bu-i | CN | Pr-i | Cl |
| VI-30 | Bu-s | CN | Pr-i | Cl |
| VI-31 | Bu-t | CN | Pr-i | Cl |
| VI-32 | Pen-n | CN | Pr-i | Cl |

TABLE 49

| Compound No. | R¹ | X | R² | Q |
|---|---|---|---|---|
| VI-33 | Pen-i | CN | Pr-i | Cl |
| VI-34 | Pen-neo | CN | Pr-i | Cl |
| VI-35 | Pen-2 | CN | Pr-i | Cl |
| VI-36 | Pen-3 | CN | Pr-i | Cl |
| VI-37 | Hex-n | CN | Pr-i | Cl |
| VI-38 | CH₂CH₂C(Me)₃ | CN | Pr-i | Cl |
| VI-39 | Pen-c | CN | Pr-i | Cl |
| VI-40 | Hex-c | CN | Pr-i | Cl |
| VI-41 | CH₂Pr-c | CN | Pr-i | Cl |

TABLE 49-continued

| Compound No. | R¹ | X | R² | Q |
|---|---|---|---|---|
| VI-42 | $CH_2Bu$-c | CN | Pr-i | Cl |
| VI-43 | $CH_2Pen$-c | CN | Pr-i | Cl |
| VI-44 | $CH_2CH=CH_2$ | CN | Pr-i | Cl |
| VI-45 | $CH_2C\equiv CH$ | CN | Pr-i | Cl |
| VI-46 | $CH_2C\equiv CCH_3$ | CN | Pr-i | Cl |
| VI-47 | $CH_2CF_3$ | CN | Pr-i | Cl |
| VI-48 | Me | Me | Pr-i | Cl |
| VI-49 | Et | Me | Pr-i | Cl |
| VI-50 | Pr-n | Me | Pr-i | Cl |
| VI-51 | Pr-i | Me | Pr-i | Cl |
| VI-52 | Bu-n | Me | Pr-i | Cl |
| VI-53 | Bu-i | Me | Pr-i | Cl |
| VI-54 | Bu-s | Me | Pr-i | Cl |
| VI-55 | Bu-t | Me | Pr-i | Cl |
| VI-56 | Pen-n | Me | Pr-i | Cl |
| VI-57 | Pen-i | Me | Pr-i | Cl |
| VI-58 | Pen-neo | Me | Pr-i | Cl |
| VI-59 | Pen-2 | Me | Pr-i | Cl |
| VI-60 | Pen-3 | Me | Pr-i | Cl |
| VI-61 | Hex-n | Me | Pr-i | Cl |
| VI-62 | $CH_2CH_2C(Me)_3$ | Me | Pr-i | Cl |
| VI-63 | $CH_2Pr$-c | Me | Pr-i | Cl |
| VI-64 | $CH_2Bu$-c | Me | Pr-i | Cl |
| VI-65 | $CH_2Pen$-c | Me | Pr-i | Cl |
| VI-66 | Me | Cl | Et | Cl |
| VI-67 | Et | Cl | Et | Cl |
| VI-68 | Pr-n | Cl | Et | Cl |

TABLE 50

| Compound No. | R¹ | X | R² | Q |
|---|---|---|---|---|
| VI-69 | Pr-i | Cl | Et | Cl |
| VI-70 | Bu-n | Cl | Et | Cl |
| VI-71 | Bu-i | Cl | Et | Cl |
| VI-72 | Bu-s | Cl | Et | Cl |
| VI-73 | Bu-t | Cl | Et | Cl |
| VI-74 | Pen-n | Cl | Et | Cl |
| VI-75 | Pen-i | Cl | Et | Cl |
| VI-76 | Pen-neo | Cl | Et | Cl |
| VI-77 | Pen-2 | Cl | Et | Cl |
| VI-78 | Pen-3 | Cl | Et | Cl |
| VI-79 | Hex-n | Cl | Et | Cl |
| VI-80 | $CH_2CH_2C(Me)_3$ | Cl | Et | Cl |
| VI-81 | Pen-c | Cl | Et | Cl |
| VI-82 | Hex-c | Cl | Et | Cl |
| VI-83 | $CH_2Pr$-c | Cl | Et | Cl |
| VI-84 | $CH_2Bu$-c | Cl | Et | Cl |
| VI-85 | $CH_2Pen$-c | Cl | Et | Cl |
| VI-86 | $CH_2CH=CH_2$ | Cl | Et | Cl |
| VI-87 | $CH_2C\equiv CH$ | Cl | Et | Cl |
| VI-88 | $CH_2C\equiv CCH_3$ | Cl | Et | Cl |
| VI-89 | Me | CN | Et | Cl |
| VI-90 | Et | CN | Et | Cl |
| VI-91 | Pr-n | CN | Et | Cl |
| VI-92 | Pr-i | CN | Et | Cl |
| VI-93 | Bu-n | CN | Et | Cl |
| VI-94 | Bu-i | CN | Et | Cl |
| VI-95 | Bu-s | CN | Et | Cl |
| VI-96 | Bu-t | CN | Et | Cl |
| VI-97 | Pen-n | CN | Et | Cl |
| VI-98 | Pen-i | CN | Et | Cl |
| VI-99 | Pen-neo | CN | Et | Cl |
| VI-100 | Pen-2 | CN | Et | Cl |
| VI-101 | Pen-3 | CN | Et | Cl |
| VI-102 | Hex-n | CN | Et | Cl |
| VI-103 | $CH_2CH_2C(Me)_3$ | CN | Et | Cl |
| VI-104 | Pen-c | CN | Et | Cl |

TABLE 51

| Compound No. | R¹ | X | R² | Q |
|---|---|---|---|---|
| VI-105 | Hex-c | CN | Et | Cl |
| VI-106 | $CH_2Pr$-c | CN | Et | Cl |
| VI-107 | $CH_2Bu$-c | CN | Et | Cl |
| VI-108 | $CH_2Pen$-c | CN | Et | Cl |
| VI-109 | $CH_2CH=CH_2$ | CN | Et | Cl |
| VI-110 | $CH_2C\equiv CH$ | CN | Et | Cl |
| VI-111 | $CH_2C\equiv CCH_3$ | CN | Et | Cl |
| VI-112 | Me | Me | Et | Cl |
| VI-113 | Et | Me | Et | Cl |
| VI-114 | Pr-n | Me | Et | Cl |
| VI-115 | Pr-i | Me | Et | Cl |
| VI-116 | Bu-n | Me | Et | Cl |
| VI-117 | Bu-i | Me | Et | Cl |
| VI-118 | Bu-s | Me | Et | Cl |
| VI-119 | Bu-t | Me | Et | Cl |
| VI-120 | Pen-n | Me | Et | Cl |
| VI-121 | Pen-i | Me | Et | Cl |
| VI-122 | Pen-neo | Me | Et | Cl |
| VI-123 | Pen-2 | Me | Et | Cl |
| VI-124 | Pen-3 | Me | Et | Cl |
| VI-125 | Hex-n | Me | Et | Cl |
| VI-126 | $CH_2CH_2C(Me)_3$ | Me | Et | Cl |
| VI-127 | $CH_2Pr$-c | Me | Et | Cl |
| VI-128 | $CH_2Bu$-c | Me | Et | Cl |
| VI-129 | $CH_2Pen$-c | Me | Et | Cl |
| VI-130 | Me | Cl | Me | Cl |
| VI-131 | Et | Cl | Me | Cl |
| VI-132 | Pr-n | Cl | Me | Cl |
| VI-133 | Pr-i | Cl | Me | Cl |
| VI-134 | Bu-n | Cl | Me | Cl |
| VI-135 | Bu-i | Cl | Me | Cl |
| VI-136 | Bu-s | Cl | Me | Cl |
| VI-137 | Bu-t | Cl | Me | Cl |
| VI-138 | Pen-n | Cl | Me | Cl |
| VI-139 | Pen-i | Cl | Me | Cl |
| VI-140 | Pen-neo | Cl | Me | Cl |

TABLE 52

| Compound No. | R¹ | X | R² | Q |
|---|---|---|---|---|
| VI-141 | Pen-2 | Cl | Me | Cl |
| VI-142 | Pen-3 | Cl | Me | Cl |
| VI-143 | Hex-n | Cl | Me | Cl |
| VI-144 | $CH_2CH_2C(Me)_3$ | Cl | Me | Cl |
| VI-145 | Pen-c | Cl | Me | Cl |
| VI-146 | Hex-c | Cl | Me | Cl |
| VI-147 | $CH_2Pr$-c | Cl | Me | Cl |
| VI-148 | $CH_2Bu$-c | Cl | Me | Cl |
| VI-149 | $CH_2Pen$-c | Cl | Me | Cl |
| VI-150 | $CH_2CH=CH_2$ | Cl | Me | Cl |
| VI-151 | $CH_2C\equiv CH$ | Cl | Me | Cl |
| VI-152 | $CH_2C\equiv CCH_3$ | Cl | Me | Cl |
| VI-153 | Me | CN | Me | Cl |
| VI-154 | Et | CN | Me | Cl |
| VI-155 | Pr-n | CN | Me | Cl |
| VI-156 | Pr-i | CN | Me | Cl |
| VI-157 | Bu-n | CN | Me | Cl |
| VI-158 | Bu-i | CN | Me | Cl |
| VI-159 | Bu-s | CN | Me | Cl |
| VI-160 | Bu-t | CN | Me | Cl |
| VI-161 | Pen-n | CN | Me | Cl |
| VI-162 | Pen-i | CN | Me | Cl |
| VI-163 | Pen-neo | CN | Me | Cl |
| VI-164 | Pen-2 | CN | Me | Cl |
| VI-165 | Pen-3 | CN | Me | Cl |
| VI-166 | Hex-n | CN | Me | Cl |
| VI-167 | $CH_2CH_2C(Me)_3$ | CN | Me | Cl |
| VI-168 | Pen-c | CN | Me | Cl |
| VI-169 | Hex-c | CN | Me | Cl |
| VI-170 | $CH_2Pr$-c | CN | Me | Cl |
| VI-171 | $CH_2Bu$-c | CN | Me | Cl |
| VI-172 | $CH_2Pen$-c | CN | Me | Cl |

TABLE 52-continued

| Compound No. | R¹ | X | R² | Q |
|---|---|---|---|---|
| VI-173 | $CH_2CH=CH_2$ | CN | Me | Cl |
| VI-174 | $CH_2C\equiv CH$ | CN | Me | Cl |
| VI-175 | $CH_2C\equiv CCH_3$ | CN | Me | Cl |
| VI-176 | Me | Me | Me | Cl |

TABLE 53

| Compound No. | R¹ | X | R² | Q |
|---|---|---|---|---|
| VI-177 | Et | Me | Me | Cl |
| VI-178 | Pr-n | Me | Me | Cl |
| VI-179 | Pr-i | Me | Me | Cl |
| VI-180 | Bu-n | Me | Me | Cl |
| VI-181 | Bu-i | Me | Me | Cl |
| VI-182 | Bu-s | Me | Me | Cl |
| VI-183 | Bu-t | Me | Me | Cl |
| VI-184 | Pen-n | Me | Me | Cl |
| VI-185 | Pen-i | Me | Me | Cl |
| VI-186 | Pen-neo | Me | Me | Cl |
| VI-187 | Pen-2 | Me | Me | Cl |
| VI-188 | Pen-3 | Me | Me | Cl |
| VI-189 | Hex-n | Me | Me | Cl |

TABLE 53-continued

| Compound No. | R¹ | X | R² | Q |
|---|---|---|---|---|
| VI-190 | $CH_2CH_2C(Me)_3$ | Me | Me | Cl |
| VI-191 | $CH_2Pr$-c | Me | Me | Cl |
| VI-192 | $CH_2Bu$-c | Me | Me | Cl |
| VI-193 | $CH_2Pen$-c | Me | Me | Cl |
| VI-194 | Me | CN | Pr-n | Cl |
| VI-195 | Et | CN | Pr-n | Cl |
| VI-196 | Pr-i | CN | Pr-n | Cl |
| VI-197 | Bu-n | CN | Pr-n | Cl |
| VI-198 | Bu-i | CN | Pr-n | Cl |
| VI-199 | Bu-s | CN | Pr-n | Cl |
| VI-200 | $CH_2Pr$-c | CN | Pr-n | Cl |
| VI-201 | $CH_2CH=CH_2$ | CN | Pr-n | Cl |
| VI-202 | $CH_2C\equiv CH$ | CN | Pr-n | Cl |
| VI-203 | $CH_2CF_3$ | CN | Pr-n | Cl |
| VI-204 | Me | CN | Bu-i | Cl |
| VI-205 | Me | CN | Pen-i | Cl |
| VI-206 | Me | CN | $CH_2Pr$-c | Cl |
| VI-207 | Me | CN | Pen-c | Cl |
| VI-208 | Me | CN | $CH_2Ph$ | Cl |
| VI-209 | Me | CN | $CH_2CH_2OEt$ | Cl |
| VI-210 | Pr-i | CN | $CH_2CH=CH_2$ | Cl |
| VI-211 | Pr-i | CN | $CH_2C\equiv CH$ | Cl |
| VI-212 | Pr-i | CN | $CH_2CF_3$ | Cl |

TABLE 54

| Compound No. | R¹ | X | R² | Q |
|---|---|---|---|---|
| VI-213 | Pr-i | CN | $CH_2CH_2OEt$ | Cl |
| VI-214 | $CH_2Pr$-c | CN | $CH_2Pr$-c | Cl |
| VI-215 | $CH_2Ph$ | CN | Pr-i | Cl |
| VI-216 | Pr-i | $CONH_2$ | Bu-i | Cl |
| VI-217 | Pr-i | CN | Bu-t | Cl |
| VI-218 | Pr-i | CN | Bu-s | Cl |
| VI-219 | Pr-i | CN | $CH_2CN$ | Cl |
| VI-220 | Bu-t | CONHBu-t | Me | Cl |
| VI-221 | Pr-i | $CO_2Me$ | Pr-i | Cl |
| VI-222 | Me | 2-methylthiophen-yl | Et | Cl |
| VI-223 | Me | 3-methylpyridin-yl | Et | Cl |
| VI-224 | Pr-i | 5-methyl-1H-tetrazolyl | Pr-i | Cl |
| VI-225 | Pr-i | 2-methyl-1H-imidazolyl | Pr-i | Cl |
| VI-226 | Et | 3-(trifluoromethyl)-1,4-dimethylpyrazolyl | Et | Cl |
| VI-227 | $CH_2CH_2OCH_3$ | CN | Et | Cl |

TABLE 54-continued

| Compound No. | R¹ | X | R² | Q |
|---|---|---|---|---|
| VI-228 | 4-butoxy-benzoic acid methyl ester (MeO-C(=O)-C₆H₄-O-CH₂CH₂CH₂CH₃) | CN | Me | Cl |
| VI-229 | PhCH=CHCH₂CH₃ (1-phenyl-1-butenyl) | CN | Me | Cl |
| VI-230 | 2-ethyl-tetrahydrofuran | CN | Me | Cl |
| VI-231 | 2-ethyl-oxirane | CN | Me | Cl |
| VI-232 | CH₂CH(CH₃)CH₂CH₃ | CN | Et | Cl |
| VI-233 | CH₂C(Cl)=CH₂ | CN | Pr-i | Cl |
| VI-234 | CH₂C(Cl)=CHCl | CN | Pr-i | Cl |

TABLE 55

| Compound No. | R¹ | X | R² | Q |
|---|---|---|---|---|
| VI-235 | CH₂C(CH₃)=CH₂ | CN | Pr-i | Cl |
| VI-236 | (6-chloropyridin-3-yl)CH₂ | CN | Pr-i | Cl |
| VI-237 | (3-chloro-5-trifluoromethyl-pyridin-2-yl)methyl | CN | Pr-i | Cl |
| VI-238 | CH₂Ph(3-CF₃) | CN | Pr-i | Cl |
| VI-239 | CH₂Ph(4-CF₃) | CN | Pr-i | Cl |
| VI-240 | CH₂Ph(4-OCH₃) | CN | Pr-i | Cl |
| VI-241 | CH₂Ph(4-CN) | CN | Pr-i | Cl |
| VI-242 | CH₂Ph(4-Cl) | CN | Pr-i | Cl |
| VI-243 | CH₂Ph(4-CH₃) | CN | Pr-i | Cl |
| VI-244 | CH₂CH₂Ph | CN | Pr-i | Cl |
| VI-245 | CH₂CH₂CH₂Ph | CN | Pr-i | Cl |
| VI-246 | CH(CH₃)Ph | CN | Pr-i | Cl |
| VI-247 | Bu-c | CN | Pr-i | Cl |
| VI-248 | CH₂Si(CH₃)₃ | CN | Pr-i | Cl |
| VI-249 | (2-chloro-5-ethyl-thiazol-4-yl)methyl | CN | Pr-i | Cl |
| VI-250 | CH(CH₃)(cyclopropyl) | CN | Pr-i | Cl |
| VI-251 | CH₂CH₂-cyclopropyl | CN | Me | Cl |
| VI-252 | CH₂CH₂-cyclopropyl | ON | Et | Cl |

TABLE 55-continued

| Compound No. | R¹ | X | R² | Q |
|---|---|---|---|---|
| VI-253 | CH₂CH₂-cyclopropyl | CN | Pr-i | Cl |
| VI-254 | Pr-i | CN | CH₂C≡CCH₃ | Cl |
| VI-255 | Pr-i | CN | Pen-2 | Cl |
| VI-256 | Pr-i | CN | Pen-3 | Cl |
| VI-257 | Pen-3 | CN | Pr-n | Cl |
| VI-258 | Pen-c | CN | Pr-n | Cl |
| VI-259 | CH₂OCH₃ | CN | Et | Cl |
| VI-260 | CH₂(CH₂)₂OCH₃ | CN | Et | Cl |

TABLE 56

| Compound No. | R¹ | X | R² | Q |
|---|---|---|---|---|
| VI-261 | (1,2-dichloro-2-ethyl-cyclopropyl) | CN | Et | Cl |
| VI-262 | (1,1-difluoro-2-ethyl-cyclopropyl) | CN | Et | Cl |
| VI-263 | CH(CH₃)-cyclopropyl | CN | Me | Cl |
| VI-264 | CH(CH₃)-cyclopropyl | CN | Et | Cl |
| VI-265 | CH₂CH₂CH₂N(CH₃)₂ | CN | Me | Cl |
| VI-266 | Me | CN | Bu-t | Cl |

TABLE 56-continued

| Compound No. | R¹ | X | R² | Q |
|---|---|---|---|---|
| VI-267 | Et | CN | Bu-t | Cl |
| VI-268 | Pr-n | CN | Bu-t | Cl |
| VI-269 | Pr-i | CONH₂ | Pr-i | Cl |
| VI-270 | CH₂Ph(3-CN) | CN | Pr-i | Cl |
| VI-271 | CH₂Ph(3-OCH₃) | CN | Pr-i | Cl |
| VI-272 | CH₂(CH₂)₆CH₃ | CN | Pr-i | Cl |
| VI-273 | CH₂(CH₂)₈CH₃ | CN | Pr-i | Cl |
| VI-274 | CH₂C(CH₃)₂CH₂CH₃ | CN | Et | Cl |
| VI-275 | CH₂C(CH₃)₂CH₂CH₃ | CN | Me | Cl |
| VI-276 | CH₂(CF₂)₂CF₃ | CN | Et | Cl |
| VI-277 | CH₂Ph(4-F) | CN | Pr-i | Cl |
| VI-278 | CH₂Ph(2-CF₃) | CN | Pr-i | Cl |
| VI-279 | CH₂Ph(2-CN) | CN | Pr-i | Cl |
| VI-280 | CH₂Ph(4-CO₂CH₂CH₃) | CN | Pr-i | Cl |
| VI-281 | Pen-neo | CN | Pr-n | Cl |
| VI-282 | Pen-i | CN | Pr-n | Cl |
| VI-283 | CF₂CHFCF₃ | CN | Et | Cl |
| VI-284 | CH₂CH=C(CH₃)₂ | CN | Pr-i | Cl |
| VI-285 | CH₂C(CH₃)₂CN | CN | Me | Cl |
| VI-286 | CH₂C(CH₃)₂CH₂Cl | CN | Me | Cl |
| VI-287 | CH₂C(CH₃)₂CH₂Cl | CN | Et | Cl |
| VI-288 | CH₂(CF₂)₃CHF₂ | CN | Me | Cl |
| VI-289 | CH₂(CF₂)₂CF₃ | CN | Me | Cl |
| VI-290 | CH₂(CF₂)₃CHF₂ | CN | Et | Cl |

TABLE 57

| Compound No. | R¹ | X | R² | Q |
|---|---|---|---|---|
| VI-291 | CH₂(CH₂)₂CF₃ | CN | Me | Cl |
| VI-292 | CH₂(CH₂)₂CF₂CF₃ | CN | Me | Cl |
| VI-293 | CF₂CHFCF₃ | CN | Me | Cl |
| VI-294 | CH₂CH₂CF₃ | CN | Me | Cl |
| VI-295 | ![NC-cyclopropyl-ethyl] | CN | Me | Cl |
| VI-296 | CH(CH₂F)₂ | CN | Me | Cl |
| VI-297 | CH₂Pr-c | ![2-methyl-thiazoline] | Me | Cl |
| VI-298 | CH₂CF₂CF₃ | CN | Pr-n | Cl |
| VI-299 | CH₂CF₂CF₃ | CN | Pr-i | Cl |
| VI-300 | CH₂CH₂OCH₂CH₃ | CN | Pr-i | Cl |
| VI-301 | CH₂CCH₃(CF₃)₂ | CN | Me | Cl |
| VI-302 | CH₂CH₂OCH₂CH₃ | CN | Me | Cl |
| VI-303 | CH₂CH₂OCH₂CF₃ | CN | Me | Cl |
| VI-304 | CH₂Ph | CN | CH₂CF₃ | Cl |
| VI-305 | ![3-ethyl-furan] | CN | Me | Cl |
| VI-306 | CH₂Si(CH₃)₃ | CN | Me | Cl |
| VI-307 | CH(CH₃)CF₃ | CN | Me | Cl |
| VI-308 | Pr-n | CN | Pr-n | Cl |
| VI-309 | CH(CH₃)CF₃ | CN | Pr-i | Cl |
| VI-310 | CH₂CH₂OCH(CH₃)₂ | CN | Me | Cl |
| VI-311 | CH₂Ph(1,2,3,4,5-penta-F) | CN | Me | Cl |
| VI-312 | CH₂Ph(3-F) | CN | Me | Cl |
| VI-313 | CH₂Ph(4-F) | CN | Me | Cl |
| VI-314 | CH₂CH₂OCH(CH₃)₂ | CN | Pr-i | Cl |
| VI-315 | CH₂Ph(2,6-di-CH₃) | CN | Pr-i | Cl |

TABLE 58

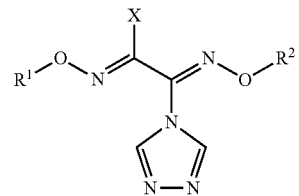

| Compound No. | R¹ | X | R² |
|---|---|---|---|
| VII-1 | Me | CN | Pr-i |
| VII-2 | Et | CN | Pr-i |
| VII-3 | Pr-n | CN | Pr-i |
| VII-4 | Pr-i | CN | Pr-i |
| VII-5 | Bu-n | CN | Pr-i |
| VII-6 | Bu-i | CN | Pr-i |
| VII-7 | Bu-s | CN | Pr-i |
| VII-8 | Bu-t | CN | Pr-i |
| VII-9 | Pen-n | CN | Pr-i |
| VII-10 | Pen-i | CN | Pr-i |
| VII-11 | Pen-neo | CN | Pr-i |
| VII-12 | Pen-2 | CN | Pr-i |
| VII-13 | Pen-3 | CN | Pr-i |
| VII-14 | Hex-n | CN | Pr-i |
| VII-15 | CH₂CH₂C(Me)₃ | CN | Pr-i |
| VII-16 | Pen-c | CN | Pr-i |
| VII-17 | Hex-c | CN | Pr-i |
| VII-18 | CH₂Pr-c | CN | Pr-i |
| VII-19 | CH₂Bu-c | CN | Pr-i |
| VII-20 | CH₂Pen-c | CN | Pr-i |
| VII-21 | CH₂CH=CH₂ | CN | Pr-i |
| VII-22 | CH₂C≡CH | CN | Pr-i |
| VII-23 | CH₂C≡CCH₃ | CN | Pr-i |
| VII-24 | Me | CONH₂ | Pr-i |
| VII-25 | Et | CONH₂ | Pr-i |
| VII-26 | Pr-n | CONH₂ | Pr-i |
| VII-27 | Pr-i | CONH₂ | Pr-i |
| VII-28 | Bu-n | CONH₂ | Pr-i |
| VII-29 | Bu-i | CONH₂ | Pr-i |
| VII-30 | Bu-s | CONH₂ | Pr-i |

| Compound No. | R¹ | X | R² |
|---|---|---|---|
| VII-31 | Bu-t | CONH₂ | Pr-i |
| VII-32 | Pen-n | CONH₂ | Pr-i |
| VII-33 | Pen-i | CONH₂ | Pr-i |
| VII-34 | Pen-neo | CONH₂ | Pr-i |
| VII-35 | Pen-2 | CONH₂ | Pr-i |
| VII-36 | Pen-3 | CONH₂ | Pr-i |
| VII-37 | Hex-n | CONH₂ | Pr-i |
| VII-38 | CH₂CH₂C(Me)₃ | CONH₂ | Pr-i |
| VII-39 | Pen-c | CONH₂ | Pr-i |
| VII-40 | Hex-c | CONH₂ | Pr-i |
| VII-41 | CH₂Pr-c | CONH₂ | Pr-i |
| VII-42 | CH₂Bu-c | CONH₂ | Pr-i |
| VII-43 | CH₂Pen-c | CONH₂ | Pr-i |
| VII-44 | CH₂CH=CH₂ | CONH₂ | Pr-i |
| VII-45 | CH₂C≡CH | CONH₂ | Pr-i |
| VII-46 | CH₂C≡CCH₃ | CONH₂ | Pr-i |
| VII-47 | Me | CN | Et |
| VII-48 | Et | CN | Et |
| VII-49 | Pr-n | CN | Et |
| VII-50 | Pr-i | CN | Et |
| VII-51 | Bu-n | CN | Et |
| VII-52 | Bu-i | CN | Et |
| VII-53 | Bu-s | CN | Et |
| VII-54 | Bu-t | CN | Et |
| VII-55 | Pen-n | CN | Et |
| VII-56 | Pen-i | CN | Et |
| VII-57 | Pen-neo | CN | Et |
| VII-58 | Pen-2 | CN | Et |
| VII-59 | Pen-3 | CN | Et |
| VII-60 | Hex-n | CN | Et |

-continued

| Compound No. | R¹ | X | R² |
|---|---|---|---|
| VII-61 | CH₂CH₂C(Me)₃ | CN | Et |
| VII-62 | Pen-c | CN | Et |
| VII-63 | Hex-c | CN | Et |
| VII-64 | CH₂Pr-c | CN | Et |
| VII-65 | CH₂Bu-c | CN | Et |
| VII-66 | CH₂Pen-c | CN | Et |

TABLE 60

| Compound No. | R¹ | X | R² |
|---|---|---|---|
| VII-67 | CH₂CH=CH₂ | CN | Et |
| VII-68 | CH₂C≡CH | CN | Et |
| VII-69 | CH₂C≡CCH₃ | CN | Et |
| VII-70 | Me | CONH₂ | Et |
| VII-71 | Et | CONH₂ | Et |
| VII-72 | Pr-n | CONH₂ | Et |
| VII-73 | Pr-i | CONH₂ | Et |
| VII-74 | Bu-n | CONH₂ | Et |
| VII-75 | Bu-i | CONH₂ | Et |
| VII-76 | Bu-s | CONH₂ | Et |
| VII-77 | Bu-t | CONH₂ | Et |
| VII-78 | Pen-n | CONH₂ | Et |
| VII-79 | Pen-i | CONH₂ | Et |
| VII-80 | Pen-neo | CONH₂ | Et |
| VII-81 | Pen-2 | CONH₂ | Et |
| VII-82 | Pen-3 | CONH₂ | Et |
| VII-83 | Hex-n | CONH₂ | Et |
| VII-84 | CH₂CH₂C(Me)₃ | CONH₂ | Et |
| VII-85 | Pen-c | CONH₂ | Et |
| VII-86 | Hex-c | CONH₂ | Et |
| VII-87 | CH₂Pr-c | CONH₂ | Et |
| VII-88 | CH₂Bu-c | CONH₂ | Et |
| VII-89 | CH₂Pen-c | CONH₂ | Et |
| VII-90 | CH₂CH=CH₂ | CONH₂ | Et |
| VII-91 | CH₂C≡CH | CONH₂ | Et |
| VII-92 | CH₂C≡CCH₃ | CONH₂ | Et |
| VII-93 | Me | CN | Me |
| VII-94 | Et | CN | Me |
| VII-95 | Pr-n | CN | Me |
| VII-96 | Pr-i | CN | Me |
| VII-97 | Bu-n | CN | Me |
| VII-98 | Bu-i | CN | Me |
| VII-99 | Bu-s | CN | Me |
| VII-100 | Bu-t | CN | Me |
| VII-101 | Pen-n | CN | Me |
| VII-102 | Pen-i | CN | Me |

TABLE 61

| Compound No. | R¹ | X | R² |
|---|---|---|---|
| VII-103 | Pen-neo | CN | Me |
| VII-104 | Pen-2 | CN | Me |
| VII-105 | Pen-3 | CN | Me |
| VII-106 | Hex-n | CN | Me |
| VII-107 | CH₂CH₂C(Me)₃ | CN | Me |
| VII-108 | Pen-c | CN | Me |
| VII-109 | Hex-c | CN | Me |
| VII-110 | CH₂Pr-c | CN | Me |
| VII-111 | CH₂Bu-c | CN | Me |
| VII-112 | CH₂Pen-c | CN | Me |
| VII-113 | CH₂CH=CH₂ | CN | Me |
| VII-114 | CH₂C≡CH | CN | Me |
| VII-115 | CH₂C≡CCH₃ | CN | Me |
| VII-116 | Me | CONH₂ | Me |
| VII-117 | Et | CONH₂ | Me |
| VII-118 | Pr-n | CONH₂ | Me |
| VII-119 | Pr-i | CONH₂ | Me |
| VII-120 | Bu-n | CONH₂ | Me |

TABLE 61-continued

| Compound No. | R¹ | X | R² |
|---|---|---|---|
| VII-121 | Bu-i | CONH₂ | Me |
| VII-122 | Bu-s | CONH₂ | Me |
| VII-123 | Bu-t | CONH₂ | Me |
| VII-124 | Pen-n | CONH₂ | Me |
| VII-125 | Pen-i | CONH₂ | Me |
| VII-126 | Pen-neo | CONH₂ | Me |
| VII-127 | Pen-2 | CONH₂ | Me |
| VII-128 | Pen-3 | CONH₂ | Me |
| VII-129 | Hex-n | CONH₂ | Me |
| VII-130 | CH₂CH₂C(Me)₃ | CONH₂ | Me |
| VII-131 | Pen-c | CONH₂ | Me |
| VII-132 | Hex-c | CONH₂ | Me |
| VII-133 | CH₂Pr-c | CONH₂ | Me |
| VII-134 | CH₂Bu-c | CONH₂ | Me |
| VII-135 | CH₂Pen-c | CONH₂ | Me |
| VII-136 | CH₂CH=CH₂ | CONH₂ | Me |
| VII-137 | CH₂C≡CH | CONH₂ | Me |
| VII-138 | CH₂C≡CCH₃ | CONH₂ | Me |

TABLE 62

| Compound No. | R¹ | X | R² |
|---|---|---|---|
| VII-139 | Me | CN | Pr-n |
| VII-140 | Et | CN | Pr-n |
| VII-141 | Pr-n | CN | Pr-n |
| VII-142 | Pr-i | CN | Pr-n |
| VII-143 | Bu-n | CN | Pr-n |
| VII-144 | Bu-i | CN | Pr-n |
| VII-145 | Bu-s | CN | Pr-n |
| VII-146 | Bu-t | CN | Pr-n |
| VII-147 | Pen-n | CN | Pr-n |
| VII-148 | Pen-i | CN | Pr-n |
| VII-149 | Pen-neo | CN | Pr-n |
| VII-150 | Pen-2 | CN | Pr-n |
| VII-151 | Pen-3 | CN | Pr-n |
| VII-152 | Hex-n | CN | Pr-n |
| VII-153 | CH₂CH₂C(Me)₃ | CN | Pr-n |
| VII-154 | Pen-c | CN | Pr-n |
| VII-155 | Hex-c | CN | Pr-n |
| VII-156 | CH₂Pr-c | CN | Pr-n |
| VII-157 | CH₂Bu-c | CN | Pr-n |
| VII-158 | CH₂Pen-c | CN | Pr-n |
| VII-159 | CH₂CH=CH₂ | CN | Pr-n |
| VII-160 | CH₂C≡CH | CN | Pr-n |
| VII-161 | CH₂C≡CCH₃ | CN | Pr-n |
| VII-162 | Me | CONH₂ | Pr-n |
| VII-163 | Et | CONH₂ | Pr-n |
| VII-164 | Pr-n | CONH₂ | Pr-n |
| VII-165 | Pr-i | CONH₂ | Pr-n |
| VII-166 | Bu-n | CONH₂ | Pr-n |
| VII-167 | Bu-i | CONH₂ | Pr-n |
| VII-168 | Bu-s | CONH₂ | Pr-n |
| VII-169 | Bu-t | CONH₂ | Pr-n |
| VII-170 | Pen-n | CONH₂ | Pr-n |
| VII-171 | Pen-i | CONH₂ | Pr-n |
| VII-172 | Pen-neo | CONH₂ | Pr-n |
| VII-173 | Pen-2 | CONH₂ | Pr-n |
| VII-174 | Pen-3 | CONH₂ | Pr-n |

TABLE 63

| Compound No. | R¹ | X | R² |
|---|---|---|---|
| VII-175 | Hex-n | CONH₂ | Pr-n |
| VII-176 | CH₂CH₂C(Me)₃ | CONH₂ | Pr-n |
| VII-177 | Pen-c | CONH₂ | Pr-n |
| VII-178 | Hex-c | CONH₂ | Pr-n |
| VII-179 | CH₂Pr-c | CONH₂ | Pr-n |
| VII-180 | CH₂Bu-c | CONH₂ | Pr-n |
| VII-181 | CH₂Pen-c | CONH₂ | Pr-n |
| VII-182 | CH₂CH=CH₂ | CONH₂ | Pr-n |

TABLE 63-continued

| Compound No. | $R^1$ | X | $R^2$ |
|---|---|---|---|
| VII-183 | $CH_2C\equiv CH$ | $CONH_2$ | Pr-n |
| VII-184 | $CH_2C\equiv CCH_3$ | $CONH_2$ | Pr-n |
| VII-185 | Bu-i | Me | Et |
| VII-186 | Pr-i | Me | Et |
| VII-187 | Pr-i | Me | Et |
| VII-188 | Pr-i | Me | Et |
| VII-189 | Pr-i | Me | Et |
| VII-190 | Pr-i | Me | Et |
| VII-191 | Pr-i | $CF_3$ | Me |

The present compound represented by the general formula [I] can be produced by the production methods shown below. However, the production is not restricted to these methods.

In the following, for example, "a compound represented by general formula [I-I]", "a compound represented by formula [I-I]" and "a compound [I-I]" mean the same compound.

Production Method 1

Of the present compounds represented by the general formula [I], a compound represented by [Ia-I] or [Ic-I] can be produced, for example, by the following method.

[Formula 5]

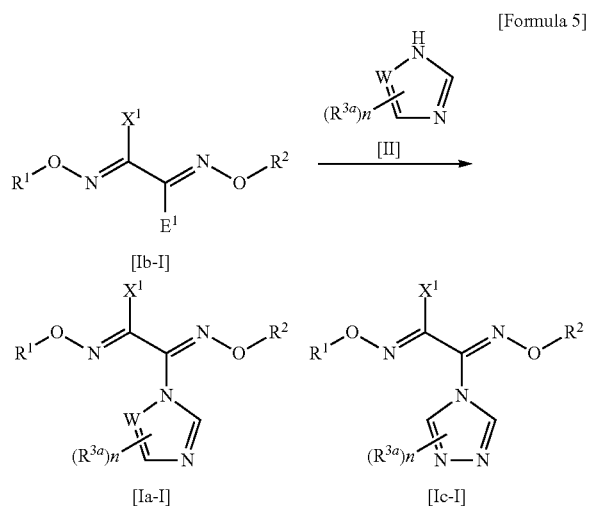

[in the above, $R^1$, $R^2$, W and n have each the above-mentioned meaning, $X^1$ is a hydrogen atom, a cyano group, a $C_1$~$C_8$ alkyl group, a $C_2$~$C_6$ alkenyl group, a $C_2$~$C_5$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkylthio group, a $C_1$~$C_6$ alkylthio $C_1$~$C_6$ alkyl group, a $C_1$~$C_6$ alkylsulfinyl $C_1$~$C_6$ alkyl group, a $C_1$~$C_6$ alkylsulfonyl $C_1$~$C_6$ alkyl group, a $C_1$~$C_6$ alkoxy group, a $C_1$~$C_6$ alkoxy $C_1$~$C_6$ alkyl group, a thiocarbamoyl group, a $R^4R^5NCO$ group, a $R^6R^7N$ group, a $C_1$~$C_5$ alkoxycarbonyl group, a carboxyl group, a $R^{80}$(HN=)C group, $R^9ON=(R^{10})C$ group, a $R^{11}S(O=)C$ group, a phenyl group which many be substituted with the substituent group α, or a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1$~$C_6$ alkyl group, $C_1$~$C_6$ haloalkyl group, $C_1$~$C_5$ alkoxy group, or cyano group), $R^4$, $R^5$, $R^6$, $R^7$, $R^8$, $R^9$, $R^{10}$, $R^{11}$ and the substituent group α have each the above-mentioned meaning, $R^{3a}$ is a hydrogen atom, a halogen atom, a cyano group, a nitro group, a $C_1$~$C_6$ alkyl group, a $C_1$~$C_6$ haloalkyl group, a $C_1$~$C_6$ alkoxy group, a $C_1$~$C_6$ alkylthio group, a $C_1$~$C_6$ alkylsulfinyl group, a $C_1$~$C_6$ alkylsulfonyl group, or formyl group, and $E^1$ is an leaving group such as chlorine atom, bromine atom, iodine atom, methanesulfonyl group, methanesulfonyloxy group, trifluoromethanesulfonyloxy group or the like.]

A compound [Ia-I] can be produced by reacting a compound [Ib-I] with a compound [II] in a solvent in the presence of a base. When W is a nitrogen atom, a compound [Ic-I] can be produced in the same manner.

In the reaction, the use amount of the compound [II] is appropriately selected ordinarily in a range of 1 to 5 equivalents relative to 1 equivalent of the compound [Ib-I], and is preferably 1 to 2 equivalents.

As the solvent used in the reaction, there can be mentioned, for example, an ether such as diethyl ether, 1,2-dimethoxyethane, tetrahydrofuran or the like; an amide such as N,N-dimethylacetamide, N,N-dimethylformamide, 1,3-dimethyl-2-imidazolidinone, N-methyl-2-pyrrolidinone or the like; a sulfur compound such as dimethyl sulfoxide, sulfolane or the like; a nitrile such as acetonitrile, propionitrile or the like; an aliphatic hydrocarbon such as hexane, heptane or the like; an aromatic hydrocarbon such as benzene, toluene, xylene or the like; a halogenated hydrocarbon such as 1,2-dichloroethane, chlorobenzene or the like; or a mixture thereof. The use amount of the solvent is ordinarily 0.1 to 50 liters, preferably 0.2 to 3.0 liters relative to 1 mol of the compound [Ib-I].

As the base usable in the reaction, there can be mentioned, for example, an inorganic base such as alkali metal hydroxide (e.g. sodium hydroxide or potassium hydroxide), alkali metal carbonate (e.g. sodium carbonate or potassium carbonate), alkali metal bicarbonate (e.g. sodium hydrogencarbonate or potassium hydrogencarbonate) or the like; a metal hydride such as sodium hydride, potassium hydride or the like; and an organic base such as triethylamine, 1,8-diazabicyclo[5.4.0]-7-undecene or the like. The use amount of the base is appropriately selected ordinarily in a range of 1 to 10 equivalents relative to 1 equivalent of the compound [Ib-I], and is preferably 1 to 5 equivalents.

The temperature of the reaction is ordinarily any desired temperature from −20° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-I], or the compound [Ia-I] and the compound [Ic-I] can be obtained. The isolated compounds [Ia-I] and [Ic-I] can be purified as necessary by column chromatography, recrystallization, etc.

Production Method 2

Of the present compounds represented by the general formula [I], a compound represented by formula [Ia-III] can be produced, for example, by the following method.

[Formula 6]

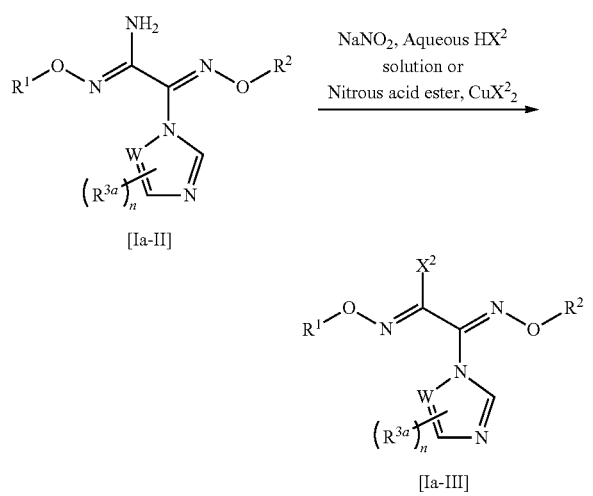

(in the above, $R^1$, $R^2$, $R^{3a}$, W and n have each the above-mentioned meaning; and $X^2$ is a halogen atom, preferably a chlorine atom or a bromine atom.)

A compound [Ia-III] can be produced by reacting a compound [Ia-II] with sodium nitrite ($NaNO_2$) in an aqueous hydrogen halide solution.

The amount of sodium nitrite used in the reaction may be appropriately selected ordinarily in a range of 1.0 to 5.0 equivalents relative to 1 equivalent of the compound [Ia-II] and is preferably 1.1 to 2.0 equivalents.

The hydrogen halide content in the aqueous hydrogen halide solution, used in the present invention, is ordinarily 2 to 200 equivalents relative to 1 mol of the compound [Ia-II], and the amount of the aqueous solution is preferably 50 to 100 liters. A solvent may be added as necessary.

As the solvent usable in the reaction, there can be mentioned, for example, an aliphatic carboxylic acid (e.g. acetic acid or trifluoroacetic acid) or an ether (e.g. 1,2-dimethoxyethane or tetrahydrofuran). The amount of the solvent is ordinarily 0.1 to 50 liters, preferably 0.2 to 3.0 liters relative to 1 mol of the compound [Ia-II].

The temperature of the reaction is ordinarily any desired temperature from –50° C. to the reflux temperature of the reaction system and is preferably a temperature of –10° C. to 100° C.

The time of the reaction differs depending upon the reaction temperature, the substrate of reaction, the amount of reaction, etc. but is ordinarily 1 to 24 hours.

After the completion of the reaction, there are conducted operations such as filtration of reaction mixture or pouring of reaction mixture into water, extraction by organic solvent, and subsequent concentration, whereby the compound [Ia-III] can be isolated. The isolated compound [Ia-III] may be purified as necessary by column chromatography, etc.

The compound [Ia-III] can also be produced by reacting the compound [Ia-II] with a nitrous acid ester in a solvent in the presence of a copper halide (II).

As the copper halide (II) used in the reaction, there can be mentioned copper bromide (II), copper chloride (II), etc. The use amount of the copper halide (II) is appropriately selected ordinarily in a range of 1.0 to 5.0 equivalents relative to 1 equivalent of the compound [Ia-II], and is preferably 1.1 to 2.0 equivalents.

As the nitrous acid ester used in the reaction, there can be mentioned tert-butyl nitrite, amyl nitrite, etc. The use amount of the nitrous acid ester is appropriately selected ordinarily in a range of 1.0 to 5.0 equivalents relative to 1 equivalent of the compound [Ia-II], and is preferably 1.1 to 2.0 equivalents.

As the solvent usable in the reaction, there can be mentioned an ether (e.g. diethyl ether, 1,2-dimethoxyethane or tetrahydrofuran), an aromatic hydrocarbon (e.g. benzene, toluene or xylene), a nitrile (e.g. acetonitrile or propionitrile), or a mixture thereof. The amount of the solvent is ordinarily 0.1 to 50 liters, preferably 0.2 to 3.0 liters relative to 1 mol of the compound [Ia-II].

The temperature of the reaction is ordinarily any desired temperature from –50° C. to the reflux temperature of the reaction system and is preferably a temperature of –10° C. to 100° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-III] can be isolated. The isolated compound [Ia-III] can be purified as necessary by column chromatography, etc.

Production Method 3

Of the present compounds represented by the general formula [I], the compound represented by formula [Ia-III] can also be produced, for example, by the following method.

[Formula 7]

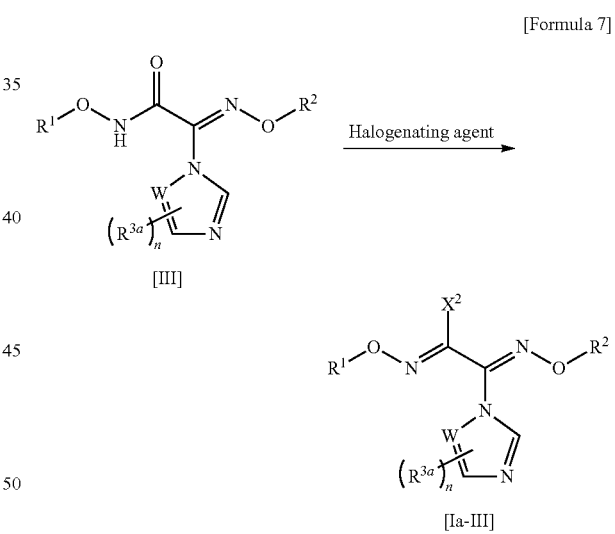

(in the above, $R^1$, $R^2$, $R^{3a}$, $X^2$, W and n have each the above-mentioned meaning.)

A compound [Ia-III] can be produced by reacting a compound [III] with a halogenating agent in a solvent.

As the halogenating agent usable in the reaction, there can be mentioned, for example, phosphorus pentachloride, thionyl chloride, or carbon tetrachloride or carbon tetrabromide in the presence of triphenylphosphine. The use amount of the halogenating agent is appropriately selected in a range of 1.0 to 20.0 mols relative to 1.0 mol of the compound [III], and is preferably 1.0 to 6.0 mols.

As the solvent usable in the reaction, there can be mentioned, for example, an aromatic hydrocarbon (e.g. benzene or toluene), a halogenated hydrocarbon (e.g. chloroform or carbon tetrachloride), or a nitrile (e.g. acetonitrile or propionitrile). The amount of the solvent is ordinarily 0.1 to 50 liters, preferably 0.2 to 10 liters relative to 1 mol of the compound [III].

The temperature of the reaction is ordinarily any desired temperature from −50° C. to the reflux temperature of the reaction system and is preferably a temperature of 0° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-III] can be isolated. The isolated compound [Ia-III] can be purified as necessary by column chromatography, recrystallization, etc.

Production Method 4

Of the present compounds represented by the general formula [I], a compound represented by formula [Ia-V] can be produced, for example, by the following method.

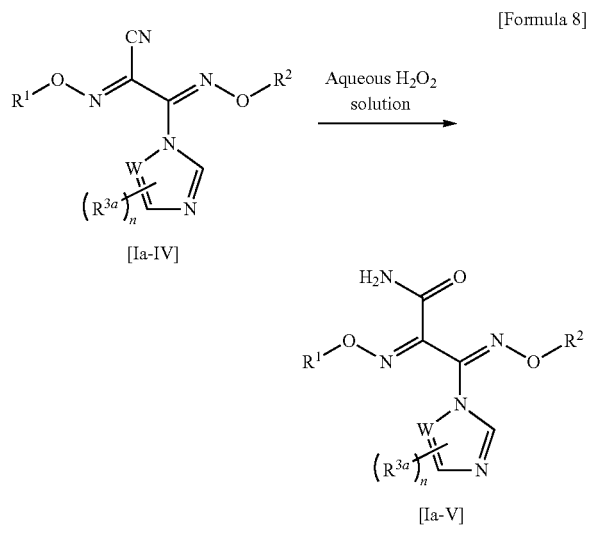

[Formula 8]

(in the above, $R^1$, $R^2$, $R^{3a}$, W and n have each the above-mentioned meaning.)

A compound [Ia-V] can be produced by reacting a compound [Ia-IV] with an aqueous hydrogen peroxide solution in the presence of a base.

The use amount of the aqueous hydrogen peroxide solution is appropriately selected in a range of 1.0 to 20.0 mols relative to 1 mol of the compound [Ia-IV], and is preferably 1.0 to 6.0 mols.

A solvent may be used as necessary in the reaction. As the solvent usable, there can be mentioned, for example, an alcohol (e.g. methanol, ethanol or propanol), a halogenated hydrocarbon (e.g. chloroform or dichloromethane), a sulfur compound (e.g. dimethyl sulfoxide or sulfolane), or a mixture thereof. The amount of the solvent is ordinarily 0.1 to 50 liters, preferably 0.2 to 3 liters relative to 1 mol of the compound [Ia-IV].

As the base usable in the reaction, there can be mentioned, for example, an inorganic base such as alkali metal hydroxide (e.g. sodium hydroxide or potassium hydroxide), alkali metal carbonate (e.g. sodium carbonate or potassium carbonate), alkali metal bicarbonate (e.g. sodium hydrogencarbonate or potassium hydrogencarbonate) or the like.

The use amount of the base is appropriately selected ordinarily in a range of 1 to 10 equivalents relative to 1 equivalent of the compound [Ia-IV], and is preferably 0.1 to 2 equivalents.

The temperature of the reaction is ordinarily any desired temperature from −50° C. to the reflux temperature of the reaction system and is preferably a temperature of 0° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-V] can be isolated. The isolated compound [Ia-V] can be purified as necessary by column chromatography, recrystallization, etc.

Production Method 5

Of the present compounds represented by the general formula [I], a compound represented by formula [Ia-VI] can be produced, for example, by a method of the following reaction formula.

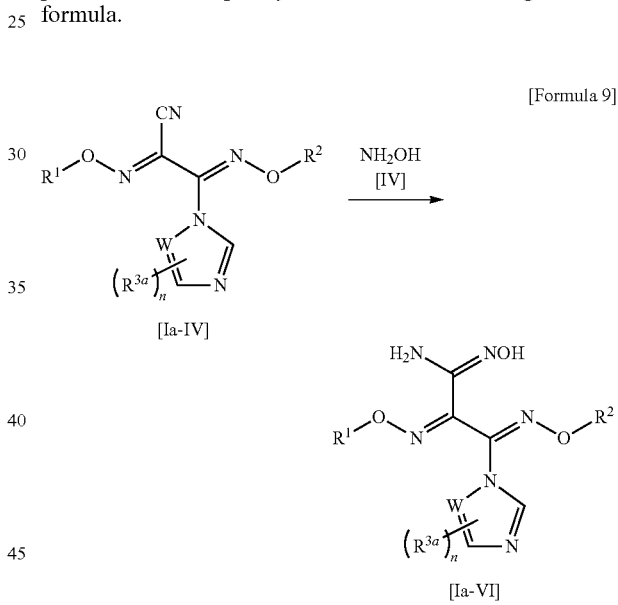

[Formula 9]

(in the above, $R^1$, $R^2$, $R^{3a}$, W and n have each the above-mentioned meaning.)

A compound [Ia-VI] can be produced by reacting a compound [Ia-IV] with a compound [IV] in a solvent. The compound [IV] may be a salt (e.g. hydrochloride or sulfate) and, in that case, the reaction may be conducted in the presence of a base.

The amount of the compound [IV] used in the reaction is appropriately selected ordinarily in a range of 1 to 5 equivalents relative to 1 equivalent of the compound [Ia-IV], and is preferably 1 to 2 equivalents.

As the solvent usable in the reaction, there can be mentioned, for example, water, an alcohol (e.g. methanol, ethanol or propanol), an amide (e.g. N,N-dimethylacetamide, N,N-dimethylformamide, 1,3-dimethyl-2-imidazolidinone or N-methyl-2-pyrrolidinone), a sulfur compound (e.g. dimethyl sulfoxide or sulfolane), or a mixture thereof. The amount of the solvent is ordinarily 0.1 to 50 liters, preferably 0.2 to 3.0 liters relative t 1 mol of the compound [Ia-IV].

As the base usable in the reaction, there can be mentioned, for example, an acetic acid base (e.g. sodium acetate or potassium acetate); an inorganic base such as alkali metal hydroxide (e.g. sodium hydroxide or potassium hydroxide), alkali metal carbonate (e.g. sodium carbonate or potassium carbonate), alkali metal bicarbonate (e.g. sodium hydrogencarbonate or potassium hydrogencarbonate) or the like; an alcohol metal salt (e.g. sodium methoxide, sodium ethoxide or potassium tert-butoxide); or an organic base (e.g. pyridine, triethylamine or 1,8-diazabicyclo[5.4.0]-7-undecene). The use amount of the base is appropriately selected in a range of 1 to 3 equivalents relative to 1 equivalent of the compound [IV], and is preferably 1 to 2 equivalents.

The temperature of the reaction is ordinarily any desired temperature from room temperature to the reflux temperature of the reaction system and is preferably a temperature of 50° C. to 100° C.

The time of the reaction differs depending upon the reaction temperature, the substrate of reaction, the amount of reaction, etc. but is ordinarily 1 to 24 hours.

After the completion of the reaction, there are conducted operations such as concentration of reaction mixture or pouring of reaction mixture into water, extraction by organic solvent, and subsequent concentration, whereby the compound [Ia-VI] can be isolated. The isolated compound [Ia-VI] can be purified as necessary by column chromatography, etc.

Production Method 6

Of the present compounds represented by the general formula [I], a compound represented by formula [Ia-II] can be produced, for example, by a method of the following reaction formula.

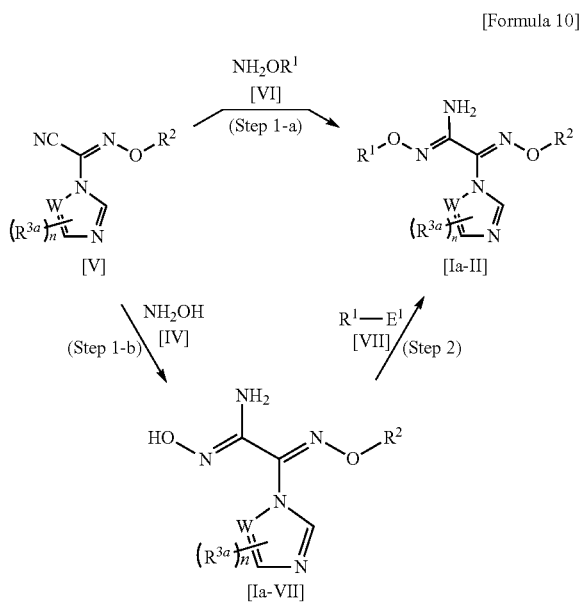

[Formula 10]

(in the above, $R^1$, $R^2$, $R^{3a}$, W, n and $E^1$ have each the above-mentioned meaning.)

(Step 1-a)

A compound [Ia-II] can be produced by reacting a compound [V] with a compound [VI] in a solvent in the presence of a base. The base [VI] may be a salt (e.g. hydrochloride or sulfate).

The amount of the compound [VI] used in the reaction is appropriately selected ordinarily in a range of 1 to 10 equivalents relative to 1 equivalent of the compound [V], and is preferably 2 to 5 equivalents.

As the solvent and base usable in the reaction, there can be mentioned the same solvents and compounds as mentioned in the production method 5. The amount of the solvent is ordinarily 0.1 to 50 liters, preferably 0.2 to 3.0 liters relative to 1 mol of the compound [V].

The use amount of the base is appropriately selected ordinarily in a range of 1 to 3 equivalents relative to 1 equivalent of the compound [VI], and is preferably 1 to 2 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-II] can be isolated. The isolated compound [Ia-II] can be purified as necessary by column chromatography, etc.

(Step 1-b)

A compound [Ia-VII] can be produced by reacting the compound [V] with a compound [IV] in a solvent. The compound [IV] may be a salt (e.g. hydrochloride or sulfate) and, in that case, the reaction may be conducted in the presence of a base.

The amount of the compound [IV] used in the reaction is appropriately selected ordinarily in a range of 1 to 5 equivalents relative to 1 equivalent of the compound [V] and is preferably 1 to 2 equivalents.

As the solvent and base usable in the reaction, there can be mentioned the same solvents and compounds as mentioned in the production method 5. The amount of the solvent is ordinarily 0.1 to 50 liters, preferably 0.2 to 3.0 liters relative to 1 mol of the compound [V].

When a base is used, the use amount of the base is appropriately selected ordinarily in a range of 1 to 3 equivalents relative to 1 equivalent of the compound [IV], and is preferably 1 to 2 equivalents.

The temperature of the reaction is ordinarily any desired temperature from room temperature to the reflux temperature of the reaction system and is preferably a temperature of 50° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-VII] can be isolated. The isolated compound [Ia-VII] can be purified as necessary by column chromatography, etc.

(Step 2)

A compound [Ia-II] can be produced by reacting the compound [Ia-VII] with a compound [VII] in a solvent in the presence of a base.

The amount of the compound [VII] used in the reaction is appropriately selected ordinarily in a range of 0.5 to 5 equivalents relative to 1 equivalent of the compound [Ia-VII] and is preferably 1.0 to 2 equivalents.

As the solvent and base usable in the reaction, there can be mentioned the same solvents and compounds as mentioned in the production method 1. The amount of the solvent is ordinarily 0.1 to 50 liters, preferably 0.2 to 3.0 liters relative to 1 mol of the compound [Ia-VII].

The use amount of the base is appropriately selected ordinarily in a range of 1 to 20 equivalents relative to 1 equivalent of the compound [Ia-VII], and is preferably 1 to 10 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-II] can be isolated. The isolated compound [Ia-II] can be purified as necessary by column chromatography, etc.

Production Method 7

A compound represented by general formula [V] can be produced, for example, by the following method.

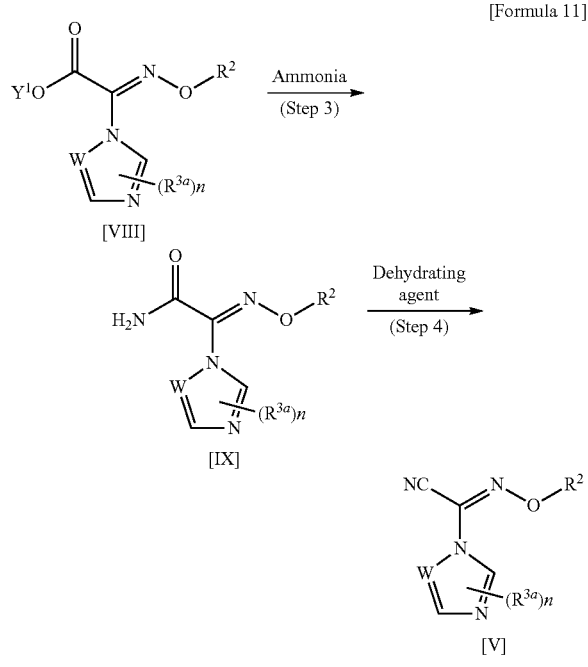

[Formula 11]

(in the above, $R^2$, $R^{3a}$, W and n have each the above-mentioned meaning, and $Y^1$ is a $C_1$~$C_6$ alkyl group.)

(Step 3)

A compound [IX] can be produced by reacting a compound [VIII] with ammonia in a solvent.

The amount of ammonia used in the reaction is appropriately selected ordinarily in a range of 1 to 10 equivalents relative to 1 equivalent of the compound [VIII] and is preferably 1 to 5 equivalents.

As the solvent usable in the reaction, there can be mentioned, for example, water, an ether (e.g. diethyl ether, 1,2-dimethoxyethane or tetrahydrofuran), an amide (e.g. N,N-dimethylacetamide, N,N-dimethylformamide, 1,3-dimethyl-2-imidazolidinone or N-methyl-2-pyrrolidinone), a sulfur compound (e.g. dimethyl sulfoxide or sulfolane), an alcohol (e.g. methanol, ethanol or propanol), or a mixture thereof. The amount of the solvent is ordinarily 0.1 to 50 liters relative to 1 mol of the compound [VIII], preferably 0.2 to 3.0 liters.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [IX] can be isolated. The isolated compound [IX] can be purified as necessary by column chromatography, etc.

(Step 4)

A compound [V] can be produced by reacting the compound [IX] with a dehydrating agent in a solvent.

As the solvent usable in the reaction, there can be mentioned, for example, an ether (e.g. diethyl ether, 1,2-dimethoxyethane or tetrahydrofuran), a nitrile (e.g. acetonitrile or propionitrile), an aromatic hydrocarbon (e.g. benzene, toluene or pyridine), or a halogenated hydrocarbon (e.g. 1,2-dichloroethane or chlorobenzene). The amount of the solvent is ordinarily 0.1 to 50 liters, preferably 0.2 to 10 liters relative to 1 mol of the compound [IX].

As the dehydrating agent usable in the reaction, there can be mentioned, for example, phosphorus pentoxide, phosphorus pentachloride, phosphorus oxychloride, triphosgene, trifluoroacetic anhydride, acetic anhydride, or thionyl chloride. The use amount of the dehydrating agent is appropriately selected ordinarily in a range of 1 to 10 equivalents relative to 1 equivalent of the compound [IX] and is preferably 1 to 5 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [V] can be isolated. The isolated compound [V] can be purified as necessary by column chromatography, recrystallization, etc.

Production Method 8

A compound represented by general formula [VIII] can be produced, for example, by the following method.

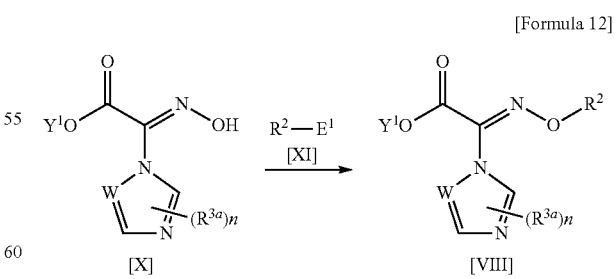

[Formula 12]

(in the above, $R^2$, $R^{3a}$, W, $Y^1$, n and $E^1$ have each the above-mentioned meaning.)

A compound [VIII] can be produced by reacting a compound [X] with a compound [XI] in a solvent in the presence of a base.

The amount of the compound [XI] used in the reaction is appropriately selected ordinarily in a range of 1.0 to 5.0 equivalents relative to 1 equivalent of the compound [X] and is preferably 1.1 to 2.0 equivalents.

As the solvent and base usable in the reaction, there can be mentioned the same solvents and compounds as mentioned in the production method 1. The amount of the solvent is ordinarily 0.1 to 50 liters, preferably 0.2 to 3.0 liters relative to 1 mol of the compound [X].

The use amount of the base is appropriately selected ordinarily in a range of 1 to 20 equivalents relative to 1 equivalent of the compound [X], and is preferably 1 to 10 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [VIII] can be isolated. The isolated compound [VIII] can be purified as necessary by column chromatography, etc.

Incidentally, the compound [X] can be produced, for example, based on the method described in Journal of the Chemical Society Perkin Transactions 1, pp. 2235~2239, (1987).

Production Method 9

A compound represented by formula [III] can be produced, for example, by the following method.

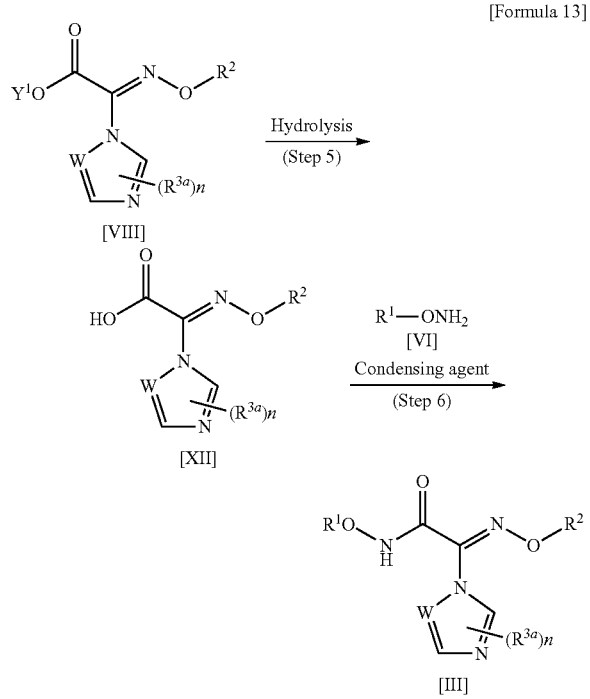

[Formula 13]

(in the above, $R^1$, $R^2$, $R^{3a}$, W, $Y^1$ and n have each the above-mentioned meaning.)

(Step 5)

A compound [XII] can be produced by hydrolyzing a compound [VIII] in a solvent in the presence of an acid or a base.

As the base usable in the reaction, there can be mentioned, for example, an inorganic base (e.g. potassium carbonate, sodium hydride or sodium hydroxide), and an organic base [e.g. 1,8-diazabicyclo[5.4.0]undeca-7-ene (DBU)]. The use amount of the base is appropriately selected in a range of 0.01 to 100 mols relative to 1 mol of the compound [VIII] and is preferably 0.1 to 10 mols.

As the acid usable in the reaction, there can be mentioned, for example, an inorganic acid (e.g. hydrochloric acid, hydrobromic acid or sulfuric acid) and an organic acid (e.g. acetic acid or trifluoroacetic acid). The use amount of the acid may be 1 mol to a large excess relative to 1 mol of the compound [VIII] and is preferably 1 to 100 mols.

As the solvent usable in the reaction, there can be mentioned, for example, an alcohol (e.g. methanol or ethanol), an ether (e.g. tetrahydrofuran), a ketone (e.g. acetone or methyl isobutyl ketone), an amide (e.g. N,N-dimethylformamide or N,N-dimethylacetamide), a sulfur compound (e.g. dimethyl sulfoxide or sulfolane), acetonitrile, water, or a mixture thereof. The use amount of the solvent is 0.01 to 100 liters, preferably 0.1 to 10 liters relative to 1 mol of the formula [VIII].

The temperature of the reaction is selected ordinarily from a range from −20° C. to the boiling point of the inert solvent and is preferably a temperature of 0° C. to 100° C.

The time of the reaction differs depending upon the reaction temperature, the substrate of reaction, the amount of reaction, etc. but is ordinarily 10 minutes to 48 hours.

(Step 6)

A compound [III] can be produced by reacting the compound [XII] with a compound [VI] in a solvent using a condensing agent. The compound [VI] may be a salt (e.g. hydrochloride or sulfate) and, in that case, the reaction may be conducted in the presence of a base.

The amount of the compound [VI] used in the reaction is appropriately selected ordinarily in a range of 1.0 to 5 equivalents relative to 1 equivalent of the compound [XII] and is preferably 1.0 to 2 equivalents.

As the condensing agent, there can be mentioned dicyclohexylcarbodiimide (DCC), N-(3-dimethylaminopropyl)-N'-ethylcarbodiimide hydrochloride (EDC or WSC), N,N-carbonyldiimidazole, 2-chloro-1,3-dimethylimidazolium chloride, 2-chloro-1-pyridinium iodide, etc. The use amount of the condensing agent is appropriately selected ordinarily in a range of 1 to 20 equivalents relative to 1 equivalent of the compound [XII] and is preferably 1.0 to 10 equivalents.

As the base usable in the reaction, there can be mentioned, for example, an acetic acid base (e.g. sodium acetate or potassium acetate), a metal salt of alcohol (e.g. sodium methoxide, sodium ethoxide or potassium tert-butoxide), or an organic base (e.g. pyridine, triethylamine or 1,8-diazabicyclo[5.4.0]-7-undecene). When a base is used, the use amount of the base is appropriately selected ordinarily in a range of 1 to 20 equivalents relative to 1 equivalent of the compound [VI] and is preferably 1 to 10 equivalents.

As the solvent usable in the reaction, there can be mentioned, for example, an ether (e.g. diethyl ether, 1,2-dimethoxyethane or tetrahydrofuran), an amide (e.g. N,N-dimethylacetamide, N,N-dimethylformamide, 1,3-dimethyl-2-imidazolidinone or N-methyl-2-pyrrlidinone), a sulfur compound (e.g. dimethyl sulfoxide or sulfolane), an aromatic hydrocarbon (e.g. benzene, toluene or xylene), a halogenated hydrocarbon (e.g. chloroform or dichloromethane), a nitrile (e.g. acetonitrile or propionitrile), or a mixture thereof. The amount of the solvent is ordinarily 0.1 to 50 liters, preferably 0.2 to 3.0 liters relative to 1 mol of the compound [XII].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [III] can be isolated. The isolated compound [III] can be purified as necessary by column chromatography, etc.

Production Method 10

Of the present compounds represented by the general formula [I], a compound represented by formula [Ia-VIII] can be produced, for example, by the following method.

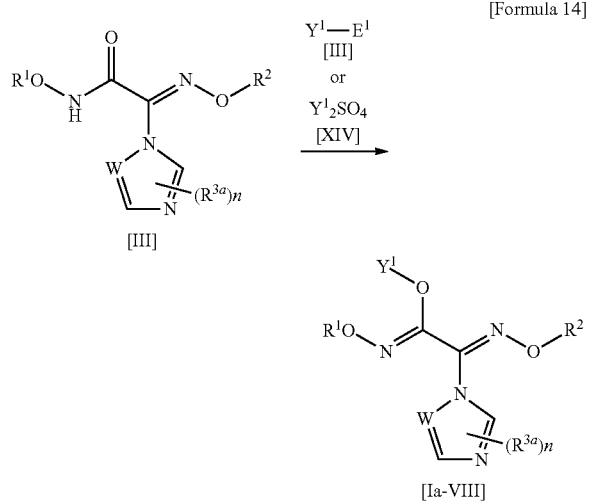

[Formula 14]

[Ia-VIII]

(in the above, $R^1$, $R^2$, $R^{3a}$, $Y^1$, W, n and $E^1$ have each the above-mentioned meaning.)

A compound [Ia-VIII] can be produced by reacting a compound [III] with a compound [XIII] or a compound [XIV] in a solvent in the presence of a base.

The amount of the compound [XIII] or the compound [XIV] used in the reaction is appropriately selected ordinarily in a range of 1.0 to 5.0 equivalents relative to 1 equivalent of the compound [III] and is preferably 1.1 to 2 equivalents.

As the solvent and base usable in the reaction, there can be mentioned the same solvents and compounds as mentioned in the production method 1. The amount of the solvent is ordinarily 0.1 to 50 liters, preferably 0.2 to 3.0 liters relative to 1 mol of the compound [III].

The use amount of the base is appropriately selected ordinarily in a range of 1 to 20 equivalents relative to 1 equivalent of the compound [III], and is preferably 1 to 10 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-VIII] can be isolated. The isolated compound [Ia-VIII] can be purified as necessary by column chromatography, etc.

Production Method 11

Of the present compounds represented by the general formula [I], a compound represented by formula [Ia-IX] can be produced, for example, by a method of the following reaction formula.

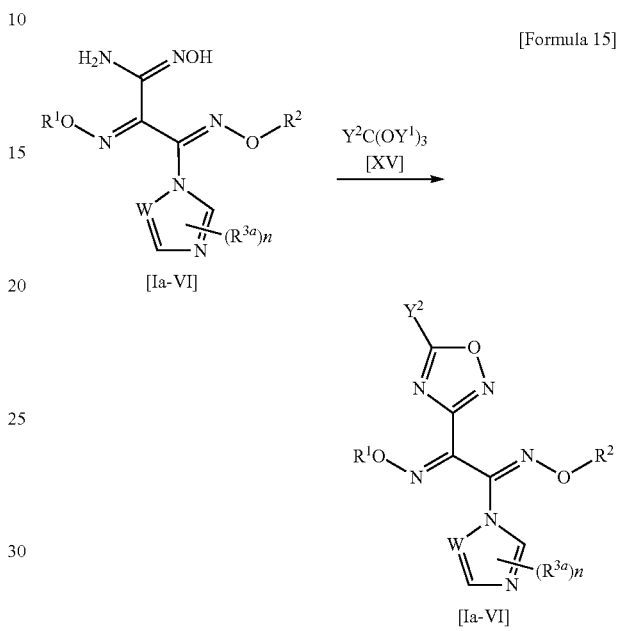

[Formula 15]

[Ia-VI]

[Ia-VI]

(in the above, $R^1$, $R^2$, $R^{3a}$, W, n and $Y^1$ have each the above-mentioned meaning, and $Y^2$ is a $C_1$~$C_6$ alkyl group.)

A compound [Ia-IX] can be produced by reacting a compound [Ia-VI] with a compound [XV] in the presence of a catalytic amount of an acid.

The amount of the compound [XV] used in the reaction is appropriately selected ordinarily in a range of 1 to 5 equivalents relative to 1 equivalent of the compound [Ia-VI] and is preferably 1 to 2 equivalents. The compound [XV] may be used also as a solvent.

A solvent may be used in the reaction. The solvent includes, for example, an alcohol (e.g. methanol, ethanol or propanol) and a sulfur compound (e.g. dimethyl sulfoxide or sulfolane). The amount of the solvent is ordinarily 0.1 to 50 liters, preferably 0.2 to 3.0 liters relative to 1 mol of the compound [Ia-VI].

As the acid usable in the reaction, there can be mentioned, for example, an inorganic acid (e.g. sulfuric acid), a sulfonic acid (e.g. p-toluenesulfonic acid), a Lewis acid (e.g. boron trifluoride) or an acetic acid (e.g. trifluoroacetic acid).

The temperature of the reaction is ordinarily any desired temperature from room temperature to the reflux temperature of the reaction system and is preferably a temperature of 50° C. to 140° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-IX] can be isolated. The isolated compound [Ia-IX] can be purified as necessary by column chromatography, etc.

Production Method 12

Of the present compounds represented by the general formula [I], a compound represented by formula [Ia-XI] can be produced, for example, by a method of the following reaction formula.

[Formula 16]

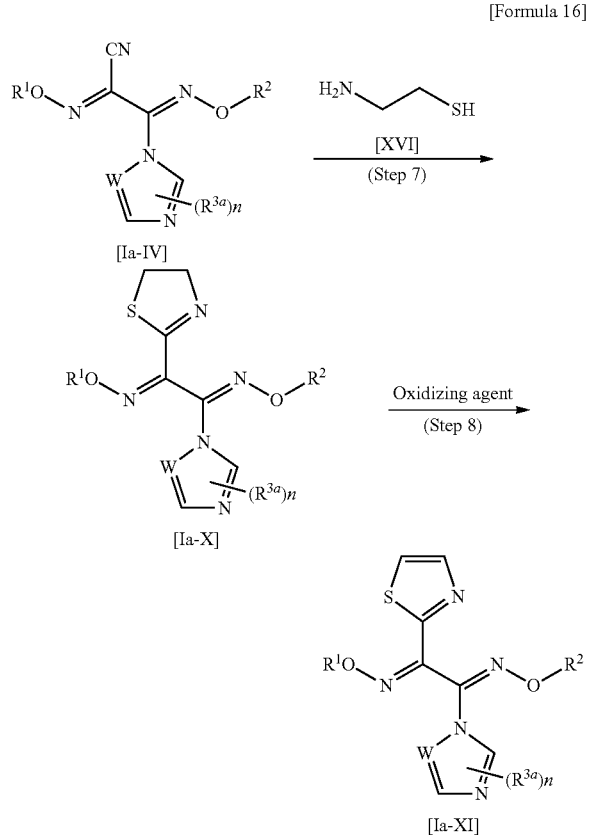

[Ia-IV]

[Ia-X]

[Ia-XI]

(in the above, $R^1$, $R^2$, $R^{3a}$, W and n have each the above-mentioned meaning.)

(Step 7)

A compound [Ia-X] can be produced b reacting a compound [Ia-IV] with a compound [XVI] in a solvent. The compound [XVI] may be a salt (e.g. hydrochloride or sulfate).

The amount of the compound [XVI] used in the reaction is appropriately selected ordinarily in a range of 1 to 10 equivalents relative to 1 equivalent of the compound [Ia-IV] and is preferably 2 to 5 equivalents.

As the solvent usable in the reaction, there can be mentioned, for example, water, an ether (e.g. diethyl ether, 1,2-dimethoxyethane or tetrahydrofuran), an alcohol (e.g. methanol, ethanol or propanol), an aromatic hydrocarbon (e.g. benzene, toluene or xylene), or a halogenated hydrocarbon (e.g. chloroform or dichloromethane). The amount of the solvent is ordinarily 0.1 to 50 liters, preferably 0.2 to 3.0 liters relative to 1 mol of the compound [Ia-IV].

A base may be used in the reaction. As the base, there can be mentioned, for example, a metal salt of alcohol (e.g. sodium methoxide, sodium ethoxide or potassium tert-butoxide), an acetic acid base (e.g. sodium acetate or ammonium acetate), or an organic base (e.g. pyridine or triethylamine). The use amount of the base is appropriately selected ordinarily in a range of 1 to 3 equivalents relative to 1 equivalent of the compound [Ia-IV] and is preferably 1 to 2 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-X] can be isolated. The isolated compound [Ia-X] can be purified as necessary by column chromatography, etc.

(Step 8)

A compound [Ia-XI] can be produced by reacting the compound [Ia-X] with an oxidizing agent in a solvent.

As the solvent usable in the reaction, there can be mentioned, for example, water, an aromatic hydrocarbon (e.g. benzene, toluene or xylene), a halogenated hydrocarbon (e.g. chloroform or dichloromethane), or a mixture thereof. The amount of the solvent is ordinarily 0.1 to 50 liters, preferably 0.2 to 10 liters relative to 1 mol of the compound [Ia-X].

As the oxidizing agent usable in the reaction, there can be mentioned, for example, potassium permanganate, manganese dioxide, nickel peroxide, or 2,3-dichloro-5,6-dicyano-p-benzoquinone (DDQ). The use amount of the oxidizing agent is appropriately selected ordinarily in a range of 1 to 10 equivalents relative to 1 equivalent of the compound [Ia-X] and is preferably 1 to 5 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-XI] can be isolated. The isolated compound [Ia-XI] can be purified as necessary by column chromatography, recrystallization, etc.

Production Method 13

Of the present compounds represented by the general formula [I], a compound represented by formula [Ia-XII] can be produced, for example, by a method of the following reaction formula.

[Formula 17]

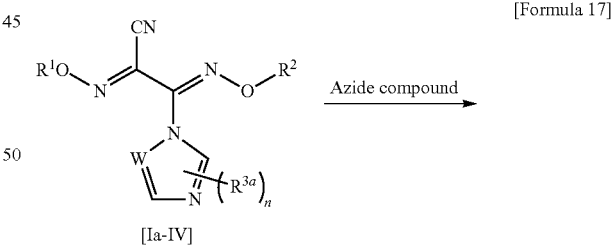

[Ia-IV]

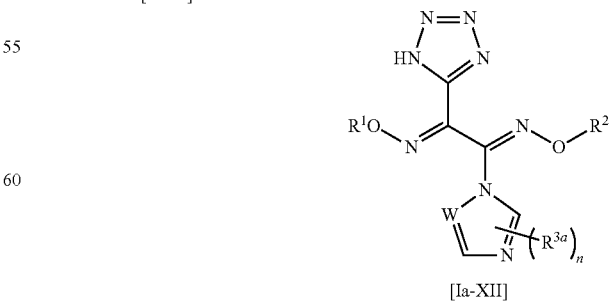

[Ia-XII]

(in the above, $R^1$, $R^2$, $R^{3a}$, W and n have each the above-mentioned meaning.)

A compound [Ia-XII] can be produced by reacting a compound [Ia-IV] with an azide compound.

The amount of the azide compound used in the reaction is appropriately selected ordinarily in a range of 1 to 5 equivalents relative to 1 equivalent of the compound [Ia-IV] and is preferably 1 to 2 equivalents.

As the azide compound usable in the reaction, there can be mentioned, for example, a trialkyl metal (e.g. trimethyltin azide or trimethylsilicon azide), or sodium azide. The reaction may be conducted in the presence of a Lewis acid (e.g. zinc bromide or aluminum chloride) or a tin compound (e.g. dibutyltin oxide).

As the solvent usable in the reaction, there can be mentioned, for example, an ether (e.g. 1,4-dioxane or tetrahydrofuran), an alcohol (e.g. methanol, ethanol or propanol), an amide (e.g. N,N-dimethylacetamide, N,N-dimethylformamide, 1,3-dimethyl-2-imidazolidinone or N-methyl-2-pyrrolidinone), an aromatic hydrocarbon (e.g. benzene, toluene or xylene), or a halogenated hydrocarbon (e.g. 1,2-dichloroethane or chlorobenzene). The amount of the solvent is ordinarily 0.1 to 50 liters, preferably 0.2 to 3.0 liters relative t 1 mol of the compound [Ia-IV].

The temperature of the reaction is ordinarily any desired temperature from room temperature to the reflux temperature of the reaction system and is preferably a temperature of 50° C. to 140° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-XII] can be isolated. The isolated compound [Ia-XII] can be purified as necessary by column chromatography, etc.

Production Method 14

Of the present compounds represented by the general formula [I], a compound represented by formula [Ia-XIII] can be produced, for example, by a method of the following reaction formula.

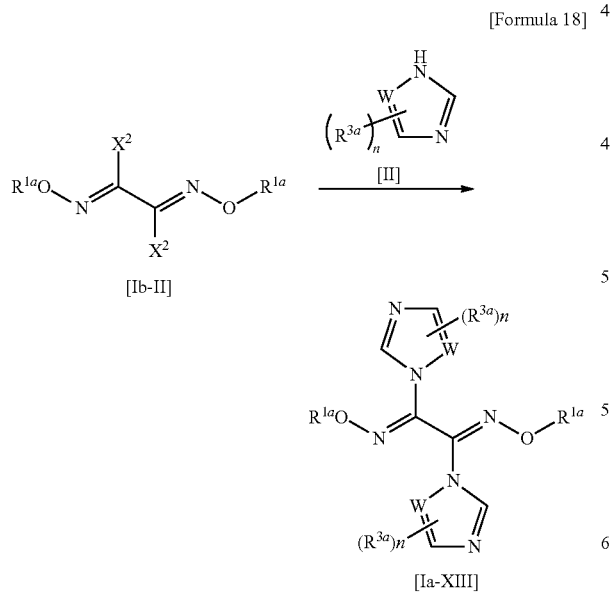

[Formula 18]

[Ib-II]

[Ia-XIII]

(in the above, $R^{1a}$, W, $X^2$ and n have each the above-mentioned meaning, and $R^{1a}$ is a $C_1$–$C_6$ alkyl group.)

A compound [Ia-XIII] can be produced by reacting a compound [Ib-II] with a compound [II] in a solvent in the presence of a base.

The amount of the compound [II] used in the reaction is appropriately selected ordinarily in a range of 1 to 5 equivalents relative to 1 equivalent of the compound [Ib-II] and is preferably 1 to 2 equivalents.

As the base usable in the reaction, there can be mentioned the same compounds as mentioned in the production method 1. The use amount of the base is appropriately selected in a range of 1.0 to 20.0 mols relative to 1 mol of the compound [Ib-II] and is preferably 1.0 to 6.0 mols.

As the solvent usable in the reaction, there can be mentioned the same solvents as mentioned in the production method 1. The use amount of the solvent is ordinarily 0.1 to 50 liters relative to 1 mol of the compound [Ib-II] and is preferably 0.2 to 3.0 liters.

The temperature of the reaction is ordinarily any desired temperature from −20° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-XIII] can be isolated. The isolated compound [Ia-XIII] can be purified as necessary by column chromatography, recrystallization, etc.

Production Method 15

Of the present compounds represented by the general formula [I], a compound represented by [Ia-XIV] can be produced, for example, by a method of the following reaction formula.

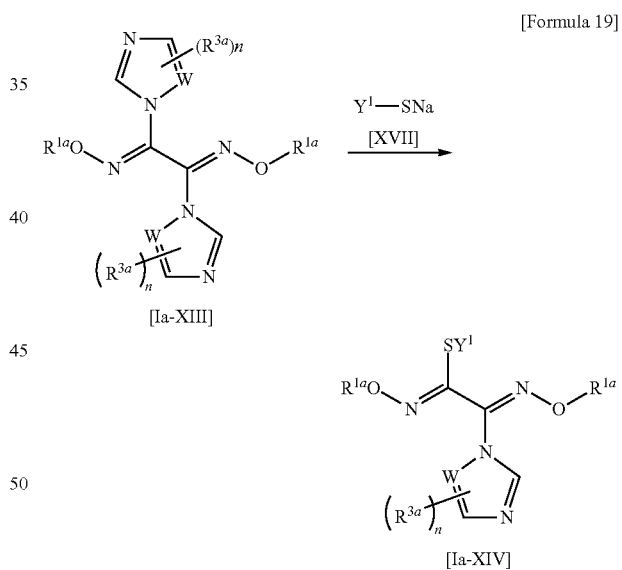

[Formula 19]

[Ia-XIII]

[Ia-XIV]

(in the above, $R^{1a}$, $R^{3a}$, W, $Y^1$ and n have each the above-mentioned meaning.)

A compound [Ia-XIV] can be produced by reacting a compound [Ia-XIII] with a compound [XVII] in a solvent.

The amount of the compound [XVII] used in the reaction is appropriately selected ordinarily in a range of 1.0 to 5.0 equivalents relative to 1.0 equivalent of the compound [Ia-XIII] and is preferably 1.0 to 1.2 equivalents.

As the solvent usable in the reaction, there can be mentioned the solvents mentioned in the production method 1. The amount of the solvent is ordinarily 0.1 to 50 liters relative to 1 mol of the compound [Ia-XIII] and is preferably 0.2 to 3.0 liters.

The temperature of the reaction is ordinarily any desired temperature from −20° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [Ia-XIV] can be isolated. The isolated compound [Ia-XIV] can be purified as necessary by column chromatography, recrystallization, etc.

Production Method 16

Of the present compounds represented by the general formula [I], a compound represented by [Ia-XV] can be produced, for example, by a method of the following reaction formula.

[Formula 20]

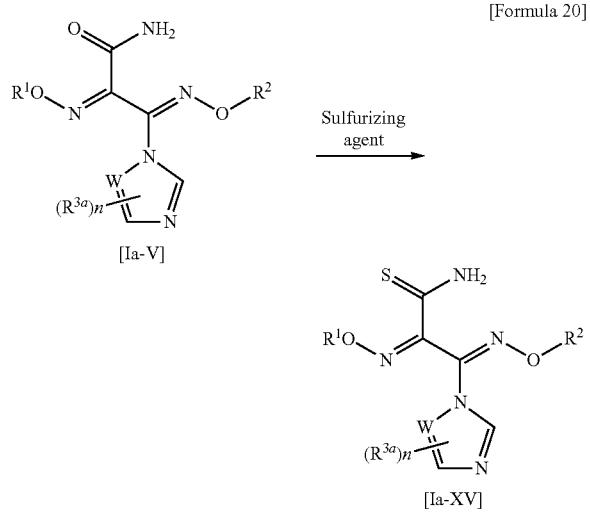

[Ia-V]

[Ia-XV]

(in the above, $R^1$, $R^2$, $R^{3a}$, W and n have each the above-mentioned meaning.)

A compound [Ia-XV] can be produced by reacting a compound [Ia-V] with a sulfurizing agent.

The amount of the sulfurizing agent used in the reaction is appropriately selected ordinarily in a range of 1 to 5 equivalents relative to 1 equivalent of the compound [Ia-V] and is preferably 1 to 2 equivalents.

As the sulfurizing agent usable in the reaction, there can be mentioned a Lawesson's reagent, 2,4-bis(4-methoxyphenyl)-1,3,2,4-dithiadiphophetane-2,4-disulfide, diphosphorus pentasulfide, etc.

As the solvent usable in the reaction, there can be mentioned, for example, an ether (e.g. diethyl ether, 1,2-dimethoxyethane or tetrahydrofuran), a nitrile (e.g. acetonitrile or propionitrile), an aromatic hydrocarbon (e.g. benzene, toluene, xylene or pyridine), or a halogenated hydrocarbon (e.g. 1,2-dichloroethane or chlorobenzene). The amount of the solvent is ordinarily 0.1 to 50 liters, preferably 0.2 to 3.0 liters relative to 1 mol of the compound [Ia-V].

The temperature of the reaction is ordinarily any desired temperature from room temperature to the reflux temperature of the reaction system and is preferably a temperature of 20° C. to 140° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-XV] can be isolated. The isolated compound [Ia-XV] can be purified as necessary by column chromatography, etc.

Production Method 17

Of the present compounds represented by the general formula [I], a compound represented by [Ia-XVII] can be produced, for example, by a method of the following reaction formula.

[Formula 21]

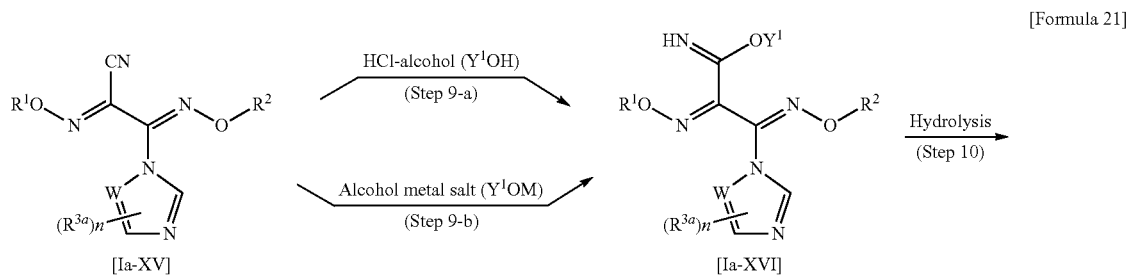

[Ia-XV]    [Ia-XVI]

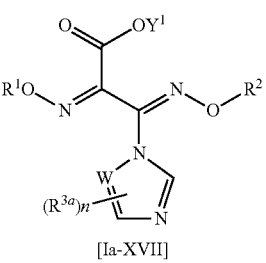

[Ia-XVII]

(in the above, $R^1$, $R^2$, $R^{3a}$, W, $Y^1$ and n have each the above-mentioned meaning, and M is an alkali metal such as sodium, potassium or the like.)

(Step 9-a)

A compound [Ia-XVI] can be produced by reacting a compound [Ia-IV], hydrogen chloride and a $C_1$–$C_6$ alcohol ($Y^1$OH) such as methanol, ethanol or the like.

The amount of the hydrogen chloride used in the reaction is appropriately selected ordinarily in a range of 1 to 10 equivalents relative to 1 equivalent of the compound [Ia-IV] and is preferably 1 to 5 equivalents. The use amount of the alcohol is ordinarily 0.1 to 50 liters, preferably 0.2 to 10 liter relative to 1 mol of the compound [Ia-IV].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, the reaction mixture may be concentrated and the concentrate per se may be used in the subsequent reaction. However, it is also possible to conduct operations such as pouring of reaction mixture into water, extraction by organic solvent, concentration and drying, whereby the compound [Ia-XVI] can be isolated. The isolated compound [Ia-XVI] can be purified as necessary by column chromatography, recrystallization, etc.

(Step 9-b)

The compound [Ia-XVI] may also be produced by reacting the compound [Ia-IV] with a $C_1$–$C_6$ alcohol metal salt ($Y^1$OM) such as sodium methoxide, sodium ethoxide or the like, in a $C_1$–$C_6$ alcohol ($Y^1$OH) such as methanol, ethanol or the like.

The amount of the alcohol metal salt used in the reaction is appropriately selected ordinarily in a range of a catalytic amount to 10 equivalents relative to 1 equivalent of the compound [Ia-IV] and is preferably 0.1 to 5 equivalents.

The amount of the alcohol used in the reaction is ordinarily 0.1 to 50 liters, preferably 0.2 to 3.0 liters relative to 1 mol of the compound [Ia-IV].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, the reaction mixture may be concentrated and the concentrate per se may be used in the subsequent reaction. However, it also possible to conduct operations such as pouring of reaction mixture into water, extraction by organic solvent, concentration and drying, whereby the compound [Ia-XVI] can be isolated. The isolated compound [Ia-XVI] can be purified as necessary by column chromatography, recrystallization, etc.

(Step 10)

A compound [Ia-XVII] can be produced by reacting the compound [Ia-XVI] in a solvent in the presence of an acid (e.g. hydrochloric acid or sulfuric acid).

As the solvent usable in the reaction, there can be mentioned, for example, an ether (e.g. diethyl ether, 1,2-dietoxyethane or tetrahydrofuran), an alcohol (e.g. methanol, ethanol or propanol), or water. The amount of the solvent is ordinarily 0.1 to 50 liters, preferably 0.2 to 3.0 liters relative to 1 mol of the compound [Ia-XVI].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, concentration and drying, whereby the compound [Ia-XVII] can be isolated. The isolated compound [Ia-XVII] can be purified as necessary by column chromatography, recrystallization, etc.

Production Method 18

Of the present compounds represented by the general formula [I], a compound represented by formula [Ia-XVIII] can be produced by a method of the following reaction formula.

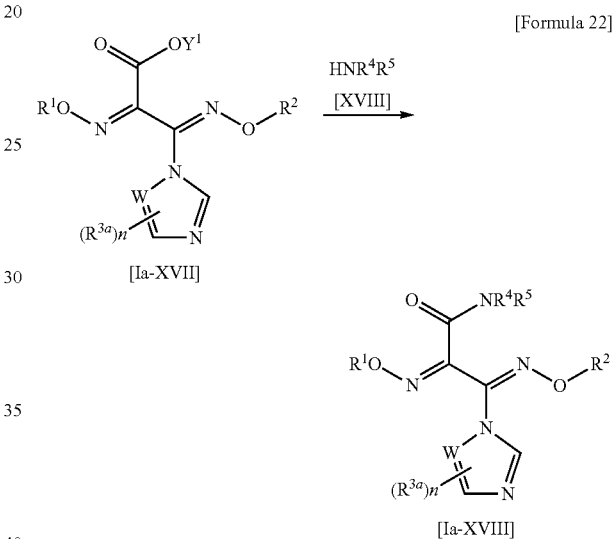

[Formula 22]

(in the above, $R^1$, $R^2$, $R^{3a}$, $R^4$, $R^5$, W, $Y^1$ and n have each the above-mentioned meaning.)

A compound [Ia-XVIII] can be produced by reacting a compound [Ia-XVII] with a compound [XVIII] in a solvent in the presence of a Lewis acid. The compound [XVIII] may be a salt (e.g. hydrochloride or sulfate).

The amount of the compound [XVIII] used in the reaction is appropriately selected ordinarily in a range of 1 to 10 equivalents relative to 1 equivalent of the compound [Ia-XVII] and is preferably 2 to 5 equivalents.

As the solvent usable in the reaction, there can be mentioned, for example, an ether (e.g. 1,4-dioxane, 1,2-dimethoxyethane or tetrahydrofuran), an aromatic hydrocarbon (e.g. benzene, toluene or xylene), or a halogenated hydrocarbon (e.g. chloroform or dichloromethane). The amount of the solvent is ordinarily 0.1 to 50 liters, preferably 0.2 to 3.0 liters relative to 1 mol of the compound [Ia-XVII].

As the Lewis acid usable in the reaction, there can be mentioned an aluminum (e.g. trimethyl aluminum or aluminum chloride). The use amount of the Lewis acid is appropriately selected ordinarily in a range of 1 to 3 equivalents relative to 1 equivalent of the compound [Ia-XVII] and is preferably 1 to 2 equivalents.

In the reaction, the compound [XVIII] may be used in an excess, or a base may be used in place of the Lewis acid. As the base, there can be mentioned, for example, an inorganic base such as alkali metal hydroxide (e.g. sodium hydroxide or potassium hydroxide), alkali metal carbonate (e.g. sodium carbonate or potassium carbonate), alkali metal bicarbonate (e.g. sodium hydrogencarbonate or potassium hydrogencarbonate) or the like; a metal salt of alcohol (e.g. sodium methoxide or sodium ethoxide); or an organic base (e.g. pyridine, triethylamine or 1,8-diazabicyclo[5.4.0]-7-undecene). The use amount of the base is appropriately selected ordinarily in a range of 1 to 3 equivalents relative to 1 equivalent of the compound [Ia-XVII] and is preferably 1 to 2 equivalents.

As the solvent usable in the reaction, there can be mentioned, for example, an alcohol (e.g. methanol, ethanol or propanol), an ether (e.g. 1,4-dioxane, 1,2-dimethoxyethane or tetrahydrofuran), an aromatic hydrocarbon (e.g. benzene, toluene or xylene), or a halogenated hydrocarbon (e.g. chloroform or dichloromethane). The amount of the solvent is ordinarily 0.1 to 50 liters, preferably 0.2 to 3.0 liters relative to 1 mol of the compound [Ia-XVII].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-XVIII] can be isolated. The isolated compound [Ia-XVIII] can be purified as necessary by column chromatography, etc.

Production Method 19

Of the present compounds represented by the general formula [I], a compound represented by formula [Ia-XIX] can be produced, for example, by a method of the following reaction formula.

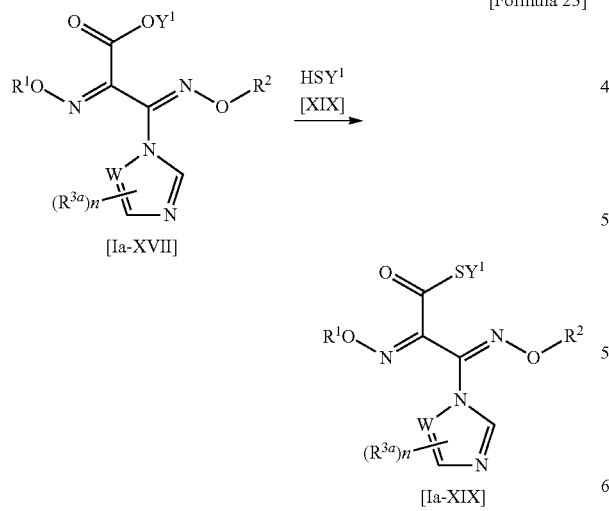

[Formula 23]

(in the above, $R^1$, $R^2$, $R^{3a}$, W, $Y^1$, $Y^2$ and n have each the above-mentioned meaning.)

A compound [Ia-XIX] can be produced by reacting a compound [Ia-XVII] with a compound [XIX] in a solvent in the presence of a Lewis acid.

The amount of the compound [XIX] used in the reaction is appropriately selected ordinarily in a range of 1 to 10 equivalents relative to 1 equivalent of the compound [Ia-XVII] and is preferably 2 to 5 equivalents.

As the solvent usable in the reaction, there can be mentioned, for example, an aromatic hydrocarbon (e.g. benzene, toluene or xylene), and a halogenated hydrocarbon (e.g. chloroform or dichloromethane). The amount of the solvent is ordinarily 0.1 to 50 liters, preferably 0.2 to 3.0 liters relative to 1 mol of the compound [Ia-XVI].

As the Lewis acid usable in the reaction, there can be mentioned an aluminum compound (e.g. trimethyl aluminum or aluminum chloride). The use amount of the Lewis acid is appropriately selected ordinarily in a range of 1 to 3 equivalents relative to 1 equivalent of the compound [Ia-XVII] and is preferably 1 to 2 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ia-XIX] can be isolated. The isolated compound [Ia-XIX] can be purified as necessary by column chromatography, etc.

Production Method 20

Of the present compounds represented by the general formula [I], a compound represented by formula [Ia-XX] can be produced, for example, by a method of the following reaction formula.

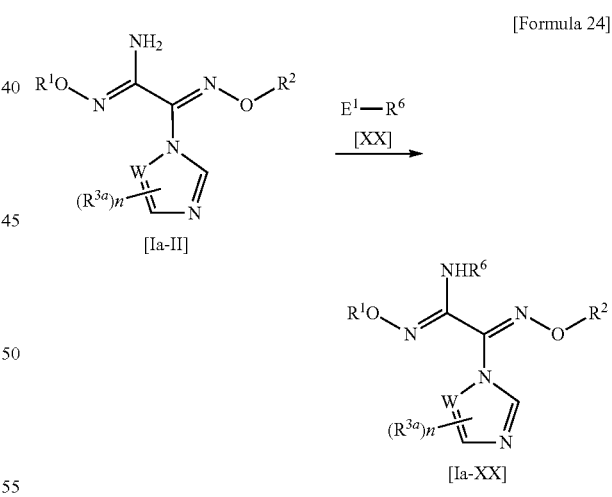

[Formula 24]

(in the above, $R^1$, $R^2$, $R^{3a}$, $R^6$, W, n and $E^1$ have each the above-mentioned meaning.)

A compound [Ia-XX] can be produced by reacting a compound [Ia-II] with a compound [XX] in a solvent in the presence of a base.

The amount of the compound [XX] used in the reaction is appropriately selected ordinarily in a range of 1.0 to 5.0 equivalents relative to 1.0 equivalent of the compound [Ia-II] and is preferably 1.1 to 2.0 equivalents.

As the solvent and base usable in the reaction, there can be mentioned the same solvents and compounds as mentioned in the production method 1. The amount of the solvent is ordinarily 0.1 to 50 liters, preferably 0.2 to 3.0 liters relative to 1 mol of the compound [Ia-II].

The use amount of the base is appropriately selected ordinarily in a range of 1 to 20 equivalents relative to 1 equivalent of the compound [Ia-II] and is preferably 1 to 10 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-XX] can be isolated. The isolated compound [Ia-XX] can be purified as necessary by column chromatography, etc.

Production Method 21

Of the present compounds represented by the general formula [I], a compound represented by formula [Ia-XXII] can be produced, for example, by a method of the following reaction formula.

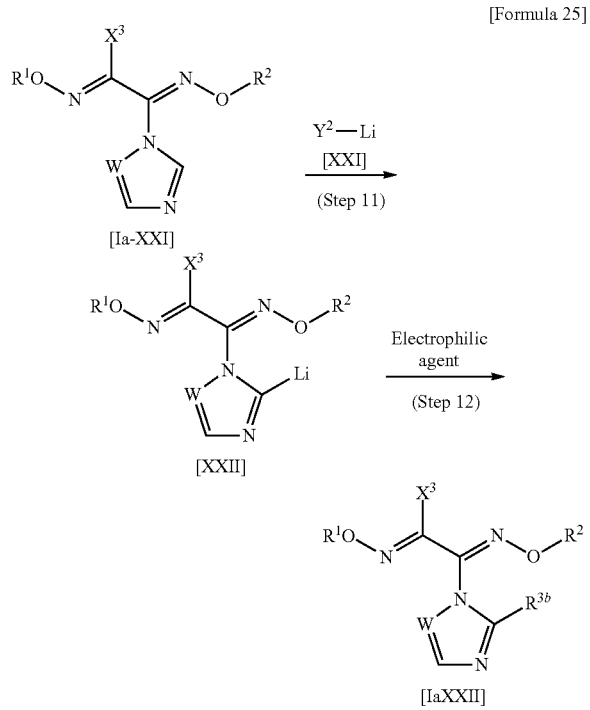

[Formula 25]

[in the above, $R^1$, $R^2$, W and $Y^2$ have each the above-mentioned meaning, $X^3$ is a hydrogen atom, a cyano group, a $C_1$~$C_8$ alkyl group, a $C_2$~$C_5$ alkenyl group, a $C_2$~$C_6$ alkynyl group, a $C_3$~$C_5$ cycloalkyl group, a $C_3$~$C_5$ cycloalkyl $C_1$~$C_6$ alkyl group, a $C_1$~$C_5$ haloalkyl group, a $C_1$~$C_6$ alkylthio group, a $C_1$~$C_6$ alkylthio $C_1$~$C_5$ alkyl group, a $C_1$~$C_6$ alkoxy group, a $C_1$~$C_5$ alkoxy $C_1$~$C_6$ alkyl group, a $R^6R^7N$ group, a $C_1$~$C_5$ alkoxycarbonyl group, a phenyl group which may be substituted with substituent group α, or a heterocyclic ring group of 1 to 9 carbon atoms, having 1 to 5 hetero atoms which may be the same or different and which are selected from oxygen atom, sulfur atom and nitrogen atom (the group may be substituted with 1 to 5 substituent(s) selected from halogen atoms, $C_1$~$C_6$ alkyl group, $C_1$~$C_6$ haloalkyl group, $C_1$~$C_6$ alkoxy group or cyano group), $R^{3b}$ is a halogen atom, a mercapto group, a $C_1$~$C_6$ alkyl group, a $C_1$~$C_6$ haloalkyl group, a $C_1$~$C_6$ alkylthio group, or a formyl group, and $R^6$, $R^7$ and the substituent group α have each the above-mentioned meaning.]

(Step 11)

A compound [XXII] can be produced by reacting a compound Ia-XXI with an alkyl lithium compound [XXI] in a solvent.

The amount of the compound [XXI] used in the reaction is appropriately selected ordinarily in a range of 1.0 to 5.0 equivalents relative to 1 equivalent of the compound [Ia-XXI] and is preferably 1.1 to 2.0 equivalents.

As the solvent usable in the reaction, there can be mentioned, for example, an ether such as diethyl ether, 1,2-dimethoxyethane, tetrahydrofuran or the like. The amount of the solvent is ordinarily 0.1 to 50 liters, preferably 0.2 to 3.0 liters relative to 1 mol of the compound [Ia-XXI].

The temperature of the reaction is ordinarily any desired temperature from −100° C. to the reflux temperature of the reaction system and is preferably a temperature of −70° C. to 0° C.

The time of the reaction differs depending upon the reaction temperature, the substrate of reaction, the amount of reaction, etc. but is ordinarily 1 to 24 hours.

After the completion of the reaction, no purification is conducted and the reaction mixture containing the compound [XXII] is used per se in the next reaction.

(Step 12)

A compound [Ia-XXII] can be produced by reacting the reaction mixture containing the compound [XXII] with an electrophilic agent in a solvent.

As the electrophilic agent usable in the reaction, there can be mentioned, for example, a halogen (e.g. chlorine or bromine), a halogenated $C_1$~$C_6$ alkyl (e.g. methyl iodide or ethyl bromide), a halogenated $C_1$~$C_6$ haloalkyl (e.g. 1-chloro-2-bromoethane or hexachloroethane), a di $C_1$~$C_6$ alkyl disulfide (e.g. dimethyl disulfide or diethyl disulfide), sulfur, or N,N-dimethylformamide. The use amount of the electrophilic agent is appropriately selected in a range of 1.0 to 5.0 mols relative to 1.0 mol of the compound [XXII] and is preferably 1.1 to 2.0 mols.

The temperature of the reaction is ordinarily any desired temperature from −100° C. to the reflux temperature of the reaction system and is preferably a temperature of −70° C. to 0° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-XXII] can be isolated. The isolated compound [Ia-XXII] can be purified as necessary by column chromatography, etc.

Production Method 22

Of the present compounds represented by the general formula [I], a compound represented by formula [Ib-III] can be produced, for example, by a method of the following reaction formula.

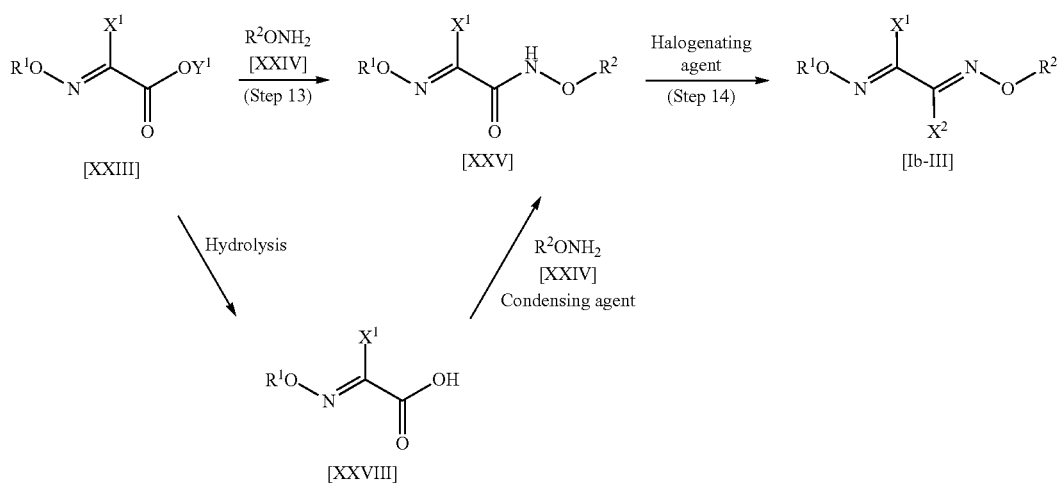

[Formula 26]

(in the above, $R^1$, $R^2$, $X^1$, $X^2$ and $Y^1$ have each the above-mentioned meaning.)

(Step 13)

A compound [XXV] can be produced by reacting a compound [XXIII] with a compound [XXIV] in a solvent in the presence of a Lewis acid.

The amount of the compound [XXIV] used in the reaction is appropriately selected ordinarily in a range of 1 to 10 equivalents relative to 1 equivalent of the compound [XXIII] and is preferably 2 to 5 equivalents.

As the solvent and Lewis acid usable in the reaction, there can be mentioned the same solvents and compounds as mentioned in the production method 18. The amount of the solvent is ordinarily 0.1 to 50 liters, preferably 0.2 to 3.0 liters relative to 1 mol of the compound [XXIII].

The use amount of the Lewis acid is appropriately selected ordinarily in a range of 1 to 3 equivalents relative to 1 equivalent of the compound [XXIII] and is preferably 1 to 2 equivalents.

In the reaction, a base may be used in place of the Lewis acid. As the base, there can be mentioned the same compounds as mentioned in the production method 18. The use amount of the base is appropriately selected ordinarily in a range of 1 to 3 equivalents relative to 1 equivalent of the compound [XXIII] and is preferably 1 to 2 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [XXV] can be isolated. The isolated compound [XXV] can be purified as necessary by column chromatography, etc.

The compound [XXV] can also be produced by hydrolyzing the compound [XXIII] in the presence of an acid or a base to obtain a compound [XXVIII] and reacting the compound [XXVIII] with a compound [XXIV] in a solvent in the presence of a condensing agent.

The amount of the compound [XXIV] used in the reaction is appropriately selected ordinarily in a range of 1.0 to 5 equivalents relative to 1 equivalent of the compound [XXVIII] and is preferably 1.1 to 2 equivalents.

As the condensing agent and solvent usable in the reaction, there can be mentioned the same compounds and solvents as mentioned in the production method 9. The use amount of the condensing agent is appropriately selected ordinarily in a range of 1 to 20 equivalents relative to 1 equivalent of the compound [XXVIII] and is preferably 1.2 to 10 equivalents. The amount of the solvent is ordinarily 0.1 to 50 liters, preferably 0.2 to 3.0 liters relative to 1 mol of the compound [XXVIII].

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [XXV] can be isolated. The isolated compound [XXV] can be purified as necessary by column chromatography, etc.

(Step 14)

A compound [Ib-III] can be produced by reacting the compound [XXV] with a halogenating agent in a solvent.

As the halogenating agent usable in the reaction, there can be mentioned the same compounds as mentioned in the production method 3. The use amount of the halogenating agent is appropriately selected in a range of 1.0 to 20.0 mols relative to 1.0 mol of the compound [XXV] and is preferably 1.0 to 6.0 mols.

As the solvent usable in the reaction, there can be mentioned the same solvents as mentioned in the production method 3. The amount of the solvent is ordinarily 0.1 to 50 liters, preferably 0.2 to 3.0 liters relative to 1.0 mol of the compound [XXV].

The temperature of the reaction is ordinarily any desired temperature from −50° C. to the reflux temperature of the reaction system and is preferably a temperature of 0° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ib-III] can be isolated. The isolated compound [Ib-III] can be purified as necessary by column chromatography, recrystallization, etc.

Incidentally, the compound [XXIII] can be produced, for example, based on the method described in Journal of Medicinal Chemistry, pp. 4608 to 4612 (1992) or Journal of Organic Chemistry, pp. 496 to 500 (2001).

Production Method 23

Of the present compounds represented by the general formula [I], a compound represented by formula [Ib-II] can be produced, for example, by a method of the following reaction formula.

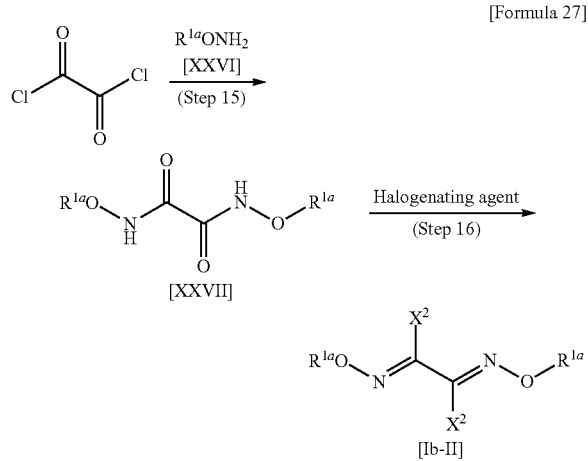

[Formula 27]

(in the above, $R^{1a}$ and $X^2$ have each the above-mentioned meaning.)

(Step 15)

A compound [XXVII] can be produced by reacting oxalyl dichloride with a compound [XXVI] in a solvent in the presence of a base.

The amount of the compound [XXVI] used in the reaction is appropriately selected ordinarily in a range of 2 to 5 equivalents relative to 1 equivalent of oxalyl dichloride and is preferably 2.0 to 3.0 equivalents.

As the solvent usable in the reaction, there can be mentioned, for example, an ether (e.g. diethyl ether, 1,2-dimethoxyethane or tetrahydrofuran), a nitrile (e.g. acetonitrile or propionitrile), an aliphatic hydrocarbon (e.g. hexane or heptane), an aromatic hydrocarbon (e.g. benzene, toluene or xylene), a halogenated hydrocarbon (e.g. 1,2-dichloroethane or chlorobenzene), or a mixture thereof. The amount of the solvent is ordinarily 0.1 to 50 liters, preferably 0.2 to 3.0 liters relative to 1 mol of oxalyl dichloride.

As the base usable in the reaction, there can be mentioned, for example, an inorganic base such as alkali metal carbonate (e.g. sodium carbonate or potassium carbonate); alkali metal bicarbonate (e.g. sodium hydrogencarbonate or potassium hydrogencarbonate); a metal hydride (e.g. sodium hydride or potassium hydride); or an organic base (e.g. triethylamine or 1,8-diazabicyclo[5.4.0]-7-undecene). The use amount of the base is appropriately selected ordinarily in a range of 2 to 10 equivalents relative to 1 equivalent of oxalyl dichloride and is preferably 2 to 5 equivalents.

The temperature of the reaction is ordinarily any desired temperature from −20° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 48 hours.

After the completion of the reaction, there are conducted operations such as pouring of reaction mixture into water, extraction by organic solvent, and subsequent concentration, whereby the compound [XXVII] can be isolated. The isolated compound [XXVII] can be purified as necessary by column chromatography, recrystallization, etc.

(Step 16)

A compound [Ib-II] can be produced by reacting the compound [XXVII] with a halogenating agent in a solvent.

As the halogenating agent usable in the reaction, there can be mentioned the same compounds as mentioned in the production method 3. The use amount of the halogenating agent is appropriately selected in a range of 1.0 to 20.0 mols relative to 1.0 mol of the general formula [XXVII] and is preferably 1.0 to 6.0 mols.

As the solvent usable in the reaction, there can be mentioned the same solvents as mentioned in the production method 3. The amount of the solvent is ordinarily 0.1 to 50 liters, preferably 0.2 to 3.0 liters relative to 1 mol of the compound [XXVII].

The temperature of the reaction is ordinarily any desired temperature from −50° C. to the reflux temperature of the reaction system and is preferably a temperature of 0° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [Ib-II] can be isolated. The isolated compound [Ib-II] can be purified as necessary by column chromatography, recrystallization, etc.

Production Method 24

Of the present compounds represented by the general formula [I], a compound represented by formula [Ia-I] can also be produced, for example, by a method of the following reaction formula.

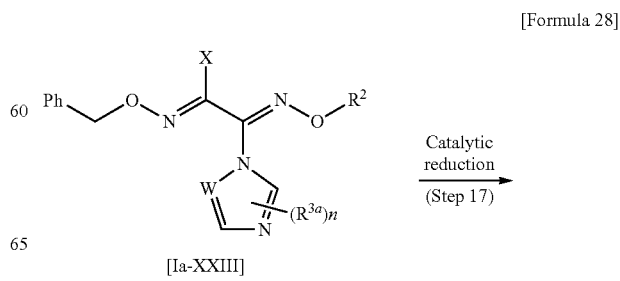

[Formula 28]

Catalytic reduction
(Step 17)

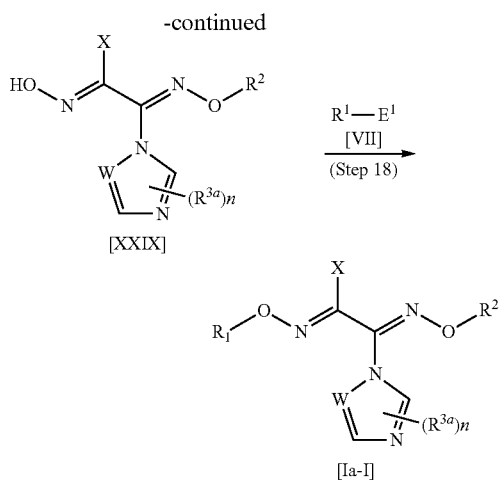

(in the above, $R^2$, $R^{3a}$, X, W, $E^1$ and n have each the above-mentioned meaning.)

(Step 17)

A compound [XXIX] can be produced by reacting a compound [Ia-XXIII] with hydrogen in a solvent in the presence of a catalyst.

As the catalyst used in the reaction, there can be mentioned, for example, palladium, palladium hydroxide, or a catalyst obtained by loading palladium or palladium hydroxide on active carbon.

The amount of the catalyst used in the reaction is appropriately selected ordinarily in a range of 0.01 to 0.1 equivalent relative to 1 equivalent of [Ia-XXIII] and is preferably 0.02 to 0.05 equivalent.

As the solvent usable in the reaction, there can be mentioned, for example, an ether (e.g. diethyl ether, 1,4-dioxane or tetrahydrofuran), an alcohol (e.g. methanol or ethanol), an acetic acid ester (e.g. ethyl acetate or butyl acetate), or acetic acid. The amount of the solvent is ordinarily 0.1 to 50 liters, preferably 0.2 to 3.0 liters relative to 1 mol of [Ia-XXIII].

The temperature of the reaction is ordinarily any desired temperature from −50° C. to the reflux temperature of the reaction system and is preferably a temperature of 0° C. to 100° C.

The time of the reaction differs depending upon the reaction temperature, the substrate of reaction, the amount of reaction, etc. but is ordinarily 1 to 48 hours.

After the completion of the reaction, there are conducted operations such as concentration of reaction mixture or pouring of reaction mixture into water, extraction by organic solvent, and subsequent concentration, whereby the compound [XXIX] can be isolated. The isolated compound [XXIX] can be purified as necessary by column chromatography, recrystallization, etc.

(Step 18)

A compound [Ia-I] can be produced by reacting the compound [XXIX] with [VII] in a solvent in the presence of a base.

The amount of the compound [VII] used in the reaction is appropriately selected ordinarily in a range of 1.0 to 5.0 equivalents relative to 1 equivalent of the compound [XXIX] and is preferably 1.0 to 2.0 equivalents.

As the solvent and base usable in the reaction, there can be mentioned the same solvents and compounds as mentioned in the production method 1. The use amount of the solvent is ordinarily 0.1 to 50 liters, preferably 0.2 to 3.0 liters relative to 1 mol of the compound [XXIX].

The use amount of the base is appropriately selected ordinarily in a range of 0.5 to 20 equivalents relative to 1 equivalent of the compound [XXIX] and is preferably 1 to 10 equivalents.

The temperature of the reaction is ordinarily any desired temperature from −50° C. to the reflux temperature of the reaction system and is preferably a temperature of −10° C. to 100° C.

The time of the reaction differs depending upon the reaction temperature, the substrate of reaction, the amount of reaction, etc. but is ordinarily 1 to 24 hours.

After the completion of the reaction, there are conducted operations such as pouring of reaction mixture into water, extraction by organic solvent, and subsequent concentration, whereby the compound [Ia-I] can be isolated. The isolated compound [Ia-I] can be purified as necessary by column chromatography, etc.

The pest control agent of the present invention is characterized by containing, as an active ingredient, an alkoxyimino derivative represented by the general formula [I] or an agriculturally acceptable salt thereof. The present pest control agent is representatively an insecticide.

The present pest control agent may as necessary contain an additive component (carrier) ordinarily used in agricultural chemical formulations.

As the additive component, there can be mentioned a carrier (e.g. solid carrier or liquid carrier), a surfactant, a binder or a tackifier, a thickening agent, a coloring agent, a spreader, a sticker, an anti-freeze, a solidification inhibitor, a disintegrator, a decomposition inhibitor, etc. As necessary, there may be used other additive components such as antiseptic, vegetable chip and the like.

These additive components may be used in one kind or in combination of two or more kinds.

The above additive components are explained.

As the solid carrier, there can be mentioned, for example, mineral carriers such as pyrophyllite clay, kaolin clay, silicastone clay, talc, diatomaceous earth, zeolite, bentonite, acid clay, active clay, Attapulgus clay, vermiculite, perlite, pumice, white carbon (e.g. synthetic silicic acid or synthetic silicate), titanium dioxide and the like; vegetable carriers such as wood flour, corn culm, walnut shell, fruit stone, rice hull, sawdust, wheat bran, soybean flour, powder cellulose, starch, dextrin, saccharide and the like; inorganic salt carriers such as calcium carbonate, ammonium sulfate, sodium sulfate, potassium chloride and the like; and polymer carriers such as polyethylene, polypropylene, polyvinyl chloride, polyvinyl acetate, ethylene-vinyl acetate copolymer, urea-aldehyde resin and the like.

As the liquid carrier, there can be mentioned, for example, monohydric alcohols such as methanol, ethanol, propanol, isopropnanol, butanol, cyclohexanol and the like; polyhydric alcohols such as ethylene glycol, diethylene glycol, propylene glycol, hexylene glycol, polyethylene glycol, polypropylene glycol, glycerine and the like; polyhydric alcohol derivatives such as propylene-type glycol ether and the like; ketones such as acetone, methyl ethyl ketone, methyl isobutyl ketone, disobutyl ketone, cyclohexanone, isophorone and the like; ethers such as ethyl ether, dioxane, cellosolve, dipropyl ether, tetrahydrofuran and the like; aliphatic hydrocarbons such as normal paraffin, naphthene, isoparaffin, kersene, mineral oil and the like; aromatic hydrocarbons such as toluene, $C_9$~$C_{10}$ alkylbenzene, xylene, solvent naphtha, alkylnaphthalene, high-boiling aromatic hydrocarbon and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, coconut oil, castor oil and the like; and water.

As to the surfactant, there is no particular restriction. However, the surfactant preferably gels or swells in water. There can be mentioned, for example, non-ionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl etherformalin condensate, polyoxyethylene polyoxypropylene block polymer, alkyl polyoxyethylene polypropylene block polymer ether, polyoxyethylene alkyl amine, polyoxyethylene fatty aci amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether type silicone, ester type silicone, fluorine-containing surfactant, polyoxyethylene castor oil, polyoxyethylene hardened castor oil and the like; anionic surfactants such as alkyl sulfate, polyoxyethylene alkyl ether sulfate, polyoxyethylene alkyl phenyl ether sulfate, polyoxyethylene styryl phenyl ether sulfate, alkylbenzenesulfonic acid salt, ligninsulfonic acid salt, alkylsulfosuccinic acid salt, naphthalenesulfonic acid salt, alkylnaphthalenesulfonic acid salt, naphthalenesulfonic acid-formalin condensate salt, alkylnaphthalenesulfonic acid-formalin condensate salt, fatty acid salt, polycarboxylic acid salt, N-methyl-fatty acid sarcosinate, resin acid salt, polyoxyethylene alkyl ether phosphate, polyoxyethylene alkylphenyl ether phosphate and the like; cationic surfactants including alkyl amine salts such as laurylamine hydrochloride, stearylamine hydrochloride, oleylamine hydrochloride, stearylamine acetate, stearylaminopropylamine acetate, alkyl trimethyl ammonium chloride, alkyl dimethyl benzalkonium chloride and the like; and ampholytic surfactants such as betaine type (e.g. dialkyldiaminoethylbetaine or alkyldimethylbenzylbetaine), amino acid type (e.g. dialkylaminoethylglycine or alkyldimethylbenzylglycine) and the like.

As the binder and tackifier, there can be mentioned, for example, carboxymethyl cellulose or a salt thereof, dextrin, water-soluble starch, xanthane gum, guar gum, sucrose, polyvinylpyrrolidone, gum arabi, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and natural phospholipid (e.g. cephalinic acid or lecithin).

As the thickening agent, there can be mentioned, for example, water-soluble polymers such as xanthan gum, guar gum, carboxymethyl cellulose, polyvinylpyrrolidone, carboxyvinyl polymer, acrylic polymer, starch derivative, polysaccharide and the like; and inorganic fine powders such as high-purity bentonite, white carbon and the like.

As the coloring agent, there can be mentioned, for example, inorganic pigments such as iron oxide, titanium oxide, Prussian Blue and the like; and organic dyes such as Alizarine dye, azo dye, metal phthalocyanine dye and the like.

As the spreader, there can be mentioned, for example, silicone-based surfactant, cellulose powder, dextrin, processed starch, polyaminocarboxylic acid chelate compound, crosslinked polyvinylpyrrolidone, maleic acid and styrene, methacrylic acid copolymer, half ester between polyhydric alcohol polymer and dicarboxylic acid anhydride, and water-soluble salt of polystyrenesulfonic acid.

As the sticker, there can be mentioned, for example, surfactant (e.g. sodium dialkylsulfosuccinate, polyoxyethylene alkyl ether, polyoxyethylene alkylphenyl ether, or polyoxyethylene fatty acid ester), paraffin, terpene, polyamide resin, polyacrylic acid salt, polyoxyethylene, wax, polyvinyl alkyl ether, alkylphenol-formalin condensate, and synthetic resin emulsion.

As the anti-freeze, there can be mentioned, for example, polyhydric alcohol (e.g. ethylene glycol, diethylene glycol, propylene glycol, or glycerine).

As the solidification inhibitor, there can be mentioned, for example, polysaccharide (e.g. starch, alginic acid, mannonse or galactose), polyvinylpyrrolidone, white carbon, ester gum and petroleum resin.

As the disintegrator, there can be mentioned, for example, sodium tripolyphosphate, sodium hexametaphosphate, stearic acid metal salt, cellulose powder, dextrin, methacrylic acid ester copolymer, polyvinylpyrrolidone, polyaminocarboxylic acid chelate compound, sulfonated styreneisobutylene-maleic anhydride copolymer, and starchpolyacrylonitrile graft copolymer.

As the decomposition inhibitor, there can be mentioned, for example, desiccants such as zeolite, quick lime, magnesium oxide and the like; antioxidants such as phenol type, amine type, sulfur type, phosphoric acid type and the like; and ultraviolet absorbents such as salicylic acid type, benzophenone type and the like.

When the present pest control agent contains the above-mentioned additive components, their contents based on mass are selected in a range of ordinarily 5 to 95%, preferably 20 to 90% in the case of carrier, ordinarily 0.1 to 30%, preferably 0.5 to 10% in the case of surfactant, and ordinarily 0.1 to 30%, preferably 0.5 to 10% in the case of other additives.

The present pest control agent is used in any formulation selected from dust formulation, dust-granule mixture, granule, wettable powder, water-soluble concentrate, water dispersible granule, tablet, Jumbo, emulsifiable concentrate, oil formulation, solution, flowable concentrate, emulsion, microemulsion, suspoemulsion, ultra-low volume formulation, microcapsule, smoking agent, aerosol, baiting agent, paste, etc.

In actual use of the formulation, the formulation can be used per se or after dilution with a diluent (e.g. water) in a given concentration. The application of the formulations containing the present compound or of its dilution product can be conducted by a method ordinarily used, such as dispersion (e.g. spraying, misting, atomizing, powder dispersion, granule dispersion, on-water-surface dispersion, or inbox dispersion), in-soil application (e.g. mixing or drenching), on-surface application (e.g. coating, dust coating or covering), immersion, poison bait, smoking and the like. It is also possible to mix the above-mentioned active ingredient with a livestock feed in order to prevent the infestation and growth of injurious pest, particularly injurious insect in the excreta of livestock.

The proportion of the active ingredient in the present pest control agent is appropriately selected so as to meet the necessity. The active ingredient is appropriately selected, for example, in the following range.

In dust formulation, dust-granule mixture, etc.
    0.01 to 20% (mass), preferably 0.05 to 10% (mass)
In granule, etc.
    0.1 to 30% (mass), preferably 0.5 to 20% (mass)

In wettable powder, water dispersible granule, etc.
  1 to 70% (mass), preferably 5 to 50% (mass)
In water-soluble concentrate, solution, etc
  1-95% (mass), preferably 10 to 80% (mass)
In emulsifiable concentrate, etc.
  5 to 90% (mass), preferably 10 to 80% (mass)
In oil formulation, etc.
  1 to 50% (mass), preferably 5 to 30% (mass)
In flowable concentrate, etc.
  5 to 60% (mass), preferably 10 to 50% (mass)
In emulsion, microemulsion, suspoemulsion, etc.
  5 to 70% (mass), preferably 10 to 60% (mass)
In tablet, baiting agent, paste, etc.
  1 to 80% (mass), preferably 5 to 50% (mass)
In smoking agent, etc.
  0.1 to 50% (mass), preferably 1 to 30% (mass)
In aerosol, etc.
  0.05 to 20% (mass), preferably 0.1 to 10% (mass)

The formulation is sprayed after dilution in an appropriate concentration, or applied directly.

When the present pest control agent is used after dilution with a diluent, the concentration of active ingredient is generally 0.1 to 5,000 ppm. When the formulation is used per se, the application amount thereof per unit area is 0.1 to 5,000 g per 1 ha in terms of active ingredient compound; however, the application amount is not restricted thereto.

Incidentally, the present pest control agent is sufficiently effective when using the present compound alone as an active ingredient. However, in the present pest control agent, there may be mixed or used in combination, as necessary, fertilizers and agricultural chemicals such as insecticide, acaricide, nematicide, synergist, fungicide, anti-viral agent, attractant, herbicide, plant growth-controlling agent and the like. In this case, a higher effect is exhibited.

Below are shown examples of the known insecticide compounds, acaricide compounds, nematicide compounds and synergist compounds, which may be mixed or used in combination.

1. Acetylcholinesterase inhibitors
  (1A) Carbamates: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb;
  (1B) Organophosphates: acephate, azamethiphos, azinphosethyl, azinphos-methyl, cadusafos, chlorethoxyfos, chlorfenvinphos, chlormephos, chlorpyrifos, chlorpyrifos-methyl, coumaphos, cyanophos, demoton-5-methyl, diamidafos, diazinon, dichlorvos, dicrotophos, dimethoate, dimethylvinphos, dioxabenzofos, disulfoton, DSP, EPN, ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-(methoxyaminothiophosphoryl)salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos, fluprazofos
2. GABA-gated chloride channel antagonists
  (2A) Cyclodiene organochlorines: chlordane, endosulfan, gamma-BCH;
  (2B) Phenylpyrazoles: acetoprol, ethiprole, fipronil, pyrafluprole, pyriprole, RZI-02-003 (code number)
3. Sodium channel modulators
  (3A) Pyrethroids/Pyrethrins: acrinathrin, allethrin (includes d-cis-trans and d-trans), bifenthrin, bioallethrin, bioallethrin S-cyclopentenyl, bioresmethrin, cycloprothrin, cyfluthrin (includes beta-), cyhalothrin (includes gamma- and lambda-), cypermethrin (includes alpha-, beta-, theta- and zeta-), cyphenothrin [includes (IR)-trans-isomers], deltamethrin, empenthrin, esfenvalerate, etofenprox, fenpropathrin, fenvalerate, flucythrinate, flumethrin, taufluvalinate (includes tau-), halfenprox, imiprothrin, metofluthrin, permethrin, phenothrin [includes (IR)-trans-isomer], prallethrin, profluthrin, pyrethrine, resmethrin, RU15525 (code number), silafluofen, tefluthrin, tetramethrin, tralomethrin, transfluthrin, ZX18901 (code number), fluvalinate, tetramethylfluthrin, meperfluthrin;
  (3B) DDT/Methoxychlor: DDT, methoxychlor
4. Nicotinic acetylcholine receptor agonist/antagonist
  (4A) Neonicotinoids: acetamiprid, clothianidin, dinotefuran, imidacloprid, nitenpyram, thiacloprid, thiamethoxam;
  (4B) Nicotine: nicotine-sulfate
5. Nicotinic acetylcholine receptor allosteric activators
  Spinosyns: spinetoram, spinosad
6. Chloride channel activators
  Avermectins, Milbemycins: abamectin, emamectin benzoate, lepimectin, milbemectin, ivermectin, polynactins
7. Juvenile hormone mimics
  diofenolan, hydroprene, kinoprene, methothrin, fenoxycarb, pyriproxyfen
8. Miscellaneous non-specific (multi-site) inhibitors
  1,3-dichloropropene, DCIP, ethylene dibromide, methyl bromide, chloropicrin, sulfuryl fluoride
9. Antifeedant
  pymetrozine, flonicamid, pyrifluquinazon
10. Mite growth inhibitors
  clofentezine, diflovidazin, hexythiazox, etoxazole
11. Microbial disruptors of insect midgut membranes
  BT agent: Bacillus sphaericus, Bacillus thuringiensis subsp. aizawai, Bacillus thuringiensis subsp. israelensis, Bacillus thuringiensis subsp. kurstaki, Bacillus thuringiensis subsp. tenebrionis, Bt crop proteins (Cry1Ab, Cry1Ac, Cry1Fa, Cry2Ab, mCry3A, Cry3Ab, Cry3Bb, Cry34/35Ab1), Bacillus popilliae, Bacillus subtillis
12. Inhibitors of mitochondrial ATP synthase
  diafenthiuron;
  Organotin miticides: azocyclotin, cyhexatin, fenbutatin oxide;
  propargite, tetradifon
13. Uncouplers of oxidative phosphorylation via disruption of the proton gradient
  chlorfenapyr, DNOC
14. Nicotinic acetylcholine receptor channel blockers
  Nereistoxin analogues: bensultap, cartap, thiocyclam, thiosultap
15. Inhibitors of chitin biosynthesis, type 0
  Benzoylureas: bistrifluoron, chlorfluazuron, diflubenzuron, flucycloxuron, flufenoxuron, hexaflumuron, lufenuron, novaluron, noviflumuron, teflubenzuron, triflumuron, fluazuron
16. Inhibitors of chitin biosynthesis, type 1
  buprofezin
17. Moulting disruptor, Dipteran
  cyromazine
18. Ecdysone receptor agonist (ecdysis acceleration)
  Diacylhydrazines: chromafenozide, halofenozide, methoxyfenozide, tebufenozide
19. Octopamine receptor agonist
  amitraz 20. Mitochondrial complex III electron transport inhibitors
cyflumetofen, hydramethylnon, acequinocyl, fluacrypyrim, cyenopyrafen
21. Mitochondrial complex I electron transport inhibitors
METI acaricides and insecticides: fenazaquin, fenpyroximate, pyridaben, pyrimidifen, tebufenpyrad, tolfenpyrad
Other: rotenone
22. Sodium channel blockers
indoxacarb, metaflumizone
23. Inhibitors of lipid synthesis
Tetronic and Tetramic acid derivatives: spirodiclofen, spiromesifen, spirotetramat
24. Mitochondrial complex IV electron transport inhibitors
aluminium phosphide, phosphine, zinc phosphide, calcium cyanide
25. Neuronal inhibitors (unknown mode of action)
bifenazate
26. Aconitase inhibitors
sodium fluoroacetate
27. Synergists
piperonyl butoxide, DEF
28. Ryanodine receptor modulators
chlorantraniliprole, flubendiamide, cyantraniliprole
29. Compounds with unknown mode of action
azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, fulsulfamide, karanjin, metham, methoprene, methoxyfenozide, methyl isothiocyanate, pyridalyl, pyrifluquinazon, sulcofuron-sodium, sulfluramid, sulfoxaflor
30. Entomopathogenic fungi, nematode-pathogenic microorganisms
*Beauveria bassiana, Beauveria tenella, Verticillium lecanii, Pacilimyces tenuipes, Paecilomyces fumosoroceus, Beauveria brongniartii, Monacrosporium phymatophagum, Pasteuriapenetrans*
31. Sex pheromone
(Z)-11-hexadecenal, (Z)-11-hexadecenyl acetate, litlure-A, litlure-B, Z-13-eicosene-10-one, (Z,E)-9,12-tetradecadienyl acetate, (Z)-9-tetradecen-1-ol, (Z)-11-tetradecenyl acetate, (Z)-9,12-tetradecadienyl acetate, (Z,E)-9,11-detradecadienyl acetate Below are shown examples of the known fungicide or disease damage control agent compounds which may be mixed or used in combination.
1. Nucleic acid biosynthesis inhibitors
Acylalanines: benalazyl, benalazyl-M, furalaxyl, metalaxyl, metalaxyl-M;
Oxazolidinones: oxadixyl;
Butyrolactones: clozylacon, ofurace;
Hydroxy-(2-amino)pyrimidines: bupirimate, dimethirimol, ethirimol;
Isoxazoles: hymexazol;
Isothiazolones: octhilinone;
Carboxylic acids: oxolinic acid
2. Mitosis and cell division inhibitors
Benzoimidazoles: benomyl, carbendazim, fuberidazole, thiabendazole;
Thiophanates: thiophanate, thiophanate-methyl;
N-phenylcarbamates: diethofencarb;
Toluamides: zoxamide;
Phenylureas: pencycuron;
Pyridinylmethylbenzamides: fluopicolide
3. Respiratory inhibitors
Pyrimidinamines: diflumetorim;
Carboxamides: benodanil, flutolanil, mepronil, fluopyram, fenfuram, carboxin, oxycarboxin, thifluzamide, bixafen, furametpyr, isopyrazam, penflufen, penthiopyrad, sedaxane, boscalid;
Methoxy-acrylates: azoxystrobin, enestroburin, picoxystrobin, pyraoxystrobin;
Methoxy-carbamates: pyraclostrobin, pyrametostrobin;
Oxyimino acetates: kresoxim-methyl, trifloxystrobin;
Oxyimino-acetamides: dimoxystrobin, metominostrobin, orysastrobin;
Oxazolidine-diones: famoxadone;
Dihydro-dioxazines: fluoxastrobin;
Imidazolinones: fenamidone;
Benzyl-carbamates: pyribencarb;
Cyano-imidazoles: cyazofamid;
Sulfamoyl-triazoles: amisulbrom;
Dinitrophenyl crotonates: binapacryl, methyldinocap, dinocap;
2,6-Dinitro-anilines: fluazinam;
Pyrimidinone hydrazones: ferimzone;
Tri phenyl tin compounds: TPTA, TPTC, TPTH;
Thiophene-carboxamides: silthiofam;
Triazolo-pyrimidylamines: ametoctradin
4. Amino acid and protein synthesis inhibitors
Anilino-pyrimidines: cyprodinil, mepanipyrim, pyrimethanil;
Enopyranuronic acid antibiotic: blasticidin-S, mildiomycin;
Hexopyranosyl antibiotic: kasugamycin;
Glucopyranosyl antibiotic: streptomycin;
Tetracycline antibiotic: oxytetracycline
5. Signal transduction inhibitors
Aryloxyquinoline: quinoxyfen;
Quinazolines: proquinazid;
Phenylpyrroles: fenpiclonil, fludioxonil;
Dicarboxylmides: chlozolinate, iprodione, procymidone, vinclozolin
6. Lipid synthesis and membrane integrity inhibitors
Phosphoro-thiolates: edifenphos, iprobenfos, pyrazophos;
Dithiolanes: isoprothiolane;
Aromatic hydrocarbons: biphenyl, chloroneb, dicloran, quintozenes, tecnazene, tolclofos-methyl;
1,2,4-Thiadiazoles: etridiazole
Carbamates: iodocarb, propamocarb-hydrochloride, prothiocarb;
Cinnamic acid amides: dimethomorph, flumorph;
Valineamide carbamates: benthiavalicarb-isopropyl, iprovalicarb, valifenalate;
Mandelic acid amides: mandipropamid;
*Bacillus subtilis* and the fungicidal lipopeptides produced:
*Bacillus subtilis* (strain: QST 713)
7. Inhibitors of sterol biosynthesis in membranes
piperazines: triforine;
Pyridines: pyrifenox;
Pyrimidines: fenarimol, nuarimol;
Imidazoles: imazalil, oxpoconazole-fumarate, pefurazoate, prochloraz, triflumizole;
Triazoles: azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, furconazole, furconazole-cis, quinconazole;

Morpholines: aldimorph, dodemorph, fenpropimorph, tridemorph;
Piperidines: fenpropidin, piperalin;
Spiroketal amines: spiroxamine;
Hydroxyanilides: fenhexamid;
Thiocarbamates: pyributicarb;
Allylamines: naftifine, terbinafine 8. Glucan synthesis inhibitors
Glucopyranosyl type antibiotic: validamycin;
Peptidylpyridine nucleotide compound: polyoxin 9. Melanine synthesis inhibitors
Isobenzo-furanones: phthalide;
Pyrrolo-quinolines: pyroquilon;
Triazolobenzo-thiazoles: tricyclazole;
Carboxamides: carpropamid, diclocymet;
Propionamides: fenoxanil 10. Host plant defence inducers
Benzo-thiadiazoles: acibenzolar-5-methyl;
Benzoisothiazoles: probenazole;
Thiadiazole-carboxamides: tiadinil, isotianil
Natural compound: laminarin 11. Compounds with unknown mode of action
Copper compound: copper hydroxide, copper dioctanoate, copper oxychloride, copper sulfate, cuprous oxide, oxine-copper, Bordeaux mixture, copper nonyl phenol sulphonate;
Sulfur compound: sulfur;
Dithiocarbamates: ferbam, mancozeb, maneb, metiram, propineb, thiram, zineb, ziram, cufraneb;
Phthalimides: captan, folpet, captafol;
Chloronitriles: chlorothalonil;
Sulfamides: dichlofluanid, tolylfluanid;
Guanidines: guazatine, iminoctadine-albesilate, iminoctadine-triacetate, dodine;
Other compound: anilazine, dithianon, cymoxanil, fosetyl (alminium, calcium, sodium), phosphorus acid and salts, tecloftalam, triazoxide, flusulfamide, diclomezine, methasulfocarb, ethaboxam, cyflufenamid, metrafenone, potassium bicarbonate, sodium bicarbonate, BAF-045 (code number), BAG-010 (code number), benthiazole, bronopol, carvone, chinomethionat, dazomet, DBEDC, debacarb, dichlorophen, difenzoquat-methyl sulfate, dimethyl disulfide, diphenylamine, ethoxyquin, flumetover, fluoroimide, flutianil, fluxapyroxad, furancarboxylic acid, metam, nabam, natamycin, nitrapyrin, nitrothalisopropyl, o-phenylphenol, oxazinylazole, oxyquinoline sulfate, phenazine oxide, polycarbamate, pyriofenone, S-2188 (code number), silver, SYP-Z-048 (code number), tebufloquin, tolnifanide, trichlamide, mineral oils, organic oils Below are shown examples of the known herbicidal compounds and plant growth-controlling compounds which may be mixed or used in combination.

A1. Acetyl CoA carboxylase (ACCase) inhibitors
(A1-1) Aryloxyphenoxy propionate: clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-etotyl, haloxyfop-P, metamifop, propaquizafop, quizalofop-ethyl, quizalofop-P-ethyl, quizalofop-P-tefuryl, fenthiaprop-ethyl;
(A1-2) Cyclohexandiones: alloxydim, butroxydim, clethodim, cycloxydim, profoxydim, sethoxydim, tepraloxydim, tralkoxydim;
(A1-3) Phenylpyrazolines: aminopyralid, pinoxaden;

B. Acetolactic synthase (ALS) inhibitors
(B-1) Imidazolinones: imazamethabenz-methyl, imazamox, imazapic (includes salts with amine, etc.), imazapyr (includes salts with isopropylamine, etc.), imazaquin, imazathapyr;
(B-2) Pyrimidinyloxy benzoate: bispyribac-sodium, pyribenzoxim, pyriftalid, pyriminobac-methyl, pyrithiobac-sodium, pyrimisulfan;
(B-3) Sulfonylaminocarbonyl-triazolinones: flucarbazonesodium, thiencarbazone (includes sodium salt, methyl ester, etc.), propoxycarbazone-sodium, procarbazone-sodium;
(B-4) Sulfonylureas: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, thifensulfuron-methyl, triasulfuron, tribenuron-methyl, trifloxysulfuron-sodium, triflusulfuron-methyl, tritosulfuron, orthosulfamuron, propgirisulfuron, metazosulfuron, flucetosulfuron;
(B-5) Triazolopyrimidines: cloransulam-methyl, diclosulam, florasulam, flumetsulam, metosulam, penoxsulam, pyroxsulam;

C1. Photosynthesis at photosystem II inhibitors (1)
(C1-1) Phenyl-carbamates: desmedipham, phenmedipham;
(C1-2) Pyridazinones: chloridazon, brompyrazon;
(C1-3) Triazines: ametryn, atrazine, cyanazine, desmetryne, dimethametryn, eglinazine-ethyl, prometon, prometryn, propazine, simazine, simetryn, terbumeton, terbuthylazine, terbutryn, trietazine;
(C1-4) Triazinones: metamitron, metribuzin;
(C1-5) Triazolinones: amicarbazone;
(C1-6) Uracils: bromacil, lenacil, terbacil;

C2. Photosynthesis at photosystem II inhibitors (2)
(C2-1) Amides: pentanochlor, propanil;
(C2-2) Ureas: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, metobenzuron;

C3. Photosynthesis at photosystem II inhibitors (3)
(C3-1) Benzothiadiazones: bentazone;
(C3-2) Nitriles: bromofenoxim, bromoxynil (includes esters of butyric acid, octanoic acid, heptanoic acid, etc.), ioxynil;
(C3-3) Phenylpyrazines: pyridafol, pyridate;

D. Photosystem-1-electron acceptors
(D-1) Bipyridyliums: diquat, paraquat dichloride;

E. Protoporphyrinogen oxidase (PPO) inhibitors
(E-1) Diphenylethers: acifluorfen-sodium, bifenox, chiomethoxyfen, ethoxyfen-ethyl, fluoroglycofen-ethyl, framesafen, lactofen, oxyfluorfen;
(E-2) N-phenylphthalimides: cinidon-ethyl, flumiciorac-pentyl, flumioxazin, chlorphthalim;
(E-3) Oxydiazoles: oxadiargyl, oxadiazon;
(E-4) Oxazolidinediones: pentoxazone;
(E-5) Phenylpyrazoles: fluazolate, pyraflufen-ethyl;
(E-6) Pyrimidinediones: benzfendizone, butafenacil, saflufenacil;
(E-7) Thiadiazoles: fluthiacet-methyl, thidiazimin;
(E-8) Triazolinones: azafenidin, carfentrazone-ethyl, sulfentrazone, bencarbazone;
(E-9) Other compound: flufenpyr-ethyl, profluazol, pyreclonil, SYP-298 (code number), SYP-300 (code number);

F1. Inhibitors of carotenoid biosynthesis at the phytoene desaturase step (PDS)
(F1-1) Pyridazinones: norflurazon;
(F1-2) Pyrimidinecarboxamides: diflufenican, picolinafen;
(F1-3) Other compound: beflubutamid, fluridone, fluorochloridone, flurtamone;
F2. 4-Hydroxyphenylpyruvate dioxygenase (HPPD) inhibitors
(F2-1) Callistemones: mesotrione;
(F2-2) Isoxazoles: pyrasulfotole, isoxaflutole, isoxachlortole;
(F2-3) Pyrazoles: benzofenap, pyrazolynate, pyrazoxyfen;
(F2-4) Ttiketones: sulcotrione, tefuryltrion, tembotrione, pyrasulfotole, topramezone, bicyclopyrone;
F3. Carotinoid biosynthesis inhibitors (unknown target)
(F3-1) Diphenylethers: acionifen;
(F3-2) Isoxazolidinones: clomazone;
(F3-3) Triazoles: amitrole;
G. EPSP synthase inhibitors (aromatic amino acid biosynthesis inhibitors)
(G-1) Glycines: glyphosate (includes salts of sodium, amine, propylamine, ispropylamine, dimethylamine, trimesium etc.);
H. Glutamine synthetase inhibitors
(H-1) Phosphinic acids: bilanafos, glufosinate (includes salts of amine, sodium, etc.);
I. Dihydropteroate (DHP) inhibitors
(I-1) Carbamates: asulam;
K1. Microtubule assembly inhibitors
(K1-1) Benzamides: propyzamide, tebutam;
(K1-2) Benzoic acids: chlorthal-dimethyl;
(K1-3) Dinitroanilines: benfluralin, butralin, dinitramine, ethalfluralin, fluchloralin, oryzalin, pendimethalin, prodiamine, trifluralin;
(K1-4) Phosphoroamidates: amiprofos-methyl, butamifos;
(K1-5) Pyridines: dithiopyr, thiazopyr;
K2. Inhibitors of mitosis/microtubule organization
(K2-1) Carbamates: carbetamide, chlorpropham, propham, swep, karbutilate;
K3. Very-long-chain fatty acids (VLCFAs) inhibitors (cell division inhibitors)
(K3-1) Acetamides: diphenamid, napropamide, naproanilide;
(K3-2) Chloroacetamides: acetochlor, alachlor, butachlor, butenachlor, diethatyl-ethyl, dimethachlor, dimethenamid, dimethenamid-P, metazachlor, metolachior, pethoxamid, pretilachlor, propachlor, propisochlor, S-metolachlor, thenylchlor;
(K3-3) Oxyacetamides: flufenacet, mefenacet;
(K3-4) Tetrazolinones: fentrazamide;
(K3-5) Other compound: anilofos, bromobutide, cafenstrole, indanofan, piperophos, fenoxasulfone, pyroxasulfone, ipfencarbazone;
L. Cellulose synthesis inhibitors
(L-1) Benzamides: isoxaben;
(L-2) Nitriles: dichiobenil, chlorthiamid;
(L-3) Triazolocarboxamides: flupoxame;
M. Uncouplers (Membrane disruptors)
(M-1) Dinitrophenols: dinoterb, DNOC (includes salts of amine, sodium, etc.);
N. Lipid synthesis inhibitors (excluding ACCase inhibitors)
(N-1) Benzofurans: benfuresate, ethofumesate;
(N-2) Halogenated carboxylic acids: dalapon, flupropanate, TCA (includes salts of sodium, calcium, ammonia, etc.);
(N-3) Phosphorodithioates: bensulide;
(N-4) Thiocarbamates: butylate, cycloate, dimepiperate, EPTC, esprocarb, molinate, orbencarb, pebulate, prosulfocarb, thiobencarb, tiocarbazil, tri-allate, vernolate
O. Synthetic auxins
(O-1) Benzoic acids: chloramben, 2,3,6-TBA, dicamba (includes salts of amine, diethylamine, isopropylamine, diglycolamine, sodium, lithium, etc.);
(O-2) Phenoxycarboxylic acids: 2,4,5-T, 2,4-D (includes salts of amine, diethylamine, triethanolamine, isopropylamine, sodium, lithium, etc.), 2,4-DB, clomeprop, dichlorprop, dichlorprop-P, MCPA, MCPA-thioethyl, MCPB (includes sodium salt, ethylester, etc.), mecoprop (includes salts of sodium, potassium, isopropylamine, trietanolamine, dimethylamine, etc.), mecoprop-P;
(O-3) Pyridine carboxylic acids: clopyralid, fluoroxypyr, picloram, triclopyr, triclopyr-butotyl;
(O-4) Quinoline carbxylic acids: quinclorac, quinmerac;
(O-5) Other compound: benazolin;
P. Auxin transport inhibitors
(P-1) Phthalamates: naptalam (includes salts with sodium, etc.);
(P-2) Semicarbazones: diflufenzopyr;
Z. Compounds with unknown mode of action
flamprop-M (includes methyl, ethyl and isopropyl esters), flamprop (includes methyl, ethyl and isopropyl esters), chlorflurenol-methyl, cinmethylin, cumyluron, daimuron, methyldymuron, difenzoquat, etobenzanid, fosamine, pyributicarb, oxaziclomefone, acrolein, AE-F-150954 (code number), aminocyclopyrachlor, cyanamide, heptamaloxyloglucan, indaziflam, triaziflam, quinoclamine, endothal-disodium, phenisopham Plant growth-controlling agent: 1-methylcyclopropene, 1-naphthylacetamide, 2,6-diisopropylnaphthalene, 4-CPA, benzylaminopurine, ancymidol, aviglycine, carvone, chiormequat, cloprop, cloxyfonac, cloxyfonac-potassium, cyclanilide, cytokinins, daminozide, dikegulac, dimethipin, ethephon, ethylchlozate, flumetralin, flurenol, flurprimidol, forchlorfenuron, gibberellin acid, inabenfide, indole acetic acid, indole butyric acid, maleic hydrazide, mefluidide, mepiquat chloride, n-decanol, paclobutrazol, prohexadione-calcium, prohydrojasmon, sintofen, thidiazuron, triacontanol, trinexapac-ethyl, uniconazole, uniconazole-P.

Below are shown examples of the known chemical injury-reducing compounds which may be mixed or used in combination.

benoxacor, furilazole, dichlormid, dicyclonone, DKA-24 (N1,N2-diallyl-N2-dichloroacetylglycineamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazoline), cloquintcet-methyl, 1,8-Naphthalic Anhydride, mefenpyrdiethyl, mefenpyr, mefenpyr-ethyl, fenchlorazole 0 ethyl, fenclorim, MG-191 (2-dichloromethyl-2-methyl-1,3-dioxane), cyometrinil, flurazole, fluxofenim, isoxadifen, isoxadifenethyl, mecoprop, MCPA, daimuron, 2,4-D, MON 4660 (code number), oxabetrinil, cyprosulfamide and TI-35 (code number)

The pest targeted by the present invention refers to pest of Orthoptera, Thysanoptera, Hemiptera, Coleoptera, Diptera, Lepidoptera, Hymenoptera, Collembola, Thysanura, Blattodea, Isoptera, Psocoptera, Mallophaga, Anoplura, plant-feeding mites, plant parasitic nematodes, plant parasitic mollusc pests, other crop pests, nuisance pests, sanitary insects, parasites, etc. As examples of such pests, the following organism species can be mentioned.

As the Orthopteran pest, there can be mentioned, for example,

Tettigoniidae: *Ruspolia lineosa*, etc.,
Gryllidae: *Teleogryllus emma*, etc.,
Gryllotalpidae: *Gryllotalpa orientalis*,
Locustidae: *Oxya hyla* intricate, *Locusta migratoria, Melanoplus sanguinipes*, etc.,
Pyrgomorphidae: *Atractomorpha lata*,
Acrididae: *Euscyrtus japonicus*
Tridactylidae: *Xya japonicus*, etc.

As the Thysanopteran pests, there can be mentioned, for example,

Thripidae: *Frankliniella intonsa, Frankliniella occidentalis, Scirtothrips dorsalis, Thrips palmi, Thrips tabaci*, etc.,
Phlaeothripidaes: *Ponticulothrips diospyrosi, Haplothrips aculeatus*, etc.

As the Hemipteran pest, there can be mentioned, for example,

Cicadidae: *Mogannia minuta*, etc.,
Cercopidae: *Aphorphora intermedia*, etc.,
Membracidae: *Machaerotypus sibiricus*, etc.,
Deltcephalidae: *Arboridia apicalis, Empoasca onukii, Nephotettix cincticeps, Recilia dorsalis*, etc.,
Cixiidae: *Pentastiridius apicalis*, etc.,
Delphacidae: *Laodelphax striatellus, Nilaparvata lugens, Sogatella furcifera*, etc.,
Meenoplidae: *Nisia nervosa*, etc.,
Derbidae: *Kamendaka saccharivora*, etc.,
*Cixidia okunii: Achilus flammeus*, etc.,
Ricamidae: *Orosanga japonicus*, etc.,
Flatidae: *Mimophantia maritima*, etc.,
Psyllidae: *Cacopsylia pyrisuga*, etc.,
Calophyidae: *Calophya mangiferae*, etc.,
Phylloxeridae: *Daktulosphaira vitifoliae*, etc.,
Chemidae: *Adelges laricis*,
Adelgidae: *Adelges tsugae*, etc.,
Aphididae: *Acyrthosiphon pisum, Aphis gossypii, Aphis spiraecola, Lipaphis erysimi, Myzuspersicae*,
Aphrastasia tsugae: *Schizaphis graminum, Rhopalosiphum padi*, etc.,
Aleyrodidae: *Aleurocanthus spiniferus, Bemisia tabaci, Bemisia argentifolii, Trialeurodes vaporariorum*, etc.,
Margarodidae: *Drosicha corpulenta, Icerya purchasi*, etc.,
Pseudococcidae: *Dysmicoccus brevipes, Planococcus citri, Pseudococcus comstocki*, etc.,
Coccidae: *Ceroplastes ceriferus*, etc.,
Aclerdidae: *Aclerda takahasii*, etc.,
Diaspididae: *Aonidella aurantii, Diaspidiotus perniciosus, Unaspis yanonensis*, etc.,
Miridae: *Lygus hesperus, Trigonotylus caelestialium*, etc.,
Tingitidae: *Stephanitis pyrioides, Stephanitis nashi*, etc.,
Pentatomidae: *Eysarcoris aeneus, Lagynotomus elongatus, Nezara viridula, Plautia crssota*, etc.,
Plataspidae: *Megacopta cribaria*, etc.,
Lygaeidae: *Cavelerius saccharivorus*, etc.,
Malcidae: *Malcus japonicus*, etc.,
Pyrrhocoridae: *Dysdercus cingulatus*, etc.,
Alydidae: *Leptocorisa acuta, Leptocorisa chinensis*, etc.,
Coreidae: *Anacanthocoris striicornis*, etc.,
Rhopalidae: *Rhopalus maculatus*, etc.,
Cimicidae: *Cimex lectularius*, etc.

As the Coleoptera pests, there can be mentioned, for example,

Scarabaeidae: *Anomara cuprea, Anomara rufocuprea, Popillia japonica, Oryctes rhinoceros*, etc.,
Elateridae: *Agriotes ogurae, Melanotus okinawensis, Melanotos fortnumi fortnumi*, etc.,
Dermestidae: *Anthrenus verbasci*, etc.,
Bostrichidae: *Heterobostrychus hamatipennis*, etc.,
Anobiidae: *Stegobium paniceum*, etc.,
Ptinidae: *Pitinus clavipes*, etc.,
Trogositidae: *Tenebroides manritanicus*, etc.,
Cleridae: *Necrobia rufipes*,
Nitidulidae: *Carpophilus hemipterus*, etc.,
Silvanidae: *Ahasverus advena*, etc.,
Laemophloeidae: *cryptolestes ferrugineus*, etc.,
Coccinellidae: *Epilachna varivestis, Henosepilachna vigintioctopunctata*, etc.,
Tenebrionidae: *Tenebrio molitor, tribolium castaneum*, etc.,
Meloidae: *Epicauta gorhami*, etc.,
Cerambycidae: *Anoplophora glabripennis, Xylotrechus pyrroderus, Monochamus alternatus*, etc.,
Bruchidae: *Callosobruchus chinensis*, etc.,
Chrysomelidae: *Leptinotarsa decemlineata, Diabrotica virgifera, Phaedon brassicae, Phyllotreta striolata*, etc.,
Brentidae: *Cylas formicarius*, etc.,
Curculionidae: *Hypera postica, Listroderes costirostris, Euscepes postfasciatus*, etc.,
Erirhinidae: *Echinocnemus bipunctatus, Lissorhoptrus oryzophilus*, etc.,
Rhynchophoridae: *Sitophilus zeamais, Sphenophrus vanetus*, etc.,
Limnoriidae: *Tomicus piniperda*, etc.,
Platypodidae: *Crossotarsus niponicus*, etc.,
Lyctidae: *Lyctus brunneus*, etc.

As the Diptera pest, there can be mentioned, for example,

Tipulidae: *Tipila aino*, etc.,
Bibionidae: *Plecia nearctica*, etc.,
Fungivoridae: *Exechia shiitakevora*, etc.,
Lycoriidae: *Pnyxiascabiei*, etc.,
Cecidomyiidae: *Asphondylia yusimai, Mayetiola destructor*, etc.,
Culicidae: *Aedes aegypti, Culex pipiens pallens*, etc.,
Simuliidae: *Simulim takahasii*, etc.,
Chironomidae: *Chironomus oryzae*, etc.,
Tabanidae: *Chrysops suavis, Tabanus trigonus*, etc.,
Syrphidae: *Eumerus strigatus*, etc.,
Trypetidae: *Bactrocera dorsalis, Euphranta japonia, Ceratitis capitata*, etc.,
Agromyzidae: *Liriomyza trifolii, Chromatomyia horticola*, etc.,
Chloropidae: *Meromyza nigriventris*, etc.,
Drosophilidae: *Drosophila suzukii, Drosophila melanogaster*, etc.,
Ephydridae: *Hydrellia griseola*, etc.,
Hippoboscidae: *Hippobosca equina*, etc.,
Scatophagidae: *Parallelpmma sasakawae*, etc.,
Anthomyiidae: *Delia antiqua, Delia platura*, etc.,
Fanniidae: *Fannia canicularis*, etc.,
Muscidae: *Musca domestica, Stomoxys calcitrans*, etc.,
Sarcophagidae: *Sarcophaga peregrina*, etc.,
Gasterophilidae: *Gasterophilus intestinalis*, etc.,
Hypodermatidae: *Hypoderma lineatum*, etc.,
Oestridae: *Oestrus ovis*, etc.

As the Lepidoptera pest, there can be mentioned, for example,

Hepialidae: *Endoclita excrescens*, etc.,
Heliozelidae: *Antispila ampelopsia*, etc.,
Cossidae: *Zeuzera leuconotum*, etc.,
Tortricidae: *Archips fuscocupreanus, Adoxophyes orana fasciata, Grapholita molesta, Homona magnanima, Leguminivora glycinivorella, Cydia pomenella*, etc., Cochylidae: *Eupoecilia ambiguella*, etc.,
Psychidae: *Bambalina* sp., *Eumeta minuscule*, etc.,
Tineidae: *Nemapogon granella*, *Tinea translucens*, etc.,
Nepticulidae: *Bucculatrix pyrivorella*, etc.,
Lyonetiidae: *Lyonetia clerkella*, etc.,
Gracilariidae: *Caloptilia theivora*, *Phyllonorycter ringoniella*, etc.,
Phyllocnistidae: *Phyllocnistis citrella*, etc.,
Acrolepiidae: *Acrolepiopsis sapporensis*, etc.,
Yponomeutidae: *Plutella xylostella*, *Yponomeuta orientalis*, etc.,
Argyresthidae: *Argyresthia conjugella*, etc.,
Aegeriidae: *Nokona regalis*, etc.,
Gelechiidae: *Phthorimaea operculella*, *Sitotroga cerealella*, *Pectinophora gossypiella*, etc.,
Carposinidae: *Carposina sasakii*, etc.,
Zygaenidae: *Illiberis pruni*, etc.,
Heterogeneidae: *Monema flavescens*, etc.,
Crambidae: *Ancylolomia japonica*, *Chile suppressalis*, *Cnaphalocrosis medinalis*, *Ostrinia furnacalis*, *Ostrinia nubilalis*, etc.,
Pyralidae: *Cadra cautella*, *Galleria mellonella*, etc.,
Pterophoridae: *Nippoptilia vitis*, etc.,
Papilionidae: *Papilio xuthus*, etc.,
Pieridae: *Pieris rapae*, etc.,
Hesperiidae: *Parnara guttata guttata*, etc.,
Geometridae: *Ascotis selenaria*, etc.,
Lasiocampidae: *Dendrolimus spectabilis*, *Malacosomaneustrium testaceum*, etc.,
Sphingidae: *Agrius convolvuli*, etc.,
Lymantriidae: *Arna pseudoconspersa*, *Lymantria dispar*, etc.,
Arctiidae: *Hyphantria cunea*, etc.,
Noctuidae: *Agrotis ipsilon*, *Autographa nigrisigna*, *Helicoverpa armigera*, *Helicoverpa zea*, *Heliothis virescens*, *Spodoptera exigua*, *Spodoptera litura*, etc.

As the Hymenoptera pest, there can be mentioned, for example,
Argidae: *Arge pagana*, etc.,
Tenthredinidae: *Apethymus kuri*, *Athaliarosae ruficornis*, etc.,
Cynipidae: *Dryocosmus kuriphilus*, etc.,
Vespidae: *Vespa simillima xanthoptera*, etc.,
Formicidae: *Solenopsis invicta*, etc.,
Megachilidae: *Megachile nipponica*, etc.

As the Order Collembola pest, there can be mentioned, for example,
Sminthuridae: *Bourletiellahortensis*, etc.

As the Order Thysanura pest, there can be mentioned, for example,
Lepismatidae: *Lepisma saccharina*, *Ctenoiepisma villosa*, etc.

As the Blattodea pest, there can be mentioned, for example,
Blattidae: *Periplaneta americana*,
Blattellidae: *Blattella germanica*, etc.

As the Order Isoptera pest, there can be mentioned, for example,
Kalotermitidae: *Incisitermes minor*, etc.,
Rhinotermitidae: *Coptotermes formosanus*, etc.,
Termitidae: *Odontotermes formosanus*, etc.

As the Order Psocoptera pest, there can be mentioned, for example,
Trogiidae: *Trogium pulsatorium*, etc.,
Liposcelidaidae: *Liposcelis corrodens*, etc.

As the Order Mallophaga pest, there can be mentioned, for example,
Menoponidae: *Lipeurus caponis*, etc.,
Trichodectidae: *Damalinia bovis*, etc.

As the Order Anoplura pest, there can be mentioned, for example,
Haematopinidae: *Haematopinus suis*, etc.,
Pediculine: *Pediculus humanus*, etc.,
Linognathidae: *Linognathus setosus*, etc.,
Pthiridae: public louse, etc.

As the Plant-feeding mites, there can be mentioned, for example,
Eupodidae: *Penthaleus major*, etc.,
Tarsonemidae: *Phytonemus pallidus*, *Polyphagotarsonemus latus*, etc.,
Pyemotidae: *Siteroptes* sp., etc.,
Tenuipalpidae: *Brevipalpus lewisi*, etc.,
Tuckerellidae: *Tuckerella pavoniformis*, etc.,
Tetranychidae: *Eotetranychusboreus*, *Panonychus citri*, *Panonychus ulmi*, *Tetranychus urticae*, *Tetranychus kanzawai*, etc.,
Nalepellidae: *Trisetacus pini*, etc.,
Eriophyidae: *Aculops pelekassi*, *Epitrimerus pyri*, *Phyllocoptruta oleivola*, etc.,
Diptilomiopidae: *Diptacus crenatae*, etc.,
Acaridae: *Aleuroglyphus ovatus*, *Tyrophagus putrescentiae*, *Rhizoglyphus robini*, etc.

As the Plant-parasitic nematodes, there can be mentioned, for example,
Longidoridae: *Xiphinema* index, etc.,
Trichodoridae: *Paratrichodorus minor*, etc.,
Rhabditidae: *Rhabditella* sp., etc.,
Tylenchidae: *Aglenchussp*., etc.,
Tylodoridae: *Cephalenchus* sp., etc.,
Anguinidae: *Nothotylenchus acris*, *Ditylenchus destructor*, etc.,
Hoplolainidae: *Rotylenchulus reniformis*, *Helicotylenchus dihystera*, etc.,
Paratylenchidae: *Paratylenchus curvitatus*, etc.,
Meloidogynidae: *Meloidogyne incognita*, *Meloidogyne hapla*, etc.,
Heteroderidae: *Globodera rostochiensis*, *Heterodera glycines*, etc.,
Telotylenchidae: *Tylenchorhynchus claytoni* etc.,
Psilenchidae: *Psilenchus* sp., etc.,
Criconematidae: *Criconemoides* sp., etc.,
Tylenchulidae: *Tylenchulus semipenetrans*, etc.,
Sphaeronematidae: *Sphaeronema camelliae*, etc.,
Pratylenchidae: *Sphaeronema camelliae*, *Radopholus citrophilus*, *Radopholus similis*, *Nacobbus aberrans*, *Pratylenchus penetrans*, *Pratylenchus coffeae*, etc.,
Iotonchiidae: *Totonchium ungulatum*, etc.,
Aphelenchidae: *Aphelenchus avenae*, etc.,
Aphelenchoididae: *Aphelenchoides besseyi*, *Aphelenchoides fragariae*, etc.,
Palasitaphelenchidae: *Bursaphelenchus xylophilus*, etc.

As the plant parasitic mollusc pests, there can be mentioned, for example,
Pilidae: *Pomacea canaliculata*, etc.,
Veronicellidae: *Leavicaulis alte*, etc.,
Achatinidae: *Achatina fulica*, etc.,
Philomycidae: *Meghimatium bilineatum*, etc.,
Succineidae: *Succinealauta*, etc.,
Didcidae: *Discus pauper*, etc.,
Zonitidae: *Zonitoides yessoensis*, etc.,
Limacidae: *Limax flavus*, *Deroceras reticulatum*, etc.,
Hehelicarionidae: *Parakaliella harimensis*, etc., Bradybaenidae: *Acusta despecta sieboldiana, Bradybaena similaris*, etc.

As other pests such as injurious animals, uncomfortable animals, sanitary insects, livestock insects, parasites and the like, there can be mentioned, for example, Acari Macronysshidae: *Ornithonyssus sylvialum*, etc.,
Varroidae: *Varroa jacobsoni*, etc.,
Dermanyssidae: *Dermanyssus gallinae*, etc.,
Macronyssidae: *Ornithonyssus sylvialum*, etc.,
Ixodidae: *Boophilus microplus, Rhipicephalussanguineus, Haemaphysalis longicornis*, etc.,
Sarcoptidae: *Sarcoptes scabiei*, etc.,
Isopoda Armadillididae: *Armadillidium vulgare*, etc.,
Decapoda Astacidae: *Procambarus clarkii*, etc.,
Porcellionidae: *Armadillidium vulgare*, etc.,
Chilopoda pests: Scutigeromorpha Sutigeridae *Thereuonema tuberculata*, Scolopendromorpha *Scolopendra subpinipes* etc.,
Diplopoda pests: Polydesmida Paradoxosomatidae *Oxidus gracilis* etc.,
Araneae *Latrodectus hasseltii: Theridiiadae hasseltii*, etc.,
Clubionidae: *Chiracanthium japonicum*, etc.,
Order Scorpionida: *Androctonus crassicauda*, etc.,
Parasitic roundworm: *Ascaris lumbricoides, Syphacia* sp., *Wucherebia bancrofti*, etc.,
Parasitic flatworm: *Distomum* sp., *Paragonimus westermanii, Metagonimus yokokawai, Schistosoma japonicum, Taenia solium, Taeniarhynchus saginatus, Echinococcus* sp., *Diphyllobothrium latum*, etc.

The pest control agent of the present invention exhibits excellent control effect to the above-mentioned pests. Further, the present pest control agent exhibits control effect also to the above-mentioned pests, etc. which already have resistances to existing pest control agents. Furthermore, the present control agent can be applied to plants which already have resistances to insects, diseases, herbicides, etc., owing to genetic recombination, artificial mating, etc.

Next, there are described the production methods, formulation methods and applications of the present compound, in detail by way of Examples. However, the present invention is in no way restricted by these Examples.

There are also described the production methods of the intermediates for production of the present compound.

EXAMPLES

Example 1

Production of 1-(2-cyano-1,2-diisopropoxyiminoethyl)-1H-1,2,4-triazole (present compound No. I-50)

(1) To 5 ml of a dichloromethane solution containing 1.0 g (5.43 mmol) of ethyl 2-cyano-2-isopropoxyiminoacetate was added 0.73 g (6.54 mmol) of O-isopropylhydroxyamine hydrochloride, followed by cooling to −20° C. Thereto was added 4.34 ml (6.08 mmol) of a trimethylaluminum (1.4 M/L) hexane solution. The mixture was heated to room temperature and stirred for 20 hours. The reaction mixture was cooled to −20° C., and 3.88 ml (5.43 mmol) of a triethylaluminum hexane solution, followed by stirring at room temperature for 6 hours. To the reaction mixture was added water, with ice-cooling. Extraction was conducted using ethyl acetate. The organic layer was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/1), to obtain 1.12 g (yield: 97%) of 2-cyano-2-isopropoxyimino-N-isopropoxyacetamide.

Incidentally, ethyl 2-cyano-2-isopropoxyiminoacetate was produced based on a method described in Journal of Medicinal Chemistry, pp. 4608~4612 (1992).

$^1$H-NMR data (CDCl$_3$/TMS δ (ppm)):

1.29 (6H, d), 1.40 (6H, d), 4.24 (1H, qq), 4.69 (1H, qq), 8.74 (1H, s)

(2) To 5 ml of an acetonitrile solution containing 0.40 g (1.88 mmol) of the 2-cyano-2-isopropoxyimino-N-isopropoxyacetamide obtained in above (1) were added 1.48 g (5.64 mmol) of triphenylphosphine and 1.73 g (11.25 mmol) of carbon tetrachloride, followed by stirring for 4 hours under heating and refluxing. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2), to obtain 0.21 g (yield: 49%) of 1-chloro-2-cyano-1,2-diisopropoxyiminoethane.

$^1$H-NMR data (CDCl$_3$/TMS δ (ppm)):

1.37 (6H, d), 1.39 (6H, d), 4.62 (1H, qq), 4.70 (1H, qq)

(3) To 5 ml of an N,N-dimethylformamide solution containing 0.21 g (0.906 mmol) of the 1-chloro-2-cyano-1,2-diisopropoxyiminoethane obtained in above (2) were added 0.10 g (1.45 mmol) of 1,2,4-triazole and 0.13 g (0.941 mmol) of potassium carbonate, followed by stirring at 90° C. for 2 hours. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/1), to obtain 0.22 g (yield: 92%) of a title compound.

$^1$H-NMR data (CDCl$_3$/TMS δ (ppm)):

1.33 (6H, d), 1.35 (6H, d), 4.54-4.71 (2H, m), 8.08 (1H, s), 8.66 (1H, s)

Example 2

Production of 1-[1,2-diisopropoxyimino-2-(1H-tetrazol-5-yl)ethyl]-1H-1,2,4-triazole (present compound No. I-213)

To 5 ml of a toluene solution containing 0.40 g (1.51 mmol) of 1-(2-cyano-1,2-diisopropoxyiminoethyl)-1H-1,2,4-triazole were added 0.35 g (3.03 mmol) of trimethylsilylazide and 0.38 g (1.51 mmol) of di-n-butyltin oxide, followed by stirring for 3 hours under heating and refluxing. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/0). The crystal obtained was washed with isopropyl ether to obtain 0.23 g (yield: 47%) of a title compound.

$^1$H-NMR data (CDCl$_3$/TMS δ (ppm)):

1.43 (6H, d), 1.49 (6H, d), 4.66 (1H, qq), 4.84 (1H, qq), 7.85 (1H, s), 9.34 (1H, s), 13.59 (1H, s)

Example 3

Production of 1-(2-carbamoyl-1,2-diisopropoxyiminoethyl)-1H-1,2,4-triazole (present compound No. I-73)

To 2 ml of a dimethyl sulfoxide solution containing 4.0 g (15.1 mmol) of 1-(2-cyano-1,2-diisopropoxyiminoethyl)-1H-1,2,4-triazole were added, with ice-cooling, 3.5 ml of hydrogen peroxide water and 2.30 g (16.6 mmol) of potassium carbonate, followed by stirring at room temperature for 10 hours. The resulting crystal was washed with water and isopropyl ether in this order, to obtain 3.28 g (yield: 77%) of a title compound.

$^1$H-NMR data (CDCl$_3$/TMS δ (ppm)):
1.38 (12H, d), 4.53-4.70 (2H, m), 6.35 (1H, s), 7.39 (1H, s), 7.95 (1H, s), 9.20 (1H, s)

Example 4

Production of 1-[2-(4,5-dihydro-1,3-thiazolin-2-yl)-1,2-diisopropoxyiminoethyl]-1H-1,2,4-triazole (present compound No. I-214) and 1-[1,2-d]isopropoxyimino-2-(thiazol-2-yl)ethyl]-1H-1,2,4-triazole (present compound No. I-215)

(1) 0.22 g (2.91 mmol) of 2-aminoethanethiole was added to 5 ml of a methanol solution containing 0.70 q (2.65 mmol) of 1-(2-cyano-1,2-diisopropoxyiminoethyl)-1H-1,2,4-triazole and 0.22 g (2.91 mmol) of ammonium acetate, followed by stirring at room temperature for 16 hours. The reaction mixture was poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=2/1), to obtain 0.47 g (yield: 55%) of 1-[2-(4,5-dihydro-1,3-thiazolin-2-yl)-1,2-diisopropoxyiminoethyl]-1H-1,2,4-triazole.

$^1$H-NMR data (CDCl$_3$/TMS δ (ppm)):
1.37 (6H, d), 1.39 (6H, d), 3.18 (2H, t), 4.05 (2H, t), 4.52-4.68 (2H, m), 9.92 (1H, s), 9.18 (1H, s)

(2) To 5 ml of a toluene solution containing 0.27 g (0.832 mmol) of the 1-[2-(4,5-dihydro-1,3-thiazolin-2-yl)-1,2-diisopropoxyiminoethyl]-1H-1,2,4-triazole obtained in above (1) were added 5 ml of water, 0.01 g (0.031 mmol) of tetra-n-butyl ammonium bromide and 0.39 g (2.47 mmol) of potassium permanganate, followed by stirring at room temperature for 2 days. To the reaction mixture was added an excess amount of sodium thiosulfate, followed by stirring for 30 minutes. The solid was removed, followed by extraction with ethyl acetate. The organic layer was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/1) to obtain 0.15 g (yield: 56%) of a title compound.

$^1$H-NMR data (CDCl$_3$/TMS δ (ppm)):
1.41 (6H, d), 1.49 (6H, d), 4.64 (1H, qq), 4.79 (1H, qq), 7.54 (1H, d), 7.82 (1H, d), 7.84 (1H, s), 9.36 (1H, s)

Example 5

Production of 1-[2-isobutoxyimino-1-isopropoxyimino-2-(1,2,4-oxadiazol-2-yl)ethyl]-1H-1,2,4-triazole (present compound No. I-209)

(1) To 10 ml of an ethanol solution containing 1.68 g (6.04 mmol) of the 1-[2-cyano-2-isobutoxyimino-1-isopropoxyiminoethyl]-1H-1,2,4-triazole produced based on Example 1 were added 0.46 g (6.62 mmol) of hydroxylamine hydrochloride and 0.54 g (6.58 mmol) of sodium acetate, followed by stirring at 50° C. for 3 hours. The solvent in the reaction mixture was distilled off under reduced pressure. The resulting crystal was washed with water and isopropyl ether, to obtain 0.91 g (yield: 48%) of 1-[2-(N-hydroxyamidino)-2-isobutyloxyimino-1-isopropoxyiminoethyl]-1H-1,2,4-triazole.

$^1$H-NMR data (CDCl$_3$/TMS δ (ppm)):
0.99 (6H, d), 1.37 (6H, d), 2.01-2.17 (1H, m), 4.11 (2H, d), 4.60 (1H, qq), 5.60 (2H, s), 7.48 (1H, s), 7.93 (1H, s), 9.13 (1H, s)

(2) 0.02 g (0.11 mmol) of p-toluenesulfonic acid monohydrate was added to 5 ml of a triethyl orthoformate solution containing 0.35 g (1.12 mmol) of the 1-[2-(N-hydroxyamidino)-2-isobutyloxyimino-1-isopropoxyiminoethyl]-1H-1,2,4-triazole obtained in above (1), followed by stirring at 150° C. for 3 hours. The reaction mixture was cooled to room temperature and poured into water. The mixture was subjected to extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2), to obtain 0.23 g (yield: 64%) of a title compound.

$^1$H-NMR data (CDCl$_3$/TMS δ (ppm));
0.98 (6H, d), 1.37 (6H, d), 2.04-2.18 (1H, m), 4.21 (2H, d), 4.61 (1H, qq), 7.89 (1H, s), 8.71 (1H, s), 9.12 (1H, s)

Example 6

Production of 1,2-diisopropoxyimino-1,2-bis(1H-1,2,4-triazol-1-yl)ethane (present compound No. I-212)

(1) To 40 ml of a tetrahydrofuran solution containing 8.79 g (78.78 mmol) of O-isopropylhydroxylamine hydrochloride were added, with ice-cooling, 21.78 g (157.59 mmol) of potassium carbonate and 5.00 g (39.39 mmol) of oxalyl chloride, followed by stirring at room temperature for 15 hours. The reaction mixture was poured into water, followed by extraction with ethyl acetate. The extract solution was washed with an aqueous saturated sodium chloride solution and dried over anhydrous magnesium sulfate. The solvent was distilled off under reduced pressure to obtain 3.39 g (yield: 42%) of N,N'-diisopropoxyoxamide.

$^1$H-NMR data (CDCl$_3$/TMS δ (ppm)):
1.29 (12H, d), 4.22 (2H, qq), 9.59 (2H, s)

(2) 2.04 g (9.79 mmol) of phosphorus pentachloride was added to 5 ml of a dichloromethane solution containing 1.0 g (4.9 mmol) of the N,N'-diisopropoxyoxamide obtained in above (1), followed by stirring at room temperature for 4 hours. The reaction mixture was poured into ice water, followed by extraction with isopropyl ether. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/4) to obtain 0.19 g (yield: 16%) of 1,2-dichloro-1,2-diisoprpoxyiminoethane.

$^1$H-NMR data (CDCl$_3$/TMS δ (ppm)):
1.35 (12H, d), 4.59 (2H, qq)

(3) To 5 ml of an N,N-dimethylformamide solution containing 0.19 g (0.788 mmol) of the 1,2-dichloro-1,2-diisoprpoxyiminoethane obtained in above (2) were added 0.16 g (2.36 mmol) of 1,2,4-triazole and 0.33 g (2.36 mmol) of potassium carbonate, followed by stirring at 100° C. for 14 hours. The reaction mixture was cooled to room temperature and poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/1) to obtain 0.20 g (yield: 83%) of a title compound.

$^1$H-NMR data (CDCl$_3$/TMS δ (ppm)):
1.43 (12H, d), 4.68 (2H, qq), 7.81 (2H, s) 9.25 (2H, s)

Example 7

Production of 1-(2-methylthio-1,2-diisopropoxyiminoethyl)-1H-1,2,4-triazole (present compound No. I-228)

Sodium thiomethoxide was added to 5 ml of a tetrahydrofuran solution (which was under heating and refluxing) containing 0.35 g (1.14 mmol) of the 1,2-diisopropoxyimino-1,2-bis(1H-1,2,4-triazol-1-yl)ethane produced in Example 6, with confirming a reaction by thin-layer chromatography. Then, stirring was conducted for 5 hours. The reaction mixture was cooled to room temperature and poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 0.17 g (yield: 52%) of a title compound.

$^1$H-NMR data (CDCl$_3$/TMS δ (ppm)):
1.31 (6H, d), 1.39 (6H, d), 2.14 (3H, s), 4.50 (1H, qq), 4.63 (1H, qq), 8.05 (1H, s), 9.23 (1H, s)

Example 8

Production of 1-(2-chloro-1,2-diisopropoxyiminoethyl)-1H-1,2,4-triazole (present compound No. I-4)

(1) 14 g (82 mmol) of isopropyl iodide and 13 g (94 mmol) of potassium carbonate were added to 100 ml of an N,N-dimethylformamide solution containing 14 g (76 mmol) of ethyl 2-hydroxyimino-2-1H-1,2,4-triazol-1-ylacetate, followed by stirring at room temperature for 5 hours. The reaction mixture was poured into water, followed by extraction with ethyl acetate. The extract solution was dried over anhydrous magnesium sulfate and concentrated under reduced pressure. The resulting residue was purified by silica gel column chromatography (elutant:ethyl acetate/hexane=1/8) to obtain 9.0 g (yield: 52%) of ethyl 2-isopropoxyimino-2-1H-1,2,4-triazol-1-ylacetate.

Incidentally, ethyl 2-hydroxyimino-2-1H-1,2,4-triazol-1-ylacetate was produced based on a method described in Journal of the Chemical Society Perkin Transactions 1, pp. 2235~2239 (1987).

$^1$H-NMR data (CDCl$_3$/TMS δ (ppm)):
1.36 (6H, d), 1.37 (3H, t), 4.43 (2H, q), 4.63 (1H, sep), 8.06 (1H, s), 8.79 (1H, s)
(2) To 60 ml of a 1,4-dioxane solution containing 13 g (57 mmol) of the ethyl 2-isopropoxyimino-2-1H-1,2,4-triazol-1-ylacetate obtained in above (1) was added 2.9 g (69 mmol) of lithium hydroxide monohydrate dissolved in 15 ml of water, followed by stirring at room temperature for 12 hours. To the reaction mixture were added hexane and an aqueous saturated sodium hydrogencarbonate solution, for phase separation. The aqueous layer was made acidic with diluted hydrochloric acid, followed by extraction with ethyl acetate. The organic layer was dried over anhydrous magnesium sulfate. The solvent was distilled off under reduced pressure to obtain 9.7 g (yield: 86%) of 2-isopropoxyimino-2-1H-1,2,4-triazol-1-ylacetic acid.

$^1$H-NMR data (CDCl$_3$/TMS δ (ppm)):
1.40 (6H, d), 4.74 (1H, sep), 8.18 (1H, s), 8.99 (1H, s)
(3) To 50 ml of a dichloromethane solution containing 5.5 g (28 mmol) of the 2-isopropoxyimino-2-1H-1,2,4-triazol-1-ylacetic acid obtained in above (2) were added 3.9 g (33 mmol) of O-isopropylhydroxyamine hydrochloride, 3.4 g (34 mmol) of N-methylmorpholine and 8.0 g (42 mmol) of N-(3-dimethylaminopropyl)-N'-ethylcarbodiimide hydrochloride (WSC), followed by stirring at room temperature for 12 hours. The reaction mixture was poured into diluted hydrochloric acid, followed by extraction with dichloromethane. The extract solution was dried over anhydrous magnesium sulfate. The solvent was distilled off under reduced pressure. The resulting crystal was washed with diisopropyl ether to obtain 3.9 g (yield: 55%) of N-isopropoxy-2-isopropoxyimino-2-(1H-1,2,4-triazol-1-yl)acetamide.

$^1$H-NMR data (CDCl$_3$/TMS δ (ppm)):
1.28-1.40 (12H, m), 1.37 (3H, t), 4.29 (1H, sep), 4.58 (1H, sep), 8.08 (1H, s), 8.82 (1H, s), 9.66 (1H, s)
(4) To 20 ml of an acetonitrile solution containing 0.74 g (2.9 mmol) of the N-isopropoxy-2-isopropoxyimino-2-(1H-1,2,4-triazol-1-yl)acetamide obtained in above (3) were added 2.3 g (8.8 mmol) of triphenylphosphine and 2.7 g (18 mmol) of carbon tetrachloride, followed by stirring for 12 hours under heating and refluxing. The reaction mixture was subjected to distillation under reduced pressure. The resulting residue was purified by silica gel column chromatography (elutant:ethyl acetate/hexane=1/8) to obtain 0.47 g (yield: 59%) of a title compound.

$^1$H-NMR data (CDCl$_3$/TMS δ (ppm)):
1.31 (6H, s), 1.35 (6H, d), 4.51 (1H, sep), 4.61 (1H, sep), 8.06 (1H, s), 8.77 (1H, s)

Example 9

Production of 1-(1,2-diisopropoxyimino-2-methoxyethyl)-1H-1,2,4-triazole (present compound No. I-165)

0.22 g (1.55 mmol) of iodomethane was added, with ice-cooling, to 5 ml of an N,N-dimethylformamide solution containing 0.22 g (1.59 mmol) of potassium carbonate and 0.4 g (1.57 mmol) of the N-isopropoxy-2-isopropoxyimino-2-(1H-1,2,4-triazol-1-yl)acetamide produced in Example 8, followed by stirring at room temperature for 20 hours. The reaction mixture was poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 0.12 g (yield: 29%) of a title compound.

$^1$H-NMR data (CDCl$_3$/TMS δ (ppm)):
0.97 (6H, d), 1.38 (6H, d), 2.01-2.16 (1H, m), 2.05 (3H, s), 4.00 (2H, d), 4.61 (1H, qq), 7.93 (1H, s), 8.24 (1 h, s), 9.22 (13, s)

Example 10

Production of 1-(2-isopropoxyimino-2-thiocarbamoyl-1-methoxyiminoethyl)-1H-1,2,4-triazole (present compound No. II-224)

0.77 g (1.9 mmol) of Lawesson's reagent was added, at room temperature, to a tetrahydrofuran (8 ml) solution containing 0.40 g (1.6 mmol) of 1-(2-carbamoyl-2-isopropoxyimino-1-methoxyiminoethyl)-1H-1,2,4-triazole, followed by stirring at 40° C. for 2 hours and then at 60° C. for 3 hours. The reaction mixture was cooled to room temperature. Thereto was added diisopropyl ether. The mixture was washed with water and an aqueous saturated sodium chloride solution and dried over anhydrous sodium sulfate. The solvent was distilled off. The resulting residue was purified by silica gel column chromatography (elutant:ethyl acetate/hexane=1/2) to obtain 0.25 g (yield: 58%) of a title compound as a yellow powder.

$^1$H-NMR data (CDCl$_3$/TMS δ (ppm)):
1.24 (6H, d), 4.15 (3H, s), 4.52 (1H, sep), 7.72 (1H, s), 7.94 (1H, s), 8.10 (1H, s), 9.24 (1H, s)

Example 11

Production of 2-isopropoxyimino-3-methoxyimino-3-1H-1,2,4-triazol-1-ylpropanecarboxymidic acid methyl ester (present compound No. II-223)

1.6 g (8.4 mmol) of a sodium methoxide 28% methanol solution was drop-wise added, with ice-cooling, into a methanol (50 ml) solution containing 5.0 g (21 mmol) of 1-(2-cyano-2-isopropoxyimino-1-methoxyiminoethyl)-1H-1,2,4-triazole, followed by stirring for 2 hours with ice-cooling. To the reaction mixture was added a small amount of an aqueous citric acid solution, followed by extraction with ethyl acetate. The extract solution was washed with an aqueous saturated sodium bicarbonate solution and an aqueous sodium chloride solution and dried over anhydrous sodium sulfate. The solvent was distilled off. The resulting residue was purified by silica gel column chromatography (elutant:ethyl acetate/hexane=1/2) to obtain 2.5 g (yield: 44%) of a title compound as a yellow oily matter.

$^1$H-NMR data (CDCl$_3$/TMS δ (ppm)):
1.36 (6H, d), 3.61 (3H, s), 4.14 (3H, s), 4.60 (1H, sep), 7.97 (1H, s), 8.92 (1H, s), 9.08 (1H, s)

Example 12

Production of 1-(2-isopropoxyimino-2-methoxycarbonyl-1-methoxyiminoethyl)-1H-1,2,4-triazole (present compound II-221)

12 ml of a 3 mol/l hydrochloric acid was added, with ice-cooling, to 20 ml of a methanol solution containing 2.5 g (9.3 mmol) of the 2-isopropoxyimino-3-methoxyimino-3-1H-1,2,4-triazol-1-ylpropanecarboxymidic acid methyl ester produced in Example 11, followed by stirring for 40 minutes. Water was added to the reaction mixture, followed by extraction with ethyl acetate. The extract solution was washed with an aqueous saturated sodium bicarbonate solution and an aqueous sodium chloride solution and dried over anhydrous sodium sulfate. The solvent was distilled off to obtain 2.4 g (yield: 95%) of a title compound as a colorless oily matter.

$^1$H-NMR data (CDCl$_3$/TMS δ (ppm)):
1.26 (6H, d), 3.86 (3H, s), 4.10 (3H, s), 4.46 (1H, sep), 8.05 (1H, s), 8.67 (1H, s)

Example 13

Production of 1-(2-isopropoxyimino-2-N,N-dimethylcarbamoyl-1-methoxyiminoethyl)-1H-1,2,4-triazole (present compound No. II-226)

4.4 ml (4.4 mmol) of a trimethylaluminum (1 mol/l) hexane solution was drop-wise added, at room temperature, into a 1,2-dichloroethane (7 ml) suspension of 0.36 g (4.4 mmol) of dimethylamine hydrochloride, followed by stirring at 80° C. for 30 minutes. To the reaction mixture was added, at 60° C., a 1,2-dichloroethane (3 ml) solution containing 0.30 g (1.1 mmol) of the 1-(2-isopropoxyimino-2-methoxycarbonyl-1-methoxyiminoethyl)-1H-1,2,4-triazole produced in Example 12, followed by stirring for 1.5 hours. The reaction mixture was cooled to room temperature and then diluted with isopropyl ether. Thereto was added a small amount of water, followed by stirring. The resulting precipitate was removed by filtration. The solvent was distilled off. The resulting reside was purified by silica gel column chromatography (elutant:ethyl acetate/hexane=2/1) to obtain 0.30 g (yield: 97%) of a title compound as a yellow oily matter.

$^1$H-NMR data (CDCl$_3$/TMS δ (ppm)):
1.23 (6H, d), 3.02 (3H, s), 3.05 (3H, s), 4.07 (3H, 4.42 (1H, sep), 8.06 (1H, s), 8.57 (1H, s)

Example 14

Production of S-ethyl 2-isopropoxyimino-3-methoxyimino-3-(1H-1,2,4-triazol-1-yl)propanethioate (present compound No. II-222

To 8 ml of 1,2-dichloroethane was added 7.5 ml (7.5 mmol) of a trimethylaluminum (1 mol/l) hexane solution. Thereinto was drop-wise added 0.47 g (7.5 mmol) of ethanethiol at room temperature, followed by stirring for 30 minutes. To this mixed solution was added, at room temperature, a 1,2-dichloroethane solution containing 0.50 g (1.9 mmol) of the 1-(2-isopropoxyimino-2-methoxycarbonyl-1-methoxyiminoethyl)-1H-1,2,4-triazole produced in Example 12, followed by stirring for 1.5 hours. The reaction mixture was diluted with isopropyl ether. Thereto was added a small amount of water, followed by stirring. The resulting precipitate was removed by filtration. The solvent was distilled off. The resulting residue was purified by silica gel column chromatography (elutant:ethyl acetate/hexane=1/2) to obtain 0.56 g (yield: 98%) of a title compound as a yellow oily matter.

$^1$H-NMR data (CDCl$_3$/TMS δ (ppm)):
1.34 (6H, d), 2.99 (2H, q), 4.12 (3H, s), 4.54 (1H, sep), 7.99 (1H, s), 8.88 (1H, s)

Example 15

Production of 1-(2-amino-1,2-diisoprooxyiminoethyl)-1H-1,2,4-triazole (present compound No. I-119)

(1) 12.13 g (213.68 mmol) of a 30% aqueous ammonia solution was added, in ice-cooling, to 40 ml of a methanol solution containing 24.17 g (106.84 mmol) of the ethyl 2-isopropoxyimino-2-1H-1,2,4-triazol-1-ylacetate produced in Example 8 (1), followed by stirring for 3 hours. The solvent in the reaction mixture was distilled off under reduced pressure. The resulting residue was dissolved in 40 ml of a dichloromethane solution. To the solution were added, in ice-cooling, 16.90 g (213.65 mmol) of pyridine and 24.68 g (117.51 mmol) of trifluoroacetic anhydride, followed by stirring for 4 hours. The reaction mixture was subjected to extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=2/1) to obtain 19.14 g (yield: 100%) of 1-(1-cyano-1-isopropoxyiminomethyl)-1H-1,2,4-triazole.

$^1$H-NMR data (CDCl$_3$/TMS δ (ppm)):
1.45 (6H, d), 4.74 (1H, qq), 8.10 (1H, s), 9.14 (1H, s)

(2) To 5 ml of an ethanol solution containing 0.4 g (2.23 mmol) of the 1-(1-cyano-1-isopropoxyiminomethyl)-1H-1,2,4-triazole obtained in above (1) were added 0.46 g (3.33 mmol) of potassium carbonate and 0.37 g (3.32 mmol) of O-isopropylhydroxyamine hydrochloride, followed by stirring for 5 hours under heating and refluxing. The reaction mixture was returned to room temperature, followed by extraction with ethyl acetate. The organic layer was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 0.09 g (yield: 16%) of a title compound.

$^1$H-NMR data (CDCl$_3$/TMS δ (ppm)):
1.19 (6H, d), 1.29 (6H, d), 4.22 (1H, qq), 4.51 (1H, qq), 4.92 (2H, s), 8.07 (1H, s), 8.38 (1H, s)

Example 16

Production of 1-(2-bromo-1,2-diisopropoxyiminoethyl)-1H-1,2,4-triazole (Present compound No. I-142)

An aqueous solution consisting of 0.04 g (0.58 mmol) of sodium nitrite and 3 ml of water was added, in ice-cooling, to a solution obtained by adding 5 ml of water and 0.5 ml of 47% hydrobromic acid to 0.13 g (0.51 mmol) of the 1-(2-amino-1,2-diisoprooxyiminoethyl)-1H-1,2,4-triazole produced in Example 15, followed by stirring. After 4 hours, the reaction mixture was subjected to extraction with ethyl acetate. The organic layer was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 0.11 g (yield: 68%) of a title compound.

$^1$H-NMR data (CDCl$_3$/TMS δ (ppm))
1.32 (6H, d), 1.36 (6H, d), 4.50-4.67 (2H, m), 8.05 (1H, s), 8.82 (1H, s)

Example 17

Production of 1-(2-amino-2-isobutoxyimino-1-isopropoxyiminoethyl)-1H-1,2,4-triazole (present compound No. I-121)

(1) 13.94 g (100.86 mmol) of potassium carbonate and 6.50 g (93.54 mmol) of hydroxylamine hydrochloride were added to 120 ml of a methanol solution containing 15.06 g (84.05 mmol) of the 1-(1-cyano-1-isopropoxyiminomethyl)-1H-1,2,4-triazole produced in Example 15 (1), followed by stirring for 2 hours under heating and refluxing. The reaction mixture was cooled to room temperature and adjusted to pH 4 using 2N HCl. Extraction with ethyl acetate was conducted. The organic layer was washed with an aqueous saturated sodium chloride solution and dried over anhydrous magnesium sulfate. The solvent was distilled off under reduced pressure to obtain 14.81 g (yield: 83%) of 1-(2-amino-2-hydroxyimino-1-isopropoxyiminoethyl)-1H-1,2,4-triazole.

$^1$H-NMR data (CDCl$_3$/TMS δ (ppm)):
1.30 (6H, d), 4.54 (1H, qq), 5.05 (2H, s), 7.98 (1H, s), 8.08 (1H, s), 8.44 (1H, s)

(2) 0.59 g (63.3 wt. %, 15.56 mmol) of sodium hydride was added, in ice-cooling, to 30 ml of an N,N-dimethylformamide solution containing 3.00 g (14.14 mmol) of the 1-(2-amino-2-hydroxyimino-1-isopropoxyiminoethyl)-1H-1,2,4-triazole obtained in above (1) and 2.13 g (15.55 mmol) of isobutyl bromide, followed by stirring at room temperature for 2 hours. The reaction mixture was poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=2/1) to obtain 2.71 g (yield: 72%) of a title compound.

$^1$H-NMR data (CDCl$_3$/TMS δ (ppm)):
0.89 (6H, d), 1.29 (6H, d), 1.88-1.99 (1H, m), 3.77 (2H, d), 4.52 (1H, qq), 4.97 (2H, s), 8.07 (1H, s), 8.39 (1H, s)

Example 18

Production of 1-[2-N-acetylamino-2-isobutyloxyimino-1-isopropoxyiminoethyl]-1H-1,2,4-triazole (present compound No. I-217)

0.58 g (7.39 mmol) of acetyl chloride was added to 5 ml of a toluene solution containing 0.4 g (1.49 mmol) of the 1-(2-amino-2-isobutoxyimino-1-isopropoxyiminoethyl)-1H-1,2,4-triazole produced in Example 17, followed by stirring at 100° C. for 10 hours. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=2/1) to obtain 0.34 g (yield: 74%) of a title compound.

$^1$H-NMR data (CDCl$_3$/TMS δ (ppm)):
0.97 (6H, d), 1.38 (6H, d), 2.01-2.16 (1H, m), 2.05 (3H, s), 4.00 (2H, d), 4.61 (1H, qq), 7.93 (1H, s), 8.24 (1H, s), 9.22 (1H, s)

Example 19

Production of 1-[2-N-methoxycarbonylamino-2-isobutyloxyimino-1-isopropoxyiminoethyl]-1H-1,2,4-triazole (present compound No. I-219)

0.06 g (1.40 mmol) of 55% sodium hydride was added, in ice-cooling, to 5 ml of an N,N-dimethylacetamide solution containing 0.34 g (1.27 mmol) of the 1-(2-amino-2-isobutoxyimino-1-isopropoxyiminoethyl)-1H-1,2,4-triazole produced in Example 17, followed by stirring at room temperature for 5 minutes. To the mixture was added, in ice-cooling, 0.13 g (1.40 mmol) of methyl chloroformate, followed by stirring at room temperature for 18 hours. The reaction mixture was subjected to extraction with ethyl acetate. The extract solution was washed with an aqueous sodium chloride solution and dried over anhydrous magnesium sulfate. The solvent was distilled off under reduced pressure. The residue was purified by silica gel column chromatography (elutant: ethyl acetate/hexane=1/2) to obtain a di-substitution product (1-[2-N,N-dimethoxycarbonylamino-2-isobutyloxyimino-1-isopropoxyiminoethyl]-1H-1,2,4-triazole). Potassium carbonate was added to 5 ml of a methanol solution of the di-substitution product until a pH of about 9 was reached, followed by stirring at 70° C. for 10 hours. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=2/1) to obtain 0.18 g (yield: 43%) of a title compound.

$^1$H-NMR data (CDCl$_3$/TMS δ (ppm)):

0.96 (6H, d), 1.39 (6H, d), 1.98-2.13 (1H, m), 3.62 (3H, s), 3.98 (2H, d), 4.62 (1H, qq), 7.79 (1H, s), 7.95 (1H, s), 9.24 (1H, s)

Example 20

Production of 1-(1,2-diisopropoxyiminopropyl)-2-mercaptoimidazole (present compound No. V-10)

(1) To 100 ml of a dichloromethane solution containing 3.00 g (34.07 mmol) of pyruvic acid were added 7.98 g (71.52 mmol) of isopropylhydroxylamine hydrochloride and 13.71 g (71.52 mmol) of N-(3-dimethylaminopropyl)-N'-ethylcarbodiimide hydrochloride (WSC). Then, 14.47 g (143.05 mmol) of N-methylmorpholine was added with ice-cooling, followed by stirring at room temperature for 20 hours. The reaction mixture was poured into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/3) to obtain 5.00 g ((yield: 73%) of 2-isopropoxyimino-Nisopropoxypropionamide.

$^1$H-NMR data (CDCl$_3$/TMS δ (ppm)):

1.27 (6H, d), 1.28 (6H, d), 2.02 (3H, s), 4.18 (1H, qq), 4.40 (1H, qq), 8.91 (1H, s)

(2) To 20 ml of an acetonitrile solution containing 3.00 g (14.83 mmol) of the 2-isopropoxyimino-N-isopropoxypropionamide obtained in above (1) were added 7.78 g (29.66 mmol) of triphenylphosphine and 9.13 g (59.36 mmol) of carbon tetrachloride, followed by stirring for 4 hours under heating and refluxing. The reaction mixture was cooled to room temperature, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 2.63 g (yield: 80%) of 1-chloro-1,2-diisopropoxyiminopropane.

$^1$H-NMR data (CDCl$_3$/TMS δ (ppm)):

1.29 (6H, d), 1.33 (6H, s), 2.10 (3H, s), 4.42-4.58 (2H, m)

(3) To 5 ml of an N,N-dimethylformamide solution containing 1.00 g (4.53 mmol) of the 1-chloro-1,2-diisopropoxyiminopropane obtained in above (2) were added 0.37 g (5.43 mmol) of imidazole and 0.75 g (5.43 mmol) of potassium carbonate, followed by stirring at 90° C. for 4 hours. The reaction mixture was cooled to room temperature and pored into water, followed by extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2) to obtain 0.83 g (yield: 73%) of 1-(1,2-diisopropoxyiminopropyl)imidazole (present compound No. I-273).

$^1$H-NMR data (CDCl$_3$/TMS δ (ppm)):

1.21 (6H, d), 1.28 (6H, d), 2.15 (3H, s), 4.32 (1H, qq), 4.46 (1H, qq), 7.05 (1H, s), 7.18 (1H, s), 7.77 (1H, s)

(4) 1.01 ml (1.59 mmol) of n-butyllithium (1.57 mol/l) was added, at −60° C., to 5 ml of a tetrahydrofuran solution containing 0.40 g (1.59 mmol) of the 1-(1,2-diisopropoxyiminopropyl)imidazole obtained in above (3), followed by stirring for 30 minutes. To the mixture was added 0.05 g (1.59 mmol) of a sulfur powder, followed by stirring at −60° C. for 3 hours. The reaction mixture was cooled to room temperature. 2N hydrochloric acid was added and the mixture was stirred overnight. The reaction mixture was subjected to extraction with ethyl acetate. The extract solution was washed with an aqueous saturated sodium chloride solution and dried over anhydrous magnesium sulfate. The solvent was distilled off under reduced pressure. The residue was purified by silica gel column chromatography (elutant:ethyl acetate/hexane=1/2). The resulting crystal, was washed with hexane to obtain 0.14 g (yield: 31%) of a title compound.

$^1$H-NMR data (CDCl$_3$/TMS δ (ppm)):

1.18 (6H, d), 1.28 (6H, d), 2.17 (3H, s), 4.27 (1H, qq), 4.50 (1H, qq), 6.57 (1H, s), 6.71 (1H, s), 11.02 (1H, s)

Example 21

Production of 1-(2-n-butoxyimino-2-cyano-1-ethoxyiminoethyl)-1H-1,2,4-triazole (present compound No. III-51)

(1) There was prepared a mixture consisting of 2.00 g (15.6 mmol) of the methyl 2-cyano-2-hydroxyiminoacetate produced by a method described in Synthesis, pp. 46~48 (1999), 2.35 g (17.2 mmol) of n-butyl bromide, 2.59 g (18.7 mmol) of potassium carbonate and 10 ml of DMF. The mixture was stirred at room temperature for 8 hours. The reaction mixture was poured into water, followed by extraction with ethyl acetate. The organic layer was washed with an aqueous saturated sodium chloride solution and dried over anhydrous magnesium sulfate. The solvent was distilled off under reduced pressure to obtain 2.05 g (yield: 71%) of methyl 2-n-butoxyimino-2-cyanoacetate.

$^1$H-NMR data (CDCl$_3$/TMS δ (ppm)):

0.94 (3H, t), 1.41 (2H, q), 1.74-1.84 (2H, m), 3.96 (3H, s), 4.53 (2H, t)

(2) To 20 ml of a 1,4-dioxane solution containing 1.00 g (5.43 mmol) of the methyl 2-n-butoxyimino-2-cyanoacetate obtained in above (1) was added 10 ml of an aqueous solution containing 0.25 g (6.0 mmol) of lithium hydroxide monohydrate, followed by stirring at room temperature for 3 hours. To the reaction mixture were added hexane and an aqueous saturated sodium hydrogencarbonate solution, for phase separation. The aqueous layer was made acidic with diluted hydrochloric acid, followed by extraction with ethyl acetate. The organic layer was dried over anhydrous magnesium sulfate. The solvent was distilled off under reduced pressure to obtain 0.90 g (yield: 98%) of 2-n-butoxyimino-2-cyanoacetic acid.

$^1$H-NMR data (CDCl$_3$/TMS δ (ppm)):

0.97 (3H, t), 1.42 (2H, q), 1.76-1.86 (2H, m), 4.56 (2H, t)

(3) To 20 ml of a dichloromethane solution containing 0.90 g (5.3 mmol) of the 2-n-butoxyimino-2-cyanoacetic acid obtained in above (2) were added 0.57 g (5.8 mmol) of Oethylhydroxyamine hydrochloride, 0.59 g (5.8 mmol) of N-methylmorpholine and 1.5 g (7.8 mmol) of N-(3-dimethylaminopropyl)-N'-ethylcarbodiimide hydrochloride (WSC), followed by stirring at room temperature for 12 hours. The reaction mixture was poured into diluted hydrochloric acid, followed by extraction with dichloromethane. The organic layer was dried over anhydrous magnesium sulfate. The solvent was distilled off under reduced pressure. The resulting residue was purified by column chromatography (elutant:ethyl acetate/hexane=1/4) to obtain 0.55 g (yield: 49%) of N-ethoxy-2-n-butoxyimino-2-cyanoacetamide.

$^1$H-NMR data (CDCl$_3$/TMS δ (ppm)):
0.97 (3H, t), 1.31 (3H, t), 1.41 (2H, q), 1.72-1.81 (2H, m), 4.06 (2H, q), 4.44 (2H, t), 8.88 (1H, s)

(4) To 20 ml of an acetonitrile solution containing 0.45 g (2.1 mmol) of the N-ethoxy-2-n-butoxyimino-2-cyanoacetamide obtained in above (3) were added 2.3 g (8.8 mmol) of triphenylphosphine and 2.7 g (18 mmol) of carbon tetrachloride, followed by stirring for 3 hours under heating and refluxing. The reaction mixture was concentrated under reduced pressure. The resulting residue was purified by column chromatography (elutant:ethyl acetate/hexane=1/9) to obtain 0.24 g (yield: 48%) of 2-n-butoxyimino-1-chloro-2-cyano-1-ethoxyiminoethane.

$^1$H-NMR data (CDCl$_3$/TMS δ (ppm)):
0.97 (3H, t), 1.40 (3H, t), 1.44 (2H, q), 1.74-1.81 (2H, m), 4.38-4.47 (4H, m)

(5) There was prepared a mixture consisting of 1.30 g (5.6 mmol) of the 2-n-butoxyimino-1-chloro-2-cyano-1-ethoxyiminoethane obtained in above (4), 0.76 g (11 mmol) of 1,2,4-triazole, 1.50 g (11 mmol) of potassium carbonate and 7 ml of DMF. The mixture was stirred at 70° C. for 2 hours. The reaction mixture was cooled to room temperature and poured into water, followed by extraction with ethyl acetate. The organic layer was washed with an aqueous saturated sodium chloride solution and dried over anhydrous magnesium sulfate. The solvent was distilled off under reduced pressure. The resulting residue was purified by column chromatography (elutant:ethyl acetate/hexane=1/9) to obtain 1.32 g (yield: 89%) of a title compound.

$^1$H-NMR data (CDCl$_3$/TMS δ (ppm)):
0.94 (3H, t), 1.35-1.46 (5H, m), 1.72 (2H, m), 4.35-4.45 (4H, m), 8.09 (1H, s), 8.66 (1H, s)

Example 22

Production of 1-(2-n-butoxyimino-2-carbamoyl-1-ethoxyiminoethyl)-1H-1,2,4-triazole (present compound No. III-74)

To 5 ml of a methanol solution containing 0.98 g (3.7 mmol) of the 1-(2-n-butoxyimino-2-cyano-1-ethoxyiminoethyl)-1H-1,2,4-triazole produced in Example 17 were added, at room temperature, 60 mg (0.19 mmol) of tetrabutylammonium bromide, 55 mg (0.40 mmol) of potassium carbonate and 1.7 g (15 mmol) of an aqueous 30 wt. % hydrogen peroxide solution, followed by stirring for 10 hours. To the reaction mixture was added sodium dithiosulfate, followed by stirring for 10 minutes. The reaction mixture was concentrated under reduced pressure. The resulting crystal was washed with an aqueous citric acid solution, cold water and isopropyl ether in this order, to obtain 0.64 g (yield: 61%) of a title compound.

$^1$H-NMR data (CDCl$_3$/TMS δ (ppm)):
0.97 (3H, t), 1.40-1.48 (5H, m), 1.76 (2H, m), 4.35-4.45 (4H, m), 6.16 (1H, s), 7.31 (1H, s), 7.96 (1H, s), 9.18 (1H, s)

Example 23

Production of 1-[2-cyano-1,2-bis(n-propoxyimino)ethyl]-1H-1,2,4-triazole (present compound No. IV-90)

(1) There was prepared a mixture consisting of 2.50 g (19.5 mmol) of methyl 2-cyano-2-hydroxyiminoacetate, 2.60 g (21.1 mmol) of n-propyl bromide, 3.20 g (23.2 mmol) of potassium carbonate and 10 ml of DMF. The mixture was stirred at room temperature for 8 hours. The reaction mixture was poured into water, followed by extraction with ethyl acetate. The organic layer was washed with an aqueous saturated sodium chloride solution and dried over anhydrous magnesium sulfate. The solvent was distilled off under reduced pressure to obtain 2.35 g (yield: 71%) of methyl 2-cyano-2-n-propoxyiminoacetate.

$^1$H-NMR data (CDCl$_3$/TMS δ (ppm)):
1.00 (3H, t), 1.78-1.90 (2H, m), 3.97 (3H, s), 4.49 (2H, t)

(2) 10 ml of an aqueous solution containing 0.41 g (9.8 mmol) of lithium hydroxide monohydrate was added to 20 ml of a 1,4-dioxane solution containing 1.50 g (8.81 mmol) of the methyl 2-cyano-2-n-propoxyiminoacetate obtained in above (1), followed by stirring at room temperature for 3 hours. To the reaction mixture were added hexane and an aqueous saturated sodium hydrogencarbonate solution, for phase separation. The aqueous layer was made acidic with diluted hydrochloric acid, followed by extraction with ethyl acetate. The organic layer was dried over anhydrous magnesium sulfate. The solvent was distilled off under reduced pressure to obtain 1.28 g (yield: 93%) of 2-cyano-2-n-propoxyiminoacetic acid.

$^1$H-NMR data (CDCl$_3$/TMS δ (ppm)):
1.00 (3H, t), 1.79-1.91 (2H, m), 4.52 (2H, t)

(3) To 20 ml of a dichloromethane solution containing 1.28 g (8.20 mmol) of the 2-cyano-2-n-propoxyiminoacetic acid obtained in above (2) were added 1.00 g (8.96 mmol) of O-npropylhydroxyamine hydrochloride, 0.91 g (9.0 mmol) of N-methylmorpholine and 2.5 g (13 mmol) of N-(3-dimethylaminopropyl)-N'-ethylcarbodiimide hydrochloride (WSC), followed by stirring at room temperature for 12 hours. The reaction mixture was poured into diluted hydrochloric acid, followed by extraction with dichloromethane. The organic layer was dried over anhydrous magnesium sulfate. The solvent was distilled off under reduced pressure. The resulting residue was purified by column chromatography (elutant:ethyl acetate/hexane=1/4) to obtain 0.77 g (yield: 44%) of N-npropoxy-2-cyano-2-n-propoxyiminoacetamide.

$^1$H-NMR data (CDCl$_3$/TMS δ (ppm)):
0.96-1.03 (6H, m), 1.66-1.87 (4H, m), 3.96 (2H, t), 4.39 (2H, t), 8.86 (1H, s)

(4) 2.2 g (8.4 mmol) of triphenylphosphine and 2.6 g (17 mmol) of carbon tetrachloride were added to 20 ml of an acetonitrile solution containing 0.59 g (2.8 mmol) of the Nn-propoxy-2-cyano-2-n-propoxyiminoacetamide obtained in above (3), followed by stirring for 3 hours under heating and refluxing. The reaction mixture was concentrated under reduced pressure. The resulting residue was purified by column chromatography (elutant:ethyl acetate/hexane=1/9) to obtain 0.45 g (yield: 69%) of 1-chloro-2-cyano-1,2-bis(n-propoxyimino)ethane.

$^1$H-NMR data (CDCl$_3$/TMS δ (ppm)):
0.96-1.02 (6H, m), 1.76-1.85 (4H, m), 4.31 (2H, t), 4.40 (2H, t)

(5) There was prepared a mixture consisting of 0.45 g (1.9 mmol) of the 1-chloro-2-cyano-1,2-bis(n-propoxyimino)

ethane obtained in above (4), 0.20 g (2.9 mmol) of 1,2,4-triazole, 0.53 g (3.8 mmol) of potassium carbonate and 10 ml of DMF. The mixture was stirred at 40° C. for 12 hours. The reaction mixture was cooled to room temperature and poured into water, followed by extraction with ethyl acetate. The organic layer was washed with an aqueous saturated sodium chloride solution and dried over anhydrous magnesium sulfate. The solvent was distilled off under reduced pressure to obtain 0.40 g (yield: 80%) of a title compound.

$^1$H-NMR data (CDCl$_3$/TMS δ (ppm)):
0.94-1.02 (6H, m), 1.70-1.84 (4H, m), 4.29-4.37 (4H, m), 8.09 (1H, s), 8.66 (1H, s)

Example 24

Production of 1-[2-carbamoyl-1,2-bis(n-propoxyimino)ethyl]-1H-1,2,4-triazole (present compound No. IV-101)

To 5 ml of a methanol solution containing 1.06 g (4.0 mmol) of the 1-[2-cyano-1,2-bis(n-propoxyimino)ethyl]-1H-1,2,4-triazole produced in Example 23 were added, at room temperature, 65 mg (0.20 mmol) of tetrabutylammonium bromide, 55 mg (0.40 mmol) of potassium carbonate and 1.8 g (16 mmol) of an aqueous 30 wt. % hydrogen peroxide solution, followed by stirring for 10 hours. To the reaction mixture was added sodium dithiosulfate, followed by stirring for 10 minutes. The reaction mixture was concentrated under reduced pressure. The resulting crystal was washed with an aqueous citric acid solution, cold water and isopropyl ether in this order to obtain 0.73 g (yield: 64%) of a title compound.

$^1$H-NMR data (CDCl$_3$/TMS δ (ppm)):
1.00 (6H, t), 1.77-1.84 (4H, m), 4.31 (2H, t), 4.35 (2H, t), 6.13 (1H, s), 7.34 (1H, s), 7.96 (1H, s), 9.18 (1H, s)

Example 25

Production of 1-[2-cyano-2-(2,2,3,3,3-pentafluoro-n-propoxyimino)-1-(2,2,2-trifluoroethoxyimino)ethyl]-1H-1,2,4-triazole (present compound No. IV-185)

(1) 0.34 g (0.16 mmol) of 5 wt. % palladium carbon was added to 1.70 g (4.83 mmol) of the 1-[2-benzyloxyimino-2-cyano-1-(2,2,2-trifluoroetoxyimino)ethyl]-1H-1,2,4-triazole (present compound No. IV-181) produced based on Example 1. Thereto was added 10 ml of ethanol in a nitrogen current. Hydrogen was added to this mixture at normal pressure at room temperature for 1.5 hours. The insoluble was removed by filtration. The filtrate was concentrated under reduced pressure. The resulting residue was purified by column chromatography (elutant:ethyl acetate/hexane=1/1) to obtain 1.26 g (yield: 100%) of 1-[2-cyano-2-hydroxyimino-1-(2,2,2-trifluoroethoxyimino)ethyl]-1H-1,2,4-triazole.

$^1$H-NMR data (CDCl$_3$/TMS δ (ppm)):
5.04 (2H, q), 8.36 (1H, s), 9.00 (1H, s)

(2) 1.26 g (4.81 mmol) of the 1-[2-cyano-2-hydroxyimino-1-(2,2,2-trifluoroethoxyimino)ethyl]-1H-1,2,4-triazole obtained in above (1) was dissolved in 10 ml of DMSO. To the solution were added 2.49 g (5.77 mmol) of 2,2,3,3,3-ptnetafluoro-n-propyl nonafluoro-n-butanesulfonate and 0.80 g (5.77 mmol) of potassium carbonate, followed by stirring at room temperature for 10 hours. To the reaction mixture were added 1.25 g (2.89 mmol) of 2,2,3,3,3-ptnetafluoro-n-propyl nonafluoro-n-butanesulfonate and 0.40 g (2.81 mmol) of potassium carbonate, followed by stirring at 70° C. for 7 hours. The reaction mixture was cooled to room temperature and poured into water, followed by extraction with ethyl acetate. The organic layer was washed with an aqueous saturated sodium chloride solution and dried over anhydrous magnesium sulfate. The solvent was distilled off under reduced pressure. The resulting residue was purified by column chromatography (elutant:ethyl acetate/hexane=1/1) to obtain 0.50 g (yield: 26%) of a title compound.

$^1$H-NMR data (CDCl$_3$/TMS δ (ppm)):
4.63-4.89 (4H, m), 8.13 (1H, s), 8.75 (1H, s)

The physical properties of the present compounds [I] produced based on the above Examples (including those compounds produced in the Examples) are shown in Table 64 to Table 72.

TABLE 64

| Compound No. | Melting point (° C.) or refractive index ($n_D^{20}$) |
| --- | --- |
| I-1 | 1.525 |
| I-4 | 1.505 |
| I-5 | 1.500 |
| I-6 | 1.497 |
| I-7 | 1.498 |
| I-8 | 1.496 |
| I-9 | 1.497 |
| I-11 | 1.494 |
| I-13 | 1.495 |
| I-14 | 1.495 |
| I-15 | 1.495 |
| I-16 | 1.517 |
| I-18 | 1.516 |
| I-19 | 1.514 |
| I-21 | 1.515 |
| I-22 | 30-32 |
| I-29 | 1.495 |
| I-47 | 1.511 |
| I-48 | 48-51 |
| I-49 | 1.502 |
| I-50 | 1.498 |
| I-51 | 1.500 |
| I-52 | 1.498 |
| I-53 | 1.497 |
| I-54 | 53-54 |
| I-55 | 1.498 |
| I-56 | 1.496 |
| I-57 | 1.492 |
| I-58 | 1.496 |
| I-59 | 1.496 |
| I-60 | 1.4950 |
| I-61 | 1.488 |
| I-62 | 1.515 |
| I-64 | 1.514 |
| I-67 | 1.512 |
| I-68 | 1.517 |
| I-69 | 1.522 |
| I-70 | 182-184 |
| I-71 | 179-181 |
| I-72 | 145-147 |
| I-73 | 165-168 |
| I-74 | 109-110 |
| I-75 | 115-117 |
| I-76 | 97-99 |
| I-77 | 128-131 |
| I-78 | 92-93 |
| I-79 | 126-127 |
| I-80 | 107-108 |
| I-81 | 80-82 |
| I-82 | 100-102 |
| I-83 | 100-101 |
| I-84 | 93-95 |
| I-85 | 103-106 |
| I-87 | 136-138 |
| I-90 | 145-146 |
| I-91 | 162-163 |

TABLE 64-continued

| Compound No. | Melting point (° C.) or refractive index ($n_D^{20}$) |
| --- | --- |
| I-92 | 133-135 |
| I-96 | 1.490 |
| I-98 | 1.489 |
| I-110 | 1.505 |
| I-119 | 1.508 |
| I-121 | 65-67 |
| I-124 | 1.509 |
| I-128 | 1.504 |
| I-129 | 1.505 |
| I-130 | 68-71 |
| I-131 | 68-70 |
| I-133 | 52-54 |
| I-134 | 1.525 |
| I-136 | 1.529 |
| I-142 | 1.509 |
| I-165 | 1.489 |
| I-167 | 1.488 |
| I-179 | 1.504 |
| I-186 | 144-147 |
| I-188 | 156-158 |
| I-190 | 173-176 |
| I-199 | 145-148 |

TABLE 65

| Compound No. | Melting point (° C.) or refractive index ($n_D^{20}$) |
| --- | --- |
| I-208 | 120-123 |
| I-209 | 70-73 |
| I-210 | 1.506 |
| I-211 | 1.503 |
| I-212 | 114-117 |
| I-213 | 163-166 |
| I-214 | 112-115 |
| I-215 | 72-75 |
| I-217 | 118-121 |
| I-218 | 131-134 |
| I-219 | 1.504 |
| I-220 | 1.497 |
| I-221 | 68-71 |
| I-223 | 93-96 |
| I-224 | 178-181 |
| I-225 | 118-119 |
| I-226 | 89-90 |
| I-228 | 48-51 |
| I-230 | 30 |
| I-231 | 1.479 |
| I-233 | 1.493 |
| I-234 | 51-52 |
| I-235 | 1.490 |
| I-236 | 1.468 |
| I-237 | 126-128 |
| I-238 | 1.462 |
| I-239 | 1.548 |
| I-240 | 1.545 |
| I-241 | 142-144 |
| I-242 | 1.510 |
| I-243 | 1.498 |
| I-244 | 1.500 |
| I-245 | 1.503 |
| I-246 | 1.492 |
| I-247 | 1.503 |
| I-248 | 1.523 |
| I-249 | 1.530 |
| I-250 | 1.520 |
| I-251 | 96-99 |
| I-254 | 1.552 |
| I-255 | 165-168 |
| I-256 | 139-140 |
| I-257 | 69-72 |
| I-258 | 1.495 |
| I-259 | 1.501 |
| I-260 | 1.492 |

TABLE 65-continued

| Compound No. | Melting point (° C.) or refractive index ($n_D^{20}$) |
| --- | --- |
| I-261 | 1.503 |
| I-262 | 76-78 |
| I-263 | 1.502 |
| I-264 | 81-82 |
| I-266 | 1.512 |
| I-267 | 1.492 |
| I-268 | 110-113 |
| I-269 | 1.517 |
| I-270 | 1.504 |
| I-271 | 86-88 |
| I-272 | 139-142 |
| I-273 | 1.495 |
| I-274 | 65-67 |
| I-275 | 165-168 |
| I-278 | 125-127 |
| I-279 | 140-142 |
| I-280 | 195-198 |
| I-282 | 136-139 |
| I-283 | 110-113 |
| I-284 | 94-97 |
| I-285 | 108-110 |
| I-286 | 1.516 |
| I-287 | 111-113 |
| I-288 | 1.496 |
| I-289 | 70-72 |
| I-290 | 169-172 |
| I-296 | 1.512 |
| I-297 | 110-112 |
| I-298 | 1.521 |
| I-299 | 95-98 |
| I-300 | 1.534 |
| I-301 | 112-114 |

TABLE 66

| Compound No. | Melting point (° C.) or refractive index ($n_D^{20}$) |
| --- | --- |
| I-302 | 110-112 |
| I-304 | 121-123 |
| I-305 | 76-78 |
| I-306 | 146-149 |
| I-307 | 1.516 |
| I-308 | 169-171 |
| I-309 | 1.500 |
| I-310 | 99-102 |
| I-311 | 1.536 |
| I-313 | 55-58 |
| I-314 | 83-86 |
| I-315 | 111-114 |
| I-316 | 1.518 |
| I-318 | 1.499 |
| I-319 | 121-122 |
| I-320 | 1.481 |
| I-321 | 150-151 |
| I-322 | 73-76 |
| I-323 | 1.505 |
| I-324 | 54-57 |
| I-325 | 1.510 |
| I-326 | 96-97 |
| I-327 | 94-96 |
| I-329 | 1.511 |
| I-330 | 131-133 |
| I-331 | 1.508 |
| I-332 | 130-132 |
| I-333 | 1.550 |
| I-334 | 141-142 |
| I-335 | 72-73 |
| I-336 | 141-142 |
| I-337 | 1.545 |
| I-338 | 162-163 |
| I-339 | 1.541 |
| I-340 | 94-95 |
| I-341 | 1.539 |

TABLE 66-continued

| Compound No. | Melting point (° C.) or refractive index ($n_D^{20}$) |
|---|---|
| I-342 | 99-100 |
| I-343 | 1.535 |
| I-345 | 66-69 |
| I-346 | 1.5290 |
| I-347 | 1.5460 |
| I-348 | 1.5480 |
| I-349 | 132-135 |
| I-351 | 1.4870 |
| I-352 | 81-84 |
| I-353 | 59-62 |
| I-354 | 83-86 |
| I-355 | 1.4890 |
| I-356 | 86-89 |
| I-357 | 1.5370 |
| I-358 | 125-126 |
| I-359 | 1.4330 |
| I-360 | 117-119 |
| I-361 | 1.5130 |
| I-362 | 113-114 |
| I-363 | 75-78 |
| I-365 | 1.5380 |
| I-367 | 1.5480 |
| I-368 | 159-162 |
| I-369 | 1.5140 |
| I-370 | 123-126 |
| I-371 | 77-79 |
| I-372 | 54-57 |
| I-373 | 123-126 |
| I-374 | 1.4470 |
| I-375 | 117-120 |
| I-376 | 1.4980 |
| I-377 | 84-85 |
| I-378 | 1.5360 |
| I-379 | 1.4700 |
| I-380 | 123-126 |
| I-381 | 1.4930 |
| I-382 | 78-80 |
| I-383 | 1.5440 |
| I-384 | 140-143 |
| I-385 | 1.5440 |
| I-386 | 148-150 |
| I-387 | 1.5430 |
| I-388 | 167-170 |
| I-389 | 1.5440 |
| I-390 | 1.5100 |
| I-391 | 1.4940 |
| I-392 | 1.4950 |
| I-393 | 69-72 |
| I-394 | 57-60 |
| I-395 | 68-71 |
| I-396 | 95-98 |
| I-397 | 83-86 |
| I-398 | 1.5290 |

TABLE 67

| Compound No. | Melting point (° C.) or refractive index ($n_D^{20}$) |
|---|---|
| II-4 | 1.516 |
| II-6 | 1.508 |
| II-10 | 1.507 |
| II-15 | 1.504 |
| II-47 | 89-90 |
| II-48 | 71-73 |
| II-49 | 47-50 |
| II-50 | 1.509 |
| II-51 | 1.511 |
| II-52 | 1.508 |
| II-53 | 1.507 |
| II-54 | 85-88 |
| II-55 | 1.508 |
| II-56 | 1.507 |
| II-57 | 1.503 |

TABLE 67-continued

| Compound No. | Melting point (° C.) or refractive index ($n_D^{20}$) |
|---|---|
| II-58 | 1.503 |
| II-59 | 1.507 |
| II-60 | 1.504 |
| II-61 | 1.503 |
| II-62 | 1.524 |
| II-63 | 1.5240 |
| II-64 | 1.529 |
| II-65 | 1.527 |
| II-66 | 1.524 |
| II-67 | 1.531 |
| II-68 | 1.536 |
| II-70 | 175-178 |
| II-71 | 174-176 |
| II-72 | 132-135 |
| II-73 | 179-182 |
| II-74 | 134-137 |
| II-75 | 122-124 |
| II-76 | 158-161 |
| II-77 | 41-44 |
| II-78 | 104-107 |
| II-79 | 105-106 |
| II-80 | 156-158 |
| II-81 | 115-116 |
| II-82 | 122-125 |
| II-83 | 79-81 |
| II-84 | 127-129 |
| II-85 | 141-144 |
| II-86 | 97-100 |
| II-87 | 126-129 |
| II-88 | 120-123 |
| II-89 | 105-107 |
| II-90 | 126-129 |
| II-91 | 128-131 |
| II-121 | 77-80 |
| II-125 | 1.516 |
| II-130 | 1.512 |
| II-133 | 110-112 |
| II-185 | 180-183 |
| II-188 | 142-144 |
| II-190 | 153-156 |
| II-194 | 103-105 |
| II-199 | 110-113 |
| II-208 | 87-88 |
| II-214 | 134-137 |
| II-215 | 105-107 |
| II-221 | 1.500 |
| II-222 | 1.526 |
| II-223 | 1.505 |
| II-224 | 133-136 |
| II-225 | 119-122 |
| II-226 | 1.511 |
| II-227 | 1.500 |
| II-235 | 1.499 |
| II-236 | 1.494 |
| II-237 | 63-66 |
| II-238 | 65-67 |
| II-240 | 1.475 |
| II-241 | 154-157 |
| II-244 | 1.564 |
| II-245 | 123-126 |
| II-246 | 39-42 |
| II-247 | 154-157 |
| II-266 | 1.507 |
| II-267 | 99-102 |
| II-268 | 1.517 |
| II-269 | 1.523 |
| II-271 | 82-84 |
| II-278 | 1.523 |
| II-279 | 118-120 |
| II-280 | 1.542 |
| II-281 | 153-155 |

TABLE 68

| Compound No. | Melting point (° C.) or refractive index ($n_D^{20}$) |
|---|---|
| II-282 | 1.532 |
| II-283 | 117-120 |
| II-284 | 1.5270 |
| II-285 | 109-112 |
| II-286 | 62-65 |
| II-287 | 158-161 |
| II-288 | 1.524 |
| II-289 | 89-92 |
| II-290 | 175-178 |
| II-299 | 1.509 |
| II-301 | 1.503 |
| II-302 | 111-114 |
| II-303 | 1.522 |
| II-304 | 138-140 |
| II-305 | 1.518 |
| II-306 | 138-140 |
| II-307 | 1.522 |
| II-308 | 117-119 |
| II-309 | 1.514 |
| II-311 | 103-104 |
| II-312 | 1.5020 |
| II-313 | 110-111 |
| II-314 | 1.5350 |
| II-316 | 1.5300 |
| II-317 | 154-155 |
| II-318 | 1.5580 |
| II-319 | 1.5090 |
| II-320 | 129-131 |
| II-321 | 1.5150 |
| II-322 | 93-96 |
| II-323 | 132-134 |
| II-324 | 1.4390 |
| II-325 | 146-149 |
| II-326 | 1.4540 |
| II-327 | 123-126 |
| II-328 | 1.4760 |
| II-329 | 120-123 |
| II-330 | 1.4560 |
| II-331 | 104-107 |
| II-332 | 1.5330 |
| II-333 | 135-138 |
| II-334 | 1.4810 |
| II-335 | 157-158 |
| II-338 | 48-51 |
| II-339 | 147-150 |
| II-340 | 1.5710 |
| II-341 | 124-127 |
| II-342 | 101-104 |
| II-343 | 154-157 |
| II-344 | 1.5020 |
| II-345 | 157-159 |
| II-346 | 1.5330 |
| II-347 | 1.5680 |
| II-348 | 146-149 |
| II-349 | 1.4550 |
| II-350 | 110-112 |
| II-351 | 61-64 |
| II-352 | 127-130 |
| II-353 | 1.5440 |
| II-354 | 161-164 |
| II-355 | 1.5080 |
| II-356 | 98-101 |
| II-357 | 1.4740 |
| II-358 | 92-95 |
| II-359 | 1.4750 |
| II-360 | 150-153 |
| II-361 | 1.5040 |
| II-362 | 100-102 |
| II-363 | 80-83 |
| II-364 | 153-156 |
| II-365 | 47-49 |
| II-366 | 103-106 |
| II-367 | 99-102 |
| II-368 | 116-119 |
| II-369 | 1.5470 |
| II-370 | 133-136 |
| II-371 | 1.5760 |
| II-372 | 105-108 |
| II-374 | 130-133 |
| II-375 | 96-97 |
| II-376 | 104-107 |
| II-377 | 1.5100 |
| II-378 | 81-84 |
| II-379 | 1.4390 |
| II-380 | 128-131 |
| II-381 | 148-151 |

TABLE 69

| Compound No. | Melting point (° C.) or refractive index ($n_D^{20}$) |
|---|---|
| III-4 | 1.507 |
| III-47 | 1.521 |
| III-48 | 85-87 |
| III-49 | 1.508 |
| III-50 | 1.505 |
| III-51 | 1.505 |
| III-52 | 1.503 |
| III-53 | 1.501 |
| III-54 | 70-73 |
| III-55 | 1.5010 |
| III-56 | 1.500 |
| III-57 | 1.498 |
| III-58 | 1.501 |
| III-59 | 1.501 |
| III-60 | 1.501 |
| III-61 | 1.501 |
| III-62 | 1.523 |
| III-64 | 1.519 |
| III-65 | 1.520 |
| III-66 | 1.519 |
| III-67 | 1.521 |
| III-68 | 1.526 |
| III-70 | 162-164 |
| III-71 | 168-171 |
| III-72 | 155-157 |
| III-73 | 172-175 |
| III-74 | 111-114 |
| III-75 | 134-137 |
| III-76 | 121-123 |
| III-77 | 126-129 |
| III-78 | 95-97 |
| III-79 | 104-107 |
| III-80 | 155-156 |
| III-81 | 61-64 |
| III-82 | 91-94 |
| III-83 | 97-100 |
| III-84 | 82-84 |
| III-85 | 140-143 |
| III-87 | 142-145 |
| III-88 | 112-115 |
| III-89 | 106-107 |
| III-90 | 149-152 |
| III-91 | 141-144 |
| III-233 | 1.495 |
| III-234 | 79-82 |
| III-238 | 72-74 |
| III-239 | 142-145 |
| III-242 | 1.556 |
| III-243 | 120-122 |
| III-262 | 1.511 |
| III-263 | 90-93 |
| III-264 | 109-111 |
| III-265 | 1.574 |
| III-266 | 1.570 |
| III-267 | 95-98 |
| III-268 | 121-124 |
| III-269 | 1.535 |
| III-270 | 162-165 |
| III-272 | 1.501 |

TABLE 69-continued

| Compound No. | Melting point (° C.) or refractive index ($n_D^{20}$) |
| --- | --- |
| III-273 | 91-93 |
| III-277 | 1.507 |
| III-278 | 144-147 |
| III-279 | 1.505 |
| III-280 | 76-78 |
| III-281 | 1.512 |
| III-282 | 92-95 |
| III-283 | 1.532 |
| III-285 | 1.514 |
| III-287 | 1.499 |
| III-288 | 121-122 |
| III-289 | 1.515 |
| III-290 | 100-103 |
| III-293 | 1.517 |
| III-294 | 101-104 |
| III-295 | 1.4980 |
| III-296 | 102-104 |
| III-297 | 1.4370 |
| III-298 | 114-117 |
| III-299 | 1.4470 |
| III-300 | 1.5050 |
| III-301 | 147-150 |
| III-302 | 1.5140 |
| III-303 | 106-107 |
| III-304 | 1.4510 |
| III-305 | 150-152 |
| III-306 | 1.4990 |
| III-307 | 1.4970 |
| III-308 | 1.4410 |
| III-309 | 88-91 |

TABLE 70

| Compound No. | Melting point (° C.) or refractive index ($n_D^{20}$) |
| --- | --- |
| IV-4 | 1.495 |
| IV-6 | 1.516 |
| IV-14 | 1.495 |
| IV-15 | 129-131 |
| IV-17 | 136-139 |
| IV-18 | 95-98 |
| IV-19 | 74-77 |
| IV-20 | 119-120 |
| IV-21 | 141-142 |
| IV-22 | 125-128 |
| IV-23 | 136-138 |
| IV-24 | 172-174 |
| IV-25 | 165-168 |
| IV-27 | 75-78 |
| IV-30 | 1.502 |
| IV-32 | 1.495 |
| IV-33 | 1.499 |
| IV-34 | 1.493 |
| IV-35 | 1.496 |
| IV-36 | 1.514 |
| IV-37 | 1.512 |
| IV-38 | 1.520 |
| IV-39 | 1.524 |
| IV-40 | 1.467 |
| IV-42 | 1.496 |
| IV-59 | 133-134 |
| IV-61 | 135-136 |
| IV-62 | 211-214 |
| IV-63 | 127-128 |
| IV-64 | 159-162 |
| IV-65 | 132-135 |
| IV-71 | 102-103 |
| IV-74 | 1.515 |
| IV-76 | 1.506 |
| IV-77 | 74-76 |
| IV-78 | 1.503 |
| IV-79 | 1.529 |
| IV-80 | 1.527 |

TABLE 70-continued

| Compound No. | Melting point (° C.) or refractive index ($n_D^{20}$) |
| --- | --- |
| IV-86 | 1.510 |
| IV-89 | 60-62 |
| IV-90 | 1.504 |
| IV-91 | 1.501 |
| IV-92 | 1.500 |
| IV-93 | 1.501 |
| IV-95 | 1.517 |
| IV-96 | 1.515 |
| IV-97 | 1.524 |
| IV-98 | 1.472 |
| IV-99 | 1.555 |
| IV-100 | 138-141 |
| IV-101 | 127-128 |
| IV-102 | 105-106 |
| IV-103 | 122-125 |
| IV-104 | 86-88 |
| IV-106 | 123-126 |
| IV-107 | 131-133 |
| IV-108 | 121-124 |
| IV-109 | 159-160 |
| IV-110 | 107-109 |
| IV-111 | 1.493 |
| IV-112 | 114-116 |
| IV-113 | 1.511 |
| IV-114 | 147-150 |
| IV-115 | 1.492 |
| IV-116 | 45-48 |
| IV-117 | 1.530 |
| IV-118 | 154-156 |
| IV-119 | 1.529 |
| IV-120 | 111-113 |
| IV-122 | 130-132 |
| IV-127 | 1.539 |
| IV-128 | 144-147 |
| IV-129 | 1.506 |
| IV-130 | 1.525 |
| IV-131 | 1.508 |
| IV-132 | 122-125 |
| IV-133 | 132-133 |
| IV-134 | 103-104 |

TABLE 71

| Compound No. | Melting point (° C.) or refractive index ($n_D^{20}$) |
| --- | --- |
| IV-135 | 83-86 |
| IV-146 | 1.518 |
| IV-147 | 1.539 |
| IV-148 | 1.522 |
| IV-149 | 1.510 |
| IV-151 | 171-173 |
| IV-153 | 110-112 |
| IV-155 | 1.572 |
| IV-164 | 1.520 |
| IV-165 | 129-131 |
| IV-164 | 1.499 |
| IV-165 | 85-86 |
| IV-166 | 1.498 |
| IV-167 | 166-167 |
| IV-168 | 1.495 |
| IV-169 | 116-117 |
| IV-170 | 1.494 |
| IV-171 | 79-81 |
| IV-172 | 1.494 |
| IV-173 | 63-66 |
| IV-174 | 1.4940 |
| IV-175 | 92-95 |
| IV-176 | 1.4980 |
| IV-177 | 108-111 |
| IV-178 | 148-151 |
| IV-179 | 1.4520 |
| IV-180 | 129-130 |
| IV-181 | 75-77 |

TABLE 71-continued

| Compound No. | Melting point (° C.) or refractive index ($n_D^{20}$) |
|---|---|
| IV-182 | 82-85 |
| IV-183 | 1.4380 |
| IV-184 | 86-87 |
| IV-185 | 1.4210 |
| V-10 | 143-145 |
| V-181 | 1.466 |
| V-182 | 113-115 |
| V-26 | 1.482 |
| VI-27 | 42-45 |
| VI-28 | 1.481 |
| VI-30 | 1.479 |
| VI-31 | 1.473 |
| VI-32 | 1.4850 |
| VI-34 | 1.477 |
| VI-37 | 1.4830 |
| VI-39 | 1.500 |
| VI-41 | 1.494 |
| VI-44 | 1.497 |
| VI-45 | 1.497 |
| VI-46 | 1.512 |
| VI-51 | 1.470 |
| VI-63 | 1.486 |
| VI-89 | 56-58 |
| VI-99 | 1.496 |
| VI-110 | 34-35 |
| VI-153 | 96-98 |
| VI-155 | 1.491 |
| VI-156 | 34-36 |
| VI-157 | 1.490 |
| VI-161 | 1.487 |
| VI-163 | 51-54 |
| VI-166 | 1.484 |
| VI-172 | 1.526 |
| VI-173 | 48-50 |
| VI-194 | 1.492 |
| VI-195 | 1.488 |
| VI-200 | 1.499 |
| VI-202 | 31-32 |
| VI-203 | 1.442 |
| VI-206 | 1.511 |
| VI-207 | 1.513 |
| VI-208 | 87-89 |
| VI-209 | 1.492 |
| VI-211 | 1.499 |
| VI-213 | 1.484 |
| VI-215 | 1.539 |
| VI-216 | 51-53 |
| VI-218 | 1.478 |
| VI-219 | 1.492 |
| VI-220 | 148-151 |
| VI-221 | 1.468 |
| VI-222 | 1.562 |
| VI-223 | 1.540 |
| VI-224 | 89-92 |

TABLE 72

| Compound No. | Melting point (° C.) or refractive index ($n_D^{20}$) |
|---|---|
| VI-225 | 103-106 |
| VI-226 | 58-61 |
| VI-227 | 36-37 |
| VI-228 | 82-83 |
| VI-229 | 98-99 |
| VI-230 | 1.5150 |
| VI-231 | 86-88 |
| VI-232 | 1.483 |
| VI-233 | 1.505 |
| VI-234 | 1.519 |
| VI-235 | 1.492 |
| VI-236 | 97-98 |
| VI-237 | 97-98 |
| VI-238 | 1.499 |

TABLE 72-continued

| Compound No. | Melting point (° C.) or refractive index ($n_D^{20}$) |
|---|---|
| VI-239 | 1.498 |
| VI-240 | 1.540 |
| VI-241 | 57-59 |
| VI-242 | 1.546 |
| VI-243 | 1.536 |
| VI-244 | 1.533 |
| VI-245 | 1.529 |
| VI-246 | 1.530 |
| VI-247 | 1.505 |
| VI-248 | 1.480 |
| VI-249 | 40-42 |
| VI-250 | 1.494 |
| VI-251 | 1.505 |
| VI-252 | 1.499 |
| VI-253 | 1.495 |
| VI-254 | 54-57 |
| VI-255 | 1.475 |
| VI-256 | 1.478 |
| VI-257 | 1.481 |
| VI-258 | 1.503 |
| VI-261 | 1.515 |
| VI-263 | 1.506 |
| VI-264 | 1.509 |
| VI-266 | 1.482 |
| VI-269 | 116-118 |
| VI-270 | 1.5490 |
| VI-271 | 1.5380 |
| VI-273 | 1.4770 |
| VI-275 | 58-60 |
| VI-277 | 1.5260 |
| VI-278 | 1.5030 |
| VI-279 | 89-91 |
| VI-280 | 1.5360 |
| VI-286 | 1.5050 |
| VI-288 | 1.4170 |
| VI-290 | 1.4110 |
| VI-291 | 50-52 |
| VI-292 | 34-35 |
| VI-294 | 31-34 |
| VI-295 | 72-74 |
| VI-296 | 1.4840 |
| VI-297 | 1.5520 |
| VI-301 | 1.4240 |
| VI-302 | 51-52 |
| VI-303 | 1.4510 |
| VI-305 | 67-69 |
| VI-306 | 50-53 |
| VI-308 | 1.4820 |
| VI-309 | 1.4490 |
| VI-310 | 1.4830 |
| VI-311 | 66-69 |
| VI-312 | 69-72 |
| VI-313 | 85-87 |
| VI-315 | 97-98 |
| VII-4 | 130-133 |
| VII-27 | 198-201 |
| VII-51 | 192-195 |
| VII-141 | 70-73 |
| VII-164 | 204-207 |

Shown below are the $^1$H-NMR data (TMS/δ (ppm) data) for compound Nos. I-120, I-229, I-265, I-281, I-312, II-232, II-336, II-373, III-284, IV-1, IV-11, IV-121, IV-152, VI-25, VI-29, VI-33, VI-38, VI-47, VI-53, VI-93, VI-96, VI-97, VI-103, VI-196, VI-197, VI-198, VI-199, VI-201, VI-204, VI-205, VI-210, VI-212, VI-214, VI-217, VI-259, VI-260, VI-262, VI-265, VI-267, VI-268, VI-272, VI-274, VI-276, VI-281, VI-282, VI-283, VI-284, VI-285, VI-287, VI-289, VI-293, VI-298, VI-299, VI-300, VI-304, VI-307 and VI-314.

Compound No. I-120 (CDCl$_3$): 0.91 (3H, t), 1.29 (6H, d), 1.30-1.41 (2H, m), 1.55-1.64 (2H, m), 4.00 (2H, t), 4.52 (1H, sept), 4.95 (1H, s), 8.07 (1H, s), 8.40 (1H, s)

Compound No. I-229 (CDCl$_3$): 1.30-1.41 (12H, m), 4.56-4.70 (2H, m), 8.01 (1H, s), 9.20 (1H, s)

Compound No. I-265 (CDCl$_3$): 0.92 (9H, s), 1.28-1.33 (9H, m), 1.60 (2H, t), 4.25-4.32 (4H, m), 4.59 (1H, sept), 8.04 (1H, s), 8.74 (1H, s)

Compound No. I-281 (CDCl$_3$): 1.36 (6H, d), 1.71 (3H, d), 4.60 (1H, sept), 5.49 (1H, q), 5.94 (1H, s), 7.36-7.39 (6H, m), 7.94 (1H, s), 9.14 (1H, s)

Compound No. I-312 (CDCl$_3$): 1.20-1.49 (12H, m), 3.69 (2H, s), 4.50-4.80 (2H, m), 7.87 and 7.94 (1H, s), 9.29 and 9.49 (1H, s)

Compound No. II-232 (CDCl$_3$): 1.01 (6H, d), 1.27 (9H, s), 4.08 (3H, s), 4.23 (1H, sept), 7.93 (1H, s), 9.11 (1H, s)

Compound No. II-336 (CDCl$_3$): 4.27 (3H, s), 5.01-5.22 (1H, m), 8.13 (1H, s), 8.78 (1H, s)

Compound No. II-373 (CDCl$_3$): 4.18 (3H, s), 4.79 (2H, t), 7.16 (2H, m), 7.79 (1H, s)

Compound No. III-284 (CDCl$_3$): 1.43 (3H, t), 1.75-1.81 (2H, m), 2.05-2.18 (1H, m), 4.38-4.63 (4H, m), 6.02 (1H, s), 7.26 (1H, s), 7.98 (1H, s), 9.17 (1H, s)

Compound No. IV-1 (CDCl$_3$): 0.96 (3H, t), 1.31 (6H, d), 1.73-1.81 (2H, m), 4.29 (2H, t), 4.54 (1H, sept), 8.07 (1H, s), 8.73 (1H, s)

Compound No. IV-11 (CDCl$_3$): 1.33 (6H, d), 3.40 (3H, s), 3.70 (2H, t), 4.40-4.58 (3H, m), 8.07 (1H, s), 8.85 (1H, s)

Compound No. IV-121 (CDCl$_3$): 4.19 (3H, s), 5.35 (2H, s), 7.39 (5H, s), 8.07 (1H, s), 8.65 (1H, s)

Compound No. IV-152 (CDCl$_3$): 0.92 (6H, d), 1.56-1.72 (3H, m), 4.03 (3H, s), 4.27 (2H, t), 6.09 (1H, s), 6.46 (1H, s), 7.07 (1H, s), 7.30 (1H, s), 7.89 (1H, s)

Compound No. VI-25 (CDCl$_3$): 1.37 (6H, d), 1.41 (3H, t), 4.50 (2H, q), 4.63 (1H, sept)

Compound No. VI-29 (CDCl$_3$): 0.99 (6H, d), 1.38 (6H, d), 2.04-2.18 (1H, m), 4.21 (2H, d), 4.63 (1H, sept)

Compound No. VI-33 (CDCl$_3$): 0.97 (6H, d), 1.38 (6H, d), 1.57-1.82 (3H, m), 4.47 (2H, t), 4.63 (1H, sept)

Compound No. VI-38 (CDCl$_3$): 0.97 (9H, d), 1.37 (6H, d), 1.72 (2H, t), 4.52 (2H, t), 4.62 (1H, sept)

Compound No. VI-47 (CDCl$_3$): 1.38 (6H, d), 4.65-4.80 (3H, m)

Compound No. VI-53 (CDCl$_3$): 0.94 (6H, d), 1.33 (6H, d), 1.99-2.12 (1H, m), 2.13 (3H, s), 4.00 (2H, d), 4.51 (1H, sept)

Compound No. VI-93 (CDCl$_3$): 0.96 (3H, t), 1.36 (3H, t), 1.40-1.49 (2H, m), 1.70-1.81 (2H, m), 4.53-4.46 (4H, m)

Compound No. VI-96 (CDCl$_3$): 1.39 (3H, t), 1.41 (9H, s) 4.40 (2H, q)

Compound No. VI-97 (CDCl$_3$): 0.92 (3H, t), 1.36-1.41 (7H, m), 1.74-1.81 (2H, m), 4.37-4.46 (4H, m)

Compound No. VI-103 (CDCl$_3$): 0.97 (9H, s), 1.39 (3H, t), 1.72 (2H, t), 4.41 (2H, q), 4.51 (2H, t)

Compound No. VI-196 (CDCl$_3$): 0.98 (3H, t), 1.39 (6H, d), 1.73-1.85 (2H, m), 4.31 (2H, t), 4.71 (1H, sept)

Compound No. VI-197 (CDCl$_3$): 0.95-1.00 (6H, m), 1.40-1.49 (2H, m), 1.74-1.84 (4H, m), 4.31 (2H, t), 4.45 (2H, t)

Compound No. VI-198 (CDCl$_3$): 0.36-0.67 (4H, m), 0.98 (3H, t), 1.22-1.31 (1H, m), 1.74-1.85 (2H, m), 4.26 (2H, d), 4.31 (1H, t)

Compound No. VI-199 (CDCl$_3$): 0.95-1.00 (6H, m), 1.36 (3H, d), 1.61-1.87 (4H, m), 4.31 (2H, t), 4.47-4.55 (1H, m)

Compound No. VI-201 (CDCl$_3$): 0.98 (3H, t), 1.73-1.85 (2H, m), 4.32 (2H, t), 4.91 (2H, d), 5.34-5.49 (2H, m), 5.96-6.09 (1H, m)

Compound No. VI-204 (CDCl$_3$): 0.97 (6H, d), 2.10 (1H, sept), 4.14 (2H, d), 4.25 (3H, s)

Compound No. VI-205 (CDCl$_3$): 0.95 (6H, d), 1.63-1.78 (3H, m), 4.25 (3H, s), 4.40 (2H, t)

Compound No. VI-210 (CDCl$_3$): 1.39 (6H, d), 4.71 (1H, sept), 4.83 (2H, d), 5.32-5.42 (2H, m), 5.98-6.08 (1H, m)

Compound No. VI-212 (CDCl$_3$): 1.41 (6H, d), 4.65-4.84 (3H, m),

Compound No. VI-214 (CDCl$_3$): 0.35-0.67 (4H, m), 1.19-1.31 (2H, m), 4.17 (2H, d), 4.26 (2H, d)

Compound No. VI-217 (CDCl$_3$): 1.40 (9H, s), 4.70 (1H, sept)

Compound No. VI-259 (CDCl$_3$): 1.40 (3H, t), 3.54 (3H, s), 4.43 (2H, q), 5.4 (2H, s)

Compound No. VI-260 (CDCl$_3$): 1.39 (3H, t), 2.04-2.08 (2H, m), 3.35 (3H, s), 3.50 (2H, t), 4.41 (2H, q), 4.54 (2H, t)

Compound No. VI-262 (CDCl$_3$): 1.40 (3H, t), 1.55-1.66 (2H, m), 2.04-2.14 (1H, m), 4.43 (2H, q), 4.39-4.59 (2H, m)

Compound No. VI-265 (CDCl$_3$): 1.92-1.97 (2H, m), 2.23 (6H, s), 2.37-2.40 (2H, t), 3.88 and 4.17 (3H, s), 4.42, 4.50 (2H, s)

Compound No. VI-267 (CDCl$_3$): 1.40 (9H, s), 1.41 (3H, t), 4.49 (2H, q)

Compound No. VI-268 (CDCl$_3$): 1.00 (3H, t), 1.40 (9H, s), 1.82 (2H, m), 4.39 (2H, t)

Compound No. VI-272 (CDCl$_3$): 0.89 (3H, t), 1.20-1.43 (16H, m), 1.74-1.81 (2H, m), 4.42 (2H, t), 4.63 (1H, sept)

Compound No. VI-274 (CDCl$_3$): 0.85 (3H, t), 0.96 (6H, s), 1.26-1.43 (5H, m), 4.20 (2H, s), 4.41 (2H, q)

Compound No. VI-276 (CDCl$_3$): 1.40 (3H, t), 4.45 (2H, q), 4.90 (2H, t)

Compound No. VI-281 (CDCl$_3$): 0.97 (3H, t), 1.01 (9H, s). 1.73-1.85 (1H, m), 4.11 (2H, s), 4.31 (2H, t)

Compound No. VI-282 (CDCl$_3$): 0.92-1.01 (9H, m), 1.65-1.85 (5S, m), 4.31 (2H, t), 4.48 (2H, t)

Compound No. VI-283 (CDCl$_3$): 1.43 (3S, t), 4.53 (2H, q), 5.07-5.27 (1S, m)

Compound No. VI-284 (CDCl$_3$): 1.36 (6H, d), 1.78 (6H, d), 4.61 (2H, sept), 4.65-4.92 (2H, m), 5.45-5.49 (1H, m)

Compound No. VI-285 (CDCl$_3$): 1.47 (6H, s), 4.19 (3H, s), 4.43 (2H, s)

Compound No. VI-287 (CDCl$_3$): 1.10 (6H, s), 1.39 (3H, t), 3.48 (2H, s), 4.33 (3H, s), 4.43 (2H, q)

Compound No. VI-289 (CDCl$_3$): 4.20 (3H, s), 4.90 (2H, t)

Compound No. VI-293 (CDCl$_3$): 4.26 (3H, s), 5.08-5.26 (1H, m)

Compound No. VI-298 (CDCl$_3$): 0.97 (3H, t), 1.76-1.85 (2H, m), 4.35 (2H, t), 4.86 (2H, t)

Compound No. VI-299 (CDCl$_3$): 1.38 (6H, d), 4.67 (1H, sept), 4.85 (2H, t)

Compound No. VI-300 (CDCl$_3$): 1.23 (3H, t), 1.37 (6H, d), 3.56 (2H, q), 3.78 (2H, t), 4.57 (2H, t), 4.67 (1H, sept)

Compound No. VI-304 (CDCl$_3$): 4.79 (2H, q), 5.46 (2H, s), 7.40 (5H, s)

Compound No. VI-307 (CDCl$_3$): 1.60 (3H, d), 4.19 (3H, s), 4.90 (1H, sept)

Compound No. VI-314 (CDCl$_3$): 1.18 (6H, d), 1.35 (6H, d), 3.63 (1H, sept), 3.75-3.77 (2H, m), 4.54-4.56 (2H, m), 4.63 (1H, sept)

Next, the method for formulation is specifically explained by showing representative formulation examples. The kinds and proportions of compounds and additives used in each formulation are not restricted to those shown in the following formation examples and may be varied in a wide range. In the following explanation, parts (part) refer (refers) to mass parts (mass part).

Formulation Example 1

Emulsifiable Concentrate

| A compound described in Table 1 to Table 51 | 10 parts |
| --- | --- |
| Cyclohexanone | 30 parts |
| Polyoxyethylene alkyl aryl ether | 11 parts |
| Calcium alkylbenzenesulfonate | 4 parts |
| Methylnaphthalene | 45 parts |

The above materials were made into a uniform solution, to prepare an emulsifiable concentrate.

Formulation Example 2

Wettable Powder

| A compound described in Table 1 to Table 51 | 10 parts |
| --- | --- |
| Sodium salt of naphthalenesulfonic acid-formalin condensate | 0.5 part |
| Polyoxyethylene alkyl aryl ether | 0.5 part |
| Diatomaceous earth | 24 parts |
| Clay | 65 parts |

The above materials were mixed and ground to prepare a wettable powder.

Formulation Example 3

Dust Formulation

| A compound described in Table 1 to Table 51 | 2 parts |
| --- | --- |
| Diatomaceous earth | 5 parts |
| Clay | 93 parts |

The above materials were mixed and ground to prepare a dust formulation.

Formulation Example 4

Granule

| A compound described in Table 1 to Table 51 | 5 parts |
| --- | --- |
| Sodium salt of lauryl alcohol sulfate | 2 parts |
| Sodium ligninsulfonate | 5 parts |
| Carboxymethyl cellulose | 2 parts |
| Clay | 86 parts |

The above materials were mixed and ground. Thereto was added 20 parts of water, followed by kneading. The kneaded material was passed through an extrusion granulator to obtain granules of 14 to 32 meshes. The granules were dried to prepare a granule.

Next, the effect of the pest control agent containing the present compound as an active ingredient is shown by Test Examples.

Test Example 1

Insecticidal Action Test for *Aphis gossipii* Glover (Cotton Aphid, Melon Aphid)

A wettable powder prepared based on Formulation Example 2 was diluted with water so that the concentration of active ingredient became 500 ppm. In the resulting liquid were immersed cucumber seedlings on which the hatchlings of *Aphis gossipii* Glover were parasitic, after which the cucumber seedlings were dried in the air. The resulting cucumber seedlings were placed in a thermostat of 25° C. After 3 days, the number of living insects was calculated and the mortality of insect was calculated using the calculation formula of the following Mathematical Expression 1.

$$\text{Insect mortality (\%)} = [1-(\text{number of living insects})/(\text{number of tested insects})] \times 100 \quad \text{[Mathematical Expression 1]}$$

The compounds which gave an insect mortality of 90% or higher in the above test, are shown below.

I-1, I-4, I-5, I-6, I-7, I-8, I-9, I-11, I-13, I-14, I-15, I-18, I-19, I-21, I-22, I-29, I-48, I-49, I-50, I-52, I-54, I-55, I-56, I-57, I-58, I-59, I-60, I-61, I-62, I-64, I-67, I-68, I-69, I-71, I-72, I-75, I-76, I-78, I-80, I-81, I-87, I-98, I-110, I-120, I-121, I-124, I-128, I-129, I-130, I-131, I-134, I-136, I-142, I-165, I-167, I-179, I-190, I-208, I-209, I-212, I-214, I-215, I-217, I-223, I-224, I-228, I-229, I-230, I-235, I-236, I-239, I-240, I-243, I-246, I-247, I-249, I-250, I-257, I-258, I-259, I-260, I-267, I-269, I-270, I-271, I-273, I-274, I-281, I-286, I-288, I-289, I-296, I-298, I-300, I-301, I-302, I-305, I-307, I-309, I-311, I-318, I-319, I-323, I-324, I-331, I-333, I-335, I-339, I-343, I-345, I-347, I-348, I-351, I-355, I-357, I-358, I-359, I-360, I-361, I-363, I-365, I-367, I-369, I-370, I-371, I-372, I-374, I-375, I-376, I-379, I-381, I-383, I-385, I-387, I-393, I-395, I-396, I-397, II-4, II-6, II-10, II-15, II-48, II-49, II-51, II-52, II-53, II-54, II-55, II-56, II-57, II-58, II-59, II-60, II-61, II-62, II-63, II-64, II-65, II-66, II-67, II-68, II-71, II-72, II-73, II-76, II-77, II-78, II-79, II-80, II-81, II-82, II-83, II-86, II-87, II-88, II-89, II-91, II-130, II-133, II-188, II-190, II-194, II-199, II-208, II-214, II-215, II-221, II-222, II-223, II-224, II-225, II-226, II-235, II-236, II-240, II-241, II-244, II-246, II-266, II-267, II-271, II-278, II-280, II-281, II-284, II-285, II-288, II-289, II-301, II-302, II-303, II-304, II-306, II-309, II-311, II-312, II-313, II-314, II-316, II-317, II-318, II-319, II-320, II-321, II-322, II-324, II-325, II-326, II-327, II-328, II-329, II-330, II-331, II-332, II-333, II-334, II-335, II-338, II-340, I-342, II-343, II-344, II-345, II-346, II-349, II-351, II-352, II-353, II-355, II-356, II-357, II-359, II-360, II-361, II-365, II-367, II-369, II-371, II-373, II-374, II-375, II-376, II-377, II-378, II-379, III-4, III-48, III-49, III-50, III-51, III-53, III-54, III-55, III-56, III-57, III-58, III-59, III-60, III-61, III-62, III-64, III-65, III-66, III-67, III-68, III-70, III-71, III-72, III-73, III-76, III-77, III-78, III-79, III-80, III-81, III-82, III-83, III-84, III-85, III-87, III-88, III-90, III-233, III-238, III-239, III-242, III-262, III-269, III-272, III-273, III-277, III-279, III-280, III-281, III-282, III-283, III-284, III-287, III-288, III-289, III-290, III-295, III-296, III-297, III-298, III-300, III-301, III-302, III-303, III-304, III-305, III-306, III-307, III-308, III-309, IV-1, IV-6, IV-22, IV-30, IV-33, IV-36, IV-37, IV-38, IV-39, IV-79, IV-89, IV-90, IV-91, IV-92, IV-95, IV-97, IV-98, IV-99, IV-102, IV-104, IV-107, IV-115, IV-117, IV-119, IV-152, IV-164, IV-170, IV-172, IV-176, IV-177, IV-178, IV-179, IV-180, IV-181, V-10, VI-96, VI-199, VI-217, VI-221, VI-222, VI-223, VI-269, VI-276, VI-291, VI-297

Test Example 2

Insecticidal Action Test for *Aphis gossipii* Glover (Cotton Aphid, Melon Aphid)

A wettable powder prepared based on Formulation Example 2 was diluted with water so that the concentration of active ingredient became 500 ppm. 5 ml of the resulting diluted formulation was drenched to the rice-plant foot of cucumber seedlings on which the hatchlings of *Aphis* gossipii Glover were parasitic. The resulting cucumber seedlings were placed in a thermostat of 25° C. After 3 days, the number of living insects was calculated and the mortality of insect was calculated using the calculation formula of Mathematical Expression 1.

The compounds which gave an insect mortality of 90% or higher in the above test, are shown below.

I-4, I-5, I-55, I-233, II-57, II-63, II-64, II-80, II-301, II-316, II-326, II-332, II-334, II-346, II-367, II-371, III-49, III-60, III-61, III-64, III-68, III-87, III-281, III-283, III-287, III-300, III-304, IV-95

Test Example 3

Insecticidal Action Test for *Nilaparvata lugens* Stål (Brown Rice Planthopper)

A wettable powder prepared based on Formulation Example 2 was diluted with water so that the concentration of active ingredient became 500 ppm. In the diluted formulation were immersed sprouting unhulled rice. The immersed rice was placed in a plastic cup of 60 ml. Into the plastic cup were released 10 3-age larvae of *Nilaparvata lugens* Stål (brown rice planthopper). The cup was covered with a cap and placed in a thermostat of 25° C. After 6 days, the number of living insects was counted and the mortality of insect was calculated using the calculation formula of Mathematical Expression 1.

The compounds which gave an insect mortality of 90% or higher in the above test, are shown below.

I-1, I-4, I-5, I-6, I-7, I-8, I-9, I-11, I-13, I-14, I-15, I-16, I-18, I-19, I-21, I-22, I-29, I-47, I-48, I-49, I-50, I-51, I-52, I-53, I-54, I-55, I-56, I-57, I-58, I-59, I-60, I-61, I-62, I-64, I-67, I-68, I-69, I-70, I-71, I-72, I-73, I-74, I-75, I-76, I-77, I-78, I-79, I-80, I-81, I-82, I-83, I-84, I-85, I-87, I-90, I-91, I-92, I-96, I-98, I-110, I-119, I-120, I-121, I-124, I-128, I-129, I-130, I-131, I-133, I-134, I-136, I-142, I-165, I-167, I-179, I-186, I-188, I-190, I-199, I-208, I-209, I-210, I-211, I-212, I-213, I-214, I-215, I-217, I-218, I-219, I-220, I-221, I-223, I-224, I-225, I-226, I-228, I-229, I-230, I-231, I-233, I-234, I-235, I-236, I-237, I-239, I-240, I-241, I-242, I-243, I-244, I-245, I-246, I-247, I-249, I-250, I-251, I-254, I-255, I-256, I-257, I-258, I-259, I-260, I-261, I-262, I-263, I-264, I-265, I-266, I-267, I-268, I-269, I-270, I-271, I-272, I-273, I-274, I-275, I-278, I-279, I-281, I-282, I-285, I-286, I-287, I-288, I-289, I-290, I-296, I-297, I-298, I-299, I-300, I-301, I-302, I-304, I-305, I-306, I-307, I-308, I-309, I-310, I-311, I-312, I-313, I-315, I-318, I-319, I-321, I-322, I-323, I-324, I-327, I-331, I-332, I-333, I-335, I-336, I-339, I-343, I-345, I-346, I-347, I-348, I-351, I-353, I-354, I-355, I-357, I-358, I-359, I-360, I-361, I-365, I-367, I-369, I-370, I-371, I-372, I-373, I-374, I-375, I-376, I-377, I-378, I-379, I-380, I-381, I-382, I-383, I-384, I-385, I-386, I-387, I-389, I-390, I-391, I-392, I-393, I-394, I-395, I-396, I-397, I-398, II-4, II-6, II-10, II-15, II-47, II-48, II-49, II-50, II-51, II-52, II-53, II-54, II-55, II-56, II-57, II-58, II-59, II-60, II-61, II-62, II-63, II-64, II-65, II-66, II-67, II-68, II-70, II-71, II-72, II-73, II-74, II-75, II-76, II-77, II-78, II-79, II-80, II-81, II-82, II-83, II-84, II-85, II-86, II-87, II-88, II-89, II-90, II-91, II-121, II-125, II-130, II-133, II-185, II-188, II-190, II-194, II-199, II-208, II-214, II-215, II-221, II-222, II-223, II-224, II-225, II-226, II-227, II-232, II-235, II-236, II-238, II-240, II-241, II-244, II-245, II-246, II-247, II-266, II-267, II-268, II-269, II-271, II-278, II-279, II-280, II-281, II-282, II-283, II-284, II-285, II-286, II-288, II-289, II-301, II-302, II-303, II-304, II-306, II-311, II-312, II-313, II-314, II-316, II-317, II-318, II-319, II-320, II-321, II-322, II-323, II-324, II-325, II-326, II-327, II-328, II-329, II-330, II-331, II-332, II-333, II-334, II-335, II-336, II-338, II-339, II-340, II-341, II-342, II-343, II-344, II-345, II-346, II-347, II-348, II-349, II-350, II-351, II-352, II-353, II-354, II-355, II-356, II-357, II-358, II-359, II-360, II-361, II-362, II-365, II-366, II-367, II-368, II-369, II-370, II-371, II-372, II-373, II-374, II-375, II-376, II-377, II-378, II-379, II-380, II-381, III-4, III-47, III-48, III-49, III-50, III-51, III-52, III-53, III-54, III-55, III-56, III-57, III-58, III-59, III-60, III-61, III-62, III-64, III-65, III-66, III-67, III-68, III-70, III-71, III-72, III-73, III-74, III-75, III-76, III-77, III-78, III-79, III-80, III-81, III-82, III-83, III-84, III-85, III-87, III-88, III-89, III-90, III-91, III-233, III-234, III-238, III-239, III-242, III-243, III-262, III-263, III-264, III-266, III-267, III-269, III-270, III-272, III-273, III-279, III-280, III-281, III-282, III-283, III-284, III-287, III-288, III-289, III-290, III-295, III-296, III-297, III-298, III-299, III-300, III-301, III-302, III-303, III-304, III-305, III-306, III-307, III-308, III-309, IV-1, IV-4, IV-6, IV-11, IV-14, IV-15, IV-17, IV-18, IV-19, IV-20, IV-21, IV-22, IV-23, IV-25, IV-27, IV-30, IV-32, IV-33, IV-34, IV-35, IV-36, IV-37, IV-38, IV-39, IV-40, IV-42, IV-59, IV-61, IV-62, IV-64, IV-65, IV-74, IV-76, IV-77, IV-78, IV-79, IV-80, IV-86, IV-89, IV-90, IV-91, IV-92, IV-93, IV-95, IV-96, IV-97, IV-98, IV-99, IV-100, IV-101, IV-102, IV-103, IV-104, IV-106, IV-107, IV-108, IV-109, IV-110, IV-111, IV-112, IV-113, IV-114, IV-115, IV-116, IV-117, IV-118, IV-119, IV-120, IV-127, IV-129, IV-130, IV-131, IV-133, IV-134, IV-135, IV-146, IV-147, IV-149, IV-164, IV-165, IV-166, IV-167, IV-168, IV-169, IV-170, IV-171, IV-172, IV-173, IV-176, IV-177, IV-178, IV-179, IV-180, IV-181, IV-182, IV-183, IV-184, IV-185, IV-186, IV-187, V-10, V-181, VI-25, VI-26, VI-27, VI-28, VI-29, VI-30, VI-31, VI-32, VI-33, VI-34, VI-37, VI-38, VI-39, VI-41, VI-44, VI-45, VI-46, VI-53, VI-63, VI-89, VI-93, VI-96, VI-97, VI-99, VI-103, VI-110, VI-153, VI-155, VI-156, VI-157, VI-161, VI-163, VI-166, VI-172, VI-173, VI-194, VI-195, VI-196, VI-197, VI-198, VI-199, VI-200, VI-201, VI-202, VI-203, VI-204, VI-205, VI-206, VI-207, VI-209, VI-210, VI-211, VI-213, VI-214, VI-215, VI-217, VI-218, VI-221, VI-222, VI-223, VI-230, VI-232, VI-233, VI-234, VI-235, VI-239, VI-244, VI-246, VI-247, VI-248, VI-250, VI-255, VI-256, VI-257, VI-258, VI-259, VI-260, VI-261, VI-262, VI-263, VI-264, VI-267, VI-268, VI-274, VI-275, VI-277, VI-278, VI-281, VI-282, VI-283, VI-284, VI-286, VI-287, VI-290, VI-292, VI-294, VI-297, VI-300, VI-302, VI-303, VI-304, VI-305, VI-306, VI-307, VI-308, VI-309, VI-310, VI-314, VII-164

Test Example 4

Trial of Systematic Insecticidal Activity Against Brown Planthopper (*Nilaparvata lugens*)

A wettable powder prepared based on Formulation Example 2 was diluted with water so that the concentration of active ingredient became 1,800 ppm. 250 μl of the diluted formulation was poured to the rice-plant foot of 2.5-leaf age rice seedlings planted in a paper pot of 1.5 cm (length)×1.5 cm (width)×3 cm (height). Then, the paper pot was placed in a plastic cup of 700 ml. Into the plastic cup were released 5 3-age larvae of *Nilaparvata lugens* Stål (brown rice planthopper). The cup was covered with a cap and placed in a thermostat of 25° C. After 6 days, the number of living insects was counted and the mortality of insect was calculated using the calculation formula of Mathematical Expression 1.

The compounds which gave an insect mortality of 90% or higher in the above test, are shown below.
I-4, I-5, I-6, I-7, I-8, I-9, I-11, I-13, I-16, I-18, I-19, I-21, I-22, I-48, I-50, I-52, I-53, I-56, I-64, I-71, I-72, I-74, I-75, I-76, I-87, I-90, I-91, I-96, I-98, I-110, I-133, I-142, I-165, I-167, I-179, I-186, I-190, I-199, I-208, I-218, I-223, I-228, I-229, I-230, I-231, I-233, I-236, I-237, I-246, I-273, II-4, II-6, II-52, II-56, II-61, II-75, II-79, II-81, II-84, II-85, II-199, II-224, II-271, III-4, III-49, III-73, III-75, IV-4, IV-6, IV-25, IV-36, IV-40, IV-101

Test Example 5

Insecticidal Action Test for *Plutella xylostella* Linné (Diamondback Moth)

A wettable powder prepared based on Formulation Example 2 was diluted with water so that the concentration of active ingredient became 500 ppm. In the diluted formulation were immersed cabbage leaves, followed by drying in the air. The resulting cabbage leaves were placed in a plastic cup of 60 ml. Into the plastic cup were released 10 2-age larvae of *Plutella xylostella* Linné (diamondback moth). The plastic cup was covered with a cap and placed in a thermostat of 25° C. After 6 days, the number of living insects was counted and the mortality of insect was calculated using the calculation formula of Mathematical Expression 1.

The compounds which gave an insect mortality of 90% or higher in the above test, are shown below.
I-378, II-353, II-355, III-78, IV-121, IV-155, VI-25, VI-28, VI-33, VI-46, VI-63, VI-110, VI-153, VI-172, VI-196, VI-201, VI-210, VI-215, VI-223, VI-232, VI-233, VI-255, VI-256, VI-260, VI-265

Test Example 6

Insecticidal Action Test for *Helicoverpa armigera* Hubner (Corn Earworm)

A wettable powder prepared based on Formulation Example 2 was diluted with water so that the concentration of active ingredient became 500 ppm. In the diluted formulation were immersed cabbage leaves, followed by drying in the air. The resulting cabbage leaves were placed in a plastic cup of 60 ml. Into the plastic cup were released 5 hatchlings of *Plutella xylostella* Linné (diamondback moth). The plastic cup was covered with a cap and placed in a thermostat of 25° C. After 6 days, the number of living insects was counted and the mortality of insect was calculated using the calculation formula of Mathematical Expression 1.

The compounds which gave an insect mortality of 90% or higher in the above test, are shown below.
I-374, II-353, III-78, VI-28, VI-46, VI-63, VI-212, VI-215, VI-222, VI-223, VI-231

The invention claimed is:
1. An alkoxyimino compound of the following general formula [I] or an agriculturally acceptable salt thereof,

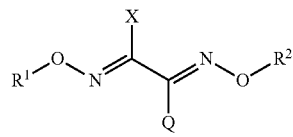

[I]

wherein:
X is a hydrogen atom, a halogen atom, a cyano group, a $C_1$~$C_8$ alkyl group, a $C_2$~$C_6$ alkenyl group, a $C_2$~$C_6$ alkynyl group, a $C_3$~$C_6$ cycloalkyl group, a ($C_3$~$C_6$ cycloalkyl)-($C_1$~$C_6$ alkyl) group, a $C_1$~$C_6$ haloalkyl group, a $C_1$~$C_6$ alkylthio group, a $C_1$~$C_6$ alkylsulfinyl group, a $C_1$~$C_6$ alkylsulfonyl group, a ($C_1$~$C_6$ alkylthio)-($C_1$~$C_6$ alkyl) group, a ($C_1$~$C_6$ alkylsulfinyl)-($C_1$~$C_6$ alkyl) group, a ($C_1$~$C_6$ alkylsulfonyl)-($C_1$~$C_6$ alkyl) group, a $C_1$~$C_6$ alkoxy group, a ($C_1$~$C_6$ alkoxy)-($C_1$~$C_6$ alkyl) group, a thiocarbamoyl group, a $R^4R^5NC$(=O) group, a $R^6R^7N$ group, a $C_1$~$C_6$ alkoxycarbonyl group, a carboxyl group, a $R^8O(HN=)C$ group, a $R^9ON=(R^{10})C$ group, a $R^{11}S(O=)C$ group, a $R^{12}R^{13}NSO_2NH$ group, a $C_1$~$C_6$ alkyl group wherein the alkyl moiety is substituted with a hydroxyl group, a cyano $C_1$~$C_6$ alkyl group, a $C_1$~$C_6$ alkylcarbonyl group, a phenyl group which may be substituted with substituent(s) selected from a substituent group α, or a heterocyclic ring of 1 to 9 carbon atoms, having 1 to 5 hetero atoms which may be the same or different and which are selected from the group consisting of an oxygen atom, sulfur atom and nitrogen atom, wherein a heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, oxo group and cyano group;
$R^1$ is a $C_1$~$C_{10}$ alkyl group, a $C_2$~$C_6$ alkenyl group, a $C_2$~$C_6$ alkynyl group, a $C_3$~$C_6$ cycloalkyl group, a ($C_3$~$C_6$ cycloalkyl)-($C_1$~$C_6$ alkyl) group, a $C_1$~$C_6$ haloalkyl group, a $C_2$~$C_6$ haloalkenyl group, a $C_2$~$C_6$ haloalkynyl group, a ($C_1$~$C_6$ alkylthio)-($C_1$~$C_6$ alkyl) group, a ($C_1$~$C_6$ alkylsulfinyl)-($C_1$~$C_6$ alkyl) group, a ($C_1$~$C_6$ alkylsulfonyl)-($C_1$~$C_6$ alkyl) group, a ($C_1$~$C_6$ alkoxy)-($C_1$~$C_6$ alkyl) group, a ($C_1$~$C_6$ haloalkoxy)-($C_1$~$C_6$ alkyl) group, a ($C_1$~$C_6$ alkoxyimino)-($C_1$~$C_6$ alkyl) group, a (tri($C_1$~$C_6$ alkyl)silyl)-($C_1$~$C_6$ alkyl) group, a cyano $C_1$~$C_6$ alkyl group, a (gem-di($C_1$~$C_6$ alkoxy)-($C_1$~$C_6$ alkyl) group, a $C_1$~$C_6$ alkyl group wherein the alkyl moiety is substituted with a hydroxyl group, an amino $C_1$~$C_6$ alkyl group (the group may be substituted with $R^{14}$ and $R^{15}$), a phenyl group which may be substituted with substituent(s) selected from the group consisting of a halogen atom, $C_1$~$C_6$ haloalkyl group, $C_1$~$C_6$ alkoxy group, $C_1$~$C_6$ haloalkoxy group, $C_1$~$C_6$ alkoxycarbonyl group, nitro group, and a cyano group, a phenyl $C_1$~$C_6$ alkyl group which may be substituted with substituent(s) selected from the group consisting of a halogen atom, $C_1$~$C_6$ haloalkyl group, $C_1$~$C_6$ alkoxy group, $C_1$~$C_6$ haloalkoxy group, $C_1$~$C_6$ alkoxycarbonyl group, nitro group, and a cyano group, a phenyl $C_2$~$C_6$ alkenyl group which may be substituted with substituent(s) selected from the substituent group α, a phenoxy $C_1$~$C_6$ alkyl group which may be substituted with substituent(s) selected from the substituent group α, a heterocyclic ring of 1 to 9 carbon atoms, having 1 to 5 hetero atoms which may be the same or different and which are selected from the group consisting of an oxygen atom, sulfur atom and nitrogen atom, wherein the heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, and cyano group, a $C_1$~$C_6$ alkyl group substituted with a heterocyclic ring of 1 to 9 carbon atoms, having 1 to 5 hetero atoms which may be the same or different and which are selected from the group consisting of an oxygen atom, sulfur atom and nitrogen atom, wherein a heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, and cyano group, or a $C_2$~$C_6$ alkenyl group substituted with a heterocyclic ring may be substituted of 1 to 9 carbon atoms, having 1 to 5 hetero atoms which may be the same or different and which are selected from the group consisting of an oxygen atom, sulfur atom and nitrogen atom, wherein a heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, and cyano group;

when the heterocyclic ring contains nitrogen atom, the nitrogen atom may be oxidized to form N-oxide;

$R^2$ is a $C_1$~$C_6$ alkyl group, a $C_2$~$C_6$ alkenyl group, a $C_2$~$C_6$ alkynyl group, a $C_3$~$C_6$ cycloalkyl group, a $C_1$~$C_6$ haloalkyl group, a $C_2$~$C_6$ haloalkenyl group, a $C_2$~$C_6$ haloalkynyl group, a ($C_1$~$C_6$ alkylthio)-($C_1$~$C_6$ alkyl) group, a ($C_1$~$C_6$ alkylsulfinyl)~($C_1$~$C_6$ alkyl) group, a ($C_1$~$C_6$ alkylsulfonyl)-($C_1$~$C_6$ alkyl) group, a ($C_1$~$C_6$ alkoxy)-($C_1$~$C_6$ alkyl) group, a ($C_1$~$C_6$ haloalkoxy)-($C_1$~$C_6$ alkyl) group, a cyano $C_1$~$C_6$ alkyl group, or a phenyl $C_1$~$C_6$ alkyl group which may be substituted with the substituent group α;

Q is a heterocyclic ring as set forth by the following formula [Q-1] or formula [Q-2];

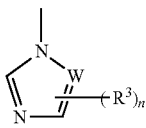
[Q-1]

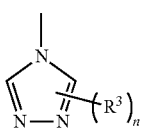
[Q-2]

or a halogen atom;

in the formula [Q-1], W is a nitrogen atom or a methine group;

the nitrogen atom(s) of a heterocyclic ring of formula [Q-1] and formula [Q-2] may be oxidized to form N-oxide;

in the formula [Q-1] and formula [Q-2], $R^3$ is a mercapto group, or a $C_1$~$C_6$ haloalkyl group;

in the formula [Q-1], n is 0, 1 or 2 when W is a nitrogen atom and 0, 1, 2 or 3 when W is a methine group;

in the formula [Q-2], n is 0, 1, 2 or 3;

$R^4$, $R^5$, $R^6$, $R^7$, $R^{12}$, $R^{13}$, $R^{14}$ and $R^{15}$ are each a hydrogen atom, a $C_1$~$C_6$ alkyl group, a $C_1$~$C_6$ alkoxy group, a ($C_1$~$C_6$ alkoxy)-($C_1$~$C_6$ alkyl) group, a $C_1$~$C_6$ alkylcarbonyl group, a $C_1$~$C_6$ alkoxycarbonyl group, a $C_1$~$C_6$ haloalkyl group, a $C_3$~$C_6$ cycloalkyl group, a ($C_3$~$C_6$ cycloalkyl)-($C_1$~$C_6$ alkyl) group, a $C_1$~$C_6$ alkylsulfonyl group, a cyano $C_1$~$C_6$ alkyl group, or a phenyl group which may be substituted with substituent(s) selected from the substituent group α;

$R^4$ and $R^5$, $R^6$ and $R^7$, $R^{12}$ and $R^{13}$, and $R^{14}$ and $R^{15}$ may respectively be combined together to form an $C_2$~$C_7$ alkylene chain and thereby may form, together with the nitrogen atom to which they bond, a 3- to 8-membered ring, wherein the alkylene chain may contain one oxygen atom, sulfur atom or nitrogen atom and also may be substituted with halogen atom, $C_1$~$C_6$ alkyl group and oxo group;

$R^8$ and $R^9$ are each a hydrogen atom, a $C_1$~$C_6$ alkyl group, a $C_1$~$C_6$ haloalkyl group, or a $C_1$~$C_6$ alkoxycarbonyl group;

$R^{10}$ is a $R^6R^7N$ group or Q;

$R^{11}$ is a $C_1$~$C_6$ alkyl group; and substituent group α is a halogen atom, $C_1$~$C_6$ alkyl group, $C_1$~$C_6$ haloalkyl group, $C_1$~$C_6$ alkoxy group, $C_1$~$C_6$ haloalkoxy group, $C_1$~$C_6$ alkoxycarbonyl group, nitro group, or cyano group.

2. An alkoxyimino compound or an agriculturally acceptable salt thereof, set forth in claim 1, wherein X is a hydrogen atom, a halogen atom, a cyano group, a $C_1$~$C_8$ alkyl group, a $C_3$~$C_6$ cycloalkyl group, a $C_1$~$C_6$ haloalkyl group, a $C_1$~$C_6$ alkylthio group, a $C_1$~$C_6$ alkylsulfinyl group, a $C_1$~$C_6$ alkylsulfonyl group, a $C_1$~$C_6$ alkoxy group, a thiocarbamoyl group, a $R^4R^5NC$(=O) group, a $R^6R^7N$ group, a $C_1$~$C_6$ alkoxycarbonyl group, a carboxyl group, a $R^8O(HN=)C$ group, a $R^9ON=(R^{10})C$ group, a $R^{11}S(O=)C$ group, a $R^{12}R^{13}NSO_2NH$ group, a $C_1$~$C_6$ alkyl group wherein the alkyl moiety is substituted with a hydroxyl group, a cyano $C_1$~$C_6$ alkyl group, a $C_1$~$C_6$ alkylcarbonyl group, a phenyl group which may be substituted with substituent(s) selected from the substituent group α, or a heterocyclic ring of 1 to 9 carbon atoms, having 1 to 5 hetero atoms which may be the same or different and which are selected from the group consisting of an oxygen atom, sulfur atom and nitrogen atom, wherein a heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, oxo group and cyano group, $R^1$ is a $C_1$~$C_{10}$ to alkyl group, a $C_2$~$C_6$ alkenyl group, a $C_2$~$C_6$ alkynyl group, a $C_3$~$C_6$ cycloalkyl group, a ($C_3$~$C_6$ cycloalkyl)-($C_1$~$C_6$ alkyl) group, a $C_1$~$C_6$ haloalkyl group, a $C_2$~$C_6$ haloalkenyl group, a ($C_1$~$C_6$ alkylthio)-($C_1$~$C_6$ alkyl) group, a ($C_1$~$C_6$ alkoxy $C_1$~$C_6$ alkyl) group, a ($C_1$~$C_6$ haloalkoxy)-($C_1$~$C_6$ alkyl) group, a (tri($C_1$~$C_6$ alkyl)silyl)-($C_1$~$C_6$ alkyl) group, a cyano $C_1$~$C_6$ alkyl group, a (gem-di($C_1$~$C_6$ alkoxy))-($C_1$~$C_6$ alkyl) group, a $C_1$~$C_6$ alkyl group wherein the alkyl moiety is substituted with a hydroxyl group, an amino $C_1$~$C_6$ alkyl group (the group may be substituted with $R^{14}$ and $R^{15}$), a phenyl group which may be substituted with substituent(s) selected from the group consisting of a halogen atom, $C_1$~$C_6$ haloalkyl group, $C_1$~$C_6$ alkoxy group, $C_1$~$C_6$ haloalkoxy group, $C_1$~$C_6$ alkoxycarbonyl group, nitro group, and a cyano group, a phenyl $C_1$~$C_6$ alkyl group which may be substituted with substituent(s) selected from the group consisting of a halogen atom, $C_1$~$C_6$ haloalkyl group, $C_1$~$C_6$ alkoxy group, $C_1$~$C_6$ haloalkoxy group, $C_1$~$C_6$ alkoxycarbonyl group, nitro group, and a cyano group, a phenyl $C_2$~$C_6$ alkenyl group which may be substituted with substituent(s) selected from the substituent group α, a phenoxy $C_1$~$C_6$ alkyl group which may be substituted with substituent(s) selected from the substituent group α, a heterocyclic ring of 1 to 9 carbon atoms, having 1 to 5 hetero atoms which may be the same or different and which are selected from the group consisting of an oxygen atom, sulfur atom and nitrogen atom, wherein a heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, and cyano group, or a $C_1$~$C_6$ alkyl group substituted with a heterocyclic ring of 1 to 9 carbon atoms, having 1 to 5 hetero atoms which may be the same or different and which are selected from the group consisting of an oxygen atom, sulfur atom and nitrogen atom, wherein the heterocyclic ring may be substituted with 1 to 5 substituent(s) selected from the group consisting of halogen atoms, $C_1$~$C_6$ alkyl group, $C_1$~$C_6$ haloalkyl group, $C_1$~$C_6$ alkoxy group, and cyano group, when the heterocyclic ring contains nitrogen atom, the nitrogen atom may be oxidized to form N-oxide, $R^2$ is a $C_1$~$C_6$ alkyl group, a $C_2$~$C_6$ alkenyl group, a $C_2$~$C_6$ alkynyl group, a $C_3$~$C_6$ cycloalkyl group, a $C_1$~$C_6$ haloalkyl group, a $C_1$~$C_6$ alkoxy $C_1$~$C_6$ alkyl group, a cyano $C_1$~$C_6$ alkyl group, or a phenyl $C_1$~$C_6$ alkyl group which may be substituted with the substituent group α, Q is a heterocyclic ring as set forth by the following formula [Q-1] or formula [Q-2],

[formula 3]

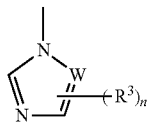
[Q-1]

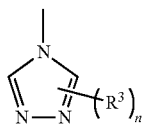
[Q-2]

or a halogen atom, in the formula [Q-1], W is a nitrogen atom or a methine group, in the formula [Q-1] and formula [Q-2], $R^3$ is a mercapto group or a $C_1$~$C_6$ haloalkyl group, in the formula [Q-1] and formula [Q-2], n is 0 or 1, $R^4$, $R^5$, $R^6$, $R^7$, $R^{12}$, $R^{13}$, $R^{14}$ and $R^{15}$ are each a hydrogen atom, a $C_1$~$C_6$ alkyl group, a $C_1$~$C_6$ alkoxy group, a $C_1$~$C_6$ alkylcarbonyl group, a $C_1$~$C_6$ alkoxycarbonyl group, a $C_1$~$C_6$ haloalkyl group, a $C_3$~$C_6$ cycloalkyl $C_1$~$C_6$ alkyl group, a cyano $C_1$~$C_6$ alkyl group, or a phenyl group which may be substituted with substituent(s) selected from the substituent group α, $R^4$ and $R^5$, $R^6$ and $R^7$, $R^{12}$ and $R^{13}$, and $R^{14}$ and $R^{15}$ may respectively be combined together to form an $C_2$~$C_7$ alkylene chain and thereby may form, together with the nitrogen atom to which they bond, a 3- to 8-membered ring, wherein the alkylene ring may contain one oxygen atom, sulfur atom or nitrogen atom, $R^8$ and $R^9$ are each a hydrogen atom, a $C_1$~$C_6$ alkyl group, or a $C_1$~$C_6$ alkoxycarbonyl group, $R^{10}$ is a $R^6R^7N$ group or Q, and $R^{11}$ is a $C_1$~$C_6$ alkyl group.

3. The alkoxyimino compound or an agriculturally acceptable salt thereof of claim 1, wherein Q is a halogen atom.

4. The alkoxyimino compound or an agriculturally acceptable salt thereof of claim 1, wherein Q is a heterocyclic ring as set forth by the following formula [Q-1],

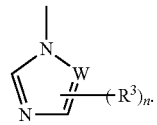
[Q-1]

5. A pest control agent characterized by containing, as an active ingredient, the alkoxyimino compound or an agriculturally acceptable salt thereof of claim 1.

6. The pest control agent of claim 5, wherein said pest control agent is formulated as an insecticide.

7. A method for pest control, comprising the step of applying an effective amount of the alkoxyimino compound or an agriculturally acceptable salt thereof of claim 1 to a pest in the form of dispersion to soil, surface application or mixing with livestock feed.

8. The method for pest control of claim 7, wherein said pest is an insect and the alkoxyimino compound or an agriculturally acceptable salt thereof is formulated as an insecticide.

9. The alkoxyimino compound or an agriculturally acceptable salt thereof of claim 2, wherein Q is a halogen atom.

10. The alkoxyimino compound or an agriculturally acceptable salt thereof of claim 2, wherein Q is a heterocyclic ring as set forth by the following formula [Q-1],

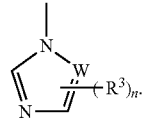
[Q-1]

11. A pest control agent characterized by containing, as an active ingredient, the alkoxyimino compound or an agriculturally acceptable salt thereof of claim 2.

12. A pest control agent characterized by containing, as an active ingredient, the alkoxyimino compound or an agriculturally acceptable salt thereof of claim 3.

13. A pest control agent characterized by containing, as an active ingredient, the alkoxyimino compound or an agriculturally acceptable salt thereof of claim 4.

14. A method for pest control, comprising the step of applying an effective amount of the alkoxyimino compound or an agriculturally acceptable salt thereof of claim 2 to a pest by dispersion, in-soil application, surface application or mixing with livestock feed.

15. A method for pest control, comprising the step of applying an effective amount of the alkoxyimino compound or an agriculturally acceptable salt thereof of claim 3 to a pest by dispersion, in-soil application, surface application or mixing with livestock feed.

16. A method for pest control, comprising the step of applying an effective amount of the alkoxyimino compound or an agriculturally acceptable salt thereof of claim 4 to a pest by dispersion, in-soil application, surface application or mixing with livestock feed.

* * * * *

UNITED STATES PATENT AND TRADEMARK OFFICE
CERTIFICATE OF CORRECTION

PATENT NO. : 8,895,035 B2  
APPLICATION NO. : 13/806317  
DATED : November 25, 2014  
INVENTOR(S) : Shunichirou Fukumoto et al.

Page 1 of 1

It is certified that error appears in the above-identified patent and that said Letters Patent is hereby corrected as shown below:

In the Claims

At column 135, line 21:

--with the substituent group α;-- should read:

--with substituent(s) selected from the substituent group α;--

At column 135, line 47:

--in the formula [Q-2], n is 0, 1, 2 or 3;-- should read:

--in the formula [Q-2], n is 0, 1 or 2;--

At column 137, line 11:

--which may be substituted with the substituent group α,-- should read:

--which may be substituted with substituent(s) selected from the substituent group α,--

Signed and Sealed this  
Twenty-fifth Day of August, 2015

Michelle K. Lee  
*Director of the United States Patent and Trademark Office*